(12) United States Patent
Markosyan et al.

(10) Patent No.: US 9,752,174 B2
(45) Date of Patent: Sep. 5, 2017

(54) HIGH-PURITY STEVIOL GLYCOSIDES

(71) Applicants: PURECIRCLE SDN BHD, Negeri Sembilian (MY); THE COCA-COLA COMPANY, NW Atlanta, GA (US)

(72) Inventors: Avetik Markosyan, Yerevan (AM); Indra Prakash, Alpharetta, GA (US); Cynthia Bunders, Atlanta, GA (US); Pankaj Soni, Kennesaw, GA (US); Jarrin Cyrille, Muret (FR); Aurélien Badie, Lebège (FR); Robert ter Halle, Baziege (FR)

(73) Assignees: PureCircle Sdn Bhd, Kuala Lumpur (MY); The Coca-Cola Company, Atlanta, GA (US)

( * ) Notice: Subject to any disclaimer, the term of this patent is extended or adjusted under 35 U.S.C. 154(b) by 47 days.

(21) Appl. No.: 14/287,837

(22) Filed: May 27, 2014

(65) Prior Publication Data

US 2014/0357588 A1 Dec. 4, 2014

Related U.S. Application Data

(60) Provisional application No. 61/827,922, filed on May 28, 2013, provisional application No. 61/843,544, filed on Jul. 8, 2013, provisional application No. 61/861,528, filed on Aug. 2, 2013, provisional application No. 61/881,166, filed on Sep. 23, 2013, provisional application No. 61/885,084, filed on Oct. 1, 2013, provisional application No. 61/904,751, filed on Nov. 15, 2013, provisional application No. 61/913,482, filed on Dec. 9, 2013, provisional application No. 61/921,635, filed on Dec. 30, 2013, provisional application No. 61/925,329, filed on Jan. 9, 2014, provisional application No. 61/939,855, filed on Feb. 14, 2014.

(51) Int. Cl.
| | | |
|---|---|---|
| *C12P 19/56* | (2006.01) |
| *A23L 2/60* | (2006.01) |
| *A24B 15/10* | (2006.01) |
| *C07H 15/256* | (2006.01) |
| *A24B 15/30* | (2006.01) |
| *A23L 27/30* | (2016.01) |

(52) U.S. Cl.
CPC ............ *C12P 19/56* (2013.01); *A23L 2/60* (2013.01); *A23L 27/33* (2016.08); *A24B 15/10* (2013.01); *A24B 15/302* (2013.01); *C07H 15/256* (2013.01); *A23V 2002/00* (2013.01); *Y02P 20/582* (2015.11)

(58) Field of Classification Search
CPC ..... A23L 1/2363; A23L 2/60; A23V 2002/00; A23V 2250/258; A24B 15/302; A24B 15/10; C12P 19/56
USPC ............ 514/34; 536/18.1; 426/48, 590, 658
See application file for complete search history.

(56) References Cited

U.S. PATENT DOCUMENTS

| | | |
|---|---|---|
| 3,723,410 A | 3/1973 | Persinos |
| 4,082,858 A | 4/1978 | Morita et al. |
| 4,171,430 A | 10/1979 | Matsushita et al. |
| 4,219,571 A | 8/1980 | Miyake |
| 4,361,697 A | 11/1982 | Dobberstein et al. |
| 4,454,290 A | 6/1984 | Dubois |
| 4,590,160 A | 5/1986 | Nishihashi et al. |
| 4,599,403 A | 7/1986 | Kumar |
| 4,612,942 A | 9/1986 | Dobberstein et al. |
| 4,657,638 A | 4/1987 | le Grand et al. |
| 4,892,938 A | 1/1990 | Giovanetto |
| 4,915,969 A * | 4/1990 | Beyts .................. A23F 5/40 426/548 |
| 4,917,916 A | 4/1990 | Hirao et al. |
| 5,112,610 A | 5/1992 | Kienle |
| 5,576,042 A | 11/1996 | Fuisz |
| 5,779,805 A | 7/1998 | Morano |
| 5,962,678 A * | 10/1999 | Payzant ............ A23L 1/2366 536/127 |
| 5,972,120 A | 10/1999 | Kutowy et al. |
| 6,031,157 A | 2/2000 | Morita et al. |
| 6,080,561 A | 6/2000 | Morita et al. |
| 6,204,377 B1 | 3/2001 | Nishimoto et al. |
| 6,228,996 B1 | 5/2001 | Zhou et al. |
| 6,706,304 B1 | 3/2004 | Ishida et al. |
| 7,807,206 B2 | 10/2010 | Magomet et al. |
| 7,838,044 B2 | 11/2010 | Abelyan et al. |
| 7,862,845 B2 | 1/2011 | Magomet et al. |
| 8,257,948 B1 | 9/2012 | Markosyan |
| 2002/0132320 A1 | 9/2002 | Wang et al. |
| 2003/0161876 A1 | 8/2003 | Hansson et al. |
| 2003/0236399 A1 | 12/2003 | Zheng et al. |
| 2006/0083838 A1 | 4/2006 | Jackson et al. |
| 2006/0134292 A1 | 6/2006 | Abelyan et al. |
| 2006/0142555 A1 | 6/2006 | Jonnala et al. |
| 2007/0082102 A1 | 4/2007 | Magomet et al. |
| 2007/0082103 A1 | 4/2007 | Magomet et al. |
| 2007/0116800 A1 | 5/2007 | Prakash |
| 2007/0116819 A1 | 5/2007 | Prakash |

(Continued)

FOREIGN PATENT DOCUMENTS

| | | |
|---|---|---|
| BR | P10701736 | 7/2008 |
| CN | 1049666 | 3/1991 |

(Continued)

OTHER PUBLICATIONS

Richman et al, The Plant Journal, 2006, 41, 56-67.*

(Continued)

*Primary Examiner* — Ganapathy Krishnan
(74) *Attorney, Agent, or Firm* — Briggs and Morgan, P.A.; Audrey J. Babcock

(57) ABSTRACT

Methods of preparing highly purified steviol glycosides, particularly rebaudiosides A, D and M are described. The methods include utilizing recombinant microorganisms for converting various staring compositions to target steviol glycosides. In addition, novel steviol glycosides reb D2 and reb M2 are disclosed, as are methods of preparing the same. The highly purified rebaudiosides are useful as non-caloric sweetener in edible and chewable compositions such as any beverages, confectioneries, bakery products, cookies, and chewing gums.

4 Claims, 69 Drawing Sheets

(56) References Cited

U.S. PATENT DOCUMENTS

| | | |
|---|---|---|
| 2007/0116820 A1 | 5/2007 | Prakash |
| 2007/0116821 A1 | 5/2007 | Prakash |
| 2007/0116822 A1 | 5/2007 | Prakash |
| 2007/0116823 A1 | 5/2007 | Prakash |
| 2007/0116824 A1 | 5/2007 | Prakash |
| 2007/0116825 A1 | 5/2007 | Prakash |
| 2007/0116826 A1 | 5/2007 | Prakash |
| 2007/0116827 A1 | 5/2007 | Prakash |
| 2007/0116828 A1 | 5/2007 | Prakash |
| 2007/0116829 A1 | 5/2007 | Prakash |
| 2007/0116830 A1 | 5/2007 | Prakash |
| 2007/0116831 A1 | 5/2007 | Prakash |
| 2007/0116832 A1 | 5/2007 | Prakash |
| 2007/0116833 A1 | 5/2007 | Prakash |
| 2007/0116834 A1 | 5/2007 | Prakash |
| 2007/0116835 A1 | 5/2007 | Prakash |
| 2007/0116836 A1 | 5/2007 | Prakash |
| 2007/0116837 A1 | 5/2007 | Prakash |
| 2007/0116838 A1 | 5/2007 | Prakash |
| 2007/0116839 A1 | 5/2007 | Prakash |
| 2007/0116840 A1 | 5/2007 | Prakash |
| 2007/0116841 A1 | 5/2007 | Prakash |
| 2007/0128311 A1 | 6/2007 | Prakash |
| 2007/0134390 A1 | 6/2007 | Prakash |
| 2007/0134391 A1 | 6/2007 | Prakash |
| 2007/0224321 A1 | 9/2007 | Prakash |
| 2007/0292582 A1 | 12/2007 | Prakash et al. |
| 2008/0064063 A1 | 3/2008 | Brandle et al. |
| 2008/0102497 A1 | 5/2008 | Wong et al. |
| 2008/0107775 A1 | 5/2008 | Prakash |
| 2008/0107776 A1 | 5/2008 | Prakash |
| 2008/0107787 A1 | 5/2008 | Prakash |
| 2008/0108710 A1 | 5/2008 | Prakash |
| 2008/0111269 A1 | 5/2008 | Politi et al. |
| 2008/0226797 A1 | 9/2008 | Lee et al. |
| 2008/0292764 A1 | 11/2008 | Prakash et al. |
| 2008/0292765 A1 | 11/2008 | Prakash |
| 2008/0292775 A1 | 11/2008 | Prakash |
| 2008/0300402 A1 | 12/2008 | Yang et al. |
| 2009/0017185 A1 | 1/2009 | Catani |
| 2009/0053378 A1 | 2/2009 | Prakash |
| 2009/0074935 A1 | 3/2009 | Lee |
| 2009/0079935 A1 | 3/2009 | Harris et al. |
| 2009/0142817 A1 | 6/2009 | Norman et al. |
| 2009/0226590 A1 | 9/2009 | Fouache et al. |
| 2010/0055752 A1 | 3/2010 | Kumar |
| 2010/0056472 A1 | 3/2010 | Duan et al. |
| 2010/0099857 A1 | 4/2010 | Evans et al. |
| 2010/0112153 A1 | 5/2010 | Abelyan et al. |
| 2010/0120710 A1 | 5/2010 | Watanabe et al. |
| 2010/0137569 A1 | 6/2010 | Prakash et al. |
| 2010/0189861 A1 | 7/2010 | Abelyan et al. |
| 2010/0227034 A1 | 9/2010 | Purkayastha et al. |
| 2010/0255171 A1 | 10/2010 | Purkayastha et al. |
| 2010/0278993 A1 | 11/2010 | Prakash et al. |
| 2010/0316782 A1 | 12/2010 | Shi et al. |
| 2011/0030457 A1 | 2/2011 | Valery et al. |
| 2011/0033525 A1 | 2/2011 | Liu |
| 2011/0092684 A1 | 4/2011 | Abelyan et al. |
| 2011/0104353 A1† | 5/2011 | Lee |
| 2011/0111115 A1 | 5/2011 | Shi et al. |
| 2011/0124587 A1 | 5/2011 | Jackson et al. |
| 2011/0160311 A1† | 6/2011 | Prakash |
| 2011/0183056 A1† | 7/2011 | Morita |
| 2011/0189360 A1 | 8/2011 | Yoo et al. |
| 2011/0195169 A1 | 8/2011 | Markosyan et al. |
| 2012/0164678 A1 | 6/2012 | Stephanopoulos et al. |
| 2012/0214752 A1 | 8/2012 | Markosyan |
| 2013/0171328 A1† | 7/2013 | Kishore |
| 2014/0329281 A1† | 11/2014 | Houghton-Larsen |

FOREIGN PATENT DOCUMENTS

| | | |
|---|---|---|
| CN | 1100727 | 3/1995 |
| CN | 1112565 | 11/1995 |
| CN | 1192447 | 9/1998 |
| CN | 1238341 | 12/1999 |
| CN | 1349997 | 5/2002 |
| CN | 101200480 | 6/2008 |
| JP | 52005800 | 1/1977 |
| JP | 52083731 | 7/1977 |
| JP | 52100500 | 8/1977 |
| JP | 52136200 | 11/1977 |
| JP | 54030199 | 3/1979 |
| JP | 54132599 | 10/1979 |
| JP | 55039731 | 3/1980 |
| JP | 55081567 | 6/1980 |
| JP | 55092400 | 7/1980 |
| JP | 55120770 | 9/1980 |
| JP | 55138372 | 10/1980 |
| JP | 55159770 | 12/1980 |
| JP | 55162953 | 12/1980 |
| JP | 56099768 | 8/1981 |
| JP | 56109568 | 8/1981 |
| JP | 56121453 | 9/1981 |
| JP | 56121454 | 9/1981 |
| JP | 56121455 | 9/1981 |
| JP | 56160962 | 12/1981 |
| JP | 57002656 | 1/1982 |
| JP | 57005663 | 1/1982 |
| JP | 57046998 | 3/1982 |
| JP | 57075992 | 5/1982 |
| JP | 57086264 | 5/1982 |
| JP | 58020170 | 2/1983 |
| JP | 58028246 | 2/1983 |
| JP | 58028247 | 2/1983 |
| JP | 58212759 | 12/1983 |
| JP | 58212760 | 12/1983 |
| JP | 59045848 | 3/1984 |
| JP | 62166861 | 7/1987 |
| JP | 63173531 | 7/1988 |
| JP | 1131191 | 5/1989 |
| JP | 3262458 | 11/1991 |
| JP | 6007108 | 1/1994 |
| JP | 6192283 | 7/1994 |
| JP | 7143860 | 6/1995 |
| JP | 7177862 | 7/1995 |
| JP | 8000214 | 1/1996 |
| JP | 9107913 | 4/1997 |
| JP | 2000236842 | 9/2000 |
| JP | 2002262822 | 9/2002 |
| JP | 2010516764 | 5/2010 |
| KR | 20070067199 | 6/2007 |
| KR | 20080071605 | 8/2008 |
| KR | 20090021386 | 3/2009 |
| RU | 2111969 | 5/1998 |
| RU | 2123267 | 12/1998 |
| RU | 2156083 | 9/2000 |
| RU | 2167544 | 5/2001 |
| RU | 2198548 | 2/2003 |
| WO | 2005089483 | 9/2005 |
| WO | 2006072878 | 7/2006 |
| WO | 2006072879 | 7/2006 |
| WO | 2008091547 | 7/2008 |
| WO | 2009108680 | 9/2009 |
| WO | WO 2010057024 | 5/2010 |
| WO | 2010118218 | 10/2010 |
| WO | 2011059954 | 5/2011 |
| WO | 2011153378 | 12/2011 |
| WO | 2012082493 | 6/2012 |
| WO | 2012082677 | 6/2012 |
| WO | 2013022989 | 2/2013 |
| WO | WO2013/110673 A1 * | 8/2013 ............. A23L 1/236 |
| WO | WO 2013/176738 A1 * | 11/2013 ............. A23L 1/236 |

OTHER PUBLICATIONS

Shi, et al., "Synthesis of bifunctional polymeric adsorbent and its application in purification of Stevia glycosides", Reactive & Functional Polymers, vol. 50 2002, 107-116.

Shibata et al., "Glucosylation of Steviol and Steviol-Glucosides in Extracts from Stevia rebaudiana Bertoni," Plant Physiol. vol. 95, (1991) 152-156.

(56) References Cited

OTHER PUBLICATIONS

Starratt, et al., "Rebaudioside F, a diterpene glycoside from Stevia Rebaudiana", Phytochemistry, vol. 59 2002, 367-370.
Sweet Green Fields, LLC, "Notice to the U.S. Food and Drug Administration (FDA) that the use of Rebiana (Rebaudiosid A) derived from Stevia rebaudiana, as a Food Ingredient is Generally Recognized as Safe (GRAS)," Jan. 15, 2009, http:/www.accessdata.fda.gov/scripts/fcn/gras_notices/grn000282.pdf (obtained from the WEB on May 8, 2012) entire document esp. p. 22, Table 1.
Tanaka, O. , "Improvement of taste of natural sweeteners", Pure & Appl. Chem., vol. 69, No. 4 1997, 675-683.
Teo, et al., "Validation of green-solvent extraction combined with chromatographic chemical fingerprint to evaluate quality of Stevia rebaudiana Bertoni", J. Sep. Sci, vol. 32 2009, 613-622.
United Nations' Food and Agriculture Organization/Joint Expert Committee on Food Additives (2010) Steviol Glycosides, Compendium of Food Additive Specifications, FAO JECFA Monographs 10, 17-21.
van der Maarel et al., "Properties and applications of starch-converting enzymes of the a-amylase family," Journal of Biotechnology, vol. 94 (2002) 137-155.
Vasquez, Stimulation of the Gerbil's Gustatory Receptors by Some Potently Sweet Terpenoids, J. Agric. Food Chem., vol. 41, 1305-1310, 1993.
Yamamoto, K. et al., "Effective Production of Glycosyl-steviosides by a-1,6 Transglucosylation of Dextrin Dextranase", Biosci. Biotech. Biochem. vol. 58, No. 9 1994, 1657-1661.
Yoda, et al., "Supercritical fluid extraction from Stevia rebaudiana Bertoni using CO2 and CO2+ water: extraction kinetics and identification of extracted components", Journal of Food Engineering, vol. 57 2003, 125-134.
Zell, et al., "Investigation of Polymorphism in Aspartame and Neotame Using Solid-State NMR Spectroscopy", Tetrahedron, vol. 56, 2000, 6603-6616.
Zhang, et al., "Membrane-based separation scheme for processing sweetener from Stevia leaves", Food Research International, vol. 33 2000, 617-620.
a-Glucosyltransferase Treated Stevia, Japan's Specifications and Standards for Food Additives, VIII edition, 2009, p. 257.
Ahmed, et al., "Use of p-Bromophenacyl Bromide to Enhance Ultraviolet Detection of Water-Soluble Organic Acids (Steviolbioside and Rebaudioside B) in High-Performance Liquid Chromatographic Analysis", Journal of Chromatography, vol. 192, 1980, 387-393.
Chang, S. S. et al., "Stability Studies of Stevioside and Rebaudioside A in Carbonated Beverages", Journal of Agricultural and Food Chemistry, vol. 31, 1983, 409-412.
Chen, et al., "Enrichment and separation of rebaudioside A from stevia glycosides by a novel adsorbent with pyridyl group", Science in China, vol. 42, No. 3 1999, 277-282.
Chen, et al., "Selectivity of polymer adsorbent in adsorptive separations of stevia diterpene glycisides", Science in China, vol. 41, No. 4 1998, 436-441.
Chen, et al., "Studies on the adsorptive selectivity of the polar resin with carbonyl group on rebaudioside A", Acta Polymeric Scnica, No. 4 1999, 398-403.
Crammer, et al., "Sweet glycosides from the Stevia plant", Chemistry in Britain, Oct. 1986, 915-916, 918.
Darise et al., "Enzymic Transglucosylation of Rubusoside and the Structure-Sweetness Relationship of Steviol Bisglycosides," Agric. Biol. Chem. vol. 48(10), 1984, 2483-2488.
Dubois et al., "Diterpenoid Sweeteners. Synthesis and Sensory Evaluation of Stevioside Analogues with Improved Organoleptic Properties," J. Med. Chem. vol. 28, (1985) 93-98.
Fuh, , "Purification of steviosides by membrane and ion exchange process", Journal of Food Science, vol. 55, No. 5 1990, 1454-1457.
Fukunaga et al., "Enzymic Transglucosylation Products of Stevioside: Separation and Sweetness-evaluation," Agric. Biol. Chem. vol. 53(6) (1989) 1603-1607.
Fullas et al., "Separation of natural product sweetening agents using overpressured layer chromatography," Journal of Chromatography vol. 464 (1989) 213-219.
Hale, et al., "Amylase of Bacillus Macerans", Cereal Chemistry, vol. 28, No. 1, Jan. 1951, 49-58.
International Search Report and Written Opinion of PCT/US2010/055960.
International Search Report and Written Opinion of PCT/US2011/028028.
International Search Report and Written Opinion of PCT/US2011/033734.
International Search Report and Written Opinion of PCT/US2011/033737.
International Search Report and Written Opinion of PCT/US2011/033912.
International Search Report and Written Opinion of PCT/US2011/035173.
International Search Report and Written Opinion of PCT/US2011/036063, dated Aug. 5, 2011.
International Search Report and Written Opinion of PCT/US2011/047498, dated Dec. 22, 2011.
International Search Report and Written Opinion of PCT/US2011/047499, dated Dec. 22, 2011.
International Search Report and Written Opinion of PCT/US2011/064343.
International Search Report and Written Opinion of PCT/US2012/024585.
International Search Report and Written Opinion of PCT/US2012/024722.
International Search Report and Written Opinion of PCT/US2012/030210.
International Search Report and Written Opinion of PCT/US2012/043294.
International Search Report and Written Opinion of PCT/US2012/051163.
International Search Report and Written Opinion of PCT/US2012/052659.
International Search Report and Written Opinion of PCT/US2012/052665.
International Search Report and Written Opinion of PCT/US2013/030439.
Jaitak, et al., "An Efficient Microwave-assisted Extraction Process of Stevioside and Rebaudioside-A from Stevia Rebaudiana (Bertoni)", Phytochem. Anal. vol. 20 2009, 240-245.
Kennelly, "Sweet and non-sweet constituents of Stevia rebaudiana", Stevia: The genus Stevia, Taylor & Francis, 2002, 68-85.
Kinghorn, "Overview", Stevia: The genus Stevia, Taylor & Francis, 2002, 1-17.
Kitahata, S. et al., "Production of Rubusoside Derivatives by Transgalactosylation of Various b-Galactosidases", Agric. Biol. Chem., vol. 53, No. 11 1989, 2923-2928.
Kobayashi, et al., "Dulcoside A and B, New diterpene glycosides from Stevia Rebaudiana", Phytochemistry, vol. 16 1977, 1405-1408.
Kochikyan, et al., "Combined Enzymatic Modification of Stevioside and Rebaudioside A", Applied Biochemistry and Microbiology, vol. 42, No. 1, 2006, 31-37.
Kohda, et al., "New sweet diterpene glucosides from Stevia Rebaudiana", Phytochemistry, vol. 15 1976, 981-983.
Kovylyaeva, et al., "Glycosides from Stevia rebaudiana", Chemistry of Natural Compounds, vol. 43, No. 1 2007, 81-85.
Liu, et al., "Study of stevioside preparation by membrane separation process", Desalination, vol. 83 1991, 375-382.
Lobov, S. V. et al., "Enzymic Production of Sweet Stevioside Derivatives: Transglucosylation of Glucosidases", Agric. Biol. Chem., vol. 55, No. 12 1991, 2959-2965.
Montovaneli, et al., "The effect of temperature and flow rate on the clarification of the aqueous Stevia-extract in fixed-bed column with zeolites", Brazilian Journal of Chemical Engineering, vol. 21, No. 3 2004, 449-458.

(56) References Cited

OTHER PUBLICATIONS

Moraes, et al., "Clarification of Stevia rebaudiana (Bert.) Bertoni extract adsorption in modified zeolites", Acta Scientiarum, vol. 23, No. 6 2001, 1375-1380.

Ohta et al., "Characterization of Novel Steviol Glycosides from Leaves of Stevia rebaudiana Morita," J. Appl. Glycosi., vol. 57, 199-209, 2010.

Ohtani et al. "Chapter 7. Methods to improve the taste of the sweet principles of Stevia rebaudiana." The Genus Stevia, edited by A. Douglas Kinghorn, CRC Press 2001, Taylor and Francis, London and New York, pp. 138-159.

Phillips, K. C., "Stevia: steps in developing a new sweetener", In T.H. Grenby, Editor, Developments in Sweeteners-3, Elsevier 1987, 1-43.

Pol, et al., "Comparison of two different solvents employed for pressurised fluid extraction of stevioside from Stevia rebaudiana: methanol versus water", Anal Bioanal Chem vol. 388 2007, 1847-1857.

Prakash et al., "Development of rebiana, a natural, non-caloric sweetener," Jul. 1, 2008, Food and Chemical Toxicology, vol. 46, Is. 7, Sup. 1, p. S75-S82.

Richman et al., "Fuctional genomics uncovers three glucosyltransferases involved in the synthesis of the major sweet glucosides of Stevia rebaudiana," The Plant Journal, vol. 41 (2005) 56-67.

Sakamoto et al., "Application of 13C NMR Spectroscopy to Chemistry of Natural Glycosides: Rebaudioside-C, a New Sweet Diterpene Glycoside of Stevia Rebaudiana", Chem. Pharm. Bull., vol. 25, 1977, 844-846.

\* cited by examiner
† cited by third party

FIG. 6 HPLC Chromatogram of Purified Rebaudioside M from Biotransformation of Rebaudioside D FIG. 7 HPLC Chromatogram of Standard Rebaudioside M Co-HPLC Chromatogram of Standard Rebaudioside M and Rebaudioside M Purified from Biotransformation of Rebaudioside D The signal at m/z 1313.52652 is consistent with the sodium adduct of a species with molecular formula $C_{56}H_{90}O_{33}$(+0.658 ppm). Sample was dissolved in methanol and eluted in 2:2:1 methanol:acetonitrile:water.

Example 6

Example 20

Example 21

Example 22

Example 24

Example 29

Example 30

Example 31 FIG. 63

Example 32

Example 35

Example 37

Example 43

HIGH-PURITY STEVIOL GLYCOSIDES

RELATED APPLICATIONS

This application claims the benefit of priority from U.S. Provisional Application No. 61/827,922, filed on May 28, 2013, U.S. Provisional Application No. 61/843,544, filed on Jul. 8, 2013, U.S. Provisional Application No. 61/861,528, filed on Aug. 2, 2013, U.S. Provisional Application No. 61/881,166, filed on Sep. 23, 2013, U.S. Provisional Application No. 61/885,084, filed on Oct. 1, 2013, U.S. Provisional Application No. 61/904,751, filed on Nov. 15, 2013, U.S. Provisional Application No. 61/913,482, filed on Dec. 9, 2013, U.S. Provisional Application No. 61/921,635, filed on Dec. 30, 2013, U.S. Provisional Application No. 61/925,329, filed on Jan. 9, 2014, and U.S. Provisional Application No. 61/939,855, filed on Feb. 14, 2014.

TECHNICAL FIELD

The present invention relates to a biocatalytic process for preparing compositions comprising steviol glycosides, including highly purified steviol glycoside compositions. The present invention also relates to novel steviol glycosides, methods for isolation of the same and uses for the novel steviol glycosides.

BACKGROUND OF THE INVENTION

High intensity sweeteners possess a sweetness level that is many times greater than the sweetness level of sucrose. They are essentially non-caloric and are commonly used in diet and reduced-calorie products, including foods and beverages. High intensity sweeteners do not elicit a glycemic response, making them suitable for use in products targeted to diabetics and others interested in controlling for their intake of carbohydrates.

Steviol glycosides are a class of compounds found in the leaves of *Stevia rebaudiana* Bertoni, a perennial shrub of the Asteraceae (Compositae) family native to certain regions of South America. They are characterized structurally by a single base, steviol, differing by the presence of carbohydrate residues at positions C13 and C19. They accumulate in *Stevia* leaves, composing approximately 10%-20% of the total dry weight. On a dry weight basis, the four major glycosides found in the leaves of *Stevia* typically include stevioside (9.1%), rebaudioside A (3.8%), rebaudioside C (0.6-1.0%) and dulcoside A (0.3%). Other known steviol glycosides include rebaudioside B, C, D, E, F and M, steviolbioside and rubusoside.

Although methods are known for preparing steviol glycosides from *Stevia rebaudiana*, many of these methods are unsuitable for use commercially.

Accordingly, there remains a need for simple, efficient, and economical methods for preparing compositions comprising steviol glycosides, including highly purified steviol glycoside compositions.

Additionally, there remains a need for novel steviol glycosides and methods of preparing and isolating the same.

SUMMARY OF THE INVENTION

The present invention provides a biocatalytic process for preparing a composition comprising a target steviol glycoside by contacting a starting composition comprising an organic substrate with a microorganism and/or biocatalyst, thereby producing a composition comprising a target steviol glycoside.

The starting composition can be any organic compound comprising at least one carbon atom. In one embodiment, the starting composition is selected from the group consisting of polyols or sugar alcohols, various carbohydrates.

The target steviol glycoside can be any steviol glycoside. In one embodiment, the target steviol glycoside is steviolmonoside, steviolbioside, rubusoside, dulcoside B, dulcoside A, rebaudioside B, rebaudioside G, stevioside, rebaudioside C, rebaudioside F, rebaudioside A, rebaudioside I, rebaudioside E, rebaudioside H, rebaudioside L, rebaudioside K, rebaudioside J, rebaudioside M, rebaudioside M2, rebaudioside D, rebaudioside D2, rebaudioside N, rebaudioside O or a synthetic steviol glycoside.

In one embodiment, the target steviol glycoside is stevioside.

In another embodiment, the target steviol glycoside is rebaudioside A.

In still another embodiment, the target steviol glycoside is rebaudioside D.

In yet another embodiment, the target steviol glycoside is rebaudioside M (also known as rebaudioside X).

The microorganism can be any microorganism possessing the necessary enzymes for converting the starting composition to target steviol glycosides.

The biocatalysts will comprise at least one enzyme for converting the starting composition to target steviol glycosides.

The biocatalysts can be located on the surface and/or inside the cell of the microorganism or can be secreted out of the microorganism.

The biocatalyst can be whole cell suspension, crude lysate or purified enzymes.

The biocatalyst can be in free form or immobilized to a solid support made from inorganic or organic materials.

The enzymes necessary for converting the starting composition to target steviol glycosides include the steviol biosynthesis enzymes, UDP-glycosyltransferases (UGTs) and/or UDP-recycling enzyme.

In one embodiment the steviol biosynthesis enzymes include mevalonate (MVA) pathway enzymes.

In another embodiment the steviol biosynthesis enzymes include non-mevalonate 2-C-methyl-D-erythritol-4-phosphate pathway (MEP/DOXP) enzymes.

In one embodiment the steviol biosynthesis enzymes are selected from the group including geranylgeranyl diphosphate synthase, copalyl diphosphate synthase, kaurene synthase, kaurene oxidase, kaurenoic acid 13-hydroxylase (KAH), steviol synthetase, deoxyxylulose 5-phosphate synthase (DXS), D-1-deoxyxylulose 5-phosphate reductoisomerase (DXR), 4-diphosphocytidyl-2-C-methyl-D-erythritol synthase (CMS), 4-diphosphocytidyl-2-C-methyl-D-erythritol kinase (CMK), 4-diphosphocytidyl-2-C-methyl-D-erythritol 2,4-cyclodiphosphate synthase (MCS), 1-hydroxy-2-methyl-2(E)-butenyl 4-diphosphate synthase (HDS), 1-hydroxy-2-methyl-2(E)-butenyl 4-diphosphate reductase (HDR), acetoacetyl-CoA thiolase, truncated HMG-CoA reductase, mevalonate kinase, phosphomevalonate kinase, mevalonate pyrophosphate decarboxylase, cytochrome P450 reductase etc.

The UDP-glucosyltransferase can be any UDP-glucosyltransferase capable of adding at least one glucose unit to the steviol and or steviol glycoside substrate to provide the target steviol glycoside.

In one embodiment, steviol biosynthesis enzymes and UDP-glucosyltransferases are produced in a microorganism. The microorganism may be, for example, *E. coli, Saccharomyces* sp., *Aspergillus* sp., *Pichia* sp, *Bacillus* sp., *Yarrowia* sp. etc. In another embodiment, the UDP-glucosyltransferases are synthesized.

In one embodiment, the UDP-glucosyltransferase is selected from group including UGT74G1, UGT85C2, UGT76G1, UGT91D2 and UGTs having substantial (>85%) identity to these polypeptides as well as isolated nucleic acid molecules that code for these UGTs.

In one embodiment, steviol biosynthesis enzymes, UGTs and UDP-glucose recycling system are present in one microorganism. The microorganism may be for example, *E. coli, Saccharomyces* sp., *Aspergillus* sp., *Pichia* sp, *Bacillus* sp., *Yarrowia* sp.

In one embodiment, the UDP-glucosyltransferase is any UDP-glucosyltransferase capable of adding at least one glucose unit to rubusoside to form stevioside. In a particular embodiment, the UDP-glucosyltransferase is UGT91D2.

In one embodiment, the UDP-glucosyltransferase is any UDP-glucosyltransferase capable of adding at least one glucose unit to stevioside to form rebaudioside A. In a particular embodiment, the UDP-glucosyltransferase is UGT76G1.

In another embodiment, the UDP-glucosyltransferase is any UDP-glucosyltransferase capable of adding at least one glucose unit to rebaudioside A to form rebaudioside D. In a particular embodiment, the UDP-glucosyltransferase is UGT91D2. In another embodiment, the UGT is an improved variant of UGT91D2 with higher activity and/or selectivity produced by directed evolution.

In yet another embodiment, the UDP-glucosyltransferase is any UDP-glucosyltransferase capable of adding at least one glucose unit to rebaudioside D to form rebaudioside M. In a particular embodiment, the UDP-glucosyltransferase is UGT76G1. In another embodiment, the UGT is an improved variant of UGT76G1 with higher activity and/or selectivity produced by directed evolution.

Optionally, the method of the present invention further comprises recycling UDP to provide UDP-glucose. In one embodiment, the method comprises recycling UDP by providing a recycling catalyst and a recycling substrate, such that the biotransformation of the steviol glycoside substrate to the target steviol glycoside is carried out using catalytic amounts of UDP-glucosyltransferase and UDP-glucose (FIG. 3).

In one embodiment, the recycling catalyst is sucrose synthase.

In one embodiment, the recycling substrate is sucrose.

Optionally, the method of the present invention further comprises separating the target steviol glycoside from the starting composition. The target steviol glycoside can be separated by at least one suitable method, such as, for example, crystallization, separation by membranes, centrifugation, extraction, chromatographic separation or a combination of such methods.

In one embodiment, the target steviol glycoside can be produced within the microorganism. In another embodiment, the target steviol glycoside can be secreted out in the medium. In one another embodiment, the released steviol glycoside can be continuously removed from the medium. In yet another embodiment, the target steviol glycoside is separated after the completion of the reaction.

In one embodiment, separation produces a composition comprising greater than about 80% by weight of the target steviol glycoside on an anhydrous basis, i.e., a highly purified steviol glycoside composition. In another embodiment, separation produces a composition comprising greater than about 90% by weight of the target steviol glycoside. In particular embodiments, the composition comprises greater than about 95% by weight of the target steviol glycoside. In other embodiments, the composition comprises greater than about 99% by weight of the target steviol glycoside.

The target steviol glycoside can be in any polymorphic or amorphous form, including hydrates, solvates, anhydrous or combinations thereof.

Purified target steviol glycosides can be used in consumable products as a sweetener. Suitable consumer products include, but are not limited to, food, beverages, pharmaceutical compositions, tobacco products, nutraceutical compositions, oral hygiene compositions, and cosmetic compositions.

The present invention also provides novel steviol glycosides rebaudioside D2 (reb D2, isomer of rebaudioside D) and rebaudioside M2 (reb M2, isomer of rebaudioside M), which are isomers of reb D and reb M, respectively. In one embodiment, isolated and purified reb D2 is provided. In another embodiment, isolated and purified reb M2 is provided. Reb D2 and reb M2 may also be present in any consumable products disclosed herein. In a particular embodiment, beverages comprising reb D2 and/or reb M2 are provided.

Methods of preparing reb D2 and reb M2 are also provided herein. Both are formed during the biotransformation of reb A to reb D. Reb M2 is believed to form from biotransformation of reb D2 in situ.

In one embodiment, the present invention is a method for the preparation of a composition comprising reb D2 comprising: (a) contacting a starting composition comprising reb A with an enzyme capable of transforming reb A to reb D2, UDP-glucose, and optionally UDP-glucose recycling enzymes, to produce a composition comprising reb D2, and (b) isolating the composition comprising reb D2.

In another embodiment, the present invention is a method for the preparation of a composition comprising reb M2 comprising (a) contacting a starting composition comprising reb D2 with an enzyme capable of transforming reb D2 to reb M2, UDP-glucose, and optionally UDP-glucose recycling enzymes, to produce a composition comprising reb M2, and (b) and isolating the composition comprising reb M2.

A further method for the preparation of a composition comprising reb M2 comprises (a) contacting a starting composition comprising reb A with an enzyme capable of transforming reb A to reb D2, UDP-glucose, and optionally UDP-glucose recycling enzymes, to produce a composition comprising reb D2, (b) optionally, isolating the composition comprising reb D2, (c) contacting the composition comprising reb D2 with an enzyme capable of transforming reb D2 to reb M2, UDP-glucose, and optionally UDP-glucose recycling enzymes to produce a composition comprising reb M2, and (d) isolating the composition comprising reb M2.

The composition can be further purified to provide reb D2 or reb M2 with purities greater than about 95% by weight on a dry basis.

BRIEF DESCRIPTION OF THE DRAWINGS

The accompanying drawings are included to provide a further understanding of the invention. The drawings illustrate embodiments of the invention and together with the description serve to explain the principles of the embodiments of the invention.

DETAILED DESCRIPTION

Figure 1:
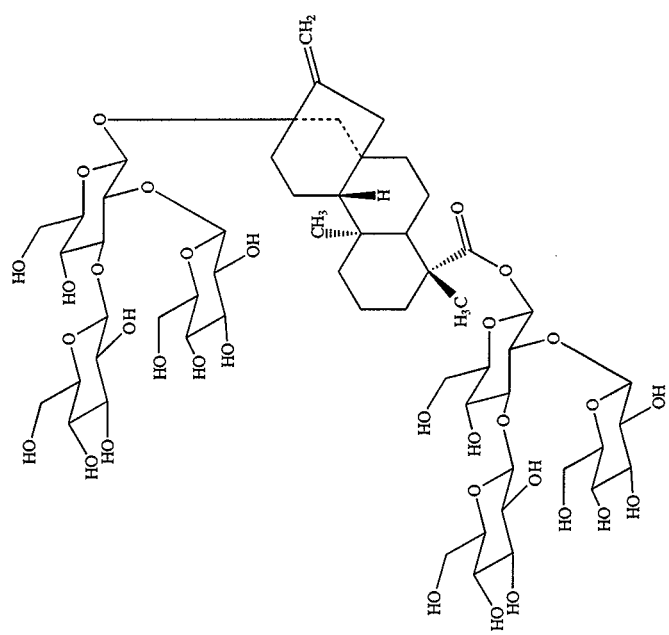
FIG. 1 shows the structure of reb M.
Figure 2:
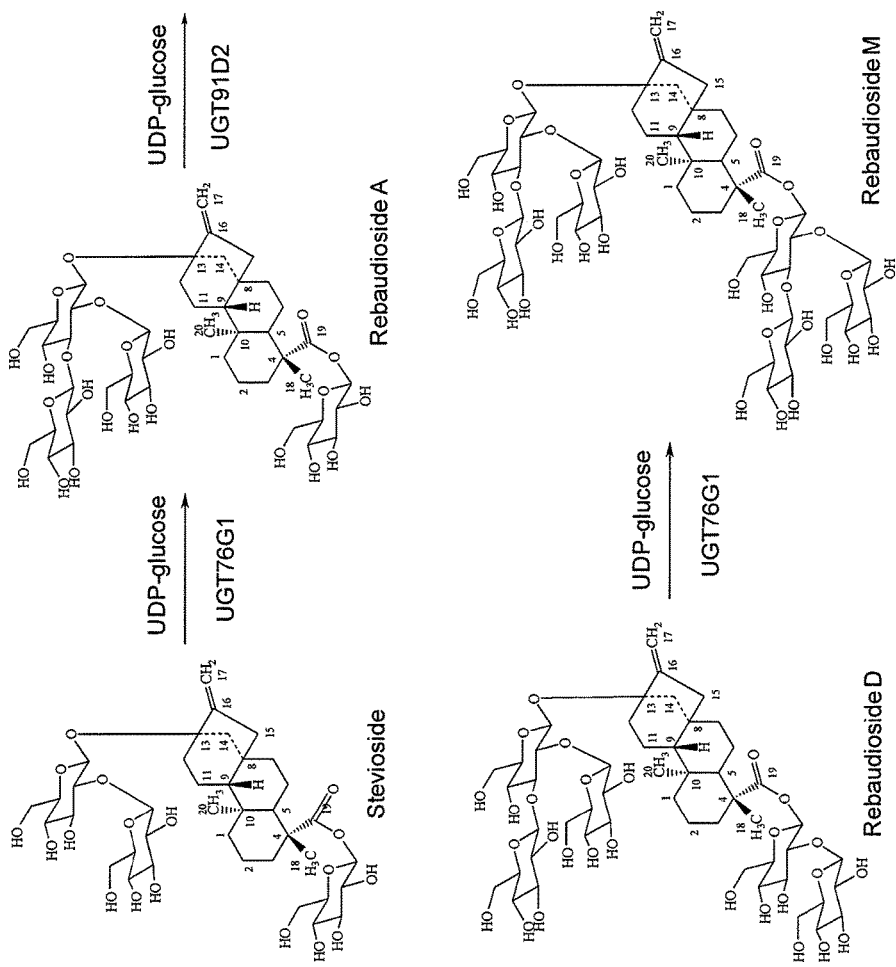
FIG. 2 shows the biocatalytic production of reb M from stevioside.

The present invention provides a biocatalytic process for preparing a composition comprising a target steviol glycoside by contacting a starting composition, comprising an organic substrate, with a microorganism and/or biocatalyst, thereby producing a composition comprising a target steviol glycoside.

One object of the invention is to provide an efficient biocatalytic method for preparing steviol glycosides, particularly stevioside, reb E, reb A, reb D, reb D2, reb M, and reb M2 from various starting compositions.

As used herein, "biocatalysis" or "biocatalytic" refers to the use of natural or genetically engineered biocatalysts, such as cells, protein enzymes, to perform single or multiple step chemical transformations on organic compounds. Biocatalysis include fermentation, biosynthesis and biotransformation processes. Both, isolated enzyme and whole-cell biocatalysis methods, using biocatalysts in free as well as immobilized forms, are known in the art. Biocatalyst protein enzymes can be naturally occurring or recombinant proteins.

As used herein, the term "steviol glycoside(s)" refers to a glycoside of steviol, including, but not limited to, naturally occurring steviol glycosides, e.g. steviolmonoside, steviolbioside, rubusoside, dulcoside B, dulcoside A, rebaudioside B, rebaudioside G, stevioside, rebaudioside C, rebaudioside F, rebaudioside A, rebaudioside I, rebaudioside E, rebaudioside H, rebaudioside L, rebaudioside K, rebaudioside J, rebaudioside M, rebaudioside M2, rebaudioside D, rebaudioside D2, rebaudioside N, rebaudioside O, synthetic steviol glycosides, e.g. enzymatically glucosylated steviol glycosides and combinations thereof.

Chemical structures of steviol and its glycosides

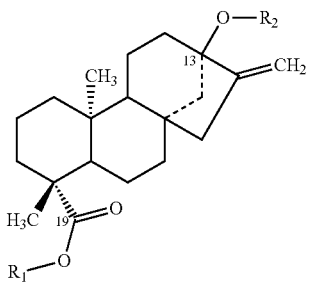

| Compound | $R_1$ | $R_2$ |
|---|---|---|
| Steviol | H | H |
| Steviolmonoside | H | β-Glc |
| Steviol monoglucosyl ester | β-Glc | H |
| Rubusoside | β-Glc | β-Glc |
| Steviolbioside | H | β-Glc-β-Glc (2→1) |
| Stevioside | β-Glc | β-Glc-β-Glc (2→1) |
| Rebaudioside A | β-Glc | β-Glc-β-Glc (2→1)<br>\|<br>β-Glc (3→1) |
| Rebaudioside D | β-Glc-β-Glc (2→1) | β-Glc-β-Glc (2→1)<br>\|<br>β-Glc (3→1) |
| Rebaudioside E | β-Glc-β-Glc (2→1) | β-Glc-β-Glc (2→1) |
| Rebaudioside M | β-Glc-β-Glc (2→1)<br>\|<br>β-Glc (3→4) | β-Glc-β-Glc (2→1)<br>\|<br>β-Glc (3→1) |

(Glc = glucose)

Starting Composition

As used herein, "starting composition" refers to any composition (generally an aqueous solution) containing one or more organic compound comprising at least one carbon atom.

In one embodiment, the starting composition is selected from the group consisting of polyols and various carbohydrates.

The term "polyol" refers to a molecule that contains more than one hydroxyl group. A polyol may be a diol, triol, or a tetraol which contain 2, 3, and 4 hydroxyl groups, respectively. A polyol also may contain more than four hydroxyl groups, such as a pentaol, hexaol, heptaol, or the like, which contain 5, 6, or 7 hydroxyl groups, respectively. Additionally, a polyol also may be a sugar alcohol, polyhydric alcohol, or polyalcohol which is a reduced form of carbohydrate, wherein the carbonyl group (aldehyde or ketone, reducing sugar) has been reduced to a primary or secondary hydroxyl group. Examples of polyols include, but are not limited to, erythritol, maltitol, mannitol, sorbitol, lactitol, xylitol, inositol, isomalt, propylene glycol, glycerol, threitol, galactitol, hydrogenated isomaltulose, reduced isomalto-oligosaccharides, reduced xylo-oligosaccharides, reduced gentio-oligosaccharides, reduced maltose syrup, reduced glucose syrup, hydrogenated starch hydrolyzates, polyglycitols and sugar alcohols or any other carbohydrates capable of being reduced.

The term "carbohydrate" refers to aldehyde or ketone compounds substituted with multiple hydroxyl groups, of the general formula $(CH_2O)_n$, wherein n is 3-30, as well as their oligomers and polymers. The carbohydrates of the present invention can, in addition, be substituted or deoxygenated at one or more positions. Carbohydrates, as used herein, encompass unmodified carbohydrates, carbohydrate derivatives, substituted carbohydrates, and modified carbohydrates. As used herein, the phrases "carbohydrate derivatives", "substituted carbohydrate", and "modified carbohydrates" are synonymous. Modified carbohydrate means any carbohydrate wherein at least one atom has been added, removed, or substituted, or combinations thereof. Thus, carbohydrate derivatives or substituted carbohydrates include substituted and unsubstituted monosaccharides, disaccharides, oligosaccharides, and polysaccharides. The carbohydrate derivatives or substituted carbohydrates optionally can be deoxygenated at any corresponding C-position, and/or substituted with one or more moieties such as hydrogen, halogen, haloalkyl, carboxyl, acyl, acyloxy, amino, amido, carboxyl derivatives, alkylamino, dialkylamino, arylamino, alkoxy, aryloxy, nitro, cyano, sulfo, mercapto, imino, sulfonyl, sulfenyl, sulfinyl, sulfamoyl, carboalkoxy, carboxamido, phosphonyl, phosphinyl, phosphoryl, phosphino, thioester, thioether, oximino, hydrazino, carbamyl, phospho, phosphonato, or any other viable functional group provided the carbohydrate derivative or substituted carbohydrate functions to improve the sweet taste of the sweetener composition.

Examples of carbohydrates which may be used in accordance with this invention include, but are not limited to, tagatose, trehalose, galactose, rhamnose, various cyclodextrins, cyclic oligosaccharides, various types of maltodextrins, dextran, sucrose, glucose, ribulose, fructose, threose, arabinose, xylose, lyxose, allose, altrose, mannose, idose, lactose, maltose, invert sugar, isotrehalose, neotrehalose, isomaltulose, erythrose, deoxyribose, gulose, idose, talose, erythrulose, xylulose, psicose, turanose, cellobiose, amylopectin, glucosamine, mannosamine, fucose, glucuronic acid, gluconic acid, glucono-lactone, abequose, galactosamine, beet oligosaccharides, isomalto-oligosaccharides (isomaltose, isomaltotriose, panose and the like), xylo-oligosaccharides (xylotriose, xylobiose and the like), xylo-terminated oligosaccharides, gentio-oligosaccharides (gentiobiose, gentiotriose, gentiotetraose and the like), sorbose, nigero-oligosaccharides, palatinose oligosaccharides, fructooligosaccharides (kestose, nystose and the like), maltotetraol, maltotriol, malto-oligosaccharides (maltotriose, maltotetraose, maltopentaose, maltohexaose, maltoheptaose and the like), starch, inulin, inulo-oligosaccharides, lactulose, melibiose, raffinose, ribose, isomerized liquid sugars such as high fructose corn syrups, coupling sugars, and soybean oligosaccharides. Additionally, the carbohydrates as used herein may be in either the D- or L-configuration.

The starting composition may be synthetic or purified (partially or entirely), commercially available or prepared.

In one embodiment, the starting composition is glycerol.

In another embodiment, the starting composition is glucose.

In still another embodiment, the starting composition is sucrose.

In yet another embodiment, the starting composition is starch.

In another embodiment, the starting composition is maltodextrin.

The organic compound(s) of starting composition serve as a substrate(s) for the production of the target steviol glycoside(s), as described herein.

Target Steviol Glycoside

The target steviol glycoside of the present method can be any steviol glycoside that can be prepared by the process disclosed herein. In one embodiment, the target steviol glycoside is selected from the group consisting of steviolmonoside, steviolbioside, rubusoside, dulcoside B, dulcoside A, rebaudioside B, rebaudioside G, stevioside, rebaudioside C, rebaudioside F, rebaudioside A, rebaudioside I, rebaudioside E, rebaudioside H, rebaudioside L, rebaudioside K, rebaudioside J, rebaudioside M, rebaudioside M2, rebaudioside D, rebaudioside D2, rebaudioside N or rebaudioside O, or other glycoside of steviol.

In one embodiment, the target steviol glycoside is stevioside. In another embodiment, the target steviol glycoside is reb A. In still another embodiment, the target steviol glycoside is reb E. In yet another embodiment, the target steviol glycoside is reb D. In yet another embodiment, the target steviol glycoside is reb D2. In a further embodiment, the target steviol glycoside is reb M. In a still further another embodiment, the target steviol glycoside is reb M2.

The target steviol glycoside can be in any polymorphic or amorphous form, including hydrates, solvates, anhydrous or combinations thereof.

In one embodiment, the present invention is a biocatalytic process for the production of reb D.

In yet another embodiment, the present invention is a biocatalytic process for the production of reb D2.

In still another embodiment, the present invention is a biocatalytic process for the production of reb M.

In a further embodiment, the present invention is a biocatalytic process for the production of reb M2.

Optionally, the method of the present invention further comprises separating the target steviol glycoside from the starting composition. The target steviol glycoside can be separated by any suitable method, such as, for example, crystallization, separation by membranes, centrifugation, extraction, chromatographic separation or a combination of such methods.

In particular embodiments, the process described herein results in a highly purified target steviol glycoside composition. The term "highly purified", as used herein, refers to a composition having greater than about 80% by weight of the target steviol glycoside on an anhydrous basis. In one embodiment, the highly purified target steviol glycoside composition contains greater than about 90% by weight of the target steviol glycoside on an anhydrous basis, such as, for example, greater than about 91%, greater than about 92%, greater than about 93%, greater than about 94%, greater than about 95%, greater than about 96%, greater than about 97%, greater than about 98% or greater than about 99% target steviol glycoside content on a dry basis.

In one embodiment, when the target steviol glycoside is reb M, the process described herein provides a composition having greater than about 90% reb M content by weight on a dry basis. In another particular embodiment, when the target steviol glycoside is reb M, the process described herein provides a composition comprising greater than about 95% reb M content by weight on a dry basis.

In another embodiment, when the target steviol glycoside is reb M2, the process described herein provides a composition having greater than about 90% reb M2 content by weight on a dry basis. In another particular embodiment, when the target steviol glycoside is reb M2, the process described herein provides a composition comprising greater than about 95% reb M2 content by weight on a dry basis.

In yet another embodiment, when the target steviol glycoside is reb D, the process described herein provides a composition greater than about 90% reb D content by weight on a dry basis. In another particular embodiment, when the target steviol glycoside is reb D, the process described herein provides a composition comprising greater than about 99% reb D content by weight on a dry basis.

In still another embodiment, when the target steviol glycoside is reb D2, the process described herein provides a composition greater than about 90% reb D2 content by weight on a dry basis. In another particular embodiment, when the target steviol glycoside is reb D2, the process described herein provides a composition comprising greater than about 95% reb D2 content by weight on a dry basis.

In a further embodiment, when the target steviol glycoside is reb A, the process described herein provides a composition comprising greater than about 90% reb A content by weight on a dry basis. In another particular embodiment, when the target steviol glycoside is reb A, the process described herein provides a composition comprising greater than about 95% reb A content by weight on a dry basis.

In a still further embodiment, when the target steviol glycoside is reb E, the process described herein provides a composition comprising greater than about 90% reb E content by weight on a dry basis. In another particular embodiment, when the target steviol glycoside is reb E, the process described herein provides a composition comprising greater than about 95% reb E content by weight on a dry basis.

In a still further embodiment, when the target steviol glycoside is reb I, the process described herein provides a composition comprising greater than about 90% reb I content by weight on a dry basis. In another particular embodiment, when the target steviol glycoside is reb I, the process described herein provides a composition comprising greater than about 95% reb I content by weight on a dry basis.

In yet a further embodiment, when the target steviol glycoside is stevioside, the process described herein provides a composition comprising greater than about 90% stevioside content by weight on a dry basis. In another particular embodiment, when the target steviol glycoside is stevioside, the process described herein provides a composition comprising greater than about 95% stevioside content by weight on a dry basis.

Microorganism and Biocatalysts

In one embodiment of present invention, a microorganism or biocatalyst is contacted with the starting composition to produce target steviol glycosides. The microorganism can be any microorganism possessing the necessary enzymes for converting the starting composition to target steviol glycosides. These enzymes are encoded within the microorganism's genome.

In one embodiment the microoganism may be, for example, *E. coli, Saccharomyces* sp., *Aspergillus* sp., *Pichia* sp., *Bacillus* sp., *Yarrowia* sp. etc.

The enzymes can be located on the surface and/or inside the cell of the microorganism and/or can be secreted out in the medium by the microorganism.

The biocatalyst comprises at least one enzyme and can be whole cell suspension, crude lysate or purified enzyme.

The enzymes necessary for converting the starting composition to target steviol glycosides include the steviol biosynthesis enzymes and UDP-glycosyltransferases (UGTs). Optionally it may include UDP recycling enzyme(s). The UDP recycling enzyme can be sucrose synthase and the recycling substrate can be sucrose.

In one embodiment the steviol biosynthesis enzymes include mevalonate (MVA) pathway enzymes.

In another embodiment the steviol biosynthesis enzymes include non-mevalonate 2-C-methyl-D-erythritol-4-phosphate pathway (MEP/DOXP) enzymes.

In one embodiment the steviol biosynthesis enzymes are selected from the group including geranylgeranyl diphosphate synthase, copalyl diphosphate synthase, kaurene synthase, kaurene oxidase, kaurenoic acid 13-hydroxylase (KAH), steviol synthetase, deoxyxylulose 5-phosphate synthase (DXS), D-1-deoxyxylulose 5-phosphate reductoisomerase (DXR), 4-diphosphocytidyl-2-C-methyl-D-erythritol synthase (CMS), 4-diphosphocytidyl-2-C-methyl-D-erythritol kinase (CMK), 4-diphosphocytidyl-2-C-methyl-D-erythritol 2,4-cyclodiphosphate synthase (MCS), 1-hydroxy-2-methyl-2(E)-butenyl 4-diphosphate synthase (HDS), 1-hydroxy-2-methyl-2(E)-butenyl 4-diphosphate reductase (HDR), acetoacetyl-CoA thiolase, truncated HMG-CoA reductase, mevalonate kinase, phosphomevalonate kinase, mevalonate pyrophosphate decarboxylase, cytochrome P450 reductase etc.

The UDP-glucosyltransferase can be any UDP-glucosyltransferase capable of adding at least one glucose unit to the steviol and or steviol glycoside substrate to provide the target steviol glycoside.

In one embodiment, the microorganism is free. In another embodiment, the microorganism is immobilized. For example, the microorganism may be immobilized to a solid support made from inorganic or organic materials. Non-limiting examples of solid supports suitable to immobilize the microorganism include derivatized cellulose or glass, ceramics, metal oxides or membranes. The microorganism may be immobilized to the solid support, for example, by covalent attachment, adsorption, cross-linking, entrapment or encapsulation.

In one embodiment the microorganism is in aqueous medium, comprising water, and various components selected form group including carbon sources, energy sources, nitrogen sources, microelements, vitamins, nucleosides, nucleoside phosphates, nucleoside diphosphates, nucleoside triphosphates, organic and inorganic salts, organic and mineral acids, bases etc. Carbon sources include glycerol, glucose, carbon dioxide, carbonates, bicarbonates. Nitrogen sources can include nitrates, nitrites, amino acids, peptides, peptones, or proteins.

In a particular embodiment, the medium comprises buffer. Suitable buffers include, but are not limited to, PIPES buffer, acetate buffer and phosphate buffer. In a particular embodiment, the medium comprises phosphate buffer.

In one embodiment, the medium can also include an organic solvent.

In one embodiment, the UDP-glucosyltransferase is any UDP-glucosyltransferase capable of adding at least one glucose unit to rubusoside, thereby producing stevioside. The UDP-glucosyltransferase may be, for example, UGT91D2.

In another embodiment, the UDP-glucosyltransferase is any UDP-glucosyltransferase capable of adding at least one glucose unit to rubusoside, thereby producing rebaudioside E. The UDP-glucosyltransferase may be, for example, UGTSL2.

In still another embodiment, the UDP-glucosyltransferase is any UDP-glucosyltransferase capable of adding at least one glucose unit to rebaudioside E, thereby producing rebaudioside D. The UDP-glucosyltransferase may be, for example, UGT76G1.

In yet embodiment, the UDP-glucosyltransferase is any UDP-glucosyltransferase capable of adding at least one glucose unit to stevioside, thereby producing rebaudioside A. The UDP-glucosyltransferase may be, for example, UGT76G1.

In a further embodiment, the UDP-glucosyltransferase is any UDP-glucosyltransferase capable of adding at least one glucose unit to rebaudioside A, thereby producing rebaudioside D and/or rebaudioside D2 and/or rebaudioside M2. The UDP-glucosyltransferase may be, for example, UGT91D2 or UGTSL2.

In another embodiment, the UDP-glucosyltransferase capable of adding at least one glucose unit to rebaudioside A is selected from the following listing of GenInfo identifier numbers, preferably from the group presented in Table 1, and more preferably the group presented in Table 2.

| | | | | | |
|---|---|---|---|---|---|
| 397567 | 30680413 | 115480946 | 147798902 | 218193594 | 225443294 |
| 454245 | 32816174 | 116310259 | 147811764 | 218193942 | 225444853 |
| 1359905 | 32816178 | 116310985 | 147827151 | 219885307 | 225449296 |
| 1685003 | 34393978 | 116788066 | 147836230 | 222615927 | 225449700 |
| 1685005 | 37993665 | 116788606 | 147839909 | 222619587 | 225454338 |
| 2191136 | 37993671 | 116789315 | 147846163 | 222623142 | 225454340 |
| 2501497 | 37993675 | 119394507 | 147855977 | 222625633 | 225454342 |
| 2911049 | 39104603 | 119640480 | 148905778 | 222625635 | 225454473 |
| 4218003 | 41469414 | 122209731 | 148905999 | 222636620 | 225454475 |
| 4314356 | 41469452 | 125526997 | 148906835 | 222636621 | 225458362 |
| 13492674 | 42566366 | 125534279 | 148907340 | 222636628 | 225461551 |
| 13492676 | 42570280 | 125534461 | 148908935 | 222636629 | 225461556 |
| 15217773 | 42572855 | 125540090 | 148909182 | 224053242 | 225461558 |
| 15217796 | 44890129 | 125541516 | 148909920 | 224053386 | 225469538 |
| 15223396 | 46806235 | 125545408 | 148910082 | 224055535 | 225469540 |
| 15223589 | 50284482 | 125547340 | 148910154 | 224056138 | 226316457 |
| 15227766 | 51090402 | 125547520 | 148910612 | 224056160 | 226492603 |
| 15230017 | 51090594 | 125554547 | 148910769 | 224067918 | 226494221 |
| 15231757 | 52839682 | 125557592 | 156138791 | 224072747 | 226495389 |
| 15234056 | 56550539 | 125557593 | 156138797 | 224080189 | 226495945 |
| 15234195 | 62734263 | 125557608 | 156138799 | 224091845 | 226502400 |
| 15234196 | 62857204 | 125559566 | 156138803 | 224094703 | 226507980 |
| 15238503 | 62857206 | 125563266 | 165972256 | 224100653 | 226531147 |
| 15239523 | 62857210 | 125571055 | 168016721 | 224100657 | 226532094 |
| 15239525 | 62857212 | 125579728 | 171674071 | 224101569 | 238477377 |
| 15239543 | 75265643 | 125588307 | 171906258 | 224103105 | 240254512 |
| 15239937 | 75285934 | 125589492 | 183013901 | 224103633 | 242032615 |
| 15240305 | 75288884 | 125599469 | 183013903 | 224103637 | 242032621 |

-continued

| | | | | | |
|---|---|---|---|---|---|
| 15240534 | 77550661 | 125601477 | 186478321 | 224109218 | 242038423 |
| 15982889 | 77556148 | 126635837 | 187373030 | 224114583 | 242043290 |
| 18086351 | 82791223 | 126635845 | 187373042 | 224116284 | 242044836 |
| 18418378 | 83778990 | 126635847 | 190692175 | 224120552 | 242051252 |
| 18418380 | 89953335 | 126635863 | 194701936 | 224121288 | 242056217 |
| 18418382 | 110741436 | 126635867 | 195620060 | 224121296 | 242056219 |
| 19743740 | 110743955 | 126635883 | 209954691 | 224121300 | 242056663 |
| 19911201 | 115438196 | 126635887 | 209954719 | 224130358 | 242059339 |
| 20149064 | 115438785 | 133874210 | 209954725 | 224140703 | 242059341 |
| 20260654 | 115441237 | 133874212 | 209954733 | 224143404 | 242060922 |
| 21435782 | 115454819 | 145358033 | 210063105 | 224143406 | 242067411 |
| 21553613 | 115456047 | 147772508 | 210063107 | 224144306 | 242067413 |
| 21593514 | 115457492 | 147776893 | 212275846 | 224285244 | 242076258 |
| 22759895 | 115459312 | 147776894 | 216296854 | 225431707 | 242076396 |
| 23955910 | 115464719 | 147776895 | 217074506 | 225435532 | 242084750 |
| 26452040 | 115471069 | 147786916 | 218185693 | 225436321 | 242091005 |
| 28393204 | 115471071 | 147798900 | 218187075 | 225440041 | 242095206 |
| 30679796 | 115474009 | 147798901 | 218189427 | 225441116 | 242345159 |
| 242345161 | 297724601 | 326492035 | 356523945 | 357140904 | 359486938 |
| 255536859 | 297725463 | 326493430 | 356523957 | 357165849 | 359487055 |
| 255538228 | 297728331 | 326500410 | 356523959 | 357165852 | 359488135 |
| 255541676 | 297738632 | 326506816 | 356523961 | 357168415 | 359488708 |
| 255547075 | 297745347 | 326507826 | 356523963 | 357437837 | 359493630 |
| 255552620 | 297745348 | 326508394 | 356524387 | 357442755 | 359493632 |
| 255552622 | 297795735 | 326509445 | 356524403 | 357442757 | 359493634 |
| 255555343 | 297796253 | 326511261 | 356527181 | 357445729 | 359493636 |
| 255555361 | 297796257 | 326511866 | 356533209 | 357445731 | 359493815 |
| 255555363 | 297796261 | 326512412 | 356533852 | 357445733 | 359495856 |
| 255555365 | 297797587 | 326517673 | 356534718 | 357446799 | 359495858 |
| 255555369 | 297798502 | 326518800 | 356535480 | 357446805 | 359495869 |
| 255555373 | 297799226 | 326521124 | 356542996 | 357452779 | 359495871 |
| 255555377 | 297805988 | 326525567 | 356543136 | 357452781 | 359497638 |
| 255556812 | 297807499 | 326525957 | 356543932 | 357452783 | 359807261 |
| 255556818 | 297809125 | 326526607 | 356549841 | 357452787 | 374256637 |
| 255563008 | 297809127 | 326527141 | 356549843 | 357452789 | 377655465 |
| 255564074 | 297811403 | 326530093 | 356554358 | 357452791 | 378405177 |
| 255564531 | 297820040 | 326534036 | 356554360 | 357452797 | 378829085 |
| 255572878 | 297821483 | 326534312 | 356558606 | 357452799 | 387135070 |
| 255577901 | 297825217 | 332071132 | 356560333 | 357470367 | 387135072 |
| 255583249 | 297832276 | 339715876 | 356560599 | 357472193 | 387135078 |
| 255583253 | 297832280 | 342306012 | 356560749 | 357472195 | 387135092 |
| 255583255 | 297832518 | 342306016 | 356566018 | 357474295 | 387135094 |
| 255585664 | 297832520 | 343457675 | 356566169 | 357474493 | 387135098 |
| 255585666 | 297840825 | 343457677 | 356566173 | 357474497 | 387135100 |
| 255634688 | 297840827 | 350534960 | 356567761 | 357474499 | 387135134 |
| 255644801 | 297847402 | 356498085 | 356574704 | 357490035 | 387135136 |
| 255645821 | 297849372 | 356499771 | 356576401 | 357493567 | 387135174 |
| 255647456 | 300078590 | 356499777 | 356577660 | 357497139 | 387135176 |
| 255648275 | 300669727 | 356499779 | 357114993 | 357497581 | 387135184 |
| 260279126 | 302142947 | 356501328 | 357115447 | 357497671 | 387135186 |
| 260279128 | 302142948 | 356502523 | 357115451 | 357500579 | 387135188 |
| 261343326 | 302142950 | 356503180 | 357115453 | 357504663 | 387135190 |
| 283132367 | 302142951 | 356503184 | 357116080 | 357504691 | 387135192 |
| 283362112 | 302765302 | 356503295 | 357116928 | 357504699 | 387135194 |
| 289188052 | 302796334 | 356504436 | 357117461 | 357504707 | 387135282 |
| 295841350 | 302811470 | 356504523 | 357117463 | 357505859 | 387135284 |
| 296088529 | 302821107 | 356504765 | 357117829 | 357510851 | 387135294 |
| 296090415 | 302821679 | 356511113 | 357117839 | 357516975 | 387135298 |
| 296090524 | 319759260 | 356515120 | 357125059 | 359477003 | 387135300 |
| 296090526 | 319759266 | 356517088 | 357126015 | 359477998 | 387135302 |
| 297599503 | 320148814 | 356520732 | 357134488 | 359478043 | 387135304 |
| 297601531 | 326489963 | 356522586 | 357135657 | 359478286 | 387135312 |
| 297611791 | 326490273 | 356522588 | 357138503 | 359484299 | 387135314 |
| 297722841 | 326491131 | 356522590 | 357139683 | 359486936 | 387135316 |
| 387135318 | 449440433 | 460376293 | 460413408 | 462423864 | 475546199 |
| 387135320 | 449445896 | 460378310 | 460416351 | 470101924 | 475556485 |
| 387135322 | 449446454 | 460380744 | 462394387 | 470102280 | 475559699 |
| 387135324 | 449447657 | 460381726 | 462394433 | 470102858 | 475578293 |
| 387135326 | 449449002 | 460382093 | 462394557 | 470104211 | 475591753 |
| 387135328 | 449449004 | 460382095 | 462395646 | 470104264 | 475593742 |
| 388493506 | 449449006 | 460382754 | 462395678 | 470104266 | 475612072 |
| 388495496 | 449451379 | 460384935 | 462396388 | 470106317 | 475622476 |
| 388498446 | 449451589 | 460384937 | 462396389 | 470106357 | 475622507 |
| 388499220 | 449451591 | 460385076 | 462396419 | 470115448 | 475623787 |
| 388502176 | 449451593 | 460385872 | 462396542 | 470130404 | 482550481 |
| 388517521 | 449453712 | 460386018 | 462397507 | 470131550 | 482550499 |
| 388519407 | 449453714 | 460389217 | 462399998 | 470136482 | 482550740 |
| 388521413 | 449453716 | 460394872 | 462400798 | 470136484 | 482550999 |
| 388827901 | 449453732 | 460396139 | 462401217 | 470136488 | 482552352 |

-continued

| | | | | | |
|---|---|---|---|---|---|
| 388827903 | 449457075 | 460397862 | 462402118 | 470136492 | 482554970 |
| 388827907 | 449467555 | 460397864 | 462402237 | 470137933 | 482555336 |
| 388827909 | 449468742 | 460398541 | 462402284 | 470137937 | 482555478 |
| 388827913 | 449495638 | 460403139 | 462402416 | 470140422 | 482556454 |
| 393887637 | 449495736 | 460403141 | 462404228 | 470140426 | 482557289 |
| 393887646 | 449499880 | 460403143 | 462406358 | 470140908 | 482558462 |
| 393887649 | 449502786 | 460403145 | 462408262 | 470141232 | 482558508 |
| 393990627 | 449503471 | 460405998 | 462409325 | 470142008 | 482558547 |
| 397746860 | 449503473 | 460407578 | 462409359 | 470142010 | 482561055 |
| 397789318 | 449515857 | 460407590 | 462409777 | 470142012 | 482561555 |
| 413924864 | 449518643 | 460409128 | 462411467 | 470143607 | 482562795 |
| 414590349 | 449519559 | 460409134 | 462414311 | 470143939 | 482562850 |
| 414590661 | 449522783 | 460409136 | 462414416 | 470145404 | 482565074 |
| 414591157 | 449524530 | 460409459 | 462414476 | 473923244 | 482566269 |
| 414879558 | 449524591 | 460409461 | 462415526 | 474114354 | 482566296 |
| 414879559 | 449528823 | 460409463 | 462415603 | 474143634 | 482566307 |
| 414879560 | 449528825 | 460409465 | 462415731 | 474202268 | 482568689 |
| 414888074 | 449534021 | 460409467 | 462416307 | 474299266 | 482570049 |
| 431812559 | 460365546 | 460410124 | 462416920 | 474363119 | 482570572 |
| 449432064 | 460366882 | 460410126 | 462416922 | 474366157 | 482575121 |
| 449432066 | 460369823 | 460410128 | 462416923 | 474429346 | |
| 449433069 | 460369829 | 460410130 | 462416924 | 475432777 | |
| 449436944 | 460369831 | 460410132 | 462417401 | 475473002 | |
| 449438665 | 460369833 | 460410134 | 462419769 | 475489790 | |
| 449438667 | 460370755 | 460410213 | 462420317 | 475511330 | |
| 449440431 | 460374714 | 460411200 | 462423366 | 475516200 | |

TABLE 1

| GI number | Accession | Origin |
|---|---|---|
| 190692175 | ACE87855.1 | *Stevia rebaudiana* |
| 41469452 | AAS07253.1 | *Oryza sativa* |
| 62857204 | BAD95881.1 | *Ipomoea nil* |
| 62857206 | BAD95882.1 | *Ipomoea purperea* |
| 56550539 | BAD77944.1 | *Bellis perennis* |
| 115454819 | NP_001051010.1 | *Oryza sativa* Japonica Group |
| 115459312 | NP_001053256.1 | *Oryza sativa* Japonica Group |
| 115471069 | NP_001059133.1 | *Oryza sativa* Japonica Group |
| 115471071 | NP_001059134.1 | *Oryza sativa* Japonica Group |
| 116310985 | CAH67920.1 | *Oryza sativa* Indica Group |
| 116788066 | ABK24743.1 | *Picea sitchensis* |
| 122209731 | Q2V6J9.1 | *Fragaria* x *ananassa* |
| 125534461 | EAY81009.1 | *Oryza sativa* Indica Group |
| 125559566 | EAZ05102.1 | *Oryza sativa* Indica Group |
| 125588307 | EAZ28971.1 | *Oryza sativa* Japonica Group |
| 148907340 | ABR16806.1 | *Picea sitchensis* |
| 148910082 | ABR18123.1 | *Picea sitchensis* |
| 148910612 | ABR18376.1 | *Picea sitchensis* |
| 15234195 | NP_194486.1 | *Arabidopsis thaliana* |
| 15239523 | NP_200210.1 | *Arabidopsis thaliana* |
| 15239937 | NP_196793.1 | *Arabidopsis thaliana* |
| 1685005 | AAB36653.1 | *Nicotiana tabacum* |
| 183013903 | ACC38471.1 | *Medicago truncatula* |
| 186478321 | NP_172511.3 | *Arabidopsis thaliana* |
| 187373030 | ACD03249.1 | *Avena strigosa* |
| 194701936 | ACF85052.1 | *Zea mays* |
| 19743740 | AAL92461.1 | *Solanum lycopersicum* |
| 212275846 | NP_001131009.1 | *Zea mays* |
| 222619587 | EEE55719.1 | *Oryza sativa* Japonica Group |
| 224055535 | XP_002298527.1 | *Populus trichocarpa* |
| 224101569 | XP_002334266.1 | *Populus trichocarpa* |
| 224120552 | XP_002318358.1 | *Populus trichocarpa* |
| 224121288 | XP_002330790.1 | *Populus trichocarpa* |
| 225444853 | XP_002281094 | *Vitis vinifera* |
| 225454342 | XP_002275850.1 | *Vitis vinifera* |
| 225454475 | XP_002280923.1 | *Vitis vinifera* |
| 225461556 | XP_002285222 | *Vitis vinifera* |
| 225469540 | XP_002270294.1 | *Vitis vinifera* |
| 226495389 | NP_001148083.1 | *Zea mays* |
| 226502400 | NP_001147674.1 | *Zea mays* |
| 238477377 | ACR43489.1 | *Triticum aestivum* |
| 240254512 | NP_565540.4 | *Arabidopsis thaliana* |
| 2501497 | Q43716.1 | *Petunia x hybrida* |
| 255555369 | XP_002518721.1 | *Ricinus communis* |
| 26452040 | BAC43110.1 | *Arabidopsis thaliana* |
| 296088529 | CBI37520.3 | *Vitis vinifera* |

TABLE 1-continued

| GI number | Accession | Origin |
|---|---|---|
| 297611791 | NP_001067852.2 | *Oryza sativa* Japonica Group |
| 297795735 | XP_002865752.1 | *Arabidopsis lyrata* subsp. *lyrata* |
| 297798502 | XP_002867135.1 | *Arabidopsis lyrata* subsp. *lyrata* |
| 297820040 | XP_002877903.1 | *Arabidopsis lyrata* subsp. *lyrata* |
| 297832276 | XP_002884020.1 | *Arabidopsis lyrata* subsp. *lyrata* |
| 302821107 | XP_002992218.1 | *Selaginella moellendorffii* |
| 30680413 | NP_179446.2 | *Arabidopsis thaliana* |
| 319759266 | ADV71369.1 | *Pueraria montana* var. *lobata* |
| 326507826 | BAJ86656.1 | *Hordeum vulgare* subsp. *Vulgare* |
| 343457675 | AEM37036.1 | *Brassica rapa* subsp. *oleifera* |
| 350534960 | NP_001234680.1 | *Solanum lycopersicum* |
| 356501328 | XP_003519477.1 | *Glycine max* |
| 356522586 | XP_003529927.1 | *Glycine max* |
| 356535480 | XP_003536273.1 | *Glycine max* |
| 357445733 | XP_003593144.1 | *Medicago truncatula* |
| 357452783 | XP_003596668.1 | *Medicago truncatula* |
| 357474493 | XP_003607531.1 | *Medicago truncatula* |
| 357500579 | XP_003620578.1 | *Medicago truncatula* |
| 357504691 | XP_003622634.1 | *Medicago truncatula* |
| 359477998 | XP_003632051.1 | *Vitis vinifera* |
| 359487055 | XP_002271587 | *Vitis vinifera* |
| 359495869 | XP_003635104.1 | *Vitis vinifera* |
| 387135134 | AFJ52948.1 | *Linum usitatissimum* |
| 387135176 | AFJ52969.1 | *Linum usitatissimum* |
| 387135192 | AFJ52977.1 | *Linum usitatissimum* |
| 387135282 | AFJ53022.1 | *Linum usitatissimum* |
| 387135302 | AFJ53032.1 | *Linum usitatissimum* |
| 387135312 | AFJ53037.1 | *Linum usitatissimum* |
| 388519407 | AFK47765.1 | *Medicago truncatula* |
| 393887646 | AFN26668.1 | *Barbarea vulgaris* subsp. *arcuata* |
| 414888074 | DAA64088.1 | *Zea mays* |
| 42572855 | NP_974524.1 | *Arabidopsis thaliana* |
| 449440433 | XP_004137989.1 | *Cucumis sativus* |
| 449446454 | XP_004140986.1 | *Cucumis sativus* |
| 449449004 | XP_004142255.1 | *Cucumis sativus* |
| 449451593 | XP_004143546.1 | *Cucumis sativus* |
| 449515857 | XP_004164964.1 | *Cucumis sativus* |
| 460382095 | XP_004236775.1 | *Solanum lycopersicum* |
| 460409128 | XP_004249992.1 | *Solanum lycopersicum* |
| 460409461 | XP_004250157.1 | *Solanum lycopersicum* |
| 460409465 | XP_004250159.1 | *Solanum lycopersicum* |
| 462396388 | EMJ02187.1 | *Prunus persica* |
| 462402118 | EMJ07675.1 | *Prunus persica* |
| 462409359 | EMJ14693.1 | *Prunus persica* |
| 462416923 | EMJ21660.1 | *Prunus persica* |
| 46806235 | BAD17459.1 | *Oryza sativa* Japonica Group |

TABLE 1-continued

| GI number | Accession | Origin |
|---|---|---|
| 470104266 | XP_004288529.1 | *Fragaria vesca* subsp. *vesca* |
| 470142008 | XP_004306714.1 | *Fragaria vesca* subsp. *vesca* |
| 475432777 | EMT01232.1 | *Aegilops tauschii* |
| 51090402 | BAD35324.1 | *Oryza sativa* Japonica Group |

TABLE 2

| GI number | Accession | Origin | Internal reference |
|---|---|---|---|
| 460409128 | XP.004249992.1 | *Solanum lycopersicum* | UGTSL |
| 460386018 | XP.004238697.1 | *Solanum lycopersicum* | — |
| 460409134 | XP.004249995.1 | *Solanum lycopersicum* | — |
| 460410132 | XP.004250485.1 | *Solanum lycopersicum* | UGTSL2 |
| 460410130 | XP.004250484.1 | *Solanum lycopersicum* | — |
| 460410128 | XP.004250483.1 | *Solanum lycopersicum* | — |
| 460378310 | XP.004234916.1 | *Solanum lycopersicum* | — |
| 209954733 | BAG80557.1 | *Lycium barbarum* | UGTLB |
| 209954725 | BAG80553.1 | *Lycium barbarum* | — |

In yet another embodiment, the UDP-glucosyltransferase is any UDP-glucosyltransferase capable of adding at least one glucose unit to rebaudioside D to form rebaudioside M and/or rebaudioside M2. The UDP-glucosyltransferase may be, for example, UGT76G1.

Figure 3:
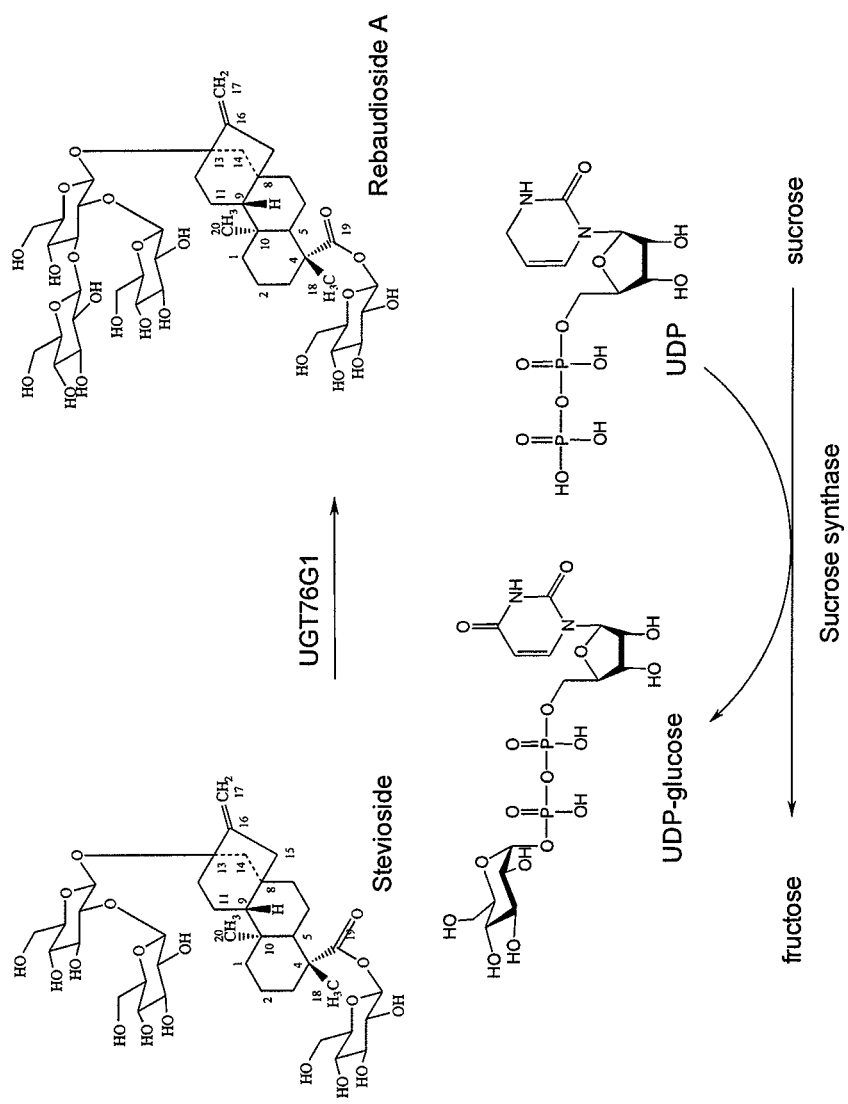
FIG. 3 shows the biocatalytic production of reb A from stevioside using the enzyme UGT76G1 and concomitant recycling of UDP to UDP glucose via sucrose synthase.

Optionally, the method of the present invention further comprises recycling UDP to provide UDP-glucose. In one embodiment, the method comprises recycling UDP by providing a recycling catalyst, i.e., a biocatalyst capable of UDP-glucose overproduction, and a recycling substrate, such that the conversion of the substrate steviol glycoside to the target steviol glycoside is carried out using catalytic amounts of UDP-glucosyltransferase and UDP-glucose (FIG. 3).

In one embodiment, the UDP-glucose recycling catalyst is sucrose synthase.

In one embodiment, the recycling substrate is sucrose.

In one embodiment the biocatalyst comprises more than one UDP-glucosyltransferase.

In embodiment the biocatalyst comprises more than one UDP-glucosyltransferase and UDP-glucose recycling catalyst.

The target steviol glycoside is optionally purified from the resulting composition. Purification of the target steviol glycoside from the reaction medium can be achieved by at least one suitable method to provide a highly purified target steviol glycoside composition. Suitable methods include crystallization, separation by membranes, centrifugation, extraction (liquid or solid phase), chromatographic separation, HPLC (preparative or analytical) or a combination of such methods.

Compounds and Methods

The present invention also provides isolated and highly purified reb D2. Reb D2 is an isomer of reb D and has the following structure:

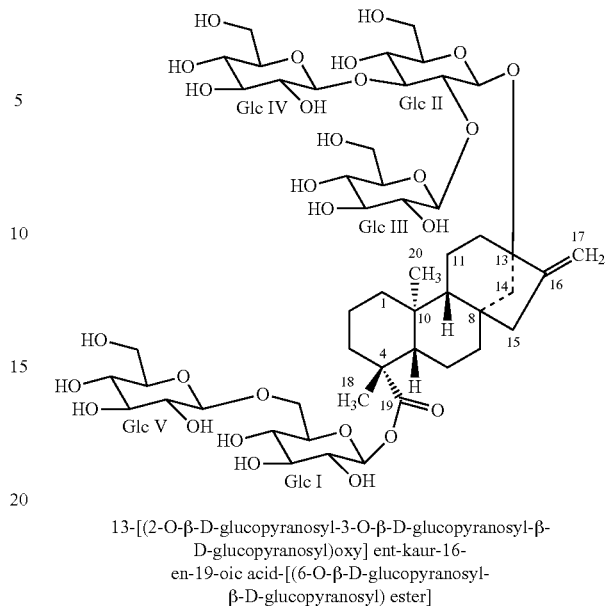

13-[(2-O-β-D-glucopyranosyl-3-O-β-D-glucopyranosyl-β-D-glucopyranosyl)oxy] ent-kaur-16-en-19-oic acid-[(6-O-β-D-glucopyranosyl-β-D-glucopyranosyl) ester]

In another embodiment, the present invention provides reb D2 having a purity greater than about 95% by weight on an anhydrous basis, such as, for example, greater than about 96% by weight, greater than about 97% by weight, greater than about 98% by weight or greater than about 99% by weight.

In still another embodiment, the present invention provides reb D2 having a purity greater than about 95% by weight in a steviol glycoside mixture, such as, for example, greater than about 96% by weight, greater than about 97% by weight, greater than about 98% by weight or greater than about 99% by weight.

The present invention also provides compositions comprising reb D2.

In one embodiment, the present invention provides a method for preparing reb D2 comprising:
 a. contacting a starting composition comprising reb A with an enzyme capable of transforming reb A to reb D2, UDP-glucose, and optionally UDP-glucose recycling enzymes, to produce a composition comprising reb D2; and
 b. isolating the composition comprising reb D2.

In some embodiments, the enzyme capable of transforming reb A to reb D2 is a UDP-glucosyltransferase, such as, for example, UGT91D2, UGTSL, UGTSL_Sc, UGTSL2 (GI No. 460410132 version XP_004250485.1), GI No. 460409128 (UGTSL) version XP_004249992.1, GI No. 115454819 version NP_001051010.1, GI No. 187373030, version ACD03249.1. GI No. 222619587 version EEE55719.1, GI No. 297795735 version XP_002865752.1 or EUGT11.

The enzyme capable of transforming reb A to reb D2 can be immobilized or in a recombinant microorganism.

In one embodiment, the enzyme is immobilized. In another embodiment, the enzyme is in a recombinant microorganism.

In one embodiment, the microorganism is free. In another embodiment, the microorganism is immobilized. For example, the microorganism may be immobilized to a solid support made from inorganic or organic materials. Non-limiting examples of solid supports suitable to immobilize the microorganism include derivatized cellulose or glass, ceramics, metal oxides or membranes. The microorganism may be immobilized to the solid support, for example, by covalent attachment, adsorption, cross-linking, entrapment or encapsulation.

Suitable microorganisms include, but are not limited to, *E. coli, Saccharomyces* sp., *Aspergillus* sp., *Pichia* sp., *Bacillus* sp., *Yarrowia* sp.

In one embodiment the microorganism is in an aqueous medium, comprising water, and various components selected form group including carbon sources, energy sources, nitrogen sources, microelements, vitamins, nucleosides, nucleoside phosphates, nucleoside diphosphates, nucleoside triphosphates, organic and inorganic salts, organic and mineral acids, bases etc. Carbon sources include glycerol, glucose, carbon dioxide, carbonates, bicarbonates. Nitrogen sources can include nitrates, nitrites, amino acids, peptides, peptones, or proteins.

In a particular embodiment, the medium comprises buffer. Suitable buffers include, but are not limited to, PIPES buffer, acetate buffer and phosphate buffer. In a particular embodiment, the medium comprises phosphate buffer.

In one embodiment the medium can also include an organic solvent.

In a particular embodiment, the enzyme is a UDP-glucosyltransferase capable of transforming reb A to reb D2.

In a more particular embodiment, the enzyme is selected from UGT91D2, UGTSL, UGTSL_Sc, UGTSL2 (GI No. 460410132 version XP_004250485.1), GI No. 460409128 (UGTSL) version XP_004249992.1, GI No. 115454819 version NP_001051010.1, GI No. 187373030, version ACD03249.1. GI No. 222619587 version EEE55719.1, GI No. 297795735 version XP_002865752.1 or EUGT11 and UGTs having substantial (>85%) sequence identity to these.

In a still more particular embodiment, the enzyme is UGTSL2 or its improved variant produced by directed evolution and having higher activity.

In one embodiment, the target steviol glycoside can be produced within the microorganism. In another embodiment, the target steviol glycoside can be secreted out in the medium. In one another embodiment, the released steviol glycoside can be continuously removed from the medium. In yet another embodiment, the target steviol glycoside is separated after the completion of the reaction.

Isolation of reb D2 from the reaction medium can be achieved by any suitable method to provide a composition comprising reb D2. Suitable methods include, but are not limited to, lysis, crystallization, separation by membranes, centrifugation, extraction (liquid or solid phase), chromatographic separation, HPLC (preparative or analytical) or a combination of such methods. In a particular embodiment, isolation can be achieved by lysis and centrifugation.

In some embodiments, isolation may result in a reb D2 purity less than about 95% by weight on an anhydrous basis, and the composition may contain, e.g., steviol glycosides and/or residual reaction products. The composition comprising reb D2 can be further purified to provide highly purified reb D2, i.e. reb D2 having a purity greater than about 95% by weight on an anhydrous basis. In some embodiments, the compositions comprising reb D2 can be further purified to provide reb D2 having a purity greater than about 96%, greater than about 97%, greater than about 98% or greater than about 99% by weight on an anhydrous basis.

Purification can be affected by any means known to one of skill in the art including, but not limited to, crystallization, separation by membranes, centrifugation, extraction (liquid or solid phase), chromatographic separation, HPLC (preparative or analytical) or a combination of such methods. In a particular embodiment, HPLC is used to purify reb D2. In a more particular embodiment, semi-preparative HPLC is used to purify reb D2.

For example, a two-step semi-preparative HPLC purification can be used. The first step utilizes a C18 column with a mobile phase containing A (25% MeCN in water) and B (30% MeCN in water) with the following gradient:

| Time (min) | % A | % B |
|---|---|---|
| 0.0-5.0 | 100 | 0 |
| 20 | 20 | 80 |
| 25 | 20 | 80 |
| 30 | 100 | 0 |

The secondary step utilizes the same column and conditions, but with only an isocratic mobile phase: 20% MeCN in water.

Those of skill in the art will recognize that the particular column, mobile phases, injection volumes and other HPLC parameters can vary.

In one embodiment, the present invention provides isolated and highly purified reb M2. Reb M2 is an isomer of reb M and has the following structure:

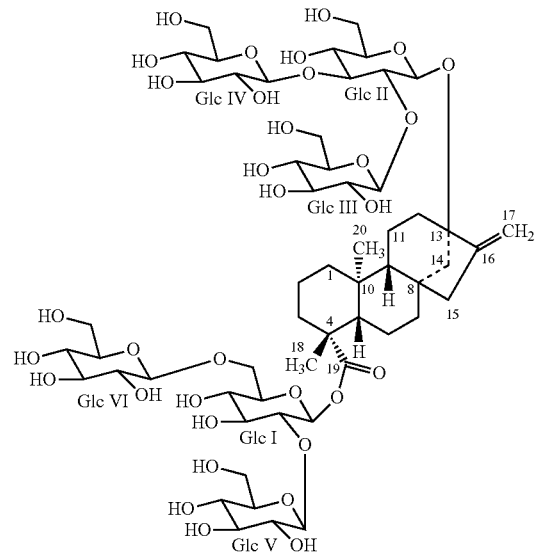

(13-[(2-O-β-D-glucopyranosyl-3-O-β-D-glucopyranosyl-β-D-glucopyranosyl)oxy] ent-kaur-16-en-19-oic acid-[(2-O-β-D-glucopyranosyl-6-O-β-D-glucopyranosyl-β-D-glucopyranosyl) ester])

In another embodiment, the present invention provides reb M2 having a purity greater than about 95% by weight on an anhydrous basis, such as, for example, greater than about 96% by weight, greater than about 97% by weight, greater than about 98% by weight or greater than about 99% by weight.

In still another embodiment, the present invention provides reb M2 having a purity greater than about 95% by weight in a steviol glycoside mixture, such as, for example, greater than about 96% by weight, greater than about 97% by weight, greater than about 98% by weight or greater than about 99% by weight.

In yet another embodiment, the present invention provides reb M2 having a purity greater than about 95% by weight in a *stevia* extract, such as, for example, greater than about 96% by weight, greater than about 97% by weight, greater than about 98% by weight or greater than about 99% by weight.

The present invention also provides compositions comprising reb M2.

It has been found that reb M2 is produced during biotransformation of reb A to reb D. As noted above, biotransformation of reb A to reb D also produces reb D2. Accordingly, in one embodiment, the present invention provides a method for preparing reb M2 comprising:
  a. contacting a starting composition comprising reb A and/or reb D2 with an enzyme capable of transforming reb A and/or reb D2 to reb M2, UDP-glucose, and optionally UDP-glucose recycling enzymes to produce a composition comprising reb M2; and
  b. isolating a composition comprising reb M2.

Not wishing to be bound by theory, it is currently believed that the pathway begins with transformation of reb A to reb D2, followed by transformation of reb D2 to reb M2. Accordingly, In one embodiment, the present invention provides a method for preparing reb M2 comprising:
  a. contacting a starting composition comprising reb D2 with an enzyme capable of transforming reb D2 to reb M2, UDP-glucose, and optionally UDP-glucose recycling enzymes to produce a composition comprising reb M2; and
  b. isolating a composition comprising reb M2.

In yet another embodiment, a method for preparing reb M2 comprises:
  a. contacting a starting composition comprising reb A with an enzyme capable of transforming reb A to reb D2, UDP-glucose, and optionally UDP-glucose recycling enzymes to produce a composition comprising reb D2;
  b. optionally, isolating a composition comprising reb D2;
  c. contacting the composition comprising reb D2 with an enzyme capable of transforming reb D2 to reb M2, UDP-glucose, and optionally UDP-glucose recycling enzymes to produce a composition comprising reb M2; and
  d. isolating a composition comprising reb M2.

The enzyme can be a UDP-glucosyltransferase, such as, for example, UGT91D2, UGTSL, UGTSL_Sc, UGTSL2 (GI No. 460410132 version XP_004250485.1), GI No. 460409128 (UGTSL) version XP_004249992.1, GI No. 115454819 version NP_001051010.1, GI No. 187373030, version ACD03249.1. GI No. 222619587 version EEE55719.1, GI No. 297795735 version XP_002865752.1 or EUGT11.

The enzyme can be immobilized or in a recombinant microorganism.

In one embodiment, the enzyme is immobilized. In another embodiment, the enzyme is in a recombinant microorganism.

In one embodiment, the microorganism is free. In another embodiment, the microorganism is immobilized. For example, the microorganism may be immobilized to a solid support made from inorganic or organic materials. Non-limiting examples of solid supports suitable to immobilize the microorganism include derivatized cellulose or glass, ceramics, metal oxides or membranes. The microorganism may be immobilized to the solid support, for example, by covalent attachment, adsorption, cross-linking, entrapment or encapsulation.

Suitable microorganisms include, but are not limited to, *E. coli, Saccharomyces* sp., *Aspergillus* sp., *Pichia* sp., *Bacillus* sp., *Yarrowia* sp.

In one embodiment the microorganism is in aqueous medium, comprising water, and various components selected form group including carbon sources, energy sources, nitrogen sources, microelements, vitamins, nucleosides, nucleoside phosphates, nucleoside diphosphates, nucleoside triphosphates, organic and inorganic salts, organic and mineral acids, bases etc. Carbon sources include glycerol, glucose, carbon dioxide, carbonates, bicarbonates. Nitrogen sources can include nitrates, nitrites, amino acids, peptides, peptones, or proteins.

In a particular embodiment, the medium comprises buffer. Suitable buffers include, but are not limited to, PIPES buffer, acetate buffer and phosphate buffer. In a particular embodiment, the medium comprises phosphate buffer.

In one embodiment the medium can also include an organic solvent.

In a particular embodiment, the enzyme is a UDP-glucosyltransferase capable of transforming reb A and/or reb D2 to reb M2 and is contained in *E. coli*.

In a more particular embodiment, the enzyme is selected from UGT91D2, UGTSL, UGTSL_Sc, UGTSL2 (GI No. 460410132 version XP_004250485.1), GI No. 460409128 (UGTSL) version XP_004249992.1, GI No. 115454819 version NP_001051010.1, GI No. 187373030, version ACD03249.1. GI No. 222619587 version EEE55719.1, GI No. 297795735 version XP_002865752.1 or EUGT11.

In a still more particular embodiment, the enzyme is UGTSL2 or its improved variant produced by directed evolution and having higher activity.

In one embodiment, the target steviol glycoside reb M2 can be produced within the microorganism. In another embodiment, the target steviol glycoside can be secreted out in the medium. In one another embodiment, the released steviol glycoside can be continuously removed from the medium. In yet another embodiment, the target steviol glycoside is separated after the completion of the reaction.

Isolation of reb M2 from the reaction medium can be achieved by any suitable method to provide a composition comprising reb M2. Suitable methods include, but are not limited to, lysis, crystallization, separation by membranes, centrifugation, extraction (liquid or solid phase), chromatographic separation, HPLC (preparative or analytical) or a combination of such methods. In a particular embodiment, isolation can be achieved by lysis and centrifugation.

In some embodiments, isolation may result in a reb M2 purity less than about 95% by weight on an anhydrous basis, and the composition may contain, e.g., steviol glycosides and/or residual reaction products.

The composition comprising reb M2 can be further purified to provide highly purified reb M2, i.e. reb M2 having a purity greater than about 95% by weight on an anhydrous basis. In some embodiments, the compositions comprising reb M2 can be further purified to provide reb M2 having a purity greater than about 96%, greater than about 97%, greater than about 98% or greater than about 99% by weight on an anhydrous basis.

Purification can be affected by any means known to one of skill in the art including, but not limited to, crystallization, separation by membranes, centrifugation, extraction (liquid or solid phase), chromatographic separation, HPLC (preparative or analytical) or a combination of such methods. In a particular embodiment, HPLC is used to purify reb M2. In a more particular embodiment, semi-preparative HPLC is used to purify reb M2.

For example, a two-step semi-preparative HPLC purification can be used. The first step utilizes a C18 column with a mobile phase containing A (25% MeCN in water) and B (30% MeCN in water) with the following gradient:

| Time (min) | % A | % B |
|---|---|---|
| 0.0-5.0 | 100 | 0 |
| 20 | 20 | 80 |
| 25 | 20 | 80 |
| 30 | 100 | 0 |

The secondary step utilizes the same column and conditions, but with only an isocratic mobile phase: 20% MeCN in water.

Those of skill in the art will recognize that the particular column, mobile phases, injection volumes and other HPLC parameters can vary.

Purified steviol glycosides, prepared in accordance with the present invention, may be used in a variety of consumable products including, but not limited to, foods, beverages, pharmaceutical compositions, tobacco products, nutraceutical compositions, oral hygiene compositions, and cosmetic compositions.

Figure 4:
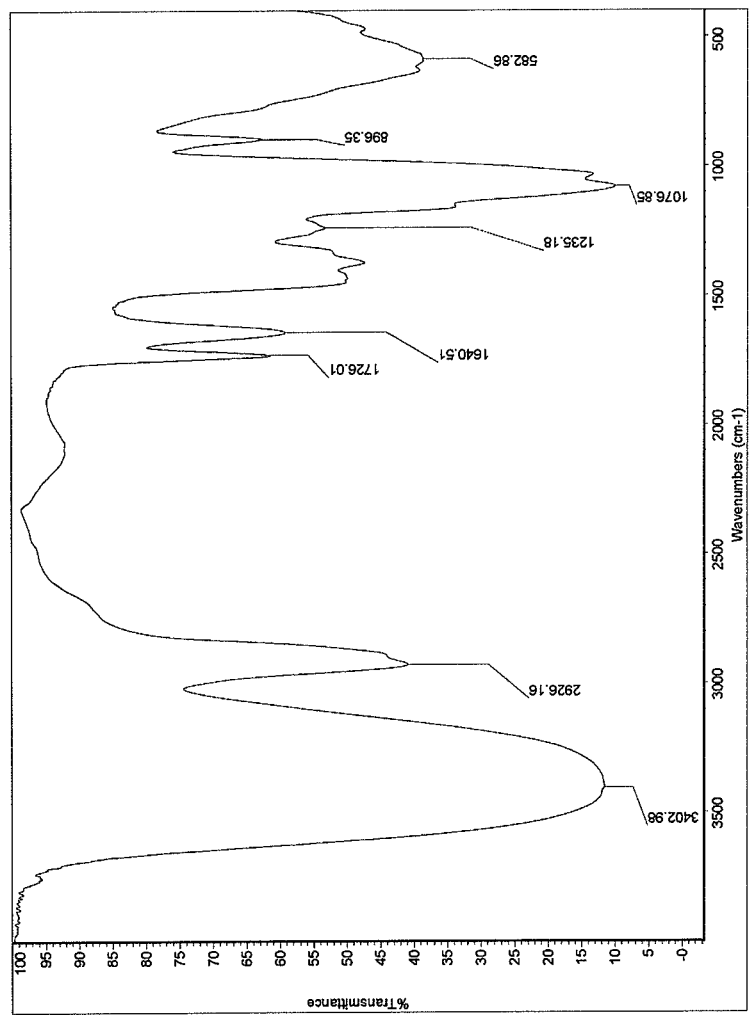
FIG. 4 shows the IR spectrum of reb M.

The high purity reb M obtained in this invention, having a molecular weight of 1291.29, a molecular formula of $C_{56}H_{90}O_{33}$, CAS registry number 1220616-44-3, and the structure presented in FIG. 1, is in the form of a white and odorless powder. The compound is about 200 times sweeter than sugar when compared to a 10% sucrose solution. The infrared absorption spectrum is shown in FIG. 4.

Other properties of the pure reb M compound include a melting point of 249-250° C., and a specific rotation of $[\alpha]_D^{25}$ −19.0° in 50% ethanol (C=1.0). The solubility of reb M in water is around 0.3%, and increases with an increase in temperature.

Reb M is soluble in diluted solutions of methanol, ethanol, n-propanol, and isopropanol. However, it is insoluble in acetone, benzene, chloroform, and ether.

Reb M obtained in accordance with the present invention is heat and pH-stable.

Highly purified target glycoside(s) particularly, reb D, reb D2, reb M and/or reb M2 obtained according to this invention can be used "as-is" or in combination with at least one sweetener, flavor, food ingredient and/or combination thereof.

Non-limiting examples of flavors include lime, lemon, orange, fruit, banana, grape, pear, pineapple, mango, berry, bitter almond, cola, cinnamon, sugar, cotton candy and vanilla flavors and/or combination thereof.

Non-limiting examples of other food ingredients include at least one selected from flavors, acidulants, organic and amino acids, coloring agents, bulking agents, modified starches, gums, texturizers, preservatives, antioxidants, emulsifiers, stabilizers, thickeners and gelling agents and/or combination thereof.

Highly purified target glycoside(s) particularly, reb D, reb D2, reb M and/or reb M2 obtained according to this invention can be prepared in various polymorphic forms, including but not limited to hydrates, solvates, anhydrous, amorphous forms and/or combination thereof.

Highly purified target steviol glycoside(s), particularly, reb D, reb D2, reb M and/or reb M2 obtained according to this invention may be incorporated as a high intensity natural sweetener in foodstuffs, beverages, pharmaceutical compositions, cosmetics, chewing gums, table top products, cereals, dairy products, toothpastes and other oral cavity compositions, etc.

Highly purified target steviol glycoside(s), particularly, reb D, reb D2, reb M and/or reb M2 as a sweetening compound may be employed as the sole sweetener, or it may be used together with at least one naturally occurring high intensity sweeteners such as stevioside, reb A, reb B, reb C, reb D, reb E, reb F, steviolbioside, dulcoside A, rubusoside, mogrosides, brazzein, neohesperidin dihydrochalcone, glycyrrhizic acid and its salts, thaumatin, perillartine, pernandulcin, mukuroziosides, baiyunoside, phlomisoside-I, dimethyl-hexahydrofluorene-dicarboxylic acid, abrusosides, periandrin, carnosiflosides, cyclocarioside, pterocaryosides, polypodoside A, brazilin, hernandulcin, phillodulcin, glycyphyllin, phlorizin, trilobatin, dihydroflavonol, dihydroquercetin-3-acetate, neoastilibin, trans-cinnamaldehyde, monatin and its salts, selligueain A, hematoxylin, monellin, osladin, pterocaryoside A, pterocaryoside B, mabinlin, pentadin, miraculin, curculin, neoculin, chlorogenic acid, cynarin, Luo Han Guo sweetener, mogroside V, siamenoside and/or combination thereof.

In a particular embodiment, reb D2 and/or reb M2 can be used together in a sweetener composition comprising a compound selected from the group consisting of reb A, reb B, reb D, NSF-02, Mogroside V, erythritol and/or combinations thereof.

Highly purified target steviol glycoside(s), particularly, reb D, reb D2, reb M and/or reb M2 may also be used in combination with synthetic high intensity sweeteners such as sucralose, potassium acesulfame, aspartame, alitame, saccharin, neohesperidin dihydrochalcone, cyclamate, neotame, dulcin, suosan advantame, salts thereof, and the like.

Moreover, highly purified target steviol glycoside(s), particularly, reb D, reb D2, reb M and/or reb M2 can be used in combination with natural sweetener suppressors such as gymnemic acid, hodulcin, ziziphin, lactisole, and others. Reb D, reb D2, reb M and/or reb M2 may also be combined with various umami taste enhancers. Reb D, reb D2, reb M and/or reb M2 can be mixed with umami tasting and sweet amino acids such as glutamate, aspartic acid, glycine, alanine, threonine, proline, serine, glutamate, lysine and tryptophan.

Highly purified target steviol glycoside(s), particularly, reb D, reb D2, reb M can be used in combination with one or more additive selected from the group consisting of carbohydrates, polyols, amino acids and their corresponding salts, poly-amino acids and their corresponding salts, sugar acids and their corresponding salts, nucleotides, organic acids, inorganic acids, organic salts including organic acid salts and organic base salts, inorganic salts, bitter compounds, flavorants and flavoring ingredients, astringent compounds, proteins or protein hydrolysates, surfactants, emulsifiers, flavonoids, alcohols, polymers and combinations thereof.

Highly purified target steviol glycoside(s), particularly, reb D, reb D2, reb M and/or reb M2 may be combined with polyols or sugar alcohols. The term "polyol" refers to a molecule that contains more than one hydroxyl group. A polyol may be a diol, triol, or a tetraol which contain 2, 3, and 4 hydroxyl groups, respectively. A polyol also may contain more than four hydroxyl groups, such as a pentaol, hexaol, heptaol, or the like, which contain 5, 6, or 7 hydroxyl groups, respectively. Additionally, a polyol also may be a sugar alcohol, polyhydric alcohol, or polyalcohol which is a reduced form of carbohydrate, wherein the carbonyl group (aldehyde or ketone, reducing sugar) has been reduced to a primary or secondary hydroxyl group. Examples of polyols include, but are not limited to, erythritol, maltitol, mannitol, sorbitol, lactitol, xylitol, inositol, isomalt, propylene glycol, glycerol, threitol, galactitol, hydrogenated isomaltulose, reduced isomalto-oligosaccharides, reduced xylo-oligosaccharides, reduced gentio-oligosaccharides, reduced maltose syrup, reduced glucose syrup, hydrogenated starch hydrolyzates, polyglycitols and sugar alcohols or any other carbohydrates capable of being reduced which do not adversely affect the taste of the sweetener composition.

Highly purified target steviol glycoside(s), particularly, reb D, reb D2, reb M and/or reb M2 may be combined with reduced calorie sweeteners such as D-tagatose, allulose, allose, L-sugars, L-sorbose, L-arabinose, and others.

Highly purified target steviol glycoside(s), particularly, reb D, reb D2, reb M and/or reb M2 may also be combined with various carbohydrates. The term "carbohydrate" generally refers to aldehyde or ketone compounds substituted with multiple hydroxyl groups, of the general formula $(CH_2O)_n$, wherein n is 3-30, as well as their oligomers and polymers. The carbohydrates of the present invention can, in addition, be substituted or deoxygenated at one or more positions. Carbohydrates, as used herein, encompass unmodified carbohydrates, carbohydrate derivatives, substituted carbohydrates, and modified carbohydrates. As used herein, the phrases "carbohydrate derivatives", "substituted carbohydrate", and "modified carbohydrates" are synonymous. Modified carbohydrate means any carbohydrate wherein at least one atom has been added, removed, or substituted, or combinations thereof. Thus, carbohydrate derivatives or substituted carbohydrates include substituted and unsubstituted monosaccharides, disaccharides, oligosaccharides, and polysaccharides. The carbohydrate derivatives or substituted carbohydrates optionally can be deoxygenated at any corresponding C-position, and/or substituted with one or more moieties such as hydrogen, halogen, haloalkyl, carboxyl, acyl, acyloxy, amino, amido, carboxyl derivatives, alkylamino, dialkylamino, arylamino, alkoxy, aryloxy, nitro, cyano, sulfo, mercapto, imino, sulfonyl, sulfenyl, sulfonyl, sulfamoyl, carboalkoxy, carboxamido, phosphonyl, phosphinyl, phosphoryl, phosphino, thioester, thioether, oximino, hydrazino, carbamyl, phospho, phosphonato, or any other viable functional group provided the carbohydrate derivative or substituted carbohydrate functions to improve the sweet taste of the sweetener composition.

Examples of carbohydrates which may be used in accordance with this invention include, but are not limited to, Psicose, turanose, allulose, allose, D-tagatose, trehalose, galactose, rhamnose, various cyclodextrins, cyclic oligosaccharides, various types of maltodextrins, dextran, sucrose, glucose, ribulose, fructose, threose, arabinose, xylose, lyxose, allose, altrose, mannose, idose, lactose, maltose, invert sugar, isotrehalose, neotrehalose, isomaltulose, erythrose, deoxyribose, gulose, idose, talose, erythrulose, xylulose, psicose, turanose, cellobiose, amylopectin, glucosamine, mannosamine, fucose, glucuronic acid, gluconic acid, glucono-lactone, abequose, galactosamine, beet oligosaccharides, isomalto-oligosaccharides (isomaltose, isomaltotriose, panose and the like), xylo-oligosaccharides (xylotriose, xylobiose and the like), xylo-terminated oligosaccharides, gentio-oligosaccharides (gentiobiose, gentiotriose, gentiotetraose and the like), sorbose, nigero-oligosaccharides, palatinose oligosaccharides, fructooligosaccharides (kestose, nystose and the like), maltotetraol, maltotriol, malto-oligosaccharides (maltotriose, maltotetraose, maltopentaose, maltohexaose, maltoheptaose and the like), starch, inulin, inulo-oligosaccharides, lactulose, melibiose, raffinose, ribose, isomerized liquid sugars such as high fructose corn syrups, coupling sugars, and soybean oligosaccharides. Additionally, the carbohydrates as used herein may be in either the D- or L-configuration.

Highly purified target steviol glycoside(s), particularly, reb D, reb D2, reb M and/or reb M2 obtained according to this invention can be used in combination with various physiologically active substances or functional ingredients. Functional ingredients generally are classified into categories such as carotenoids, dietary fiber, fatty acids, saponins, antioxidants, nutraceuticals, flavonoids, isothiocyanates, phenols, plant sterols and stanols (phytosterols and phytostanols); polyols; prebiotics, probiotics; phytoestrogens; soy protein; sulfides/thiols; amino acids; proteins; vitamins; and minerals. Functional ingredients also may be classified based on their health benefits, such as cardiovascular, cholesterol-reducing, and anti-inflammatory. Exemplary functional ingredients are provided in WO2013/096420, the contents of which is hereby incorporated by reference.

Highly purified target steviol glycoside(s), particularly, reb D, reb D2, reb M and/or reb M2 obtained according to this invention may be applied as a high intensity sweetener to produce zero calorie, reduced calorie or diabetic beverages and food products with improved taste characteristics. It may also be used in drinks, foodstuffs, pharmaceuticals, and other products in which sugar cannot be used. In addition, highly purified target steviol glycoside(s), particularly, reb D, reb D2, reb M and/or reb M2 can be used as a sweetener not only for drinks, foodstuffs, and other products dedicated for human consumption, but also in animal feed and fodder with improved characteristics.

Examples of consumable products in which highly purified target steviol glycoside(s), particularly, reb D, reb D2, reb M and/or reb M2 may be used as a sweetening compound include, but are not limited to, alcoholic beverages such as vodka, wine, beer, liquor, and sake, etc.; natural juices; refreshing drinks; carbonated soft drinks; diet drinks; zero calorie drinks; reduced calorie drinks and foods; yogurt drinks; instant juices; instant coffee; powdered types of instant beverages; canned products; syrups; fermented soybean paste; soy sauce; vinegar; dressings; mayonnaise; ketchups; curry; soup; instant bouillon; powdered soy sauce; powdered vinegar; types of biscuits; rice biscuit; crackers; bread; chocolates; caramel; candy; chewing gum; jelly; pudding; preserved fruits and vegetables; fresh cream; jam; marmalade; flower paste; powdered milk; ice cream; sorbet; vegetables and fruits packed in bottles; canned and boiled beans; meat and foods boiled in sweetened sauce; agricultural vegetable food products; seafood; ham; sausage; fish ham; fish sausage; fish paste; deep fried fish products; dried seafood products; frozen food products; preserved seaweed; preserved meat; tobacco; medicinal products; and many others. In principle it can have unlimited applications.

During the manufacturing of products such as foodstuffs, drinks, pharmaceuticals, cosmetics, table top products, and chewing gum, the conventional methods such as mixing, kneading, dissolution, pickling, permeation, percolation, sprinkling, atomizing, infusing and other methods may be used.

Moreover, the highly purified target steviol glycoside(s), particularly, reb D, reb D2, reb M and/or reb M2 obtained in this invention may be used in dry or liquid forms. In one embodiment, a tabletop sweetener comprising reb D2 is provided. In another embodiment, a tabletop sweetener comprising reb M2 is provided.

The highly purified target steviol glycoside can be added before or after heat treatment of food products. The amount of the highly purified target steviol glycoside(s), particularly, reb D, reb D2, reb M and/or reb M2 depends on the purpose of usage. As discussed above, it can be added alone or in combination with other compounds.

The present invention is also directed to sweetness enhancement in beverages using reb D2. The present invention is also directed to sweetness enhancement in beverages using reb M2. Accordingly, the present invention provides a beverage comprising a sweetener and reb D2 and/or reb M2 as a sweetness enhancer, wherein reb D2 and/or reb M2 is present in a concentration at or below their respective sweetness recognition thresholds.

As used herein, the term "sweetness enhancer" refers to a compound capable of enhancing or intensifying the perception of sweet taste in a composition, such as a beverage. The term "sweetness enhancer" is synonymous with the terms "sweet taste potentiator," "sweetness potentiator," "sweetness amplifier," and "sweetness intensifier."

The term "sweetness recognition threshold concentration," as generally used herein, is the lowest known concentration of a sweet compound that is perceivable by the human sense of taste, typically around 1.0% sucrose equivalence (1.0% SE). Generally, the sweetness enhancers may enhance or potentiate the sweet taste of sweeteners without providing any noticeable sweet taste by themselves when present at or below the sweetness recognition threshold concentration of a given sweetness enhancer; however, the sweetness enhancers may themselves provide sweet taste at concentrations above their sweetness recognition threshold concentration. The sweetness recognition threshold concentration is specific for a particular enhancer and can vary based on the beverage matrix. The sweetness recognition threshold concentration can be easily determined by taste testing increasing concentrations of a given enhancer until greater than 1.0% sucrose equivalence in a given beverage matrix is detected. The concentration that provides about 1.0% sucrose equivalence is considered the sweetness recognition threshold.

In some embodiments, sweetener is present in the beverage in an amount from about 0.5% to about 12% by weight, such as, for example, about 1.0% by weight, about 1.5% by weight, about 2.0% by weight, about 2.5% by weight, about 3.0% by weight, about 3.5% by weight, about 4.0% by weight, about 4.5% by weight, about 5.0% by weight, about 5.5% by weight, about 6.0% by weight, about 6.5% by weight, about 7.0% by weight, about 7.5% by weight, about 8.0% by weight, about 8.5% by weight, about 9.0% by weight, about 9.5% by weight, about 10.0% by weight, about 10.5% by weight, about 11.0% by weight, about 11.5% by weight or about 12.0% by weight.

In a particular embodiment, the sweetener is present in the beverage in an amount from about 0.5% of about 10%, such as for example, from about 2% to about 8%, from about 3% to about 7% or from about 4% to about 6% by weight. In a particular embodiment, the sweetener is present in the beverage in an amount from about 0.5% to about 8% by weight. In another particular embodiment, the sweetener is present in the beverage in an amount from about 2% to about 8% by weight.

In one embodiment, the sweetener is a traditional caloric sweetener. Suitable sweeteners include, but are not limited to, sucrose, fructose, glucose, high fructose corn syrup and high fructose starch syrup.

In another embodiment, the sweetener is erythritol.

In still another embodiment, the sweetener is a rare sugar. Suitable rare sugars include, but are not limited to, D-allose, D-psicose, L-ribose, D-tagatose, L-glucose, L-fucose, L-arbinose, D-turanose, D-leucrose and combinations thereof.

It is contemplated that a sweetener can be used alone, or in combination with other sweeteners.

In one embodiment, the rare sugar is D-allose. In a more particular embodiment, D-allose is present in the beverage in an amount of about 0.5% to about 10% by weight, such as, for example, from about 2% to about 8%.

In another embodiment, the rare sugar is D-psicose. In a more particular embodiment, D-psicose is present in the beverage in an amount of about 0.5% to about 10% by weight, such as, for example, from about 2% to about 8%.

In still another embodiment, the rare sugar is D-ribose. In a more particular embodiment, D-ribose is present in the beverage in an amount of about 0.5% to about 10% by weight, such as, for example, from about 2% to about 8%.

In yet another embodiment, the rare sugar is D-tagatose. In a more particular embodiment, D-tagatose is present in the beverage in an amount of about 0.5% to about 10% by weight, such as, for example, from about 2% to about 8%.

In a further embodiment, the rare sugar is L-glucose. In a more particular embodiment, L-glucose is present in the beverage in an amount of about 0.5% to about 10% by weight, such as, for example, from about 2% to about 8%.

In one embodiment, the rare sugar is L-fucose. In a more particular embodiment, L-fucose is present in the beverage in an amount of about 0.5% to about 10% by weight, such as, for example, from about 2% to about 8%.

In another embodiment, the rare sugar is L-arabinose. In a more particular embodiment, L-arabinose is present in the beverage in an amount of about 0.5% to about 10% by weight, such as, for example, from about 2% to about 8%.

In yet another embodiment, the rare sugar is D-turanose. In a more particular embodiment, D-turanose is present in the beverage in an amount of about 0.5% to about 10% by weight, such as, for example, from about 2% to about 8%.

In yet another embodiment, the rare sugar is D-leucrose. In a more particular embodiment, D-leucrose is present in the beverage in an amount of about 0.5% to about 10% by weight, such as, for example, from about 2% to about 8%.

The addition of the sweetness enhancer at a concentration at or below its sweetness recognition threshold increases the detected sucrose equivalence of the beverage comprising the sweetener and the sweetness enhancer compared to a corresponding beverage in the absence of the sweetness enhancer. Moreover, sweetness can be increased by an amount more than the detectable sweetness of a solution containing the same concentration of the at least one sweetness enhancer in the absence of any sweetener.

Accordingly, the present invention also provides a method for enhancing the sweetness of a beverage comprising a sweetener comprising providing a beverage comprising a sweetener and adding a sweetness enhancer selected from reb D2, reb M2 or a combination thereof, wherein reb D2 and reb M2 are present in a concentration at or below their sweetness recognition thresholds.

Addition of reb D2 and/or reb M2 in a concentration at or below the sweetness recognition threshold to a beverage containing a sweetener may increase the detected sucrose equivalence from about 1.0% to about 5.0%, such as, for example, about 1.0%, about 1.5%, about 2.0%, about 2.5%, about 3.0%, about 3.5%, about 4.0%, about 4.5% or about 5.0%.

The following examples illustrate preferred embodiments of the invention for the preparation of highly purified target steviol glycoside(s), particularly, reb D, reb D2, reb M and/or reb M2. It will be understood that the invention is not limited to the materials, proportions, conditions and procedures set forth in the examples, which are only illustrative.

Example 1

In-Vivo Production of UGT76G1

NcoI and NdeI restriction sides were added to the original nucleic sequence as described in Genbank accession no. AAR06912.1. After codon optimization the following nucleic sequence was obtained (SEQ ID 1):

CCATGGCCCATATGGAAAACAAAACCGAAACCACCGTTCGTCGTCGTCGC

CGTATTATTCTGTTTCCGGTTCCGTTTCAGGGTCATATTAATCCGATTCT

GCAGCTGGCAAATGTGCTGTATAGCAAAGGTTTTAGCATTACCATTTTTC

ATACCAATTTTAACAAACCGAAAACCAGCAATTATCCGCATTTTACCTTT

CGCTTTATTCTGGATAATGATCCGCAGGATGAACGCATTAGCAATCTGCC

GACACATGGTCCGCTGGCAGGTATGCGTATTCCGATTATTAACGAACATG

GTGCAGATGAACTGCGTCGTGAACTGGAACTGCTGATGCTGGCAAGCGAA

GAAGATGAAGAAGTTAGCTGTCTGATTACCGATGCACTGTGGTATTTTGC

ACAGAGCGTTGCAGATAGCCTGAATCTGCGTCGTCTGGTTCTGATGACCA

GCAGCCTGTTTAACTTTCATGCACATGTTAGCCTGCCGCAGTTTGATGAA

CTGGGTTATCTGGATCCGGATGATAAAACCCGTCTGGAAGAACAGGCAAG

CGGTTTTCCGATGCTGAAAGTGAAAGATATCAAAAGCGCCTATAGCAATT

GGCAGATTCTGAAAGAAATTCTGGGCAAAATGATTAAACAGACCAAAGCA

AGCAGCGGTGTTATTTGGAATAGCTTTAAAGAACTGGAAGAAAGCGAACT

GGAAACCGTGATTCGTGAAATTCCGGCACCGAGCTTTCTGATTCCGCTGC

CGAAACATCTGACCGCAAGCAGCAGCAGCCTGCTGGATCATGATCGTACC

GTTTTTCAGTGGCTGGATCAGCAGCCTCCGAGCAGCGTTCTGTATGTTAG

CTTTGGTAGCACCAGCGAAGTTGATGAAAAAGATTTTCTGGAAATTGCCC

GTGGTCTGGTTGATAGCAAACAGAGCTTTCTGTGGGTTGTTCGTCCGGGT

TTTGTTAAAGGTAGCACCTGGGTTGAACCGCTGCCGGATGGTTTTCTGGG

TGAACGTGGTCGTATTGTTAAATGGGTTCCGCAGCAAGAAGTTCTGGCAC

ACGGCGCAATTGGTGCATTTTGGACCCATAGCGGTTGGAATAGCACCCTG

GAAAGCGTTTGTGAAGGTGTTCCGATGATTTTTAGCGATTTTGGTCTGGA

TCAGCCGCTGAATGCACGTTATATGAGTGATGTTCTGAAAGTGGGTGTGT

ATCTGGAAAATGGTTGGGAACGTGGTGAAATTGCAAATGCAATTCGTCGT

GTTATGGTGGATGAAGAAGGTGAATATATTCGTCAGAATGCCCGTGTTCT

GAAACAGAAAGCAGATGTTAGCCTGATGAAAGGTGGTAGCAGCTATGAAA

GCCTGGAAAGTCTGGTTAGCTATATTAGCAGCCTGTAATAACTCGAG

After synthesis of the gene and subcloning into pET30A+ vector using NdeI and XhoI cloning sites, the UGT76G1_pET30a+ plasmid was introduced in *E. coli* Bl21(DE3) and *E. coli* EC100 by electroporation. The obtained cells were grown in petri-dishes in the presence of Kanamycin and suitable colonies were selected and allowed to grow in liquid LB medium (erlenmeyer flasks). Glycerol was added to the suspension as cryoprotectant and 400 μL aliquots were stored at −20° C. and at −80° C.

The storage aliquots of *E. coli* BL21(DE3) containing the pET30A+_UGT76G1 plasmid were thawed and added to 30 mL of LBGKP medium (20 g/L Luria Broth Lennox; 50 mM PIPES buffer pH 7.00; 50 mM Phosphate buffer pH 7.00; 2.5 g/L glucose and 50 mg/L of Kanamycin). This culture was allowed to shake at 135 rpm at 30° C. for 8 h.

The production medium contained 60 g/L of overnight express instant TB medium (Novagen), 10 g/L of glycerol and 50 mg/L of Kanamycin. The medium was allowed to stir at 20° C. while taking samples to measure the OD and pH. The cultures gave significant growth and a good OD was obtained. After 40 h, the cells were harvested by centrifugation and frozen to yield 12.7 g of cell wet weight.

Lysis was performed by addition of Bugbuster Master mix (Novagen) and the lysate was recovered by centrifugation and kept frozen. Activity tests were performed with thawed lysate.

Example 2

In-Vitro Production of UGT76G1

The S30 T7 High Yield Protein expression system kit from Promega was used. 4 μg of UGT76G1_pET30a+ plasmid from *E. coli* EC100 was mixed with 80 μL of S30 premix plus and 72 μL of S30 T7 extract was added. Nuclease-free water was added in order to obtain a total volume of 200 μL and the resulting solution was incubated for 2 h at 30° C. 180 μL was used in the catalytic test reaction.

Example 3

In-Vitro Production of UGT91D2

NcoI and NdeI restriction sides were added to the original nucleic sequence as described in Genbank accession no. ACE87855.1. After codon optimization the following nucleic sequence was obtained (SEQ ID 2):

CCATGGCACATATGGCAACCAGCGATAGCATTGTTGATGATCGTAAACAG

CTGCATGTTGCAACCTTTCCGTGGCTGGCATTTGGTCATATTCTGCCGTA

TCTGCAGCTGAGCAAACTGATTGCAGAAAAAGGTCATAAAGTGAGCTTTC

TGAGCACCACCCGTAATATTCAGCGTCTGAGCAGCCATATTAGTCCGCTG

ATTAATGTTGTTCAGCTGACCCTGCCTCGTGTTCAAGAACTGCCGGAAGA

TGCCGAAGCAACCACCGATGTTCATCCGGAAGATATTCCGTATCTGAAAA

AAGCAAGTGATGGTCTGCAGCCGGAAGTTACCCGTTTTCTGGAACAGCAT

AGTCCGGATTGGATCATCTATGATTATACCCATTATTGGCTGCCGAGCAT

TGCAGCAAGCCTGGGTATTAGCCGTGCACATTTTAGCGTTACCACCCCGT

GGGCAATTGCATATATGGGTCCGAGCGCAGATGCAATGATTAATGGTAGT

GATGGTCGTACCACCGTTGAAGATCTGACCACCCCTCCGAAATGGTTTCC

GTTTCCGACCAAAGTTTGTTGGCGTAAACATGATCTGGCACGTCTGGTTC

CGTATAAAGCACCGGGTATTAGTGATGGTTATCGTATGGGTCTGGTTCTG

AAAGGTAGCGATTGTCTGCTGAGCAAATGCTATCATGAATTTGGCACCCA

GTGGCTGCCGCTGCTGGAAACCCTGCATCAGGTTCCGGTTGTTCCGGTGG

GTCTGCTGCCTCCGGAAGTTCCGGGTGATGAAAAAGATGAAACCTGGGTT

AGCATCAAAAAATGGCTGGATGGTAAACAGAAAGGTAGCGTGGTTTATGT

-continued

```
TGCACTGGGTAGCGAAGTTCTGGTTAGCCAGACCGAAGTTGTTGAACTGG
CACTGGGTCTGGAACTGAGCGGTCTGCCGTTTGTTTGGGCATATCGTAAA
CCGAAAGGTCCGGCAAAAAGCGATAGCGTTGAACTGCCGGATGGTTTTGT
TGAACGTACCCGTGATCGTGGTCTGGTTTGGACCAGCTGGGCACCTCAGC
TGCGTATTCTGAGCCATGAAAGCGTTTGTGGTTTTCTGACCCATTGTGGT
AGCGGTAGCATTGTGGAAGGTCTGATGTTTGGTCATCCGCTGATTATGCT
GCCGATTTTTGGTGATCAGCCGCTGAATGCACGTCTGCTGGAAGATAAAC
AGGTTGGTATTGAAATTCCGCGTAATGAAGAAGATGGTTGCCTGACCAAA
GAAAGCGTTGCACGTAGCCTGCGTAGCGTTGTTGTTGAAAAAGAAGGCGA
AATCTATAAAGCCAATGCACGTGAACTGAGCAAAATCTATAATGATACCA
AAGTGGAAAAAGAATATGTGAGCCAGTTCGTGGATTATCTGGAAAAAAAC
ACCCGTGCAGTTGCCATTGATCACGAAAGCTAATGACTCGAG
```

After synthesis of the gene and subcloning into pET30A+ vector using NcoI and XhoI cloning sites, the UGT91D2_pET30a+ plasmid was introduced into *E. coli* EC100 by electroporation. The obtained cells were grown in the presence of Kanamycin and suitable colonies were selected and allowed to grow in liquid LB medium (erlenmeyer flasks). Glycerol was added to the suspension as cryoprotectant and 400 μL aliquots were stored at −20° C. and at −80° C.

The S30 T7 High Yield Protein expression system kit from Promega was used for the in-vitro synthesis of the protein.

4 μg of UGT91D2_pET30a+ plasmid was mixed with 80 μL of S30 premix plus and 72 μL of S30 T7 extract was added. Nuclease-free water was added in order to obtain a total volume of 200 μL and the resulting solution was incubated for 2 h at 30° C. 5 μL was used for SDS-page analysis while the remaining 45 μL was used in the catalytic test reaction.

Example 4

Catalytic Reaction with In-Vivo Produced UGT76G1

Figure 40:
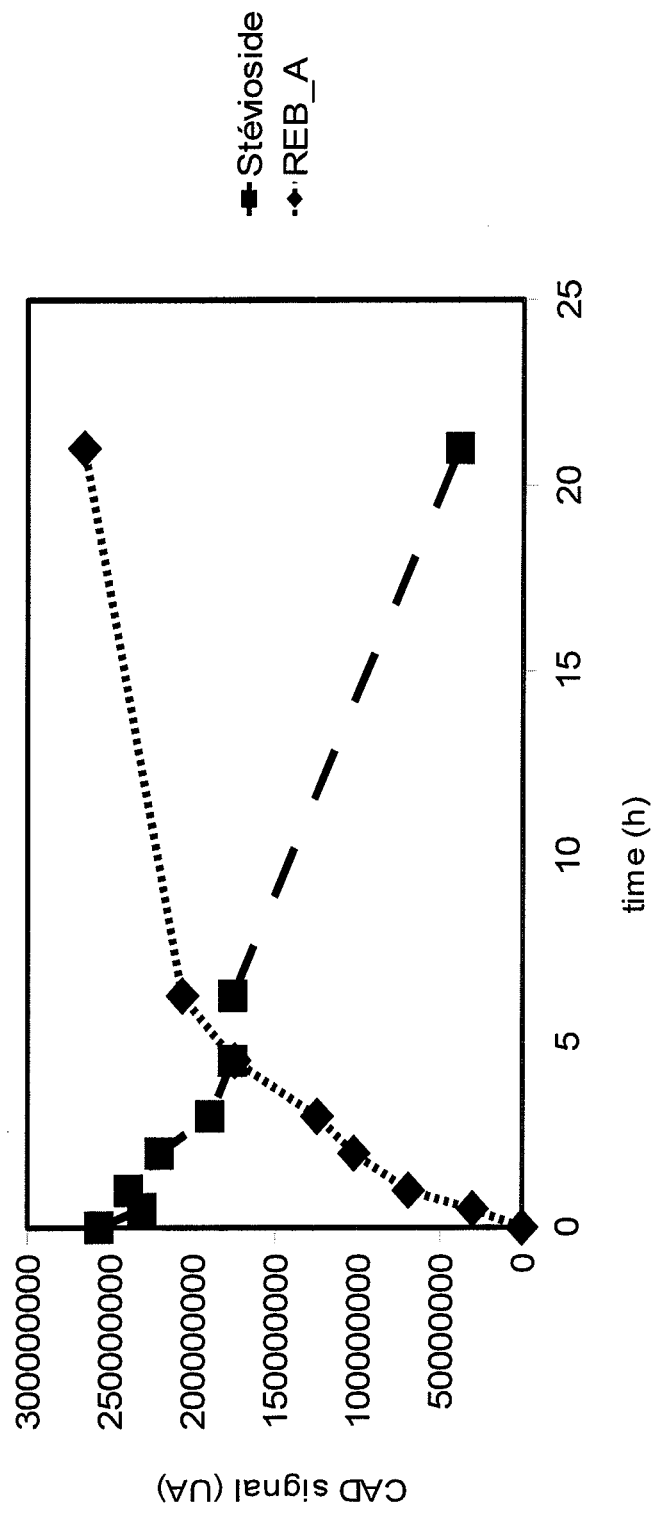
FIG. 40 shows an HPLC (CAD) analysis.

The total volume of the reaction was 5.0 mL with the following composition: 50 mM sodium phosphate buffer pH 7.2, 3 mM $MgCl_2$, 2.5 mM UDP-glucose, 0.5 mM Stevioside and 500 μL of UGT76G1 thawed lysate. The reactions were run at 30° C. on an orbitary shaker at 135 rpm. For each sample, 460 μL of the reaction mixture was quenched with 40 μL of 2N $H_2SO_4$ and 420 μL of methanol/water (6/4). The samples were immediately centrifuged and kept at 10° C. before analysis by HPLC (CAD). HPLC indicated almost complete conversion of stevioside to rebaudioside A as seen in FIG. 40.

Example 5

Catalytic Reaction with In-Vitro Produced UGT91D2

The total volume of the reaction was 0.5 mL with the following composition: 50 mM sodium phosphate buffer pH 7.2, 3 mM $MgCl_2$, 3.8 mM UDP-glucose, 0.1 mM Rebaudioside A and 180 μL of in-vitro produced UGT91D2. The reactions were run at 30° C. on an orbitary shaker at 135 rpm. For each sample, 450 μL of reaction mixture was quenched with 45 μL of 2N $H_2SO_4$ and 405 μL of 60% MeOH. After centrifugation, the supernatant was analyzed by HPLC (CAD). HPLC indicated a 4.7% conversion of rebaudioside A to rebaudioside D after 120 h.

Example 6

Catalytic Reaction with In-Vitro Produced UGT76G1

Figure 41:
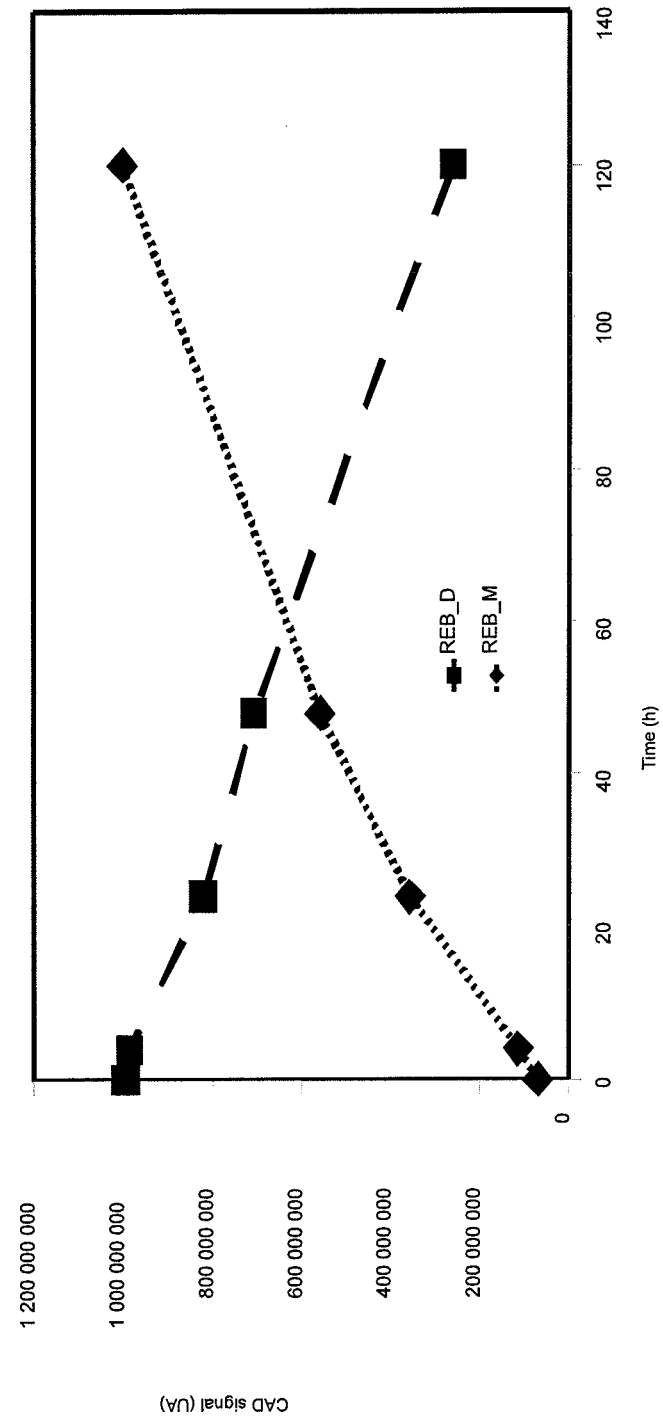
FIG. 41 shows an HPLC (CAD) analysis.

The total volume of the reaction was 2 mL with the following composition: 50 mM sodium phosphate buffer pH 7.2, 3 mM $MgCl_2$, 3.8 mM UDP-glucose, 0.5 mM Rebaudioside D and 180 μL of in-vitro produced UGT76G1. The reactions were run at 30° C. on an orbitary shaker at 135 rpm. For each sample, 400 μL of reaction mixture was quenched with 40 μL of 2N $H_2SO_4$ and 360 μL of 60% MeOH. After centrifugation, the supernatant was analyzed by HPLC (CAD). HPLC indicated 80% conversion of rebaudioside D to rebaudioside M after 120 h as seen in FIG. 41.

For examples 7 to 12, the following abbreviations were used:
LBGKP medium: 20 g/L Luria Broth Lennox; 50 mM PIPES buffer pH 7.00; 50 mM Phosphate buffer pH 7.00; 2.5 g/L glucose and 50 mg/L of Kanamycin or Ampicillin LB medium: (20 g/L Luria Broth Lennox)

Example 7

Preparation and Activity of UGT76G1 Prepared by pET30a+ Plasmid and BL21 (DE3) Expression Strain The pET30a+_UGT76G1 plasmid was transformed into BL21(DE3) expression strain (Lucigen E. Cloni® EXPRESS Electrocompetent Cells). The obtained cells were grown on LB Agar medium in petri-dishes in the presence of Kanamycin. Suitable colonies were selected and allowed to grow in liquid LBGKP medium containing Kanamycin. Glycerol was added and 400 μL aliquots were stored at −20° C. and at −80° C.

A storage aliquot was thawed and added to 30 mL of LBGKP medium. This culture was allowed to shake at 30° C. for 8 h. and subsequently used to inoculate 400 mL of production medium containing 60 g/L of "Overnight express instant TB medium" (Novagen, reference 71491-5), 10 g/L of glycerol and 50 mg/L of Kanamycin. The medium was allowed to stir at 20° C. while taking samples to measure the OD (600 nm) and pH. After 40 h, the cells were harvested by centrifugation and frozen. The obtained cell wet weight was 10.58 g.

3.24 g of obtained pellet was lysed by addition of 8.1 mL of "Bugbuster Master mix" (Novagen, reference 71456) and 3.5 mL of water. The lysate was recovered by centrifugation and kept frozen.

Example 8

Preparation and Activity of UGT76G1 Prepared by pET30a+ Plasmid and Tuner (DE3) Expression Strain The pET30a+_UGT76G1 plasmid was transformed into Tuner (DE3) expression strain (Novagen Tuner™ (DE3) Competent cells) by heat shock treatment. The obtained cells were grown on LB Agar medium in petri-dishes in the presence of Kanamycin. Suitable colonies were selected and allowed to grow in liquid LBGKP medium containing Kanamycin). Glycerol was added and 400 μL aliquots were stored at −20° C. and at −80° C.

A storage aliquot was thawed and added to 100 mL of LB medium containing 50 mg/L of Kanamycin. This culture allowed to shake at 30° C. for 15 h. 4.4 mL of this culture was used to inoculate 200 mL of production medium containing LB. This medium was allowed to stir at 37° C. until an OD (600 nm) of 0.9 was obtained, after which 400 µL of a 100 mM IPTG solution was added and the medium was allowed to stir at 30° C. for 4 h. The cells were harvested by centrifugation and frozen. The obtained cell wet weight was 1.38 g.

The obtained pellet was lysed by addition of 4.9 mL of "Bugbuster Master mix" (Novagen, reference 71456) and 2.1 mL of water. The lysate was recovered by centrifugation and kept frozen.

Example 9

Preparation and Activity of UGT76G1 Prepared by pMAL Plasmid and BL21 Expression Strain After subcloning the synthetic UGT76G1 gene into the pMAL plasmid using NdeI and SalI cloning sites, the pMAL_UGT76G1 plasmid was transformed into BL21 expression strain (New England Biolabs BL21 Competent E. coli) by heat shock treatment. The obtained cells were grown on LB Agar medium in petri-dishes in the presence of Ampicillin. Suitable colonies were selected and allowed to grow in liquid LBGKP medium containing Ampicillin). Glycerol was added and 400 µL aliquots were stored at −20° C. and at −80° C.

A storage aliquot was thawed and added to 30 mL of LBGKP medium. This culture was allowed to shake at 30° C. for 8 h. and subsequently used to inoculate 400 mL of production medium containing 60 g/L of "Overnight express instant TB medium" (Novagen, reference 71491-5), 10 g/L of glycerol and 50 mg/L of Ampicillin. The medium was allowed to stir at 20° C. while taking samples to measure the OD and pH. After 40 h, the cells were harvested by centrifugation and frozen. The obtained cell wet weight was 5.86 g.

2.74 g of obtained pellet was lysed by addition of 9.6 mL of "Bugbuster Master Mix" (Novagen, reference 71456) and 4.1 mL of water. The lysate was recovered by centrifugation and kept frozen.

Example 10

Preparation and Activity of UGT76G1 Prepared by pMAL Plasmid and ArcticExpress Expression Strain The pMAL_UGT76G1 plasmid was transformed into ArticExpress expression strain (Agilent ArcticExpress competent cells) by heat shock treatment. The obtained cells were grown on LB Agar medium in petri-dishes in the presence of Ampicillin and Geneticin. Suitable colonies were selected and allowed to grow in liquid LBGKP medium containing of Ampicillin and Geneticin. Glycerol was added and 400 µL aliquots were stored at −20° C. and at −80° C.

A storage aliquot was thawed and added to 30 mL of LBGKP medium (containing Ampicillin and Geneticin). This culture was allowed to shake at 30° C. for 8 h. and subsequently used to inoculate 400 mL of production medium containing 60 g/L of "Overnight express instant TB medium" (Novagen, reference 71491-5), 10 g/L of glycerol and 50 mg/L of Ampicillin. The medium was allowed to stir at 12° C. while taking samples to measure the OD (600 nm) and pH. After 68 h, the cells were harvested by centrifugation and frozen. The obtained cell wet weight was 8.96 g.

2.47 g of the obtained pellet was lysed by addition of 8.73 mL of "Bugbuster Master Mix" (Novagen, reference 71456) and 3.79 mL of water. The lysate was recovered by centrifugation and kept frozen.

Example 11

Preparation and Activity of UGT76G1 Prepared by pCOL-DIII Plasmid and ArcticExpress Expression Strain After subcloning the synthetic UGT76G1 gene into the pCOLDIII plasmid using Nde1 and Xho1 cloning sites, the pCOLDIII_UGT76G1 plasmid was transformed into ArcticExpress expression strain (Agilent ArcticExpress competent cells) by heat shock treatment. The obtained cells were grown on LB Agar medium in petri-dishes in the presence of Ampicillin and Geneticin. Suitable colonies were selected and allowed to grow in liquid LBGKP medium containing Ampicillin and Geneticin. Glycerol was added and 400 µL aliquots were stored at −20° C. and at −80° C.

A storage aliquot was thawed and added to 30 mL of LBGKP medium (containing Ampicillin and Geneticin). This culture was allowed to shake at 30° C. for 8 h. and subsequently used to inoculate 400 mL of production medium containing 60 g/L of "Overnight express instant TB medium" (Novagen, reference 71491-5), 10 g/L of glycerol and 50 mg/L of Kanamycin. The medium was allowed to stir at 12° C. while taking samples to measure the OD (600 nm) and pH. After 63 h, the cells were harvested by centrifugation and frozen. The obtained cell wet weight was 6.54 g.

2.81 g of the obtained pellet was lysed by addition of 9.8 mL of "Bugbuster Master Mix" (Novagen, reference 71456) and 4.2 mL of water. The lysate was recovered by centrifugation and kept frozen.

Example 12

Preparation and Activity of UGT76G1 Prepared by pCOL-DIII Plasmid and Origami2 (DE3) Expression Strain The pCOLDIII_UGT76G1 plasmid was transformed into Origami2 (DE3) expression strain (Novagen Origami™2 (DE3) Competent Cells) by heat shock treatment. The obtained cells were grown on LB Agar medium in petri-dishes in the presence of Ampicillin. Suitable colonies were selected and allowed to grow in liquid LBGKP medium containing Ampicillin. Glycerol was added and 400 µL aliquots were stored at −20° C. and at −80° C.

A storage aliquot was thawed and added to 30 mL of LBGKP medium (containing Ampicillin). This culture was allowed to shake at 30° C. for 8 h. and subsequently used to inoculate 400 mL of production medium containing 60 g/L of "Overnight express instant TB medium" (Novagen, reference 71491-5), 10 g/L of glycerol and 50 mg/L of Kanamycin. The medium was allowed to stir at 12° C. while taking samples to measure the OD (600 nm) and pH. After 68 h, the cells were harvested by centrifugation and frozen. The obtained cell wet weight was 2.53 g.

1.71 g of the obtained pellet was lysed by addition of 6.0 mL of "Bugbuster Master mix" (Novagen, reference 71456) and 1.9 mL of water. The lysate was recovered by centrifugation and kept frozen.

Example 13

Determination of Activity

Activity tests were performed on a 5 mL scale with 500 µL of thawed lysate for the transformation of Stevioside to Rebaudioside A and Rebaudioside D to Rebaudioside M using 0.5 mM of substrate, 2.5 mM of UDP-Glucose and 3 mM $MgCl_2$ in 50 mM Sodium Phosphate buffer at pH 7.2. Samples were taken and analyzed by HPLC. The results for the different preparations of UGT76G1 are summarized in the following table.

| Example | Plasmid | Expression strain | Transformation activity* | |
|---|---|---|---|---|
| | | | Stevioside to Rebaudioside A | Rebaudioside D to Rebaudioside M |
| 7 | pET30a+ | BL21 (DE3) | 29 U mL$^{-1}$ | 0.31 U mL$^{-1}$ |
| 8 | pET30a+ | Tuner (DE3) | 33 U mL$^{-1}$ | 0.40 U mL$^{-1}$ |
| 9 | pMAL | BL21 | 20 U mL$^{-1}$ | 0.15 U mL$^{-1}$ |
| 10 | pMAL | ArticExpress | 15 U mL$^{-1}$ | 0.25 U mL$^{-1}$ |
| 11 | pCOLDIII | ArticExpress | 15 U mL$^{-1}$ | 0.11 U mL$^{-1}$ |
| 12 | pCOLDIII | Origami2 (DE3) | 37 U mL$^{-1}$ | 0.20 U mL$^{-1}$ |

* Note
The activities for the transformation of Stevioside and Rebaudioside M are mentioned per mL of lysate. 1 U will transform 1 µmol of substrate in 1 hour at 30° C. and pH 7.2

Example 14

50 mL Scale Reaction for the Transformation of Rebaudioside D to Rebaudioside M 5 mL of the lysate of Example 12 was used to transform Rebaudioside D to Rebaudioside M on a 50 mL scale. The reaction medium consisted of 50 mM Sodium Phosphate buffer pH 7.2, 3 mM of MgCl$_2$, 2.5 mM of UDP-Glucose and 0.5 mM of Rebaudioside D. After allowing the reaction to be shaken at 30° C. for 90 h. 50 mL of ethanol was added and the resulting mixture was allowed to stir at −20° C. for 1 h. After centrifugation at 5000 g for 10 min. the supernatant was purified via ultrafiltration (Vivaflow MWCO 30000). 78 mL of permeate was obtained and the 9 mL of retentate was diluted with 9 mL of ethanol and resubjected to Ultrafiltration (Vivaflow MWCO 30000). Another 14 mL of filtrate was obtained, which was combined with the first permeate. The combined permeates were concentrated under reduced pressure at 30° C. until 32 mL of a clear solution was obtained.

Figure 5:
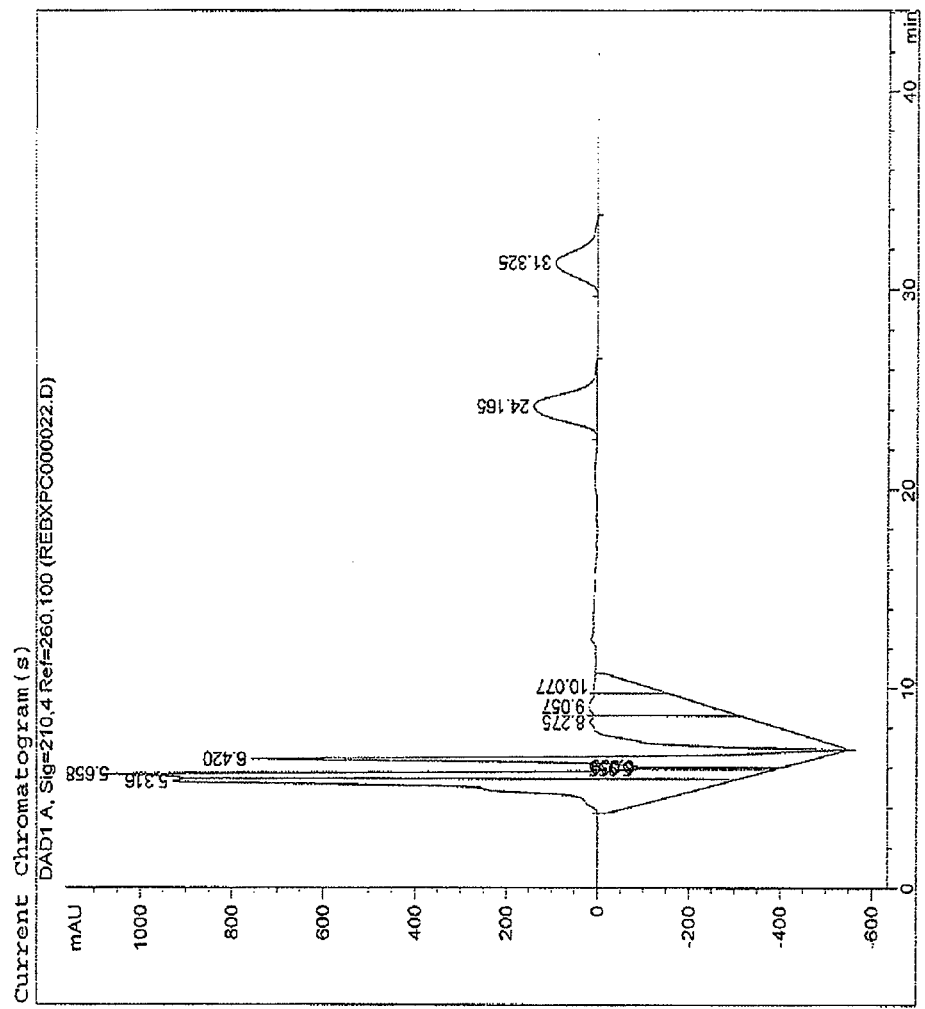
FIG. 5. shows the HPLC chromatogram of the product of the biocatalytic production of reb M from reb D, as detailed in Example 14. The peak with retention time of 24.165 minutes corresponds to unreacted reb D. The peak with retention time of 31.325 minutes corresponds to reb M.

The HPLC trace of the product mixture is shown in FIG. 5. HPLC was carried out on an Agilent 1200 series equipped with a binary pump, auto sampler, and thermostat column compartment. The method was isocratic, with a mobile phase composed of 70% water (0.1% formic acid): 30% acetonitrile. The flow rate was 0.1 µL/min. The column used was Phenomenex Prodigy 5µ ODS (3) 100 A; 250×2 mm. The column temperature was maintained at 40° C. The injection volume was 20-40 µl.

Example 15

Preparation of UGT91D2 Using pMAL Plasmid and BL21 Expression Strain

After subcloning the synthetic UGT91D2 gene into the pMAL plasmid using NdeI and SalI cloning sites, the pMAL_UGT91D2 plasmid was transformed into BL21 expression strain (New England Biolabs BL21 Competent E. coli) by heat shock treatment. The obtained cells were grown on LB Agar medium in petri-dishes in the presence of Ampicillin. Suitable colonies were selected and allowed to grow in liquid LBGKP medium containing Ampicillin). Glycerol was added and 400 µl, aliquots were stored at −20° C. and at −80° C.

A storage aliquot was thawed and added to 30 mL of LBGKP medium. This culture was allowed to shake at 30° C. for 8 h. and subsequently used to inoculate 400 mL of production medium containing 60 g/L of "Overnight express instant TB medium" (Novagen, reference 71491-5), 10 g/L of glycerol and 50 mg/L of Ampicillin. The medium was allowed to stir at 20° C. while taking samples to measure the OD and pH. After 40 h, the cells were harvested by centrifugation and frozen. The obtained cell wet weight is 12.32 g.

2.18 g of obtained pellet was lysed by addition of 7.7 mL of "Bugbuster Master Mix" (Novagen, reference 71456) and 3.2 mL of water. The lysate was recovered by centrifugation and used directly for activity testing.

Example 16

Preparation of UGT91D2 Using pMAL Plasmid and ArcticExpress Expression Strain

The pMAL_UGT91D2 plasmid was transformed into ArcticExpress expression strain (Agilent ArcticExpress competent cells) by heat shock treatment. The obtained cells were grown on LB Agar medium in petri-dishes in the presence of Ampicillin and Geneticin. Suitable colonies were selected and allowed to grow in liquid LBGKP medium containing Ampicillin and Geneticin. Glycerol was added and 400 µL aliquots were stored at −20° C. and at −80° C.

A storage aliquot was thawed and added to 30 mL of LBGKP medium (containing Ampicillin and Geneticin). This culture was allowed to shake at 30° C. for 8 h. and subsequently used to inoculate 400 mL of production medium containing 60 g/L of "Overnight express instant TB medium" (Novagen, reference 71491-5), 10 g/L of glycerol and 50 mg/L of Ampicillin. The medium was allowed to stir at 20° C. for 16 h. followed by another 50 h. at 12° C. while taking samples to measure the OD (600 nm) and pH. The cells were harvested by centrifugation and frozen. The obtained cell wet weight is 15.77 g.

2.57 g of the obtained pellet was lysed by addition of 9.0 mL of "Bugbuster Master Mix" (Novagen, reference 71456) and 3.8 mL of water. The lysate was recovered by centrifugation and used directly for activity testing.

Example 17

Preparation of UGT91D2 Using pET30a+ Plasmid and Tuner (DE3) Expression Strain

The pET30a+_UGT91D2 plasmid was transformed into Tuner (DE3) expression strain (Novagen Tuner™ (DE3) Competent cells) by heat shock treatment. The obtained cells were grown on LB Agar medium in petri-dishes in the presence of Kanamycin. Suitable colonies were selected and allowed to grow in liquid LBGKP medium (containing Kanamycin). Glycerol was added and 400 µL aliquots were stored at −20° C. and at −80° C.

A storage aliquot was thawed and added to 100 mL of LB medium containing 50 mg/L of Kanamycin. This culture allowed to shake at 30° C. for 15 h. 6.2 mL of this culture was used to inoculate 500 mL of production medium containing LB. This medium was allowed to stir at 37° C. until an OD (600 nm) of 0.9 was obtained after which 500 µL of a 100 mM IPTG solution was added (IPTG concentration in medium is 100 µM) and the medium was allowed to stir at 30° C. for 4 h, the cells were harvested by centrifugation and frozen. The obtained cell wet weight is 4.02 g.

1.92 g of the obtained pellet was lysed by addition of 6.8 mL of "Bugbuster Master mix" (Novagen, reference 71456) and 2.8 mL of water. The lysate was recovered by centrifugation and tested directly for activity.

Example 18

Preparation of UGT91D2 Using pET30a+ Plasmid and ArcticExpress Expression Strain The pET30a+_UGT91D2 plasmid was transformed into ArcticExpress (DE3) expression strain (Agilent ArcticExpress competent cells) by heat shock treatment. The obtained cells were grown on LB Agar medium in petri-dishes in the presence of Kanamycin and Geneticin. Suitable colonies were selected and allowed to grow in liquid LBGKP medium containing of Kanamycin and Geneticin. Glycerol was added and 400 μL aliquots were stored at −20° C. and at −80° C.

A storage aliquot was thawed and added to 30 mL of LBGKP medium (containing Kanamycin and Geneticin). This culture was allowed to shake at 30° C. for 8 h. and subsequently used to inoculate 400 mL of production medium containing 60 g/L of "Overnight express instant TB medium" (Novagen, reference 71491-5), 10 g/L of glycerol and 50 mg/L of Ampicillin. The medium was allowed to stir at 20° C. for 16 h. followed by another 50 h. at 12° C. while taking samples to measure the OD (600 nm) and pH. After 60 h, the cells were harvested by centrifugation and frozen. The obtained cell wet weight is 16.07 g.

3.24 g of the obtained pellet was lysed by addition of 11.4 mL of "Bugbuster Master Mix" (Novagen, reference 71456) and 4.8 mL of water. The lysate was recovered by centrifugation and used directly for activity testing.

Example 19

Determination of Activity of In-Vivo Preparations of UGT91D2

Activity tests were performed at 5 mL scale with 1000 μL of lysate for the transformation of Rubusoside to Stevioside using 0.5 mM of substrate, 2.5 mM of UDP-Glucose and 3 mM $MgCl_2$ in 50 mM Sodium Phosphate buffer at pH 7.2. Samples were taken and analyzed by HPLC. The results for the different preparations of UGT91D2 are summarized in the following table.

| Example | Plasmid | Expression strain | Transformation activity* Rubusoside to Stevioside |
|---|---|---|---|
| 15 | pMAL | BL21 | 9 mU mL$^{-1}$ |
| 16 | pMAL | ArcticExpress | 60 mU mL$^{-1}$ |
| 17 | pET30a+ | Tuner (DE3) | 28 mU mL$^{-1}$ |
| 18 | pET30a+ | ArcticExpress (DE3) | 21 mU mL$^{-1}$ |

*Note:
The activities are mentioned per mL of lysate. 1 U will transform 1 μmol of substrate in 1 hour at 30° C. and pH 7.2

Example 20

Other Enzymes for Rebaudioside A to Rebaudioside D Conversion

The following genes of UDP-glucosyltransferases were identified from public databases, synthesized by DNA2.0 and subsequently subcloned in pET30a+ vector.

| Microplate | Position | Gene Name | Internal reference | Conversion RebA to RebD |
|---|---|---|---|---|
| C908201 | A1 | gi115454819_NP_001051010.1 | S115N01 A1 | Active |
| C908201 | G2 | gi187373030_ACD03249.1 | S115N01 G2 | Active |
| C908201 | A7 | gi460409128_XP_004249992.1 | S115N05 A7 | Active |
| C912666 | E1 | gi222619587_EEE55719.1 | S115N06 E1 | Active |
| C912666 | C2 | gi297795735_XP_002865752.1 | S115N06 C2 | Active |

The aminoacid sequences are as follows:

SEQ ID 3
>gi|115454819|ref|NP_001051010.1|Os03g0702500
[Oryza sativa Japonica Group]
MDDAHSSQSPLHVVIFPWLAFGHLLPCLDLAERLAARGHRVSFVSTPRNL

ARLPPVRPELAELVDLVALPLPRVDGLPDGAEATSDVPFDKFELHRKAFD

GLAAPFSAFLDTACAGGKRPDWVLADLMHHWVALASQERGVPCAMILPCS

AAVVASSAPPTESSADQREAIVRSMGTAAPSFEAKRATEEFATEGASGVS

IMTRYSLTLQRSKLVAMRSCPELEPGAFTILTRFYGKPVVPFGLLPPRPD

GARGVSKNGKHDAIMQWLDAQPAKSVVYVALGSEAPMSADLLRELAHGLD

LAGTRFLWAMRKPAGVDADSVLPAGFLGRTGERGLVTTRWAPQVSILAHA

AVCAFLTHCGWGSVVEGLQFGHPLIMLPILGDQGPNARILEGRKLGVAVP

RNDEDGSFDRGGVAGAVRAVVVEEEGKTFFANARKLQEIVADREREERCI

DEFVQHLTSWNELKNNSDGQYP

SEQ ID 4
>gi|187373030|gb|ACD03249.1|UDP-glycosyltransferase [Avena strigosa]
MAVKDEQQSPLHILLFPFLAPGHLIPIADMAALFASRGVRCTILTTPVNA

AIIRSAVDRANDAFRGSDCPAIDISVVPFPDVGLPPGVENGNALTSPADR

LKFFQAVAELREPFDRFLADNHPDAVVSDSFFHWSTDAAAEHGVPRLGFL

GSSMFAGSCNESTLHNNPLETAADDPDALVSLPGLPHRVELRRSQMMDPK

KRPDHWALLESVNAADQKSFGEVFNSFHELEPDYVEHYQTTLGRRTWLVG

PVALASKDMAGRGSTSARSPDADSCLRWLDTKQPGSVVYVSFGTLIRFSP

AELHELARGLDLSGKNFVWVLGRAGPDSSEWMPQGFADLITPRGDRGFII

RGWAPQMLILNHRALGGFVTHCGWNSTLESVSAGVPMVTWPRFADQFQNE

KLIVEVLKVGVSIGAKDYGSGIENHDVIRGEVIAESIGKLMGSSEESDAI

QRKAKDLGAEARSAVENGGSSYNDVGRLMDELMARRSSVKVGEDIIPTND

GL

SEQ ID 5
>gi|460409128|ref|XP_004249992.1| PREDICTED: cyanidin-3-O-glucoside 2-O-glucuronosyltransferase-like [Solanum lycopersicum]
MSPKLHKELFFHSLYKKTRSNHTMATLKVLMFPFLAYGHISPYLNVAKKL

ADRGFLIYFCSTPINLKSTIEKIPEKYADSIHLIELHLPELPQLPPHYHT

TNGLPPNLNQVLQKALKMSKPNFSKILQNLKPDLVIYDILQRWAKHVANE

QNIPAVKLLTSGAAVFSYFFNVLKKPGVEFPFPGIYLRKIEQVRLSEMMS

KSDKEKELEDDDDDDDLLVDGNMQIMLMSTSRTIEAKYIDFCTALTNWKV

VPVGPPVQDLITNDVDDMELIDWLGTKDENSTVFVSFGSEYFLSKEDMEE

VAFALELSNVNFIWVARFPKGEERNLEDALPKGFLERIGERGRVLDKFAP

-continued

QPRILNHPSTGGFISHCGWNSAMESIDFGVPIIAMPMHLDQPMNARLIVE

LGVAVEIVRDDDGKIHRGEIAETLKGVITGKTGEKLRAKVRDISKNLKTI

RDEEMDAAAEELIQLCRNGN

SEQ ID 6
>gi|222619587|gb|EEE55719.1| hypothetical protein
OsJ_04191 [Oryza sativa Japonica Group]
MHVVMLPWLAFGHILPFAEFAKRVARQGHRVTLFSTPRNTRRLIDVPPSL

AGRIRVVDIPLPRVEHLPEHAEATIDLPSNDLRPYLRRAYDEAFSRELSR

LLQETGPSRPDWVLADYAAYWAPAAASRHGVPCAFLSLFGAAALCFFGPA

ETLQGRGPYAKTEPAHLTAVPEYVPFPTTVAFRGNEARELFKPSLIPDES

GVSESYRFSQSIEGCQLVAVRSNQEFEPEWLELLGELYQKPVIPIGMFPP

PPPQDVAGHEETLRWLDRQEPNSVVYAAFGSEVKLTAEQLQRIALGLEAS

ELPFIWAFRAPPDAGDGDGLPGGFKERVNGRGVVCRGWVPQVKFLAHASV

GGFLTHAGWNSIAEGLANGVRLVLLPLMFEQGLNARQLAEKKVAVEVARD

EDDGSFAANDIVDALRRVMVGEEGDEFGVKVKELAKVFGDDEVNDRYVRD

FLKCLSEYKMQRQG

SEQ ID 7
>gi|297795735|ref|XP_002865752.1| UDP-gluco-
ronosyl/UDP-glucosyl transferase family protein
[Arabidopsis lyrata subsp. lyrata]
MDDKKEEVMHIAMFPWLAMGHLLPFLRLSKLLAQKGHKISFISTPRNILR

LPKLPSNLSSSITFVSFPLPSISGLPPSSESSMDVPYNKQQSLKAAFDLL

QPPLTEFLRLSSPDWIIYDYASHWLPSIAKELGISKAFFSLFNAATLCFM

GPSSSLIEESRSTPEDFTVVPPWVPFKSTIVFRYHEVSRYVEKTDEDVTG

VSDSVRFGYTIDGSDAVFVRSCPEFEPEWFSLLQDLYRKPVFPIGFLPPV

IEDDDDDTTWVRIKEWLDKQRVNSVVYVSLGTEASLRREELTELALGLEK

SETPFFWVLRNEPQIPDGFEERVKGRGMVHVGWVPQVKILSHESVGGFLT

HCGWNSVVEGIGFGKVPIFLPVLNEQGLNTRLLQGKGLGVEVLRDERDGS

FGSDSVADSVRLVMIDDAGEEIREKVKLMKGLFGNMDENIRYVDELVGFM

RNDESSQLKEEEEEDDCSDDQSSEVSSETDEKELNLDLKEEKRRISVYKS

LSSEFDDYVANEKMG

The tested plasmids were received in a microtiterplate containing a plasmid as freeze-dried solid in each separate well.

Suspension of Plasmids.

To each well was added 24 µL of ultra-pure sterile water and the microtiter plate was shaken for 30 minutes at Room Temperature. Subsequently, the plate was incubated at 4° C. for 1 hour. The content of each well were further mixed by pipetting up and down. The plasmid quantification was performed by Qubit2.0 analysis using 1 µL of suspension. Determined quantities of plasmids were:

| Microtiter plate | Position | Internal reference | [Plasmid] ng/µL |
|---|---|---|---|
| C908201 | A1 | S115N01 A1 | 32.8 |
| C908201 | G2 | S115N01 G2 | 41.0 |
| C908201 | A7 | S115N05 A7 | 56.6 |
| C912666 | E1 | S115N06 E1 | 64.0 |
| C912666 | C2 | S115N06 C2 | 31.4 |

Transformation of Competent Cells with Plasmids.

Aliquots of chemically competent EC100 cells were taken from freezer at −80° C. and stored on ice. The cells were allowed to thaw on ice for 10 minutes. 10 µL of a dilution of above described plasmid solution was added to a sterile microtube of 1.5 mL (in order to transform each cell with 50 pg of DNA) and stored on ice. 100 µL of chemically competent cells was added to each microtube. After incubation of the chemically competent cells plasmid mixtures on ice for 20 min a thermal shock of 30 seconds at 42° C. was performed.

Further incubation was performed on ice for 2 minutes. To each microtube 300 µL of SOC medium was added and the resulting mixture was transferred to a sterile 15 mL tube. After incubate for 1 hour at 37° C. while shaking at 135 rpm, the mixture is spread on solid Luria Broth medium containing Kanamycin 50 µg/mL. The petri-dishes are allowed to incubate for 16 hours at 37° C.

Preparation of Stock Solutions in Glycerol and Purification of Plasmids.

To a 50 mL sterile Falcon Tube 10 mL of Luria Broth medium containing 50 µg/mL of Kanamycin was added. The medium was seeded with an isolated colony from the above described Petri dish and the cultures were allowed to incubate for 16 hours at 37° C. while shaking at 135 rpm.

To sterile microtube of 1.5 mL containing 300 µL of a 60% sterile glycerol solution, 600 µL of the culture was added. The stock solution was stored at −80° C.

The remainder of the culture was centrifuged at 5,525 g for 10 minutes at 10° C. and after removal of the supernatant, the pellet was stored on ice. The produced plasmids were purified according to the Qiagen Qiaprep Spin Miniprep kit (ref: 27106) and the plasmid yield was measured at 260 nm. The plasmid solution was stored at 4° C. Plasmid quantities were determined as follows:

| Microtiter plate | Position | Internal reference of test | [Plasmid] ng/µL |
|---|---|---|---|
| C908201 | A1 | S115N01 A1 | 115.7 |
| C908201 | G2 | S115N01 G2 | 120.4 |
| C908201 | A7 | S115N05 A7 | 293.8 |
| C912666 | E1 | S115N06 E1 | 126.1 |
| C912666 | C2 | S115N06 C2 | 98.8 |

In-Vitro Expression of Enzymes.

18 µL of plasmid solution (containing approximately 1.5 µg of plasmid) was used for in-vitro expression according to the Promega S30 T7 High-Yield Protein Expression System (ref: L1110) kit. The expression medium was produced as follows:

|  | S30 Premix Plus | T7 S30 Extract | Total |
|---|---|---|---|
| Trials | 30 µL | 27 µL | 57 µL |
| reference | 20 µL | 18 µL | 38 µL |

The prepared expression medium mix was added to the plasmid solution and the solution was allowed to incubate at 30° C. for 3 hours while mixing the mixture every 45 minutes. 5 µL of the mixture was frozen whereas the remainder was used for the catalytic test for the conversion of Rebaudioside A to Rebaudioside D.

Catalytic Test for Transformation of Rebaudioside A to Rebaudioside D.

430 µL of a reaction mixture containing 0.5 mM Rebaudioside A, 3 mM $MgCl_2$, 50 mM phosphate buffer (pH7.2) and 2.5 mM UDP-glucose was added to a 1.5 mL sterile microtube. 52 µL of the enzyme expression medium was added and the resulting mixture was allowed to react at 30° C. for 24 hours. 125 µL samples were taken after 2 hours, 16 hours and 24 hours and added to a 115 µL of 60% methanol and 10 µL of 2 N $H_2SO_4$. The quenched sample was centrifuged at 18,000 g for 2 minutes at RT. 200 µL was transferred to an HPLC vial and analyzed.

HPLC Analysis

The HPLC assay was performed as follows:

Apparatus

| Equipment | Supplier | Reference | Lot# |
| --- | --- | --- | --- |
| Elite | Hitachi | L-2130 | NA |
| Photodiode Array | Hitachi | L-2455 | NA |
| Corona CAD detector | ESA | 70-6186A | CO-2044 |
| Injector 100 µL | Hitachi | | NA |
| Column Synergy 4u Hydro-RP 80A (250 × 4.60 mm) | Phenomenex | 00G-4375-E0 | 588582-12 |

Instrument Conditions

| Column Temperature | 55° C. |
| --- | --- |
| Detection | UV 205 nm; bw 400 nm CAD detection |
| Analysis duration | 15 min |
| Injected volume | 10 µL |
| Flow rate | 1 mL/min |

Mobile Phase Gradient Program

| Time (min) | % Water containing 0.04% acetic acid | % methanol |
| --- | --- | --- |
| 0 | 40 | 60 |
| 8 | 25 | 75 |
| 10 | 25 | 75 |
| 11 | 40 | 60 |
| 15 | 40 | 60 |

The HPLC assay results are provided below:

| Internal reference | Steviol glycoside conversion in reaction mixture (% area) | | |
| --- | --- | --- | --- |
| | Reb D | Reb UNK | Reb A |
| S115N01 A1 | 2.1 | ND | 96.7 |
| S115N01 G2 | 0.6 | ND | 99.4 |
| S115N05 A7 | 22.4 | 23.3 | 46.7 |
| S115N06 E1 | 0.14 | 7.0 | 92.8 |
| S115N06 C2 | 0.28 | 3.9 | 95.8 |

The enzyme S115N05 A7 had the highest activity for Reb A to Reb D conversion (ca. 22.4%)

At least three enzymes produced a significant amount of an unknown glycoside (marked as Reb UNK; later identified as reb D2) along with reb D, as seen in FIGS. 42-46.

Figure 42:
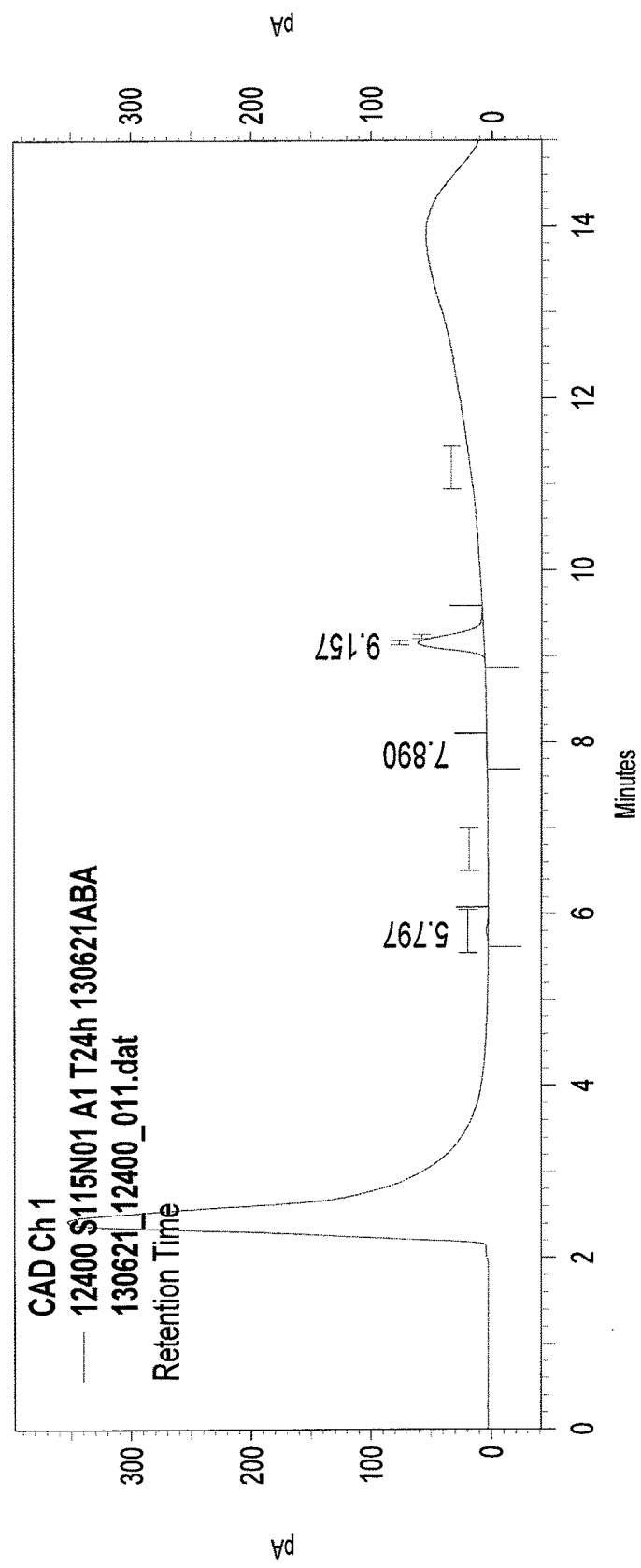
FIG. 42 shows an HPLC (CAD) analysis.

The below table accompanies FIG. 42.

Sample: 12400 S115N01A1 T24h 13062 lABA
gi|115454819|ref|NP_001051010.1| Os03g0702500 [*Oryza saliva* Japonica Group]
Filename: 130621_12400_011.dat

| CAD Ch 1 Results | | |
| --- | --- | --- |
| Compound | Retention time | Integration (area) |
| Rebaudioside D | 5.797 | 13,532,277 |
| Unknown@RT7.890 | 7.890 | 7,094,778 |
| Rebaudioside A | 9.157 | 613,483,011 |
| Total | | 634,110,066 |

Figure 43:
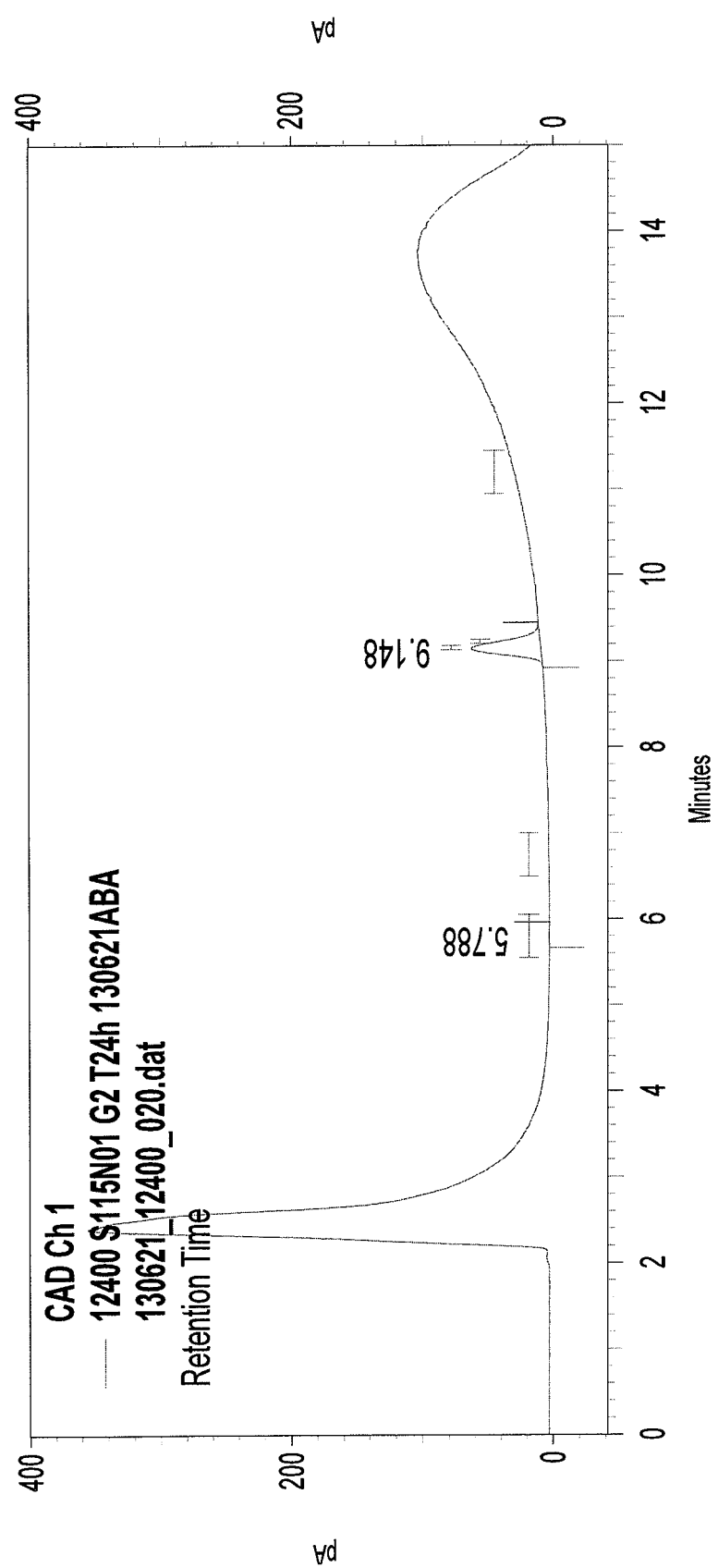
FIG. 43 shows an HPLC (CAD) analysis.

The below table accompanies FIG. 43.

Sample: 12400 S115NOIG2 T24h 130621ABA
>gi|187373030|gb|ACD03249.1| UDP-glycosyltransferase [*Avena strigosa*]
Filename: 130621_12400_020.dat

| CAD Ch 1 Results | | |
| --- | --- | --- |
| Compound | Retention time | Integration (area) |
| Rebaudioside D | 5.788 | 3,547,834 |
| Rebaudioside A | 9.148 | 585,285,463 |
| Total | | 588,833,297 |

Figure 44:
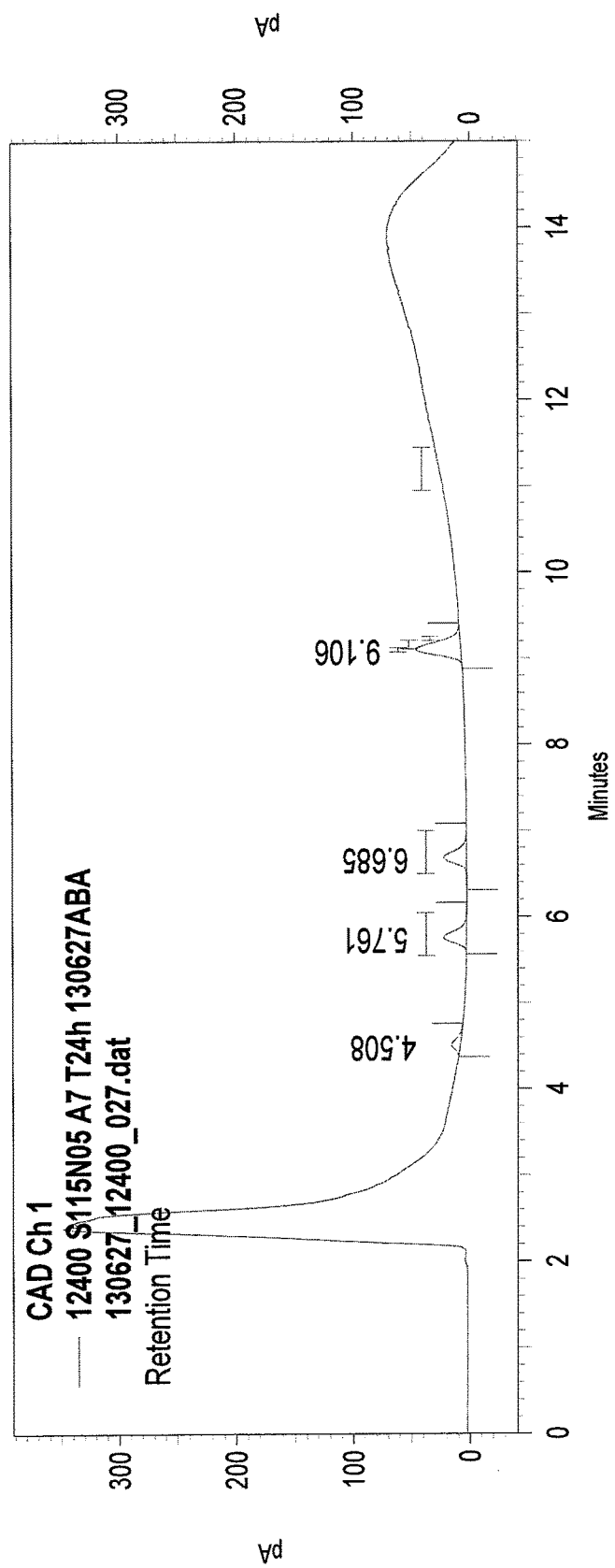
FIG. 44 shows an HPLC (CAD) analysis.

The below table accompanies FIG. 44.

Sample: 12400 S115N05A7 T24h 130627ABA
>gi|460409128|ref|XP_004249992.1| PREDICTED: cyanidin-3-O-glucoside 2-O-glucuronosyltransferase-like [*Solanum lycopersicum*]
Filename: 130627_12400_027.dat

| CAD Ch 1 Results | | |
| --- | --- | --- |
| Compound | Retention time | Integration (area) |
| Unknown@RT4.508 | 4.508 | 64,361,822 |
| Rebaudioside D | 5.761 | 191,273,935 |
| Rebaudioside UNK | 6.685 | 198,934,644 |
| Rebausioside A | 9.106 | 398,115,681 |
| Total | | 852,686,082 |

Figure 45:
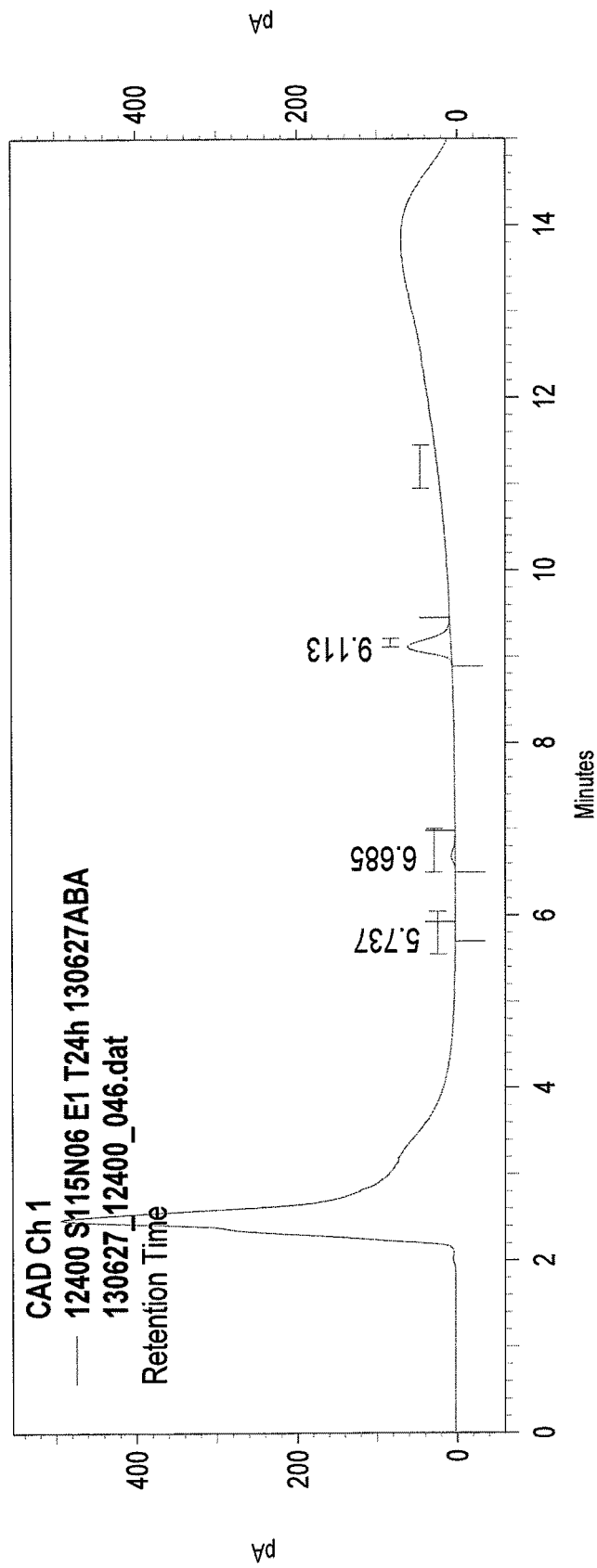
FIG. 45 shows an HPLC (CAD) analysis.

The below table accompanies FIG. 45.

Sample: 12400 S115N06E1 T24h 130627ABA
>gi|222619587|gb|EEE55719.1| hypothetical protein OsJ_04191 (*Oryza saliva* Japonica Group]
Filename: 130627_12400_046.dat

| CAD Ch 1 Results | | |
| --- | --- | --- |
| Compound | Retention time | Integration (area) |
| Rebaudioside D | 5.737 | 964,715 |
| Rebaudioside UNK | 6.685 | 46,027,361 |
| Rebausioside A | 9.113 | 606,312,523 |
| Total | | 653,304,599 |

Figure 46:
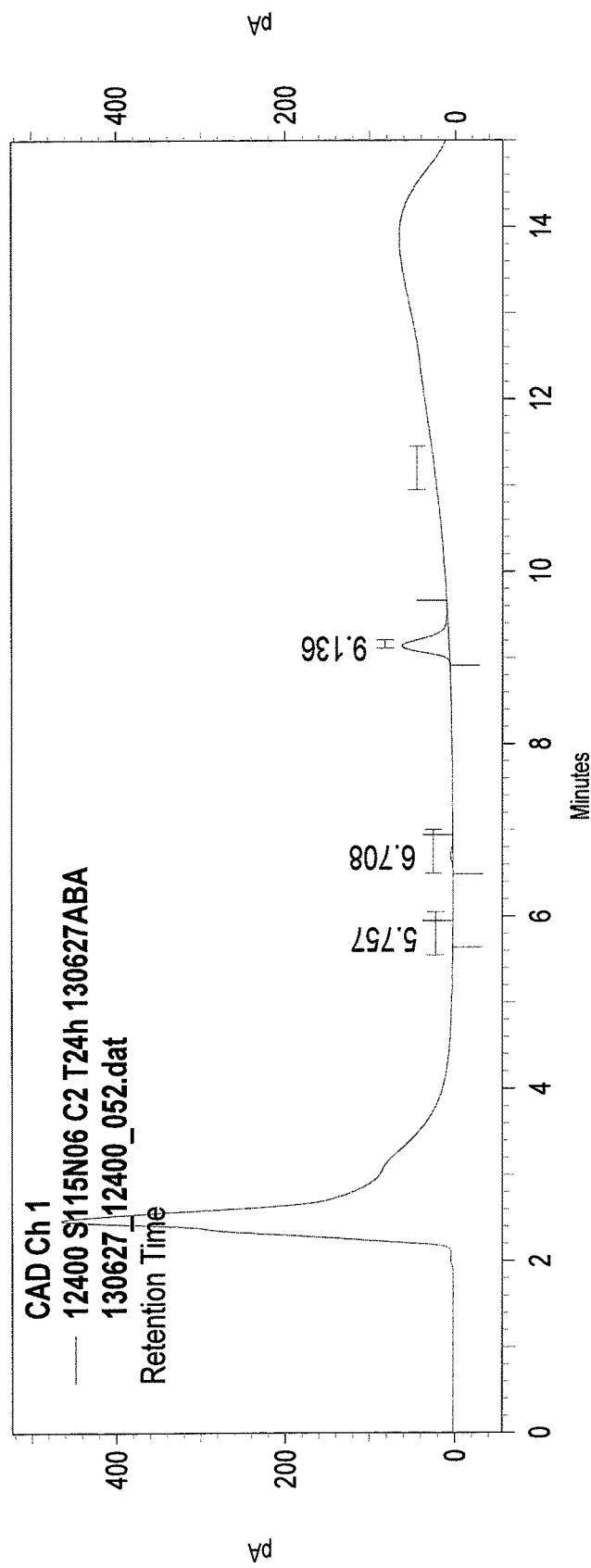
FIG. 46 shows an HPLC (CAD) analysis.

The below table accompanies FIG. 46.

Sample: 12400 S115N06C2 T24h 130627ABA
>gi|297795735|ref|XP_002865752.1| UDP-glucoronosyl/
UDP-glucosyl transferase family protein
[*Arabidopsis lyrata* subsp. lyrata]
Filename: 130627_12400_052.dat

| CAD Ch 1 Results | | |
|---|---|---|
| Compound | Retention time | Integration (area) |
| Rebaudioside D | 5.757 | 1,852,407 |
| Rebaudioside UNK | 6.708 | 26,033,636 |
| Rebausioside A | 9.136 | 633,014,654 |
| Total | | 660,900,697 |

Example 21

Activity of In-Vitro Produced EUGT11

EUGT11 gene as was described in the Patent application WO/2013/022989A2 was synthesized by DNA2.0 and subsequently subcloned in pET30a+ vector.

| Microplate | Position | GI number | Version | Internal reference | Conversion RebA to RebD |
|---|---|---|---|---|---|
| C912666 | G4 | 41469452 | AAS07253.1 | S115N08 G4 | Active |

The amino-acid sequence is as follows:

```
                                              SEQ ID 8
>gi|41469452|gb|AAS07253.1| putative UDP-gluco-
ronosyl and UDP-glucosyl transferase [Oryza sativa
Japonica Group] EUGT11 enzyme from patent
application WO/2013/022989A2
MHVVICPLLAFGHLLPCLDLAQRLACGHRVSFVSTPRNISRLPPVRPSLA

PLVSFVALPLPRVEGLPNGAESTHNVPHDRPDMVELHLRAFDGLAAPFSE

FLGTACADWVMPTSSAPRQTLSSNIHRNSSRPGTPAPSGRLLCPITPHSN

TLERAAEKLVRSSRQNARARSLLAFTSPPLPYRDVFRSLLGLQMGRKQLN

IAHETNGRRTGTLPLNLCRWMWKQRRCGKLRPSDVEFNTSRSNEAISPIG

ASLVNLQSIQSPNPRAVLPIASSGVRAVFIGRARTSTPTPPHAKPARSAA

PRAHRPPSSVMDSGYSSSYAAAAGMHVVICPWLAFGHLLPCLDLAQRLAS

RGHRVSFVSTPRNISRLPPVRPALAPLVAFVALPLPRVEGLPDGAESTND

VPHDRPDMVELHRRAFDGLAAPFSEFLGTACADWVIVDVFHHWAAAAALE

HKVPCAMMLLGSAHMIASIADRRLERAETESPAAAGQGRPAAAPTFEVAR

MKLIRTKGSSGMSLAERFSLTLSRSSLVVGRSCVEFEPETVPLLSTLRGK

PITFLGLMPPLHEGRREDGEDATVRWLDAQPAKSVVYVALGSEVPLGVEK

VHELALGLELAGTRFLWALRKPTGVSDADLLPAGFEERTRGRGVVATRWV

PQMSILAHAAVGAFLTHCGWNSTIEGLMFGHPLIMLPIFGDQGPNARLIE

AKNAGLQVARNDGDGSFDREGVAAAIRAVAVEEESSKVFQAKAKKLQEIV

ADMACHERYIDGFIQQLRSYKD
```

The tested plasmid was received in a microtiterplate containing a plasmid as freeze-dried solid in a separate well.

Suspension of Plasmid

To the well was added 24 μL of ultra-pure sterile water and the microtiter plate was shaken for 30 minutes at Room Temperature. Subsequently, the plate was incubated at 4° C. for 1 hour. The content of the well was further mixed by pipetting up and down. The plasmid quantification was performed by Qubit2.0 analysis using 1 μL of suspension. Plasmid quantity was determined as follows:

| Microtiter plate | Position | Internal reference of test | [Plasmid] ng/μL |
|---|---|---|---|
| C912666 | G4 | S115N08 G4 | 19.2 |

Transformation of Competent Cells with Plasmid.

An aliquot of chemically competent EC100 cells was taken from freezer at −80° C. and stored on ice. The cells were allowed to thaw on ice for 10 minutes. 10 μL of a dilution of above described plasmid solution was added to a sterile microtube of 1.5 mL (in order to transform each cell with 50 pg of DNA) and stored on ice. 100 μL of chemically competent cells was added to the microtube. After incubation of the chemically competent cells/plasmid mixture on ice for 20 min a thermal shock of 30 seconds at 42° C. was performed.

Further incubation was performed on ice for 2 minutes. To the microtube 300 of SOC medium was added and the resulting mixture was transferred to a sterile 15 mL tube. After incubate for 1 hour at 37° C. while shaking at 135 rpm, the mixture is spread on solid Luria Broth medium containing Kanamycin 50 μg/mL. The Petri dish is allowed to incubate for 16 hours at 37° C.

Preparation of Stock Solutions in Glycerol and Purification of Plasmid.

To a 50 mL sterile Falcon Tube 10 mL of Luria Broth medium containing 50 μg/mL of Kanamycin was added. The medium was seeded with an isolated colony from the above described Petri dish and the cultures were allowed to incubate for 16 hours at 37° C. while shaking at 135 rpm.

To sterile microtube of 1.5 mL containing 300 μL of a 60% sterile glycerol solution, 600 μL of the culture was added. The stock solution was stored at −80° C.

The remainder of the culture was centrifuged at 5,525 g for 10 minutes at 10° C. and after removal of the supernatant, the pellet was stored on ice. The produced plasmids were purified according to the Qiagen Qiaprep Spin Miniprep kit (ref: 27106) and the plasmid yield was measured at 260 nm. The plasmid solution was stored at 4° C. Plasmid quantity was determined as follows:

| Microtiter plate | Position | Internal reference of test | [Plasmid] ng/μL |
|---|---|---|---|
| C912666 | G4 | S115N08 G4 | 38.4 |

In-Vitro Expression of EUGT11.

18 μL of a diluted plasmid solution (containing approximately 1.5 μg of plasmid) was used for in-vitro expression according to the Promega S30 T7 High-Yield Protein Expression System (ref: L1110) kit. The expression medium was produced as follows:

| | S30 Premix Plus | T7 S30 Extract | DNA template | Total |
|---|---|---|---|---|
| Trials | 30 μL | 27 μL | 18 μL (~1.8 μg) | 75 μL |
| reference | 20 μL | 18 μL | 12 μL (~1.0 μg) | 50 μL |

The prepared expression medium mix was added to the plasmid solution and the solution was allowed to incubate at 30° C. for 3 hours while mixing the mixture every 45 minutes. 5 µL of the mixture was frozen whereas the remainder was used for the catalytic test for the conversion of Rebaudioside A to Rebaudioside D.

Catalytic Test for Transformation of Rebaudioside A to Rebaudioside D.

Figure 47:
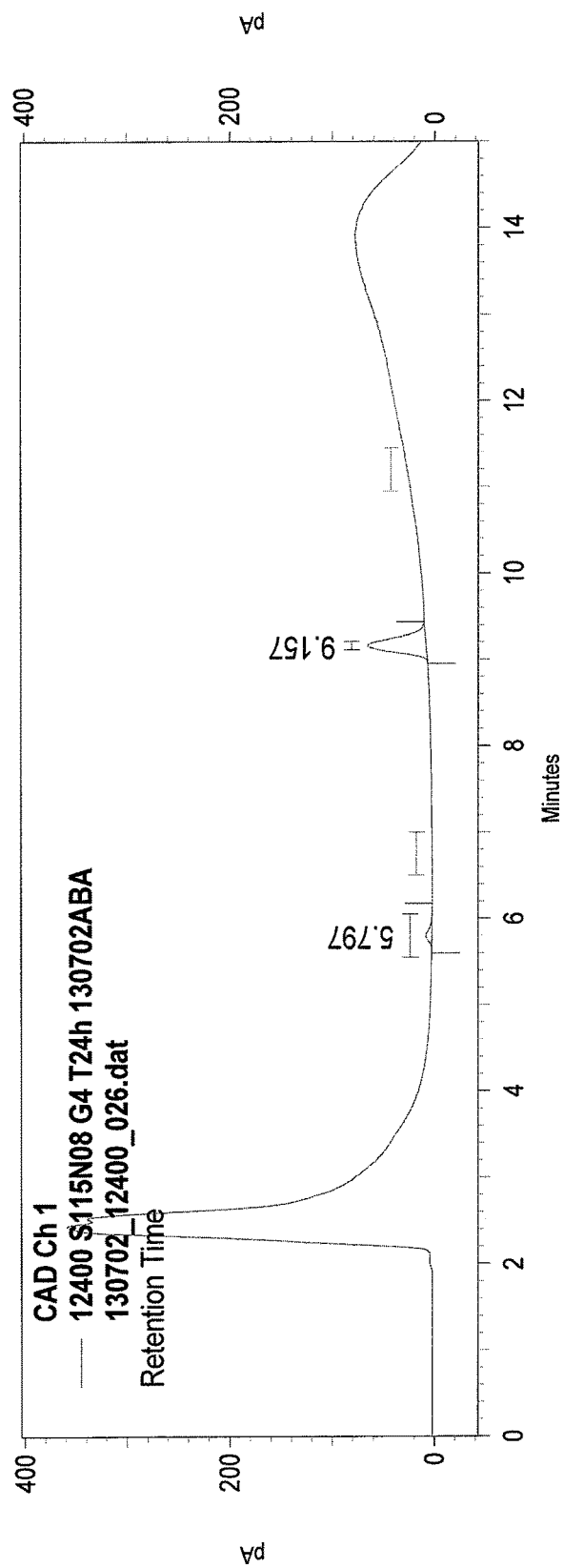
FIG. 47 shows an HPLC (CAD) analysis.

430 µL of a reaction mixture containing 0.5 mM Rebaudioside A, 3 mM MgCl$_2$, 50 mM phosphate buffer (pH7.2) and 2.5 mM UDP-glucose was added to a 1.5 mL sterile microtube. 52 µL of the enzyme expression medium was added and the resulting mixture was allowed to react at 30° C. for 24 hours. 125 µL samples were taken after 2 hours, 16 hours and 24 hours and added to a 115 µL of 60% methanol and 10 µL of 2 N H$_2$SO$_4$. The quenched sample was centrifuged at 18,000 g for 2 minutes at RT. 200 µL was transferred to HPLC vial and analyzed as seen in FIG. 47.

HPLC Analysis.

The HPLC assay was performed as described in EXAMPLE 20.

The HPLC assay results are provided below:

Sample: 12400 S115N08G4 T24h 130702CJA
>gi|41469452|gb|AAS07253.1| putative UDP-glucoronosyl a and UDP-glucosyl transferase [*Oryza sativ* Japonica Group] (EUGT11 enzyme from patent application WO/2013/022989A2)
Filename: 130702_12400_026.dat

| CAD Ch 1 Results | | |
|---|---|---|
| Compound | Retention time | Integration (area) |
| Rebaudioside D | 5.797 | 54,654,810 |
| Rebaudioside A | 9.157 | 633,926,835 |
| Total | | 688,581,645 |

Example 22

In-Vivo Production of Enzymes

The enzymes described in EXAMPLE 20 were produced in vivo.

The pET30A+ vector containing the gene corresponding to the enzyme was introduced in *E. coli* BL21(DE3) by heat shock. The obtained cells were grown in Petri dishes in the presence of Kanamycin and suitable colonies were selected and allowed to grow in liquid LB medium (Erlenmeyer flasks). Glycerol was added to the suspension as cryoprotector and 400 µL aliquots were stored at −20° C. and at −80° C.

The storage aliquots of *E. coli* BL21(DE3) containing the pET30A+_UGT plasmids were thawed and added to 30 mL of LBGKP medium (20 g/L Luria Broth Lennox; 50 mM PIPES buffer pH 7.00; 50 mM Phosphate buffer pH 7.00; 2.5 g/L glucose and 50 mg/L of Kanamycine). This culture was allowed to shake at 135 rpm at 30° C. for 8 hrs.

The production medium contained 60 g/L of overnight express instant TB medium (Novagen), 10 g/L of glycerol and 50 mg/L of Kanamycine. The preculture was added to 400 mL of this medium and the solution was allowed to stir at 20° C. while taking samples to measure the OD and pH. The cultures gave significant growth and a good OD was obtained. After 40 hrs, the cells were harvested by centrifugation and frozen. The following yields of cell wet weights (CWW) are mentioned below.

| GI number | Version | CWW |
|---|---|---|
| 115454819 | NP_001051010.1 | 9.2 g |
| 187373030 | ACD03249.1 | 7.4 g |
| 460409128 | XP_004249992.1 | 6.8 g |
| 222619587 | EEE55719.1 | 7.5 g |
| 297795735 | XP_002865752.1 | 8.8 g |

Lysis was performed by addition of Bugbuster Master mix (Novagen) and the lysate was recovered by centrifugation and used fresh.

Determination of Activity.

Activity tests were performed at 5 mL scale with 1,000 µL of thawed lysate for the transformation of Rebaudioside A using 0.5 mM of substrate, 2.5 mM of UDP-Glucose and 3 mM MgCl$_2$ in 50 mM Sodium Phosphate buffer at pH 7.2. Samples were taken and analyzed by HPLC as seen in FIGS. 48-52.

HPLC Analysis.

The HPLC assay was performed as described in EXAMPLE 20.

The results for the different enzymes are provided below.

| GI Number | Version | Conversion after 45 hrs. | Reb D selectivity |
|---|---|---|---|
| 115454819 | NP_001051010.1 | 1.1% | 100% |
| 187373030 | ACD03249.1 | 0.8% | 100% |
| 460409128 | XP_004249992.1 | 62.1% | 43.6% |
| 222619587 | EEE55719.1 | 2.9% | Reb D Not detected |
| 297795735 | XP_002865752.1 | 0.0% | Reb D Not detected |

Figure 48:
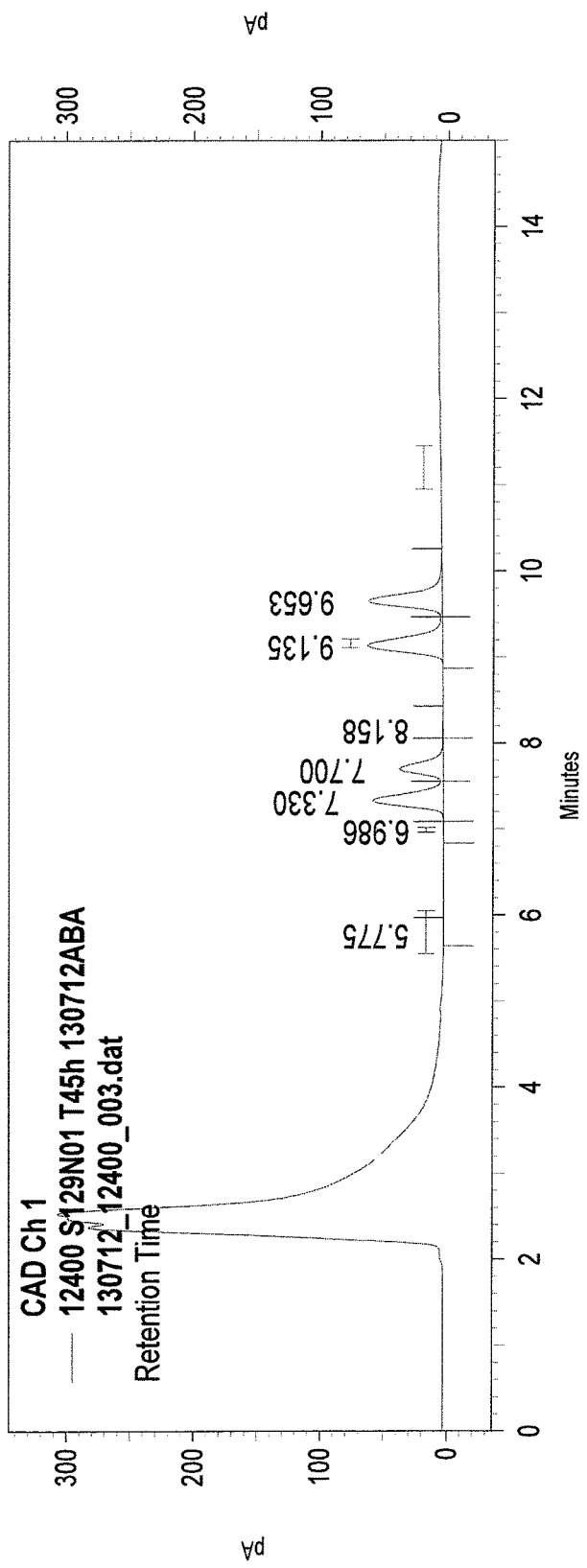
FIG. 48 shows an HPLC (CAD) analysis.

The below table accompanies FIG. 48.

SAMPLE: 12400 S129N01 T45h 130712ABA
>gi115454819 / NP_001051010.1
Filename: 130712_12400_003.dat

| CAD Ch 1 Results | | |
|---|---|---|
| Compound | Retention time | Integration (area) |
| Rebaudioside D | 5.775 | 3,264,475 |
| Unknown@RT6.986 | 6.986 | 4,110,607 |
| Unknown@RT7.330 | 7.330 | 564,033,104 |
| Unknown@RT7.700 | 7.700 | 328,710,539 |
| Unknown@RT8.158 | 8.158 | 6,344,796 |
| Rebaudioside A | 9.135 | 673,271,863 |
| Unknown@RT9.653 | 9.653 | 616,489,141 |
| Total | | 2,196,224,525 |

Figure 49:
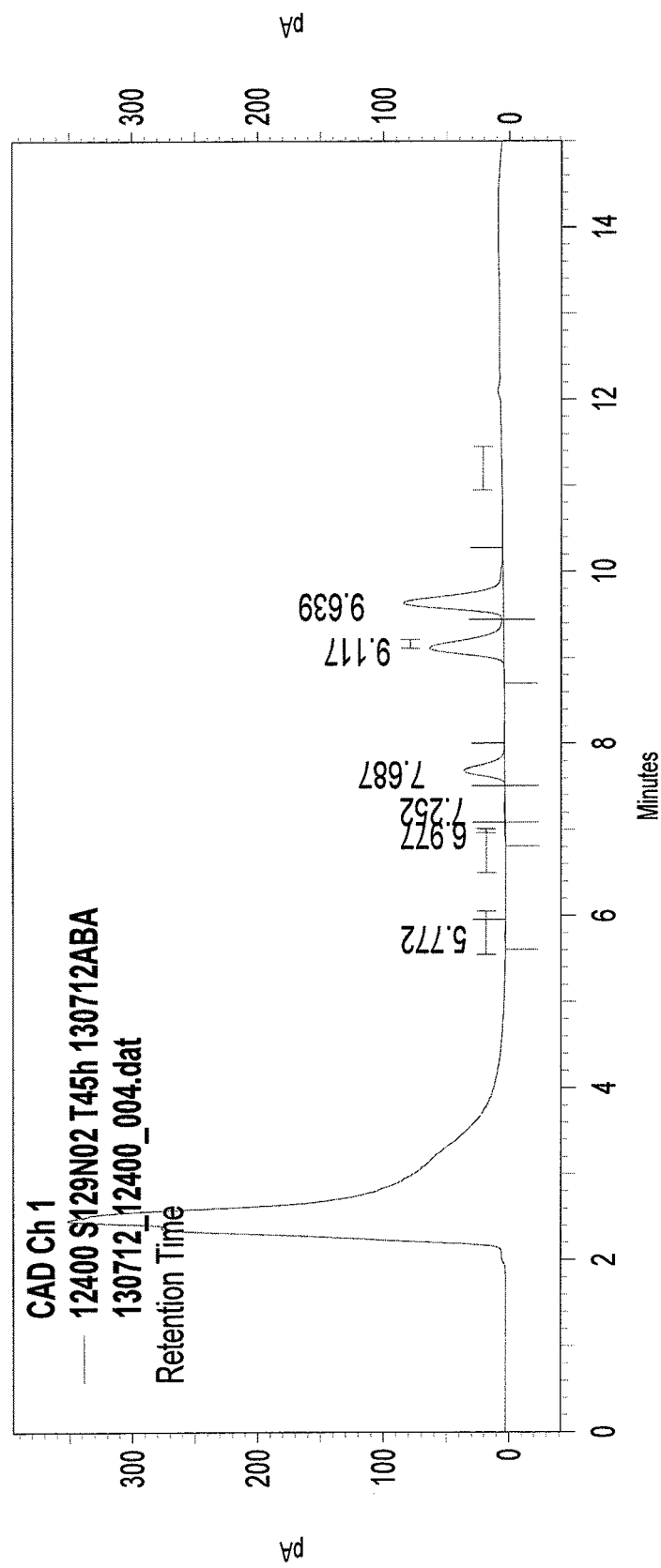
FIG. 49 shows an HPLC (CAD) analysis.

The below table accompanies FIG. 49.

Sample: 12400 S129N02 T45h 130712ABA
>gi187373030 / ACD03249.1
Filename: 130712_12400_004.dat

| CAD Ch 1 Results | | |
|---|---|---|
| Compound | Retention time | Integration (area) |
| Rebaudioside D | 5.772 | 1,997,401 |
| Unknown@RT6.977 | 6.977 | 3,341,419 |
| Unknown@RT7.252 | 7.252 | 10,576,676 |
| Unknown@RT7.687 | 7.687 | 298,862,034 |

| | | |
|---|---|---|
| Rebaudioside A | 9.117 | 675,210,845 |
| Unknown@RT9.639 | 9.639 | 874,680,345 |
| Total | | 1,864,668,720 |

Figure 50:
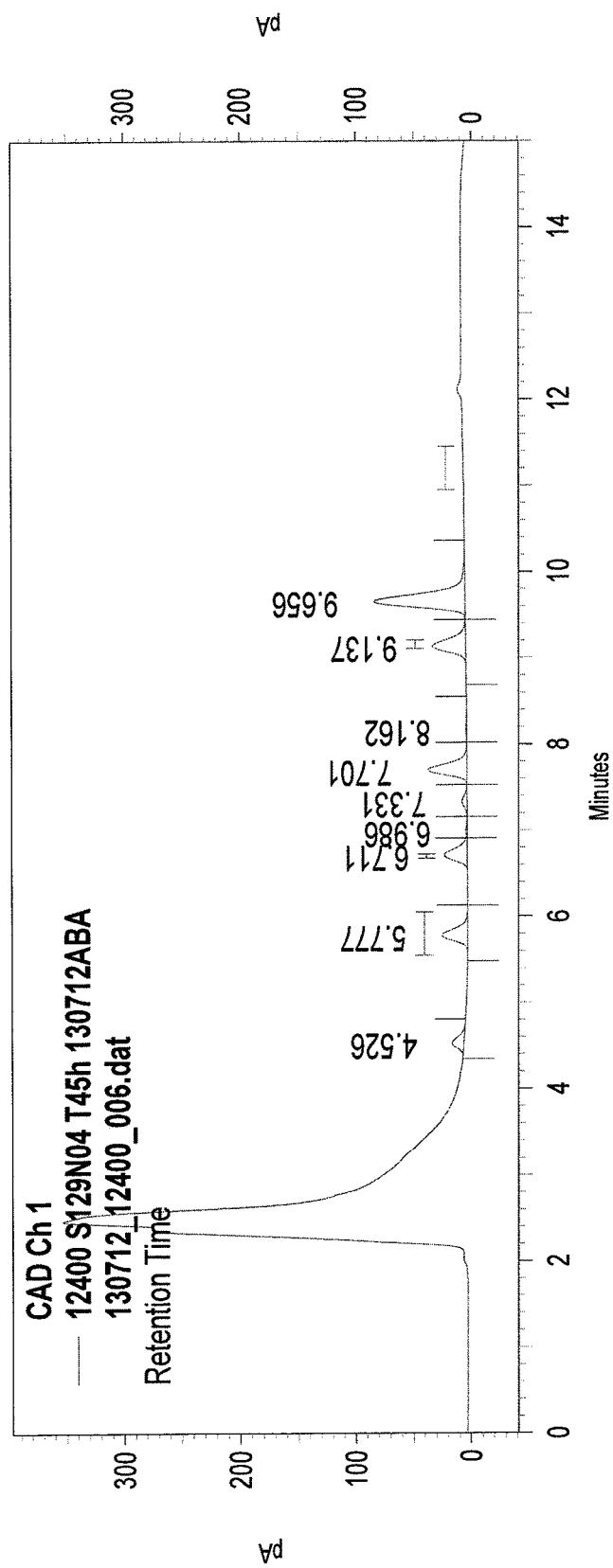
FIG. 50 shows an HPLC (CAD) analysis.

The below table accompanies FIG. 50.

Sample: 12400 S129N04 T45h 130712ABA
>gi460409128 / XP_004249992.1
Filename: 130712_12400_006.dat

| CAD Ch 1 Results | | |
|---|---|---|
| Compound | Retention time | Integration (area) |
| Unknown@RT4.526 | 4.526 | 89,809,997 |
| Rebaudioside D | 5.777 | 217,830,913 |
| Rebaudioside UNK | 6.711 | 192,129,243 |
| Unknown@RT6.986 | 6.986 | 10,241,417 |
| Unknown@RT7.331 | 7.331 | 41,195,765 |
| Unknown@RT7.701 | 7.701 | 310,640,254 |
| Unknown@RT8.162 | 8.162 | 7,950,609 |
| Rebaudioside A | 9.137 | 304,611,760 |
| Unknown@RT9.656 | 9.656 | 863,496,704 |
| Total | | 2,037,906,662 |

Figure 51:
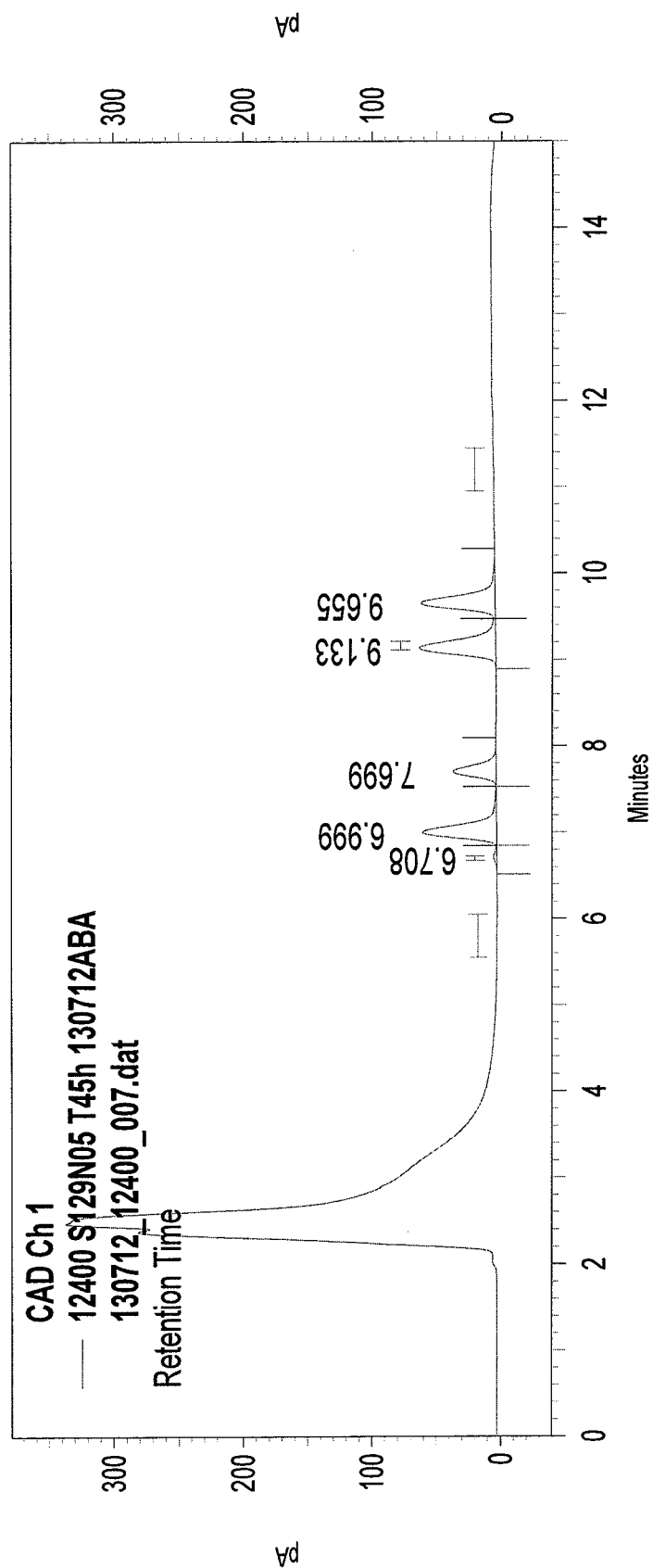
FIG. 51 shows an HPLC (CAD) analysis.

The below table accompanies FIG. 51.

Sample: 12400 S129N05 T45h 130712ABA
>gi222619587 / EEE55719.1
Filename: 130712_12400_007.dat

| CAD Ch 1 Results | | |
|---|---|---|
| Compound | Retention time | Integration (area) |
| Rebaudioside UNK | 6.708 | 20,047,847 |
| Unknown@RT6.999 | 6.999 | 598,924,958 |
| Unknown@RT7.699 | 7.699 | 303,182,042 |
| Rebaudioside A | 9.133 | 672,777,773 |
| Unknown@RT9.655 | 9.655 | 606,371,969 |
| Total | | 2,201,304,589 |

Figure 52:
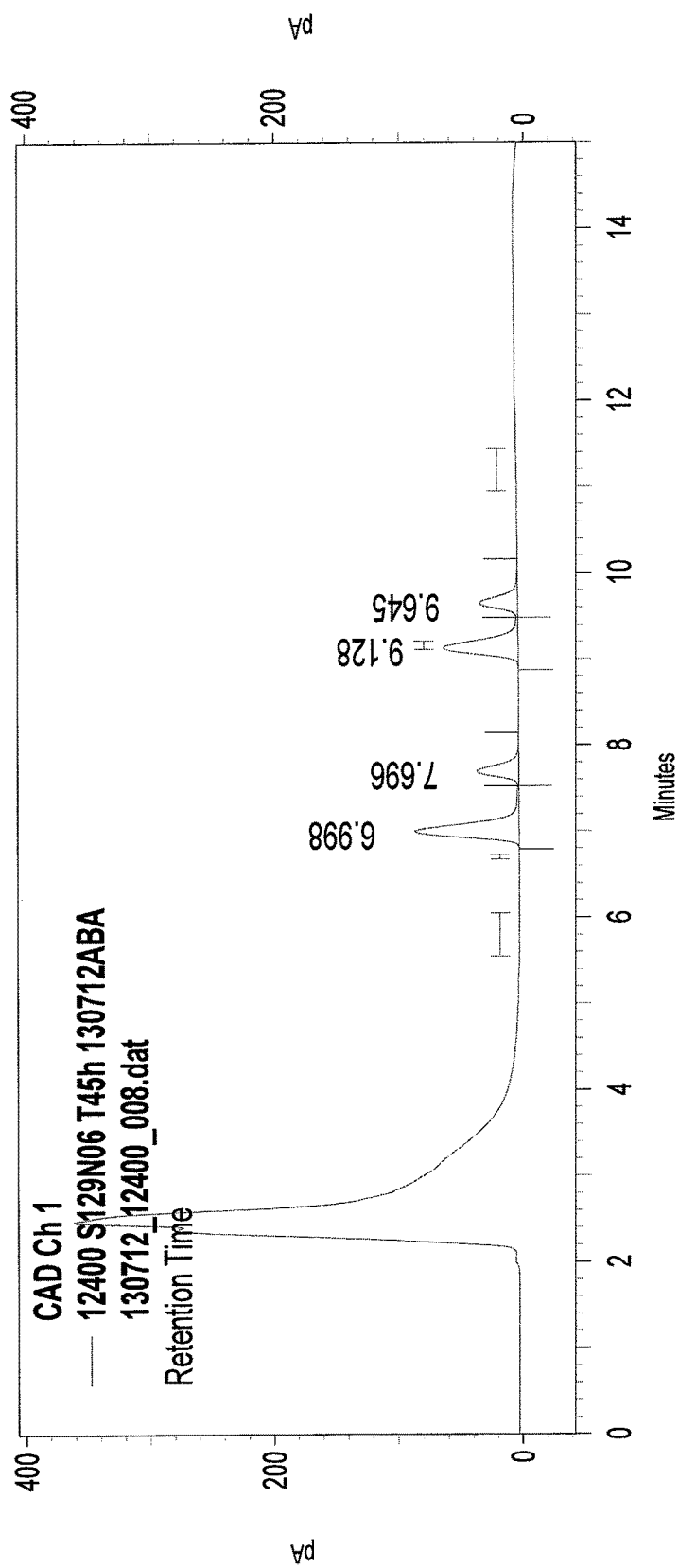
FIG. 52 shows an HPLC (CAD) analysis.

The below table accompanies FIG. 52.

Sample: 12400 S129N06 T45h 130712ABA
>gi297795735 / XP_002865752.1
Filename: 130712_12400_008.dat

| CAD Ch 1 Results | | |
|---|---|---|
| Compound | Retention time | Integration (area) |
| Unknown@RT6.998 | 6.998 | 920,620,332 |
| Unknown@RT7.696 | 7.696 | 314,421,575 |
| Rebaudioside A | 9.128 | 688,195,594 |
| Unknown@RT9.645 | 9.645 | 308,115,680 |
| Total | | 2,231,353,181 |

Example 23

Identification of Glycosides

The reaction mixtures representing GI No. 460409128, particularly the sample "12400 S115N05A7 T24 h 130627ABA" of EXAMPLE 20 (hereinafter S115N05A7), and the sample "12400 S129N04 T45h 130712ABA" of EXAMPLE 22 (hereinafter S129N04) were additionally assayed by LC-MS to identify the unknown glycosides. An Agilent 1200 series HPLC system, equipped with binary pump (G1312B), autosampler (G1367D), thermostatted column compartment (G1316B), DAD detector (G1315C), connected with Agilent 6110A MSD, and interfaced with "LC/MSD Chemstation" software, was used.

Instrument Conditions

| | |
|---|---|
| Column | Phenomenex Kinetex 2.6u C18 100A, 4.6 mm × 150 mm, 2.6 μm |
| Column Temperature | 55° C. |
| Detection | DAD at 210 nm bw 360 nm |
| | MSD (Scan and SIM mode) |
| | Mode: ES-API, Negative Polarity |
| | Drying gas flow: 13.0 L/min |
| | Nebulizer pressure: 30 psig |
| | Drying gas temperature: 270° C. |
| Analysis duration | 25 min |
| Injected volume | 2 μL |
| Flow rate | 1 mL/min |

Mobile Phase Gradient Program

| Time (min) | A (%): Formic acid 0.1% | B (%): Acetonitrile |
|---|---|---|
| 0 | 75 | 25 |
| 8.5 | 75 | 25 |
| 10.0 | 71 | 29 |
| 16.5 | 70 | 30 |

The compound observed on LCMS system at 3.5 min, corresponds to compound "Unknown@4.508" in sample "S115N05A7" (EXAMPLE 20), and compound "Unknown@RT4.526" in sample "S129N04" (EXAMPLE 22). The LCMS data suggests that this compound has six glucosidic residues ($C_{56}H_{90}O_{33}$) in its structure, and was found to be an isomer form of reb M, namely reb M2 (see Example 40 for discussion).

Figure 53:
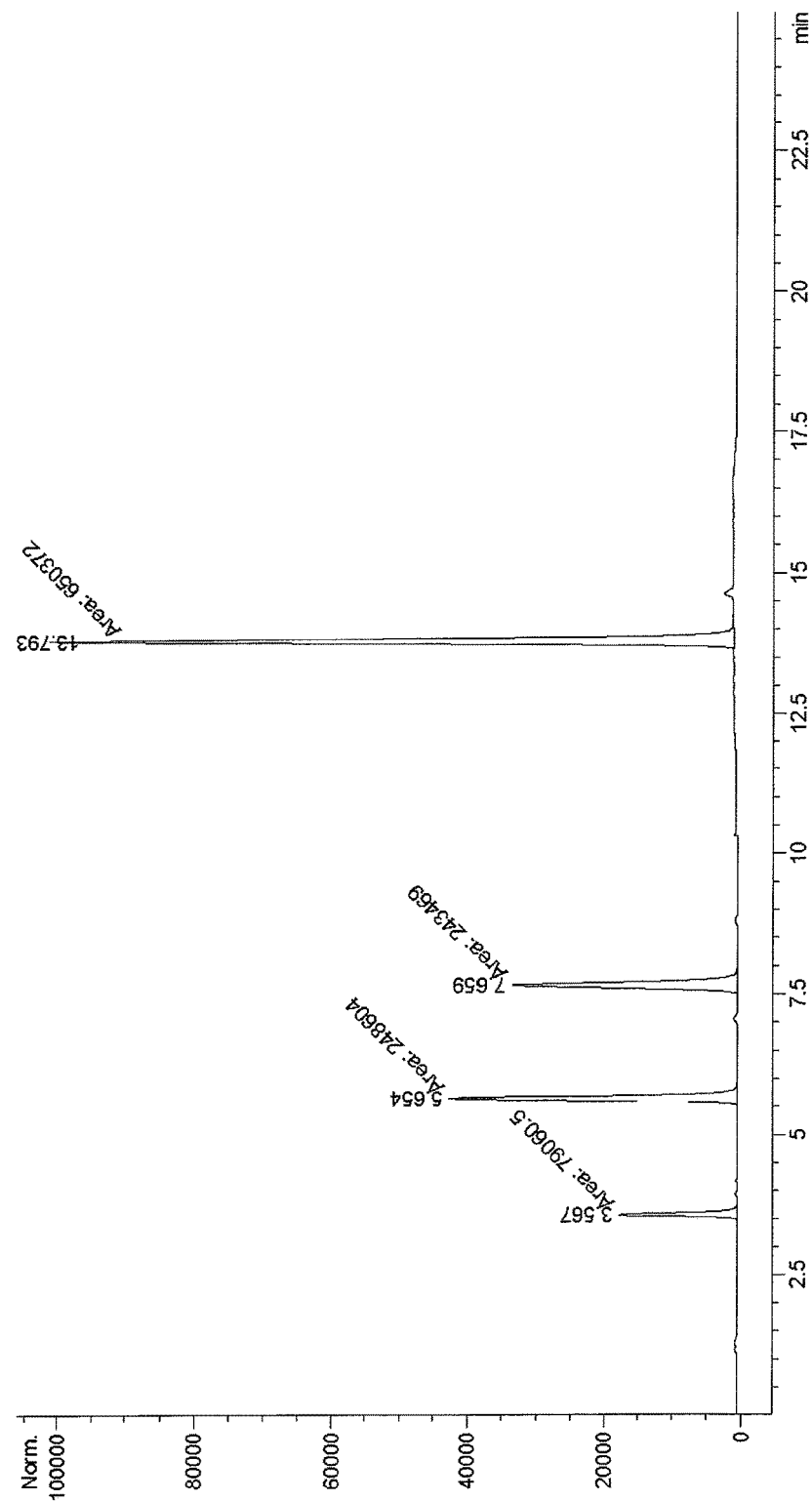
FIG. 53 shows an LCMS chromatogram.
Figure 54:
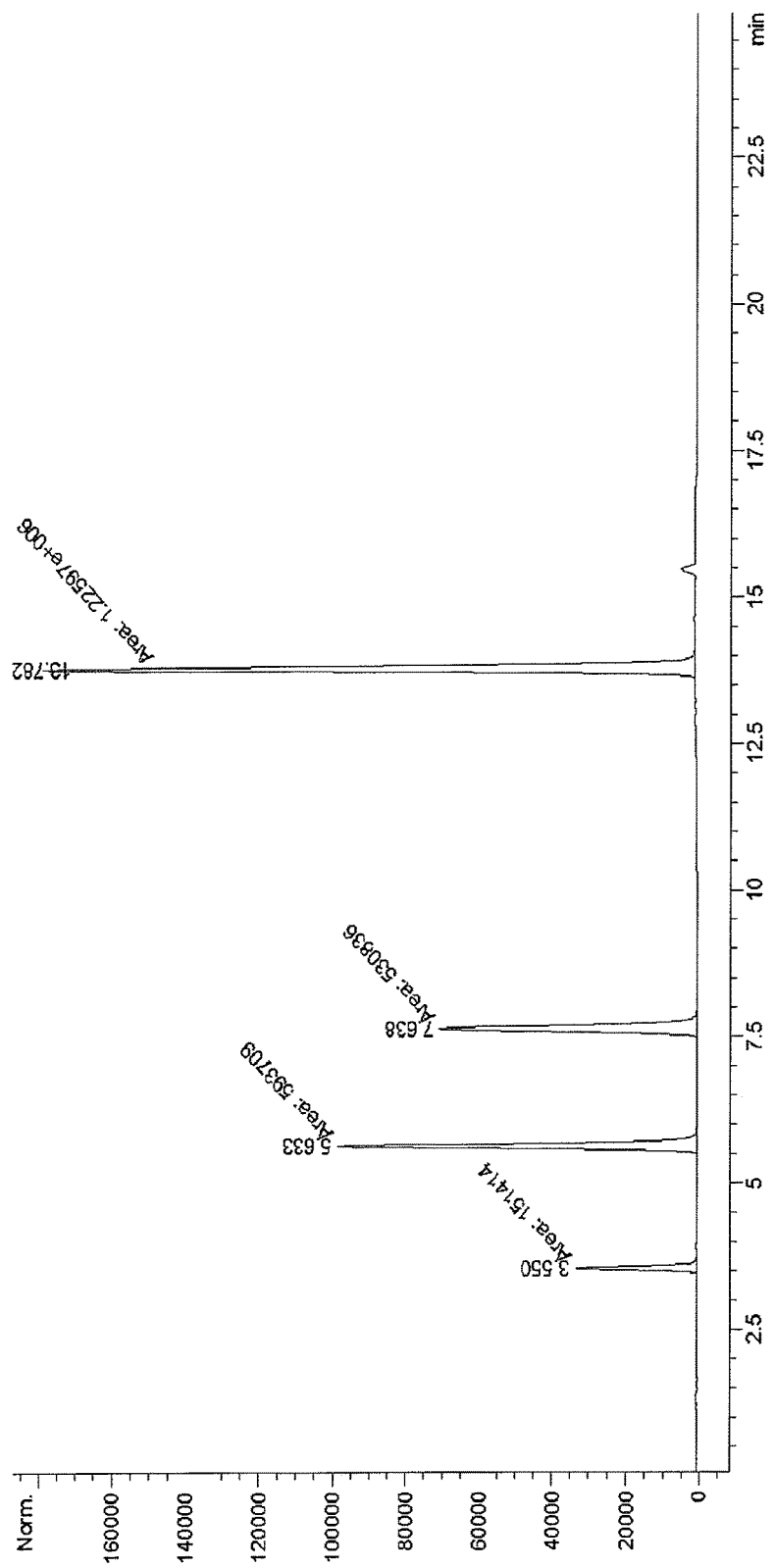
FIG. 54 shows an LCMS chromatogram.

Whereas the compound observed on LCMS system at 7.6 min, corresponds with compound "reb UNK" in sample "S115N05A7" (EXAMPLE 20), and compound "reb UNK" in sample "S129N04" (EXAMPLE 22), The LCMS data suggests that "reb UNK" has five glucosidic residues ($C_{50}H_{80}O_{28}$) in its structure, and was found to be an isomer form of reb D, namely reb D2 (see Example 39 for discussion). The ratio of these compounds and the LCMS chromatograms are provided below and as shown in FIGS. 53-54.

| | Steviol glycoside conversion in reaction mixture (% area) | | | |
|---|---|---|---|---|
| Sample | Unknown@RT 3.5 | Reb D | Reb UNK | Reb A |
| S115N05A7 | 6.47 | 20.35 | 19.93 | 53.24 |
| S129N04 | 6.05 | 23.73 | 21.22 | 49.00 |

The below table accompanies FIG. 53.

Sample: 12400 S115N05A7 T24h 130627ABA
>gi460409128/XP_004249992.1
MSD SIM Results

| Compound | Retention time | MW | Integration (area) |
|---|---|---|---|
| Unknown@RT3.567 | 3.567 | 1,291 | 79,060 |
| Rebaudioside D | 5.654 | 1,129 | 248,604 |

Sample: 12400 S115N05A7 T24h 130627ABA
>gi|460409128/XP_004249992.1
MSD SIM Results

| Compound | Retention time | MW | Integration (area) |
|---|---|---|---|
| Rebaudioside UNK | 7.659 | 1,129 | 243,469 |
| Rebausioside A | 13.793 | 967 | 650,372 |
| Total | | | 1,221,505 |

The below table accompanies FIG. 54.

Sample: 12400 S129N04 T45h 130712ABA >
gi460409128/XP_004249992.1
MSD SIM Results

| Compound | Retention time | MW | Integration (area) |
|---|---|---|---|
| Unknown@RT3.550 | 3.550 | 1,291 | 151,414 |
| Rebaudioside D | 5.633 | 1,129 | 593,709 |
| Rebaudioside UNK | 7.638 | 1,129 | 530,836 |
| Rebaudioside A | 13.782 | 967 | 1,225,970 |
| Total | | | 2,501,929 |

Example 24

Identification of Glycosides

Figure 55:
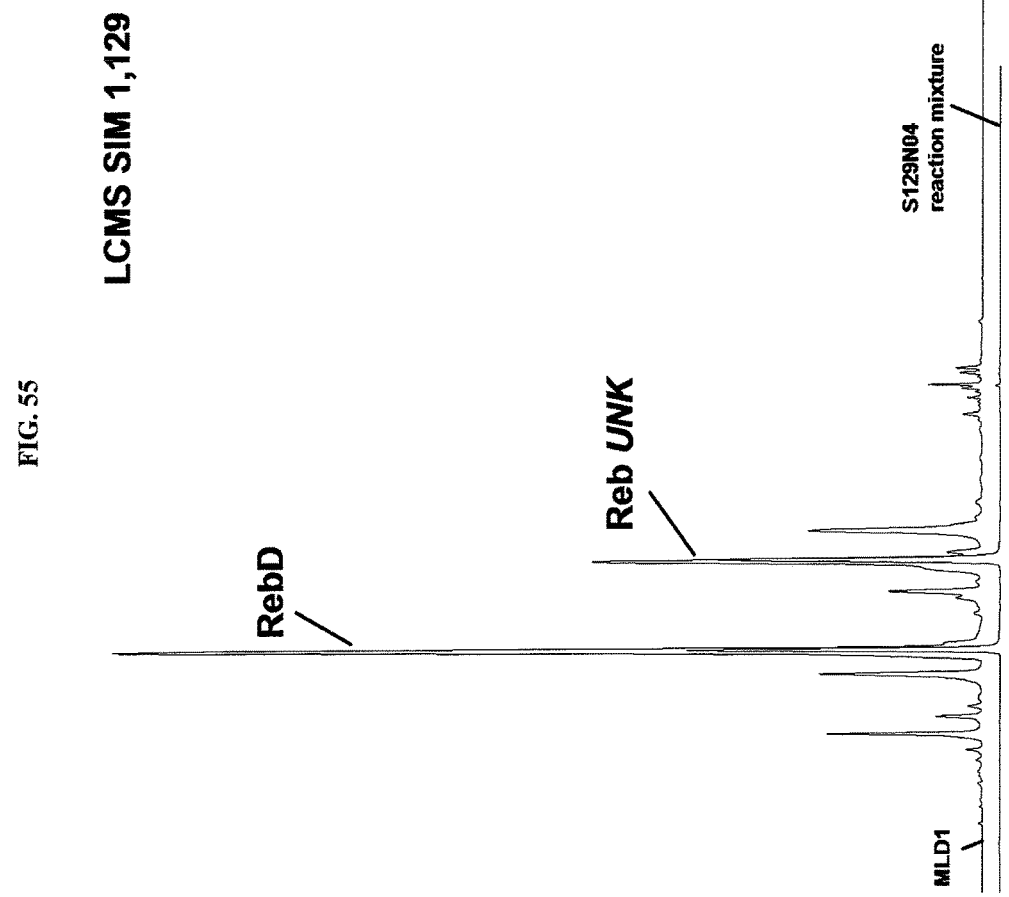
FIG. 55 shows an LCMS chromatogram.
Figure 56:
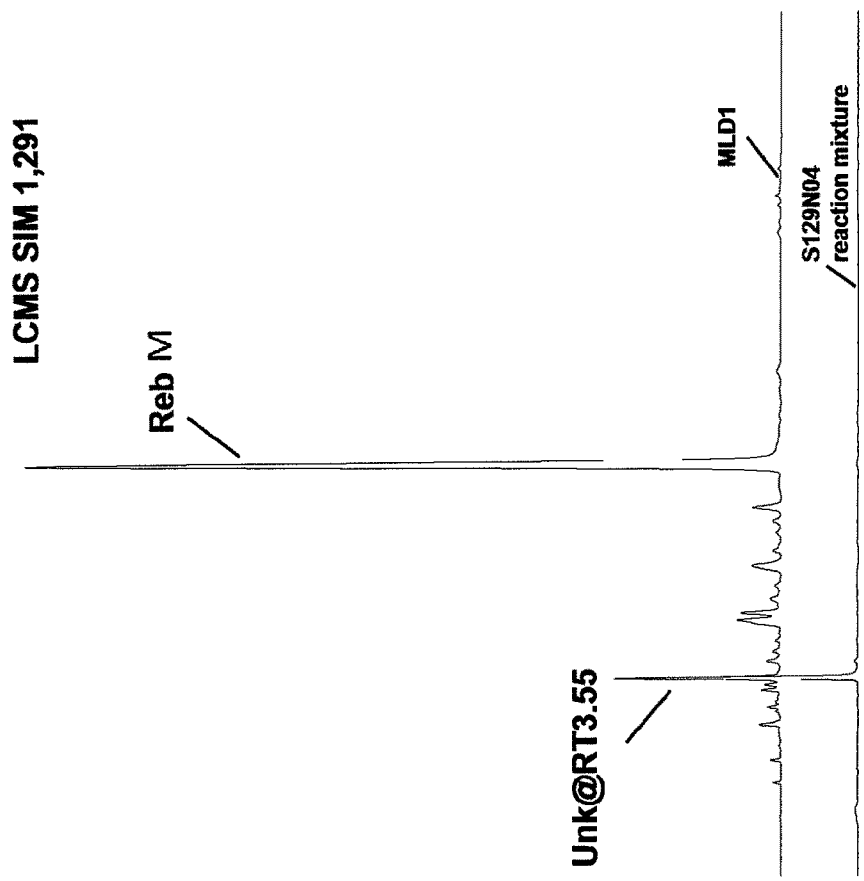
FIG. 56 shows an LCMS chromatogram.

The reaction mixture representing GI No. 460409128, particularly the sample "12400 S129N04 T45h 130712ABA" of EXAMPLE 22 (hereinafter S129N04) were additionally assayed by LC-MS, as seen in FIGS. 55-56, along with Stevia rebaudiana Bertoni leaf extract "MLD1" produced by PureCircle Sdn Bhd (Malaysia) to determine the occurrence of S129N04 glycosides in nature.

The below table accompanies FIG. 55.

Samples:
1) 12400 S129N04 T45h 130712ABA >
gi460409128/XP_004249992.1
2) MLD1 Stevia rebaudiana Bertoni extract
MSD SIM 1,129 Results

| Compound | MW |
|---|---|
| Rebaudioside D | 1,129 |
| Rebaudioside UNK | 1,129 |

The below table accompanies FIG. 56.

Samples:
1) 12400 S129N04 T45h 130712ABA >
gi460409128/XP_004249992.1
2) MLD1 Stevia rebaudiana Bertoni extract
MSD SIM 1,291 Results

| Compound | MW |
|---|---|
| Unknown@RT3.550 | 1,291 |
| Rebaudioside M | 1,291 |

The assay shows that the compound observed on LCMS system at 3.5 min, in EXAMPLE 23 ($C_{56}H_{90}O_{33}$; later confirmed as reb M2), and the compound observed on LCMS system at 7.6 min, in EXAMPLE 23 ($C_{50}H_{80}O_{28}$, reb UNK; later confirmed as reb D2) occur in the extract of Stevia rebaudiana Bertoni plant.

Example 25

Conversion of Rebaudioside E to Rebaudioside D

Figure 57:
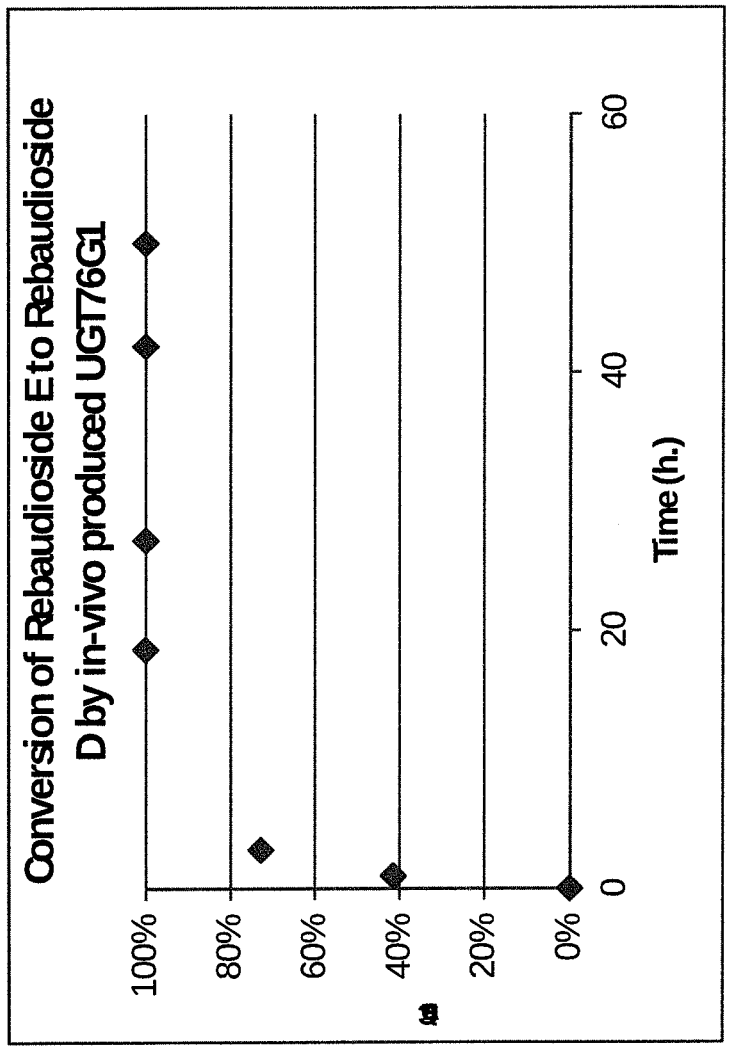
FIG. 57 shows a reaction profile.

The total volume of the reaction was 5.0 mL with the following composition: 100 mM potassium phosphate buffer pH 7.5, 3 mM $MgCl_2$, 2.5 mM UDP-glucose, 0.5 mM Rebaudioside E and 500 µL of UGT76G1 thawed lysate (UGT76G1 gene was cloned in pET30a+ vector and expressed in E. coli BL21 (DE3)). The reactions were run at 30° C. on an orbitary shaker at 135 rpm. For sampling 300 µL of the reaction mixture was quenched with 30 µl of 2N $H_2SO_4$ and 270 µL of methanol/water (6/4). The samples were immediately centrifuged and kept at 10° C. before analysis by HPLC (CAD detection). The following reaction profile was obtained corresponding to a complete conversion of Rebaudioside E to Rebaudioside D as seen in FIG. 57.

Example 26

Directed Evolution of UGT76G1 for the Conversion of Rebaudioside D to Rebaudioside M Starting from the amino acid sequence of UGT76G1, as is described in Genbank (AAR06912.1), different mutations at various amino acid positions were identified that could alter the activity of the enzyme for the transformation of Rebaudioside D (Reb D) to Rebaudioside M (Reb M). This list of mutations, designed by DNA2.0 ProteinGPS™ strategy, was subsequently used to synthesize 96 variant genes that contained 3, 4 or 5 of these mutations that were codon-optimized for expression in E. coli. The genes were subcloned in the pET30a+ plasmid and used for transformation of E. coli BL21 (DE3) chemically competent cells. The obtained cells were grown in Petri-dishes on solid LB medium in the presence of Kanamycin. Suitable colonies were selected and allowed to grow in liquid LB medium in tubes. Glycerol was added to the suspension as cryoprotectant and 400 µL aliquots were stored at −20° C. and at −80° C.

These storage aliquots of E. coli BL21(DE3) containing the pET30a+_UGT76G1var plasmids were thawed and added to LBGKP medium (20 g/L Luria Broth Lennox; 50 mM PIPES buffer pH 7.00; 50 mM Phosphate buffer pH 7.00; 2.5 g/L glucose and 50 mg/L of Kanamycine). This culture was allowed to shake in a 96 microtiter plate at 135 rpm at 30° C. for 8 h.

3.95 mL of production medium containing 60 g/L of Overnight Express™ Instant TB medium (Novagen®), 10 g/L of glycerol and 50 mg/L of Kanamycin was inoculated with 50 µL of above described culture. In a 48 deepwell plate the resulting culture was allowed to stir at 20° C. The cultures gave significant growth and a good OD (600 nm; 1 cm) was obtained. After 44 h, the cells were harvested by centrifugation and frozen.

Lysis was performed by addition of Bugbuster® Master mix (Novagen®) to the thawed cells and the lysate was recovered by centrifugation. Activity tests were performed with 100 µL of fresh lysate that was added to a solution of Rebaudioside D (final concentration 0.5 mM), $MgCl_2$ (final concentration 3 mM) and UDP-Glucose (final concentration 2.5 mM) in 50 mM phosphate buffer pH 7.2.

The reaction was allowed to run at 30° C. and samples were taken after 2, 4, 7 and 24 h. to determine conversion and initial rate by HPLC (CAD detection) using the analytical method that was described above for the transformation of Rebaudioside D to Rebaudioside M. The results are depicted in the following table.

| Clone | Mutations* | conversion Reb D to Reb M after 24 h (%) | initial rate (Reb M area/min) |
|---|---|---|---|
| UGT76G1var1 | E224A_F314S_R334K | 51.8 | 5.5E+07 |
| UGT76G1var2 | S274G_T284I_L379G | 49.3 | 4.7E+07 |
| UGT76G1var3 | I295T_S357C_V366I | 9.6 | 1.6E+06 |
| UGT76G1var4 | E224D_E231A_F265I | 14.7 | 8.6E+06 |
| UGT76G1var5 | F22Y_I373L_P382M | 3.5 | 2.3E+06 |
| UGT76G1var6 | Q266S_S357N_I373L | 0.5 | 1.8E+06 |
| UGT76G1var7 | F22L_I43V_A239V | 0.2 | −6.0E+04 |
| UGT76G1var8 | E224A_Q266S_Q342E | 0.5 | 2.3E+04 |
| UGT76G1var9 | E231A_D301N_G348P | 52.0 | 4.9E+07 |
| UGT76G1var10 | A33G_L246F_Q342E | 0.3 | −7.7E+02 |
| UGT76G1var11 | F22L_A33G_V310I | 0.4 | 3.8E+04 |
| UGT76G1var12 | L243P_K303G_A352G | 0.5 | 8.7E+04 |
| UGT76G1var13 | L243A_S357C_A385T | 0.2 | −3.3E+04 |
| UGT76G1var14 | A239I_F265I_V396F | 5.3 | 1.5E+06 |
| UGT76G1var15 | F41L_L246F_Q425E | 5.6 | 1.5E+06 |
| UGT76G1var16 | F265I_P272A_I335V | 18.6 | 5.8E+06 |
| UGT76G1var17 | F265L_Q266E_Q342K | 0.7 | 7.2E+05 |
| UGT76G1var18 | L243P_S274G_N409R | 1.9 | 5.0E+05 |
| UGT76G1var19 | E224D_E229A_Q432E | 10.5 | 5.5E+06 |
| UGT76G1var20 | S375M_K393G_Y397E | 1.8 | 1.9E+06 |
| UGT76G1var21 | A239V_V300A_K303G | 41.9 | 3.3E+07 |
| UGT76G1var22 | E231A_V310I_R334K | 34.4 | 2.4E+07 |
| UGT76G1var23 | T263S_G348P_A352G | 47.8 | 4.1E+07 |
| UGT76G1var24 | A239I_P272A_Q425E | 31.0 | 2.1E+07 |
| UGT76G1var25 | T284L_Q342K_Y397Q | 0.9 | 6.3E+04 |
| UGT76G1var26 | S241I_F265L_F377C | 1.8 | 7.5E+05 |
| UGT76G1var27 | A239I_L379A_V394I | 29.0 | 1.5E+07 |
| UGT76G1var28 | L243A_S274G_P382M | 6.1 | 2.4E+06 |
| UGT76G1var29 | F22Y_V279I_N409R | 41.0 | 2.9E+07 |
| UGT76G1var30 | I43V_E224A_S241I | 13.6 | 5.6E+06 |
| UGT76G1var31 | E224D_L243P_V300A | 0.4 | 2.4E+05 |
| UGT76G1var32 | A239V_L243A_S375M | 0.0 | −4.4E+04 |
| UGT76G1var33 | A33G_R334H_Y397Q | 1.0 | 7.5E+06 |
| UGT76G1var34 | I43V_T284I_I295T | 3.4 | 1.5E+06 |
| UGT76G1var35 | T284L_F314S_S357N | 0.5 | 1.8E+05 |
| UGT76G1var36 | F265L_L379A_V396F | 20.0 | 8.8E+06 |
| UGT76G1var37 | E229A_L379G_I407V | 39.1 | 2.8E+07 |
| UGT76G1var38 | F41L_I295M_F377C | 8.2 | 3.7E+06 |
| UGT76G1var39 | F22Y_F41L_V366I | 7.2 | 3.3E+06 |
| UGT76G1var40 | T263S_Q266E_S375R | 47.6 | 3.3E+07 |
| UGT76G1var41 | L246F_A385T_K393G | 0.8 | 1.4E+06 |
| UGT76G1var42 | T263S_Q266S_R334H | 34.6 | 2.2E+07 |
| UGT76G1var43 | S241I_P272A_V279I | 19.9 | 9.4E+06 |
| UGT76G1var44 | I335V_S375R_I407V | 35.3 | 2.3E+07 |
| UGT76G1var45 | V279I_D301N_S389E | 38.6 | 2.3E+07 |
| UGT76G1var46 | F22L_Q266E_I295M | 0.6 | 9.8E+05 |
| UGT76G1var47 | E229A_T284I_S389E | 4.8 | 2.7E+06 |
| UGT76G1var48 | V394I_Y397E_Q432E | 47.6 | 3.8E+07 |
| UGT76G1var49 | F41L_Q266E_T284I_Y397Q | 2.6 | 1.1E+06 |
| UGT76G1var50 | F22Y_V310I_S375M_F377C | 1.9 | −7.9E+05 |
| UGT76G1var51 | K303G_S357C_S389E_V396F | 18.7 | 9.5E+06 |
| UGT76G1var52 | D301N_I373L_F377C_I407V | 12.9 | 4.6E+06 |
| UGT76G1var53 | R334K_A352G_P382M_S389E | 9.3 | 4.1E+06 |
| UGT76G1var54 | E229A_T284L_R334K_Q342E | 0.7 | 4.3E+05 |
| UGT76G1var55 | I295M_Q342E_V366I_N409R | 1.0 | 2.2E+05 |
| UGT76G1var56 | L246F_A352G_S357N_Q432E | 0.4 | 4.1E+04 |
| UGT76G1var57 | S241I_T263S_L379G_A385T | 0.8 | 1.5E+05 |
| UGT76G1var58 | S357C_S375M_N409R_Q425E | 7.5 | 2.2E+06 |
| UGT76G1var59 | I335V_K393G_V394I_Y397Q | 33.0 | 2.7E+07 |
| UGT76G1var60 | E231A_L243A_V279I_S357N | 0.5 | 9.5E+04 |
| UGT76G1var61 | I43V_F265I_Q266S_L379A | 6.4 | 2.0E+06 |
| UGT76G1var62 | L243P_P272A_V394I_V396F | 0.1 | 3.4E+04 |
| UGT76G1var63 | F314S_R334H_Q342K_L379G | 3.4 | 1.2E+06 |
| UGT76G1var64 | F22L_A239I_R334H_I407V | 0.3 | 3.1E+04 |
| UGT76G1var65 | A33G_A239V_P382M_Q425E | 1.2 | 3.3E+05 |
| UGT76G1var66 | F265L_V310I_V366I_A385T | 0.8 | 3.7E+05 |
| UGT76G1var67 | E224A_F314S_S375R_Y397E | −2.1 | −5.6E+05 |
| UGT76G1var68 | Q342K_G348P_I373L_Y397E | −1.4 | −1.1E+05 |
| UGT76G1var69 | S274G_I295T_I335V_L379A | 24.7 | 8.3E+06 |
| UGT76G1var70 | E224A_I295T_V300A_G348P | 24.0 | 8.4E+06 |
| UGT76G1var71 | I295M_V300A_K393G_Q432E | 42.9 | 2.1E+07 |
| UGT76G1var72 | T284L_D301N_K303G_S375R | 19.2 | 9.1E+06 |
| UGT76G1var73 | F22Y_D301N_R334H_Q342E_V396F | 0.8 | 8.7E+05 |
| UGT76G1var74 | I295T_I373L_S375R_Y397Q_Q432E | 0.6 | 9.6E+04 |
| UGT76G1var75 | F41L_A239I_Q266S_S375M_P382M | 0.8 | −1.3E+05 |
| UGT76G1var76 | F22Y_A239I_L246F_I295M_R334K | 2.6 | 7.2E+05 |

-continued

| Clone | Mutations* | conversion Reb D to Reb M after 24 h (%) | initial rate (Reb M area/min) |
|---|---|---|---|
| UGT76G1var77 | A239V_F265I_I295T_D301N_K393G | 1.9 | 4.4E+05 |
| UGT76G1var78 | V279I_V300A_V310I_I335V_S357C | 3.2 | 8.2E+05 |
| UGT76G1var79 | E224D_T284I_V366I_I373L_K393G | 8.5 | 3.8E+06 |
| UGT76G1var80 | L243P_L379A_S389E_Q425E_Q432E | 1.0 | 2.1E+05 |
| UGT76G1var81 | A33G_T263S_S274G_V279I_Y397E | 15.0 | 6.5E+06 |
| UGT76G1var82 | E224D_L243A_F265L_R334H_A352G | 1.1 | 2.5E+05 |
| UGT76G1var83 | I43V_Q342E_S357N_S375R_L379G | 0.5 | 4.3E+04 |
| UGT76G1var84 | F22L_Q266S_F314S_A352G_S357C | 1.2 | 2.3E+05 |
| UGT76G1var85 | T284L_G348P_F377C_P382M_N409R | 1.8 | 4.0E+05 |
| UGT76G1var86 | E224A_T284L_V396F_Y397E_I407V | 1.6 | 3.8E+05 |
| UGT76G1var87 | S241I_L243A_V300A_F314S_N409R | 35.7 | 2.1E+07 |
| UGT76G1var88 | A239V_T284I_V310I_Q342K_L379A | 1.6 | 3.8E+05 |
| UGT76G1var89 | F41L_E229A_E231A_F265L_P272A | 1.2 | 2.1E+05 |
| UGT76G1var90 | E231A_S241I_S274G_Y397Q_Q425E | 34.5 | 1.9E+07 |
| UGT76G1var91 | E224A_L246F_T263S_F265I_Q342K | 1.2 | 2.3E+05 |
| UGT76G1var92 | K303G_S357N_V366I_V394I_I407V | 1.6 | 3.6E+05 |
| UGT76G1var93 | I43V_Q266E_S375M_S389E_V394I | 1.8 | 4.5E+05 |
| UGT76G1var94 | Q266E_P272A_R334K_G348P_L379G | 72.0 | 7.9E+07 |
| UGT76G1var95 | A33G_I295M_K303G_I335V_A385T | −1.3 | −1.7E+05 |
| UGT76G1var96 | F22L_E229A_L243P_F377C_A385T | 1.2 | 2.7E+05 |

*Mutations are noted as follows: original amino acid-position-new amino acid: For example the mutation of an alanine at position 33 to a glycine is noted as A33G.

Example 27

In-Vivo Production of UGTSL2

```
                                          SEQ ID 9
UGTSL2 (GI_460410132 / XP_004250485.1) amino acid
sequence:
MATNLRVLMFPWLAYGHISPFLNIAKQLADRGFLIYLCSTRINLESIIKK

IPEKYADSIHLIELQLPELPELPPHYHTTNGLPPHLNPTLHKALKMSKPN

FSRILQNLKPDLLIYDVLQPWAEHVANEQNIPAGKLLTSCAAVFSYFFSF

RKNPGVEFPFPAIHLPEVEKVKIREILAKEPEEGGRLDEGNKQMMLMCTS

RTIEAKYIDYCTELCNWKVVPVGPPFQDLITNDADNKELIDWLGTKHENS

TVFVSFGSEYFLSKEDMEEVAFALELSNVNFIWVARFPKGEERNLEDALP

KGFLERIGERGRVLDKFAPQPRILNHPSTGGFISHCGWNSAMESIDFGVP

IIAMPIHNDQPINAKLMVELGVAVEIVRDDDGKIHRGEIAETLKSVVTGE

TGEILRAKVREISKNLKSIRDEEMDAVAEELIQLCRNSNKSK
```

The pET30A+ vector containing the UGTSL2 gene was introduced in *E. coli* B121(DE3) by heat shock. The obtained cells were grown in petri-dishes in the presence of Kanamycin and suitable colonies were selected and allowed to grow in liquid LB medium (erlenmeyer flasks). Glycerol was added to the suspension as cryoprotecteur and 400 µL aliquots were stored at −20° C. and at −80° C.

The storage aliquots of *E. coli* BL21(DE3) containing the pET30A+_UGTSL2 plasmids were thawed and added to 30 mL of LBGKP medium (20 g/L Luria Broth Lennox; 50 mM PIPES buffer pH 7.00; 50 mM Phosphate buffer pH 7.00; 2.5 g/L glucose and 50 mg/L of Kanamycin). This culture was allowed to shake at 135 rpm at 30° C. for 8 h.

The production medium contained 60 g/L of overnight express instant TB medium (Novagen), 10 g/L of glycerol and 50 mg/L of Kanamycin. The preculture was added to 200 mL of this medium and the solution was allowed to stir at 20° C. while taking samples to measure the OD and pH. The culture gave significant growth and a good OD was obtained. After 40 h, the cells were harvested by centrifugation and frozen to obtain 6.22 g of cell wet weight.

Lysis was performed on 1.4 g of cells by addition of Bugbuster Master mix (Novagen) and the lysate was recovered by centrifugation and used fresh.

Example 28

Determination of Activity for Stevioside to Rebaudioside E Conversion with UGTSL and UGTSL2

UGTSL was prepared according to EXAMPLE 22, and UGTSL2 was prepared according to EXAMPLE 27.

Figure 58:
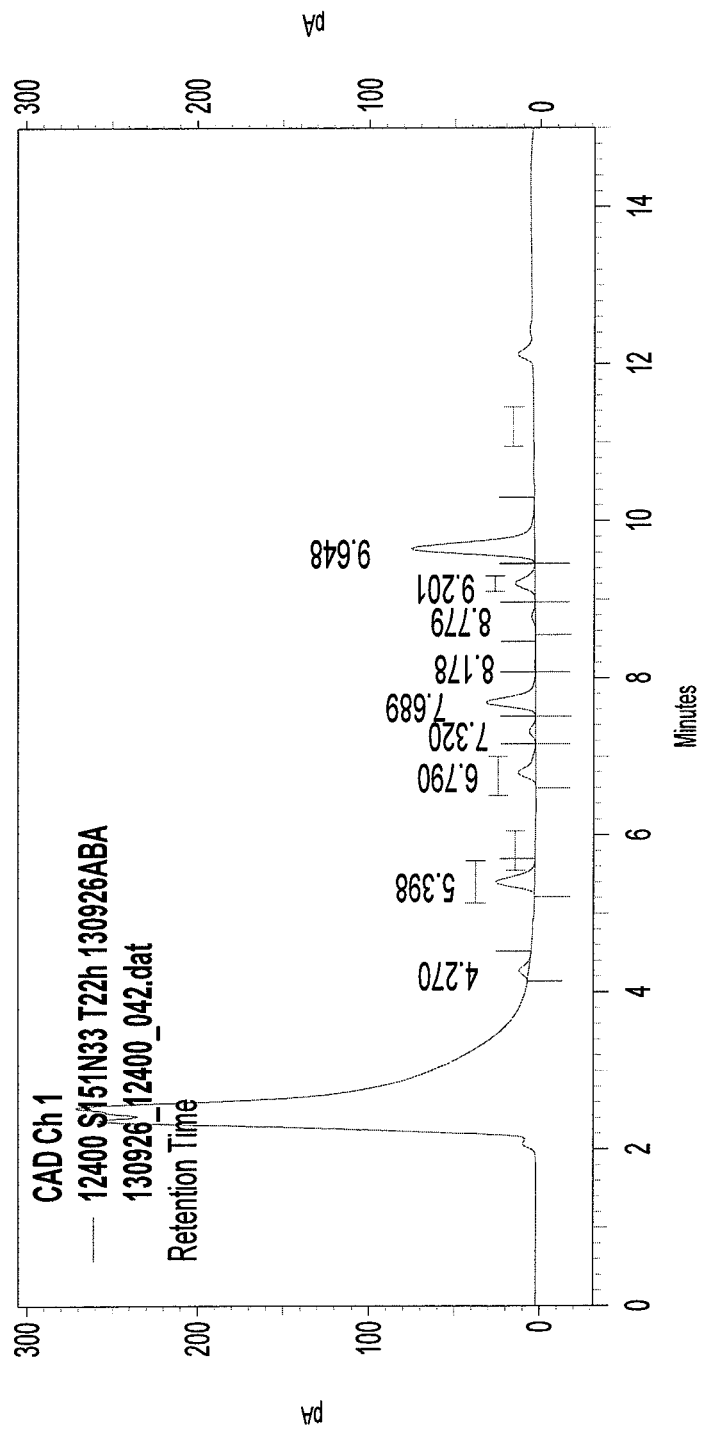
FIG. 58 shows an HPLC (CAD) analysis.
Figure 59:
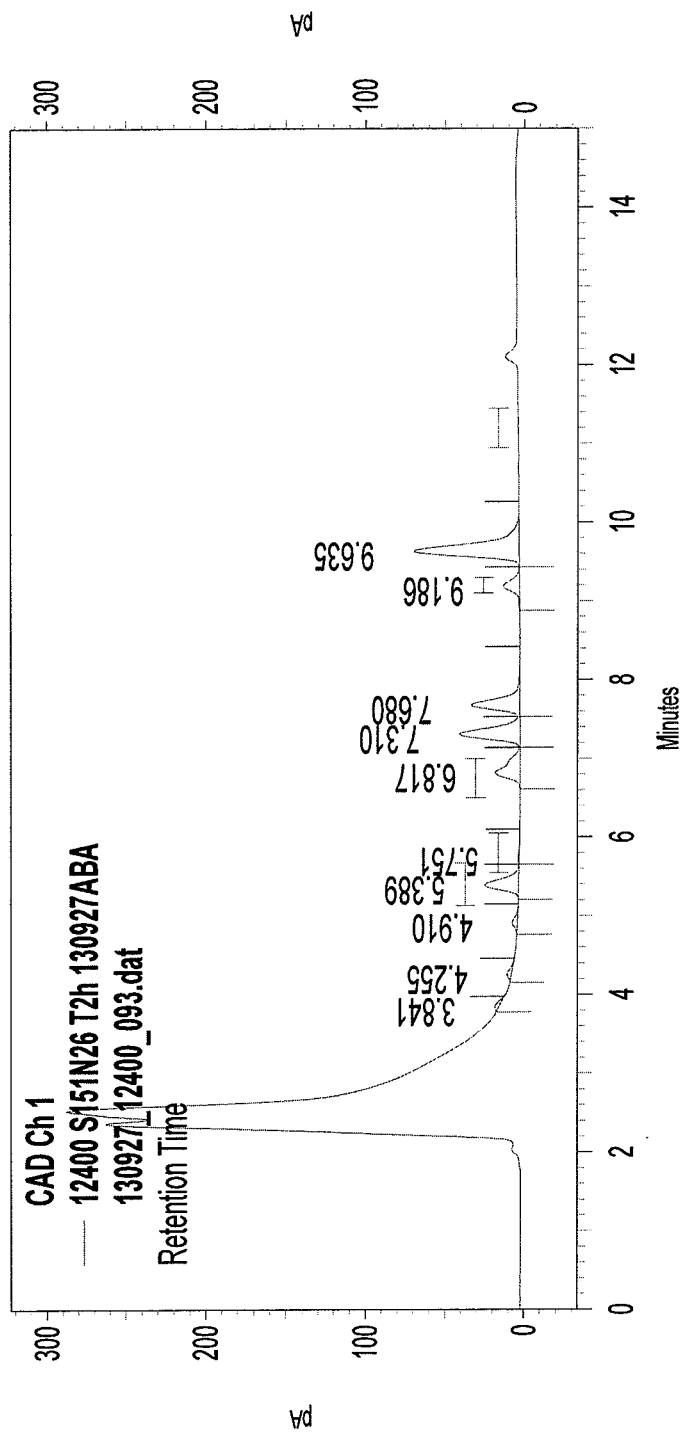
FIG. 59 shows an HPLC (CAD) analysis.

Activity tests were performed at 3 mL scale with 600 µL of lysate for the transformation of Stevioside using 0.5 mM of substrate, 2.5 mM of UDP-Glucose and 3 mM MgCl$_2$ in 50 mM Sodium Phosphate buffer at pH 7.2. Samples were taken and analyzed by HPLC. HPLC Analysis as shown in FIGS. 58-59. The HPLC assay was performed as described in EXAMPLE 20.

The results for the different enzymes and the corresponding chromatograms are provided below.

| Enzyme internal reference | GI Number | Version | Stevioside conv.[1] (reaction time) | Rebaudioside E formation[1] |
|---|---|---|---|---|
| UGTSL | 460409128 | XP_004249992.1 | 74% (22 h.) | 46% |
| UGTSL2 | 460410132 | XP_004250485.1 | 77% (2 h.) | 50% |

Note:
[1]Based on initial concentration of Stevioside

The below table accompanies FIG. 58.

SAMPLE: 12400 S151N33 T22h 130926ABA
Gene references: UGTSL (XP_004249992.1)
Filename: 130926_12400_042.dat
CAD Ch 1 Results

| Compound | Retention time | Integration (area) |
|---|---|---|
| Unknown@RT4.27 | 4.270 | 45,634,692 |
| Rebaudioside E | 5.398 | 215,079,800 |

SAMPLE: 12400 S151N33 T22h 130926ABA
Gene references: UGTSL (XP_004249992.1)
Filename: 130926_12400_042.dat
CAD Ch 1 Results

| Compound | Retention time | Integration (area) |
|---|---|---|
| Unknown@RT6.79 | 6.790 | 11,0326,212 |
| Unknown@RT7.32 | 7.320 | 33,855,010 |
| Unknown@RT7.69 | 7.689 | 271,186,269 |
| Unknown@RT8.18 | 8.178 | 6,003,490 |
| Unknown@RT8.78 | 8.779 | 20,739,231 |
| Stevioside | 9.201 | 114,734,548 |
| Unknown@RT9.65 | 9.648 | 779,225,521 |
| Total | | 1,596,784,773 |

The below table accompanies FIG. 59.

SAMPLE: 12400 S151N26 T2h 130927ABA
Gene references: UGTSL2 (XP_004250485.1)
Filename: 130927_12400_093.dat
CAD Ch 1 Results

| Compound | Retention time | Integration (area) |
|---|---|---|
| Unknown@RT3.84 | 3.841 | 16,182,482 |
| Unknown@RT4.25 | 4.255 | 20,078,830 |
| Unknown@RT4.91 | 4.910 | 27,630,795 |
| Rebaudioside E | 5.389 | 203,768,956 |
| Unknown@RT5.75 | 5.751 | 8,018,638 |
| Unknown@RT6.82 | 6.817 | 200,959,602 |
| Unknown@RT7.31 | 7.310 | 370188401 |
| Unknown@RT7.68 | 7.680 | 294,963,186 |
| Stevioside | 9.186 | 101,729,292 |
| Unknown@RT9.63 | 9.635 | 727,903,255 |
| Total | | 1,971,423,437 |

Example 29

Determination of Activity for Rubusoside to Rebaudioside E Conversion with UGTSL and UGTSL2

UGTSL was prepared according to EXAMPLE 22, and UGTSL2 was prepared according to EXAMPLE 27.

Figure 60:
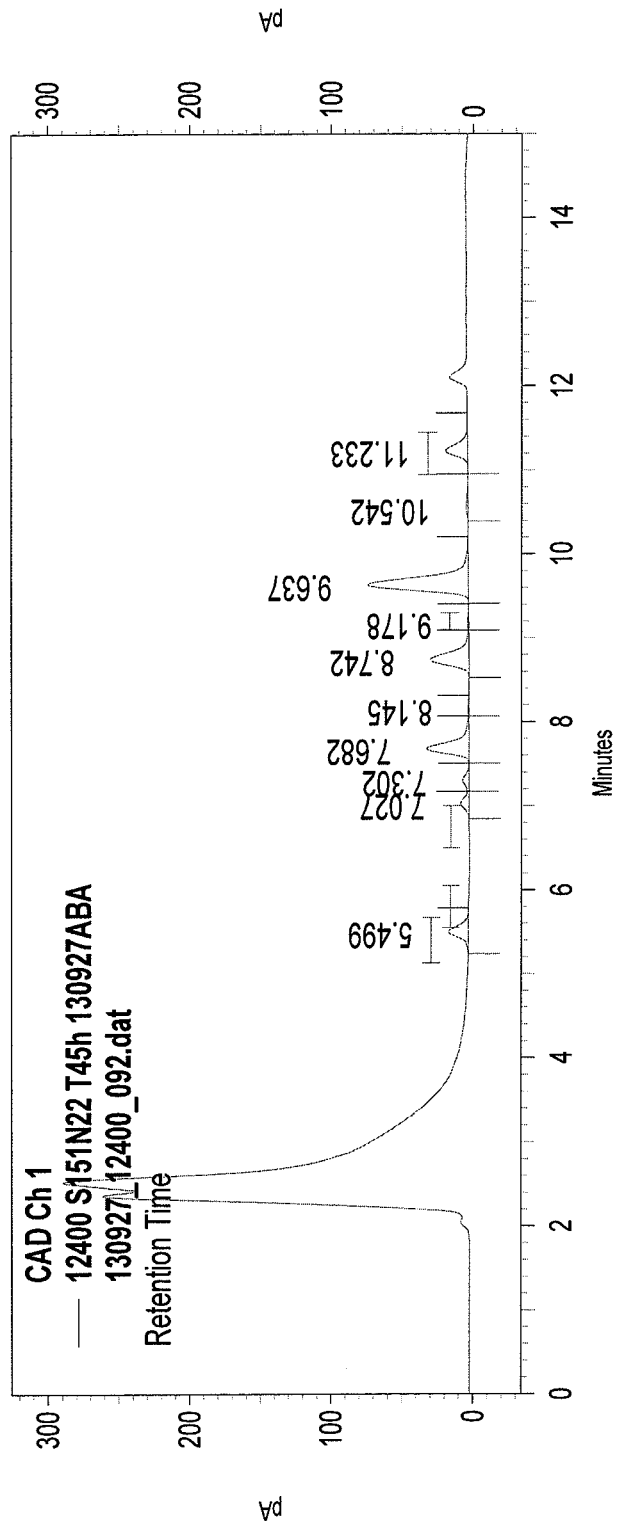
FIG. 60 shows an HPLC (CAD) analysis.
Figure 61:
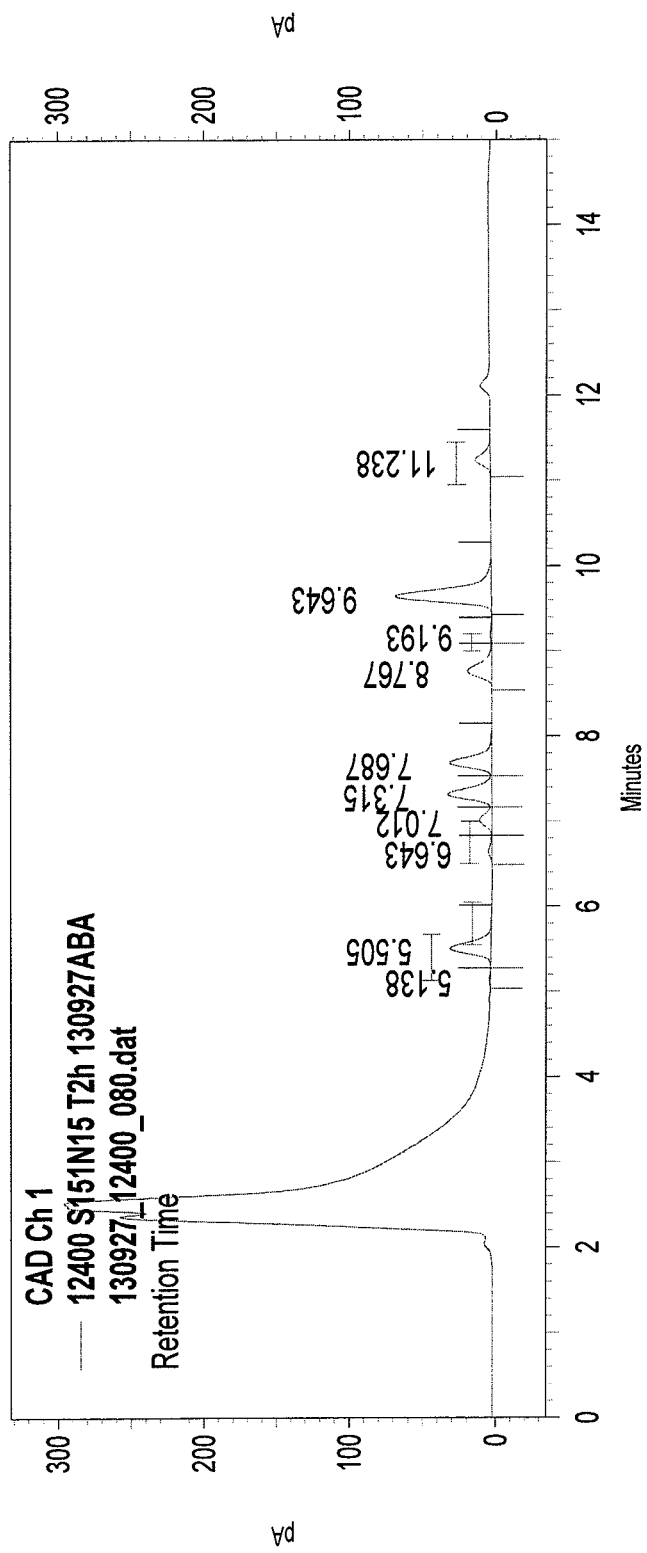
FIG. 61 shows an HPLC (CAD) analysis.

Activity tests were performed at 3 mL scale with 600 μL of lysate for the transformation of Rubusoside using 0.5 mM of substrate, 2.5 mM of UDP-Glucose and 3 mM $MgCl_2$ in 50 mM Sodium Phosphate buffer at pH 7.2. Samples were taken and analyzed by HPLC as shown in FIGS. 60-61. The HPLC assay was performed as described in EXAMPLE 20.

The results for the different enzymes and the corresponding chromatograms are provided below.

| Enzyme internal reference | GI Number | Version | Rubusoside conv.[1] (reaction time) | Rebaudioside E formation[1] |
|---|---|---|---|---|
| UGTSL | 460409128 | XP_004249992.1 | 70% (45 h.) | 27% |
| UGTSL2 | 460410132 | XP_004250485.1 | 80% (2 h.) | 55% |

Note:
[1] Based on initial concentration of Rubusoside

The below table accompanies FIG. 60.

SAMPLE: 12400 S151N22 T45h 130927ABA
Gene references: UGTSL (XP_004249992.1)
Filename: 130927_12400_092.dat
CAD Ch 1 Results

| Compound | Retention time | Integration (area) |
|---|---|---|
| Rebaudioside E | 5.499 | 135,984,743 |
| Unknown@RT7.03 | 7.027 | 54,448,761 |
| Unknown@RT7.30 | 7.302 | 41,308,528 |
| Unknown@RT7.68 | 7.682 | 283,852,603 |
| Unknown@RT8.14 | 8.145 | 5,484,731 |
| Unknown@RT8.74 | 8.742 | 290,946,055 |
| Stevioside | 9.178 | 8,774,098 |
| Unknown@RT9.64 | 9.637 | 761,299,117 |
| Unknown@RT10.54 | 10.542 | 18,276,224 |
| Rubusoside | 11.233 | 155,492,389 |
| Total | | 1,755,867,249 |

The below table accompanies FIG. 61.

SAMPLE: 12400 S151N15 T2h 130927ABA
Gene references: UGTSL2 (XP_004250485.1)
Filename: 130927_12400_080.dat
CAD Ch 1 Results

| Compound | Retention time | Integration (area) |
|---|---|---|
| Unknown@RT5.14 | 5.138 | 5,555,472 |
| Rebaudioside E | 5.505 | 278,529,547 |
| Unknown@RT6.64 | 6.643 | 23,812,633 |
| Unknown@RT7.01 | 7.012 | 84,543,823 |
| Unknown@RT7.31 | 7.315 | 283,724,517 |
| Unknown@RT7.69 | 7.687 | 264,400,008 |
| Unknown@RT8.78 | 8.767 | 188,634,123 |
| Stevioside | 9.193 | 9,365,107 |
| Unknown@RT9.64 | 9.643 | 700,878,865 |
| Rubusoside | 11.238 | 102,484,386 |
| Totals | | 1,941,928,481 |

Example 30

Determination of Activity for Rebaudioside A to Rebaudioside D Conversion with UGTSL2

UGTSL2 was prepared according to EXAMPLE 27.

Figure 62:
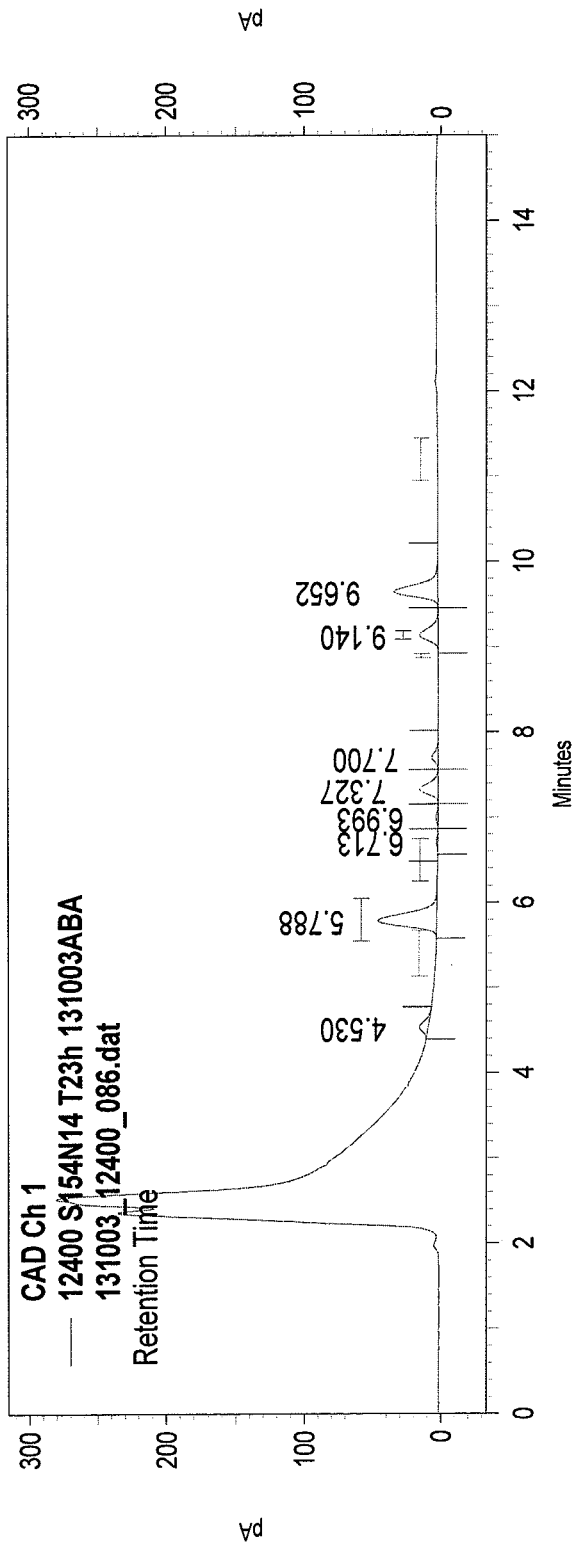
FIG. 62 shows an HPLC (CAD) analysis.

Activity tests were performed at 3 mL scale with 60 μL of lysate for the transformation of Rebaudioside A using 0.5 mM of substrate, 2.5 mM of UDP-Glucose and 3 mM $MgCl_2$ in 50 mM Sodium Phosphate buffer at pH 7.2. Samples were taken and analyzed by HPLC as shown in FIG. 62. The HPLC assay was performed as described in EXAMPLE 20.

The result after 23 h. of reaction and the corresponding chromatogram is provided below.

| Enzyme internal reference | GI Number | Version | Rebaudioside A conv.[1] (reaction time) | Rebaudioside D formation[1] |
|---|---|---|---|---|
| UGTSL2 | 460410132 | XP_004250485.1 | 78% (23 h.) | 75% |

Note:
[1] Based on initial concentration of Rebaudioside A

The below table accompanies FIG. 62.

| SAMPLE: 12400 S154N14 T23h 131003ABA<br>Gene references: UGTSL2 (XP_004250485.1)<br>Filename: 131003_12400_086.dat<br>CAD Ch 1 Results | | |
|---|---|---|
| Compound | Retention time | Integration (area) |
| Unknown@RT4.53 | 4.530 | 55,894,278 |
| Rebaudioside D | 5.788 | 461,768,318 |
| Unknown@RT6.71 | 6.713 | 7,942,480 |
| Unknown@RT6.99 | 6.993 | 11,192,896 |
| Unknown@RT7.33 | 7.327 | 120,255,606 |
| Unknown@RT7.70 | 7.700 | 38,994,186 |
| Rebaudioside A | 9.140 | 137,037,966 |
| Unknown@RT9.65 | 9.652 | 314,468,535 |
| Total | | 1,147,554,265 |

Example 31

Identification of Glycosides

The reaction mixtures prepared according to EXAMPLE 30 and incubated for 45 hrs was analyzed by LC-MS, along with Stevia rebaudiana Bertoni leaf extract "MLD1" produced by PureCircle Sdn Bhd (Malaysia), to determine the occurrence of formed glycosides in nature.

Figure 63:
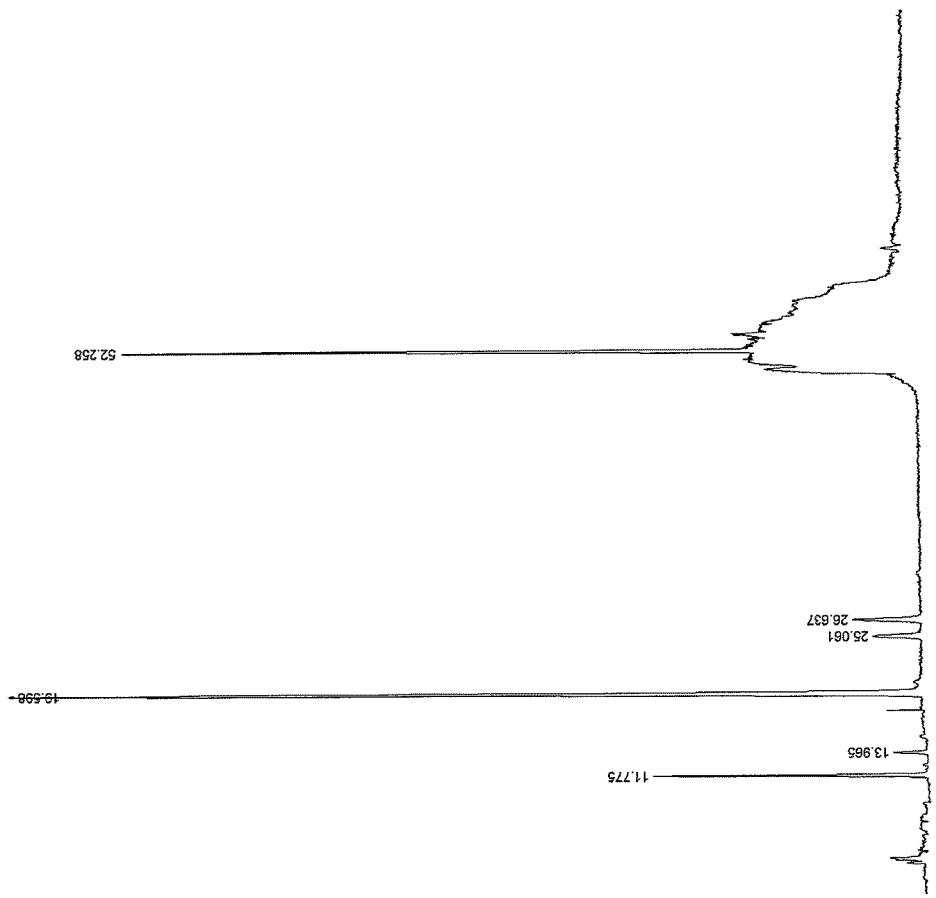
FIG. 63 shows an LCMS chromatogram.

An Agilent 1200 series HPLC system, equipped with binary pump (G1312B), autosampler (G1367D), thermostatted column compartment (G1316B), DAD detector (G1315C), connected with Agilent 6110A MSD, and interfaced with "LC/MSD Chemstation" software, was used, and the chromatogram is shown in FIG. 63.

Instrument Conditions

| Instrument conditions | |
|---|---|
| Column | Phenomenex Prodigy 3u C18 100A,<br>4.6 mm × 250 mm, 3 μm |
| Column Temperature | 55° C. |
| Detection | DAD at 210 nm bw 360 nm<br>MSD (Scan and SIM mode)<br>Mode: ES-API, Negative Polarity<br>Drying gas flow: 13.0 L/min<br>Nebulizer pressure: 30 psig<br>Drying gas temperature: 270° C. |
| Analysis duration | 75 min |
| Injected volume | 10 μL |
| Flow rate | 0.5 mL/min |

Mobile Phase Gradient Program

| Time (min) | A (%): Formic acid 0.1% | B (%): Acetonitrile |
|---|---|---|
| 0 | 75 | 25 |
| 30 | 75 | 25 |
| 33 | 68 | 32 |
| 75 | 68 | 32 |

The assay shows that the compound observed on LC-MS system at 11.77 min is the same as the compound at 3.5 min, in EXAMPLE 23 ($C_{56}H_{90}O_{33}$; later confirmed as reb M2), and the compound observed at 26.64 min is the same as the compound at 7.6 min, in EXAMPLE 23 ($C_{50}H_{80}O_{28}$, reb UNK; later confirmed as reb D2). Other isomers of reb M were observed at 13.96 min and also another isomer form of reb D was observed at 25.06 min. All observed compounds occurred in the extract of Stevia rebaudiana Bertoni plant.

The below table accompanies FIG. 63.

| SAMPLE: UGTSL2 T45h<br>Gene references: UGTSL2 (XP_004250485.1)<br>MSD SIM Results | | |
|---|---|---|
| Compound | Retention time | MW |
| Unknown@RT11.77 | 11.775 | 1,291 |
| Unknown@RT13.96 | 13.965 | 1,291 |
| Rebaudioside D | 19.598 | 1,129 |
| Unknown@RT25.06 | 25.061 | 1,129 |
| Unknown@RT26.64 | 26.637 | 1,129 |
| Rebausioside A | 52.258 | 967 |

Example 32

In Vivo Preparation and Activity Determination of UGTLB

```
                                                SEQ ID 10
UGTLB (GI_209954733 / BAG80557.1) amino acid
sequence
MGTEVTVHKNTLRVLMFPWLAYGHISPFLNVAKKLVDRGFLIYLCSTAIN

LKSTIKKIPEKYSDSIQLIELHLPELPELPPHYHTTNGLPPHLNHTLQKA

LKMSKPNFSKILQNLKPDLVIYDLLQQWAEGVANEQNIPAVKLLTSGAAV

LSYFFNLVKKPGVEFPFPAIYLRKNELEKMSELLAQSAKDKEPDGVDPFA

DGNMQVMLMSTSRIIEAKYIDYFSGLSNWKVVPVGPPVQDPIADDADEME

LIDWLGKKDENSTVFVSFGSEYFLSKEDREEIAFGLELSNVNFIWVARFP

KGEEQNLEDALPKGFLERIGDRGRVLDKFAPQPRILNHPSTGGFISHCGW

NSVMESVDFGVPIIAMPIHLDQPMNARLIVELGVAVEIVRDDYGKIHREE

IAEILKDVIAGKSGENLKAKMRDISKNLKSIRDEEMDTAAEELIQLCKNS

PKLK
```

The pET30A+ vector containing the UGTLB gene was introduced in E. coli Bl21(DE3) by heat shock. The obtained cells were grown in petri-dishes in the presence of Kanamycin and suitable colonies were selected and allowed to grow in liquid LB medium (erlenmeyer flasks). Glycerol was added to the suspension as cryoprotecteur and 400 μL aliquots were stored at −20° C. and at −80° C.

The storage aliquots of E. coli BL21(DE3) containing the pET30A+_UGTLB plasmids were thawed and added to 30 mL of LBGKP medium (20 g/L Luria Broth Lennox; 50 mM PIPES buffer pH 7.00; 50 mM Phosphate buffer pH 7.00; 2.5 g/L glucose and 50 mg/L of Kanamycine). This culture was allowed to shake at 135 rpm at 30° C. for 8 h.

The production medium contained 60 g/L of overnight express instant TB medium (Novagen), 10 g/L of glycerol and 50 mg/L of Kanamycine. The preculture was added to 200 mL of this medium and the solution was allowed to stir at 20° C. while taking samples to measure the OD and pH. The culture gave significant growth and a good OD was obtained. After 40 h, the cells were harvested by centrifugation and frozen to obtain 5.7 g of cell wet weight.

Lysis was performed on 1.2 g of cells by addition of 6 mL Bugbuster Master mix (Novagen) and the lysate was recovered by centrifugation and used fresh.

Figure 64:
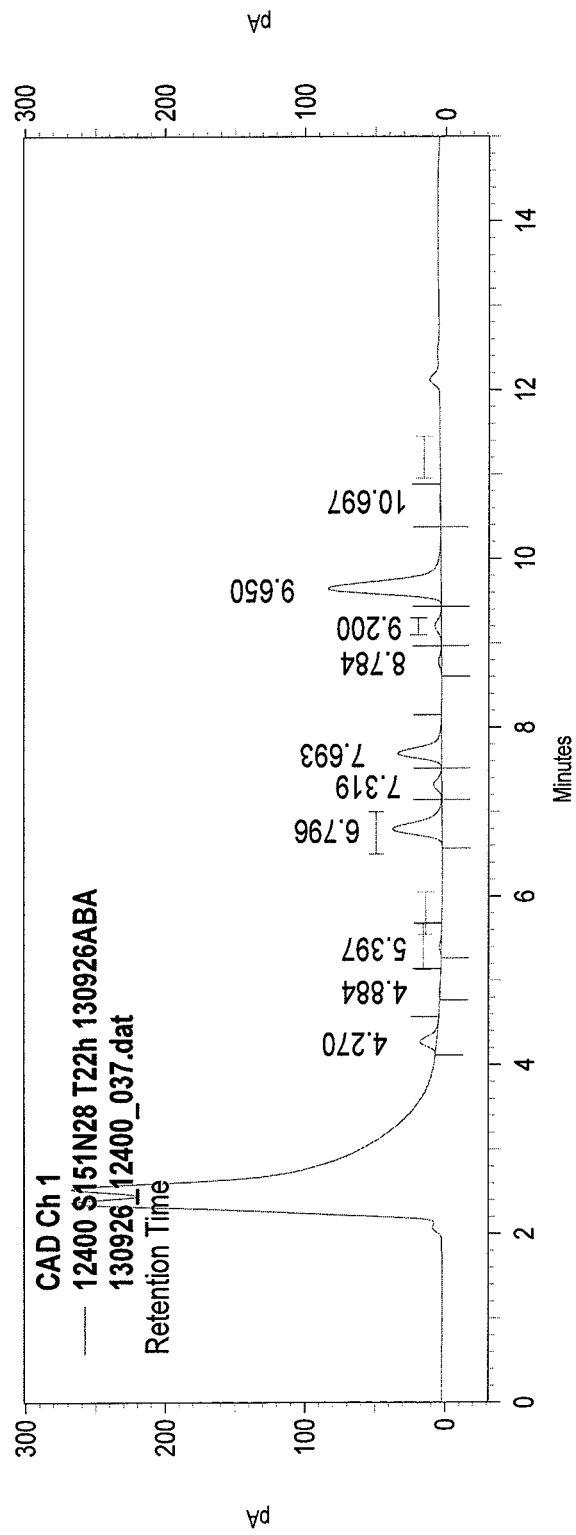
FIG. 64 shows an HPLC (CAD) analysis.
Figure 65:
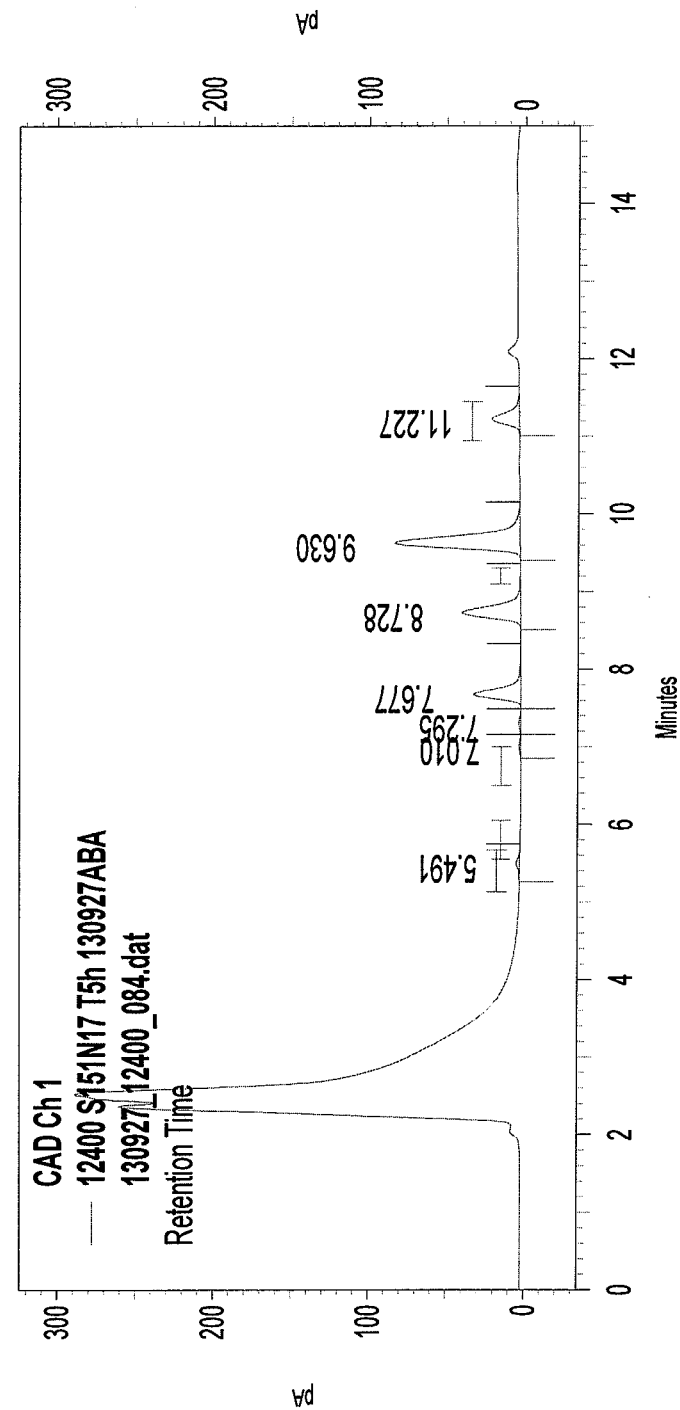
FIG. 65 shows an HPLC (CAD) analysis.
Figure 66:
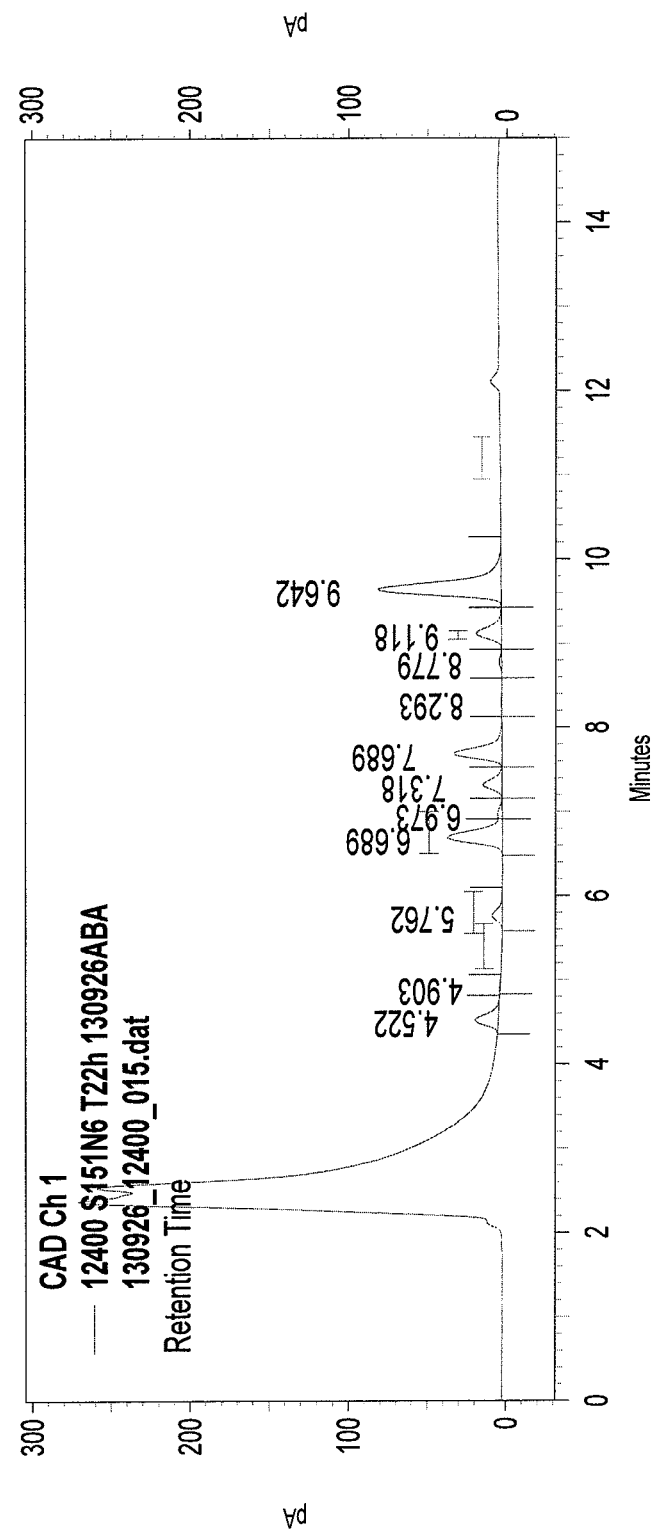
FIG. 66 shows an HPLC (CAD) analysis.

Determination of Activity for Stevioside to Rebaudioside E Conversion with UGTLB Activity tests were performed at 3 mL scale with 600 μL of lysate for the transformation of Stevioside using 0.5 mM of substrate, 2.5 mM of UDP-Glucose and 3 mM MgCl$_2$ in 50 mM Sodium Phosphate buffer at pH 7.2. Samples were taken and analyzed by HPLC as shown in FIGS. 64-66. The corresponding chromatograms are depicted in FIGS. 64-66.

| Enzyme internal reference | GI Number Version | Stevioside conv.[1] (reaction time) | Rebaudioside E formation[1] |
|---|---|---|---|
| UGTLB | 209954733 BAG80557.1 | 89% (22 h.) | 3% |

Note:
[1]Based on initial concentration of Stevioside

The below table accompanies FIG. 64.

SAMPLE: 12400 S151N28 T22h 130926ABA
Gene references: UGTLB (BAG80557.1)
Filename: 130926_12400_037.dat
CAD Ch 1 Results

| Compound | Retention time | Integration (area) |
|---|---|---|
| Unknown@4.27 | 4.270 | 101,580,340 |
| Unknown@4.88 | 4.884 | 2,979,482 |
| Rebaudioside E | 5.397 | 13,747,837 |
| Unknown@6.80 | 6.796 | 378,936,196 |
| Unknown@7.32 | 7.319 | 54,838,779 |
| Unknown@7.69 | 7.693 | 291,189,747 |
| Unknown@8.78 | 8.784 | 21,079,018 |
| Stevioside | 9.200 | 50,143,248 |
| Unknown@9.65 | 9.650 | 888,211,556 |
| Unknown@10.70 | 10.697 | 5,878,160 |
| Totals | | 1,808,584,363 |

Determination of Activity for Rubusoside to Rebaudioside E Conversion with UGTLB Activity tests were performed at 3 mL scale with 600 µL of lysate for the transformation of Rubusoside using 0.5 mM of substrate, 2.5 mM of UDP-Glucose and 3 mM MgCl$_2$ in 50 mM Sodium Phosphate buffer at pH 7.2. Samples were taken and analyzed by HPLC. The corresponding chromatogram is depicted in FIG. 65.

| Enzyme internal reference | GI Number Version | Rubusoside conv.[1] (reaction time) | Rebaudioside E formation[1] |
|---|---|---|---|
| UGTLB | 209954733 BAG80557.1 | 65% (5 h.) | 4% |

Note:
[1]Based on initial concentration of Rubusoside

The below table accompanies FIG. 65.

SAMPLE: 12400 S151N17 T5h 130927ABA
Gene references: UGTLB (BAG80557.1)
Filename: 130927_12400_084.dat
CAD Ch 1 Results

| Compound | Retention time | Integration (area) |
|---|---|---|
| Rebaudioside E | 5.491 | 21921232 |
| Unknown@7.01 | 7.010 | 9764063 |
| Unknown@7.29 | 7.295 | 12510947 |
| Unknown@7.68 | 7.677 | 283386906 |
| Unknown@8.73 | 8.728 | 402240506 |

SAMPLE: 12400 S151N17 T5h 130927ABA
Gene references: UGTLB (BAG80557.1)
Filename: 130927_12400_084.dat
CAD Ch 1 Results

| Compound | Retention time | Integration (area) |
|---|---|---|
| Unknown@9.63 | 9.630 | 878990745 |
| Rubusoside | 11.227 | 176000085 |
| Totals | | 1784814484 |

Determination of Activity for Rebaudioside A to Rebaudioside D Conversion with UGTLB Activity tests were performed at 3 mL scale with 600 µL of lysate for the transformation of Rebaudioside A using 0.5 mM of substrate, 2.5 mM of UDP-Glucose and 3 mM MgCl$_2$ in 50 mM Sodium Phosphate buffer at pH 7.2. Samples were taken and analyzed by HPLC. The corresponding chromatogram after 23 h. of reaction is depicted in FIG. 66.

| Enzyme internal reference | GI Number Version | Rebaudioside A conv.[1] (reaction time) | Rebaudioside D formation[1] |
|---|---|---|---|
| UGTLB | 209954733 BAG80557.1 | 72% (22 h.) | 10% |

Note:
[1]Based on initial concentration of Rebaudioside A

The below table accompanies FIG. 66.

SAMPLE: 12400 S154N6 T22h 130926ABA
Gene references: UGTLB (BAG80557.1)
Filename: 130926_12400_015.dat
CAD Ch 1 Results

| Compound | Retention time | Integration (area) |
|---|---|---|
| Unknown@4.42 | 4.522 | 137,916,950 |
| Unknown@4.90 | 4.903 | 2,015,271 |
| Rebaudioside D | 5.762 | 59,876,764 |
| Unknown@6.69 | 6.689 | 364,185,331 |
| Unknown@6.97 | 6.973 | 26,368,965 |
| Unknown@7.32 | 7.318 | 110,284,197 |
| Unknown@7.69 | 7.689 | 294,579,799 |
| Unknown@8.29 | 8.293 | 7,867,452 |
| Unknown@8.78 | 8.779 | 15,928,550 |
| Rebausioside A | 9.118 | 165,602,247 |
| Unknown@9.64 | 9.642 | 868,327,712 |
| Totals | | 2,052,953,238 |

Example 33

Determination of Reaction Products for Rubusoside and Stevioside Conversion with UGTSL, UGTSL2, and UGTLB Conversion of stevioside with UGTSL and UGTSL2 was conducted in similar manner to Example 28, and the conversion of rubusoside with UGTSL and UGTSL2 was conducted similarly to Example 29. Conversions of rubusoside and stevioside with UGTLB was conducted similarly to Example 32.

The reaction mixtures were analyzed by LCMS to determine all reaction products.

Rubusoside conversion products

| Sample ID | UGT (reaction time) | Rub | Stev | Reb E | Reb D | Unknown peak #1 (MW804) RT 30.70 min | Unknown peak #2 (MW804) RT 49.50 min | Unknown peak #3 (MW804) RT 50.40 min |
|---|---|---|---|---|---|---|---|---|
| S151N15 | UGTSL2 (2 hrs) | 3.54 | 2.12 | 52.88 | 6.73 | 12.02 | 9.94 | 12.77 |
| S151N17 | UGTLB (5 hrs) | 13.49 | ND | 9.21 | 1.29 | 4.07 | 66.67 | 5.27 |
| S151N22 | UGTSL (45 hrs) | 7.82 | 2.37 | 35.88 | 3.45 | 20.38 | 27.75 | 2.35 |

Stevioside conversion products

| Sample ID | UGT (reaction time) | Stev | Reb E | Reb D | Unknown peak #1 (MW966) RT = 22.60 min | Unknown peak #2 (MW966) RT = 26.50 min | Unknown peak #3 (MW966) RT = 29.50 min |
|---|---|---|---|---|---|---|---|
| S151N26 | UGTSL2 (2 hrs) | 20.01 | 42.56 | 1.70 | 4.48 | 5.56 | 25.70 |
| S151N28 | UGTLB (2 hrs) | 43.11 | 3.12 | ND | ND | 53.78 | ND |
| S151N33 | UGTSL (22 hrs) | 25.24 | 49.68 | 0.54 | 3.97 | 20.56 | ND |

It can be seen that amongst Rubusoside conversion products, besides Stevioside, Reb E and Reb D, there are at least 3 additional compounds with Molecular Weight of 804. The retention time of these compounds do not match with Reb B which is known to have same Molecular Weight as Stevioside. Since these compounds have same molecular weight with Stevioside it can be assumed that these novel steviol glycosides are isomers of Stevioside. On the other hand amongst Stevioside conversion products, besides Reb E and Reb D, there are at least 3 additional compounds with Molecular Weight of 966. The retention time of these compounds do not match with Reb A which is known to have same Molecular Weight as Reb E. Since these compounds have same molecular weight with Reb A and Reb E it can be assumed that these novel steviol glycosides are isomers of Reb A (Reb E).

Example 34

In Vivo Production of UGT76G1 in S. cerevisiae

SEQ ID 11
UGT76G1 [Stevia rebaudiana] (gi_37993653 /gb_AAR06912.1)
MENKTETTVRRRRRIILFPVPFQGHINPILQLANVLYSKGFSITIFHTNF

NKPKTSNYPHFTFRFILDNDPQDERISNLPTHGPLAGMRIPIINEHGADE

LRRELELLMLASEEDEEVSCLITDALWYFAQSVADSLNLRRLVLMTSSLF

NFHAHVSLPQFDELGYLDPDDKTRLEEQASGFPMLKVKDIKSAYSNWQIL

KEILGKMIKQTKASSGVIWNSFKELEESELETVIREIPAPSFLIPLPKHL

TASSSSLLDHDRTVFQWLDQQPPSSVLYVSFGSTSEVDEKDFLEIARGLV

DSKQSFLWVVRPGFVKGSTWVEPLPDGFLGERGRIVKWVPQQEVLAHGAI

GAFWTHSGWNSTLESVCEGVPMIFSDFGLDQPLNARYMSDVLKVGVYLEN

GWERGEIANAIRRVMVDEEGEYIRQNARVLKQKADVSLMKGGSSYESLES

LVSYISSL

The above mentioned amino acid sequence was codon optimized for expression in S. cerevisiae. Furthermore the yeast consensus sequence AACACA was added before the ATG start codon. The synthetic gene was subcloned in the pYES2 vector using Hind III and Xba I restriction sites. The pYES2_UGT76G1_Sc vector was used to transform chemically competent S. cerevisiae INVSc1 cells (Invitrogen).

The cells were grown on a solid synthetic minimal medium containing 2% glucose lacking Uracil and a single colony was picked and allowed to grow in liquid synthetic minimal medium lacking Uracil (SC-U containing 2% glucose). After centrifugation, the cells were suspended with SC-U (containing 2% glucose) and 60% glycerol/water. Aliquots were stored at −80° C. and one aliquot was used to start a culture in SC-U (containing 2% glucose) for 43 h at 30° C. Part of this culture was centrifuged and suspended in induction medium (SC-U containing 2% galactose) for 19 h30 at 30° C.

Cells were obtained by centrifugation and lysis with five volumes of CelLytic™ Y Cell Lysis Reagent (Sigma). The lysates were used directly for activity testing (UGT76G1_Sc).

Example 35

Figure 67:
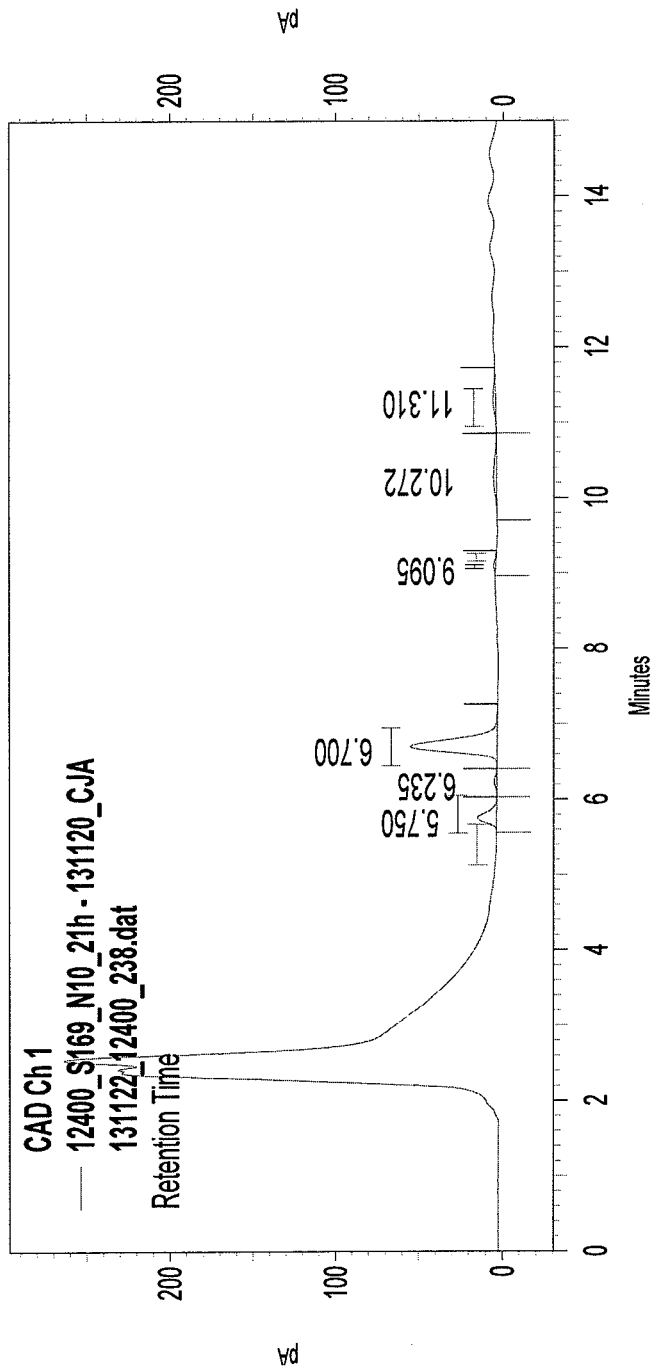
FIG. 67 shows an HPLC (CAD) analysis.

Determination of Activity of UGT76G1_Sc for the Conversion of Rebaudioside D to Rebaudioside M UGT76G1_Sc was prepared according to EXAMPLE 34. Activity tests were performed at 2 mL scale with 200 μL of lysate for the transformation of Rebaudioside D using 0.5 mM of substrate, 2.5 mM of UDP-Glucose and 3 mM $MgCl_2$ in 50 mM Sodium Phosphate buffer at pH 7.2. Samples were taken and analyzed by HPLC as shown in FIG. 67. The corresponding chromatogram is depicted in FIG. 67.

| Enzyme internal reference | Rebaudioside D conv.[1] (reaction time) | Rebaudioside M selectivity[1] |
|---|---|---|
| UGT76G1_Sc | 85% (21 h.) | 100% |

Note:
[1] Based on initial concentration of Rebaudioside D

The below table accompanies FIG. 67.

SAMPLE: 12400 S169N10 T21h 131119CJA
Gene references: UGT76G1_Sc
Filename: 131122_12400_238.dat
CAD Ch 1 Results

| Compound | Retention time | Integration (area) |
|---|---|---|
| Rebaudioside D | 5.750 | 112,094,430 |
| Unknown@6.23 | 6.235 | 17,886,043 |
| Rebaudioside M | 6.700 | 616,583,935 |
| Rebaudioside A | 9.095 | 11,183,884 |
| Unknown@10.27 | 10.272 | 62,863,156 |
| Unknown@11.31 | 11.310 | 35,839,478 |
| Total | | 856,450,926 |

Example 36

In Vivo Production of UGTSL in *S. cerevisiae*

```
                                                 SEQ ID 12
UGTSL [Solanum lycopersicum] (gi_460409128 / XP_
004249992.1
MSPKLHKELFFHSLYKKTRSNHTMATLKVLMFPPFLAYGHISPYLNVAKKL

ADRGFLIYFCSTPINLKSTIEKIPEKYADSIHLIELHLPELPQLPPHYHT

TNGLPPNLNQVLQKALKMSKPNFSKILQNLKPDLVIYDILQRWAKHVANE

QNIPAVKLLTSGAAVFSYFFNVLKKPGVEFPFPGIYLRKIEQVRLSEMMS

KSDKEKELEDDDDDDDLLVDGNMQIMLMSTSRTIEAKYIDFCTALTNWKV

VPVGPPVQDLITNDVDDMELIDWLGTKDENSTVFVSFGSEYFLSKEDMEE

VAFALELSNVNFIWVARFPKGEERNLEDALPKGFLERIGERGRVLDKFAP

QPRILNHPSTGGFISHCGWNSAMESIDFGVPIIAMPMHLDQPMNARLIVE

LGVAVEIVRDDDGKIHRGEIAETLKGVITGKTGEKLRAKVRDISKNLKTI

RDEEMDAAAEELIQLCRNGN
```

The above mentioned amino acid sequence was codon optimized for expression in *S. cerevisiae*. Furthermore the yeast consensus sequence AACACA was added before the ATG start codon. The synthetic gene was subcloned in the pYES2 vector using Hind III and Xba I restriction sites. The pYES2_UGTSL_Sc vector was used to transform chemically competent *S. cerevisiae* INVSc1 cells (Invitrogen).

The cells were grown on a solid synthetic minimal medium containing 2% glucose, lacking Uracil and a single colony was picked and allowed to grow in liquid synthetic minimal medium lacking Uracil (SC-U containing 2% glucose). After centrifugation, the cells were suspended with SC-U (containing 2% glucose) and 60% glycerol/water. Aliquots were stored at −80° C. and one aliquot was used to start a culture in SC-U (containing 2% glucose) for 43 h at 30° C. Part of this culture was centrifuged and suspended in induction medium (SC-U containing 2% galactose) for 19 h30 at 30° C.

Cells were obtained by centrifugation and lysis with five volumes of CelLytic™ Y Cell Lysis Reagent (Sigma). The lysates were used directly for activity testing (UGTSL_Sc).

Example 37

Figure 68:
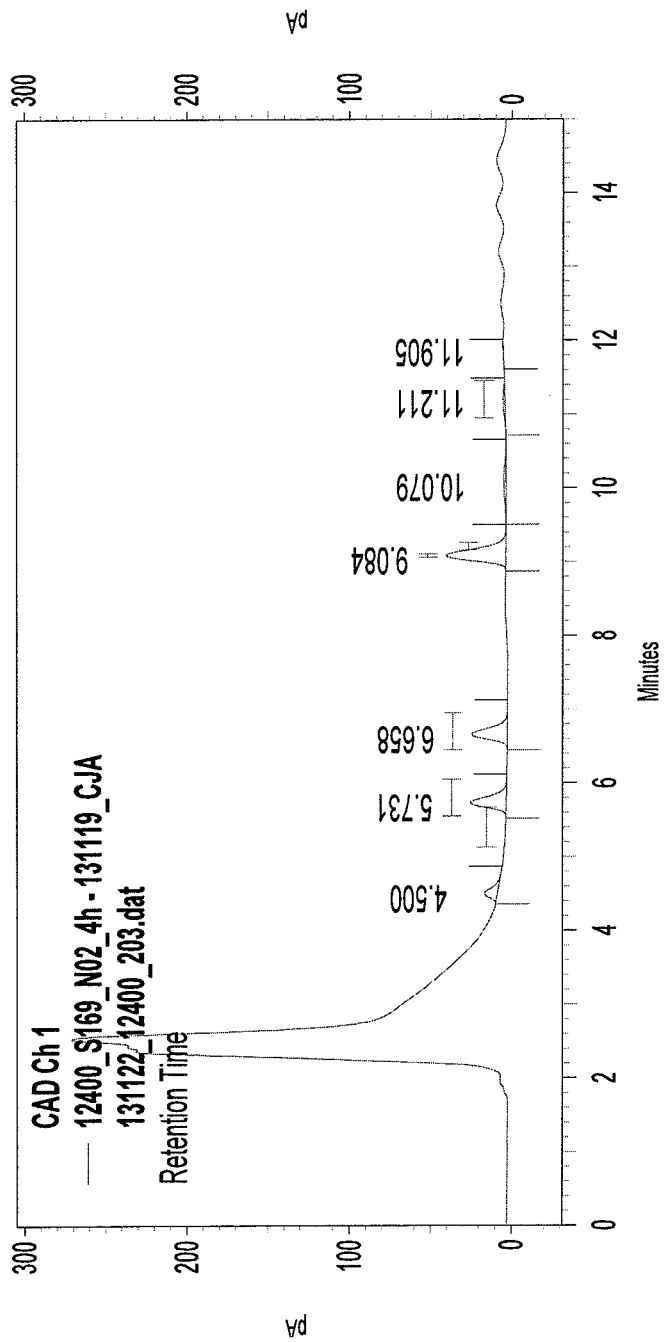
FIG. 68 shows an HPLC (CAD) analysis.

Determination of Activity of UGTSL_Sc for the Conversion of Rebaudioside A to Rebaudioside D UGTSL_Sc was prepared according to EXAMPLE 36. Activity tests were performed at 2 mL scale with 200 µL of lysate for the transformation of Rebaudioside A using 0.5 mM of substrate, 2.5 mM of UDP-Glucose and 3 mM MgCl$_2$ in 50 mM Sodium Phosphate buffer at pH 7.2. Samples were taken and analyzed by HPLC as shown in FIG. 68. The corresponding chromatogram is depicted in FIG. 68.

| Enzyme internal reference | Rebaudioside A conv.[1] (reaction time) | Rebaudioside D selectivity[1] |
|---|---|---|
| UGTSL_Sc | 46% (4 h) | 42% |

Note:
[1] Based on initial concentration of Rebaudioside A

The below table accompanies FIG. 68.

SAMPLE: 12400 S169N02 T4h 131119CJA
Gene references: UGTSL_Sc
Filename: 131122_12400_203.dat
CAD Ch 1 Results

| Compound | Retention time | Integration (area) |
|---|---|---|
| Unknown@4.50 | 4.500 | 75,046,986 |
| Rebaudioside D | 5.731 | 223,409,643 |
| Unknown@6.66 | 6.658 | 228,651,278 |
| Rebaudioside A | 9.084 | 404,642,305 |
| Unknown@10.08 | 10.079 | 43,992,253 |
| Unknown@11.21 | 11.211 | 29,776,761 |
| Unknown@11.90 | 11.905 | 2,185,316 |
| Total | | 1,007,704,542 |

Example 38

Isolation of Rebaudioside M

The amount of the product mixture of Example 14 was not large enough to separate via preparative HPLC methods. Accordingly, analytical HPLC with a series of injections was used to separate the components of the mixture. Separation was conducted according to the method described above in Example 14 to provide two fractions corresponding to the two main peaks in the HPLC trace of FIG. 5: Fraction A (retention time 24.165 minutes) and Fraction B (retention time 31.325 minutes).

The retention time of Fraction A was consistent with reb D, indicating unreacted starting material from the biotransformation reaction.

Figure 6:
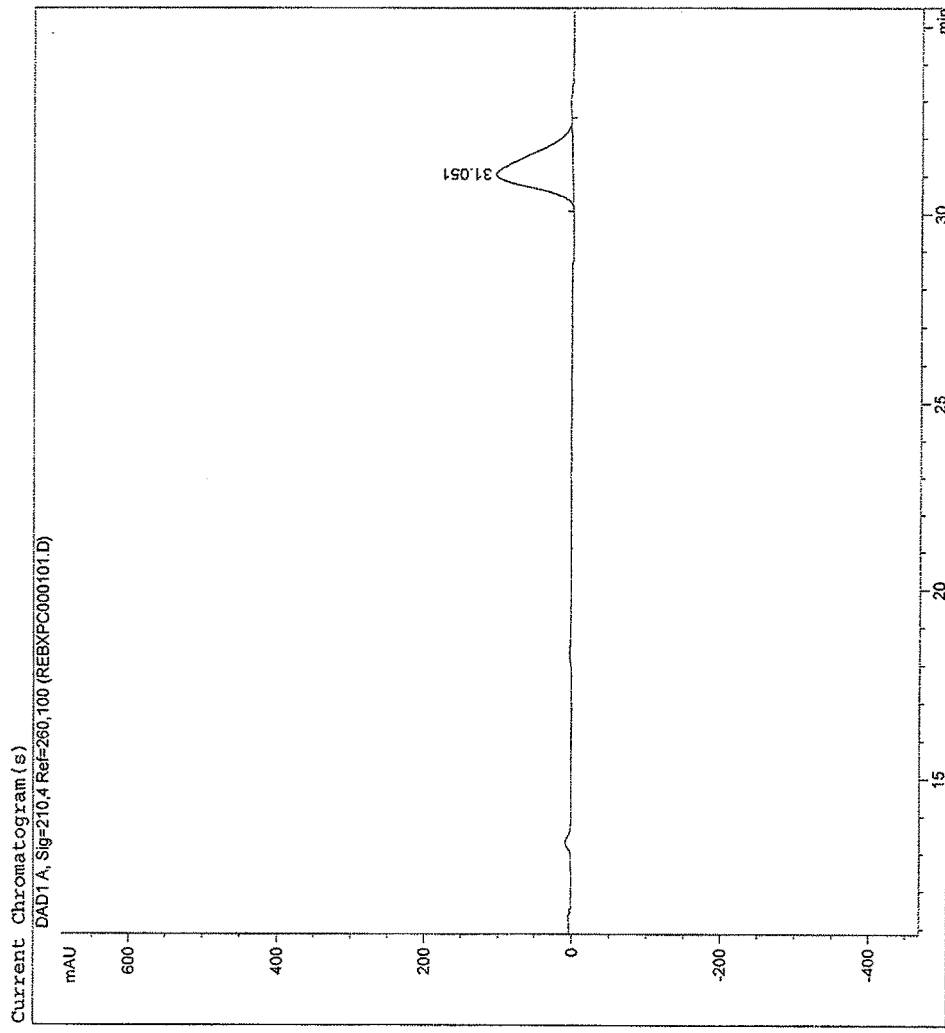
FIG. 6. shows the HPLC chromatogram of purified reb M produced by biocatalysts from reb D.
Figure 7:
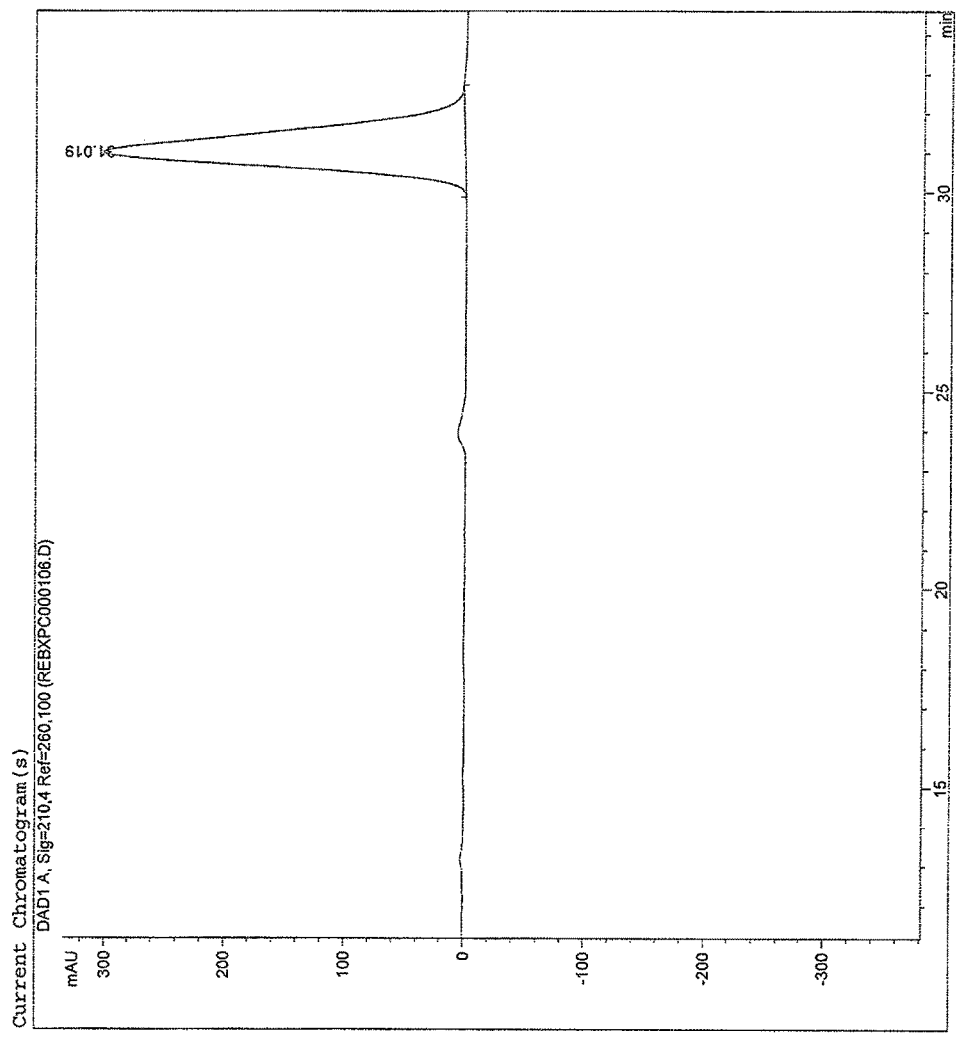
FIG. 7 shows the HPLC chromatogram of a reb M standard.
Figure 8:
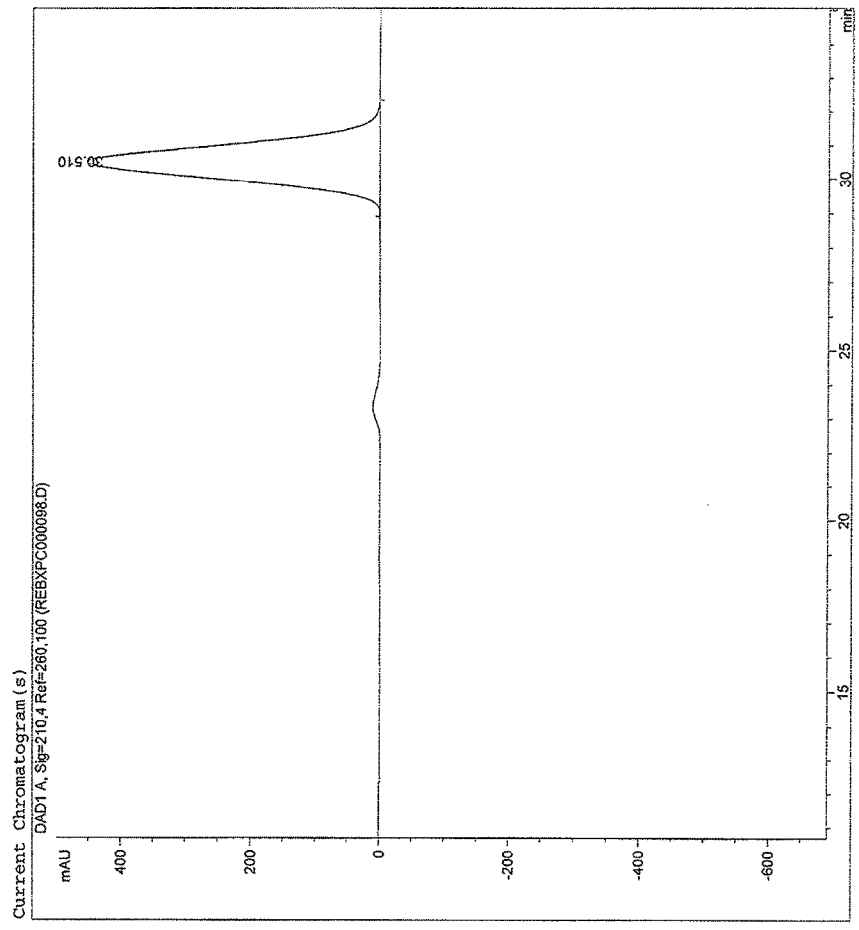
FIG. 8 shows the HPLC chromatogram of co-injection of a reb M standard and reb M purified from biotransformation from reb D.

The retention time of purified Fraction B (FIG. 6) was consistent with reb M, indicating successful biotransformation from reb D. The identity of the material collected in Fraction B as reb M was confirmed by co-injection of purified Fraction B with a reb M standard (available from PureCircle, HPLC trace of reb M standard shown in FIG. 7). Both Fraction B and the reb M standard were found to elute at the same retention time (FIG. 8), indicating Fraction B was reb M.

The identity of Fraction B as reb M was also separately confirmed by NMR and HRMS. For sampling, Fraction B was concentrated under rotary evaporator, freeze dried and dried for 40 h at 40° C.

Figure 9:
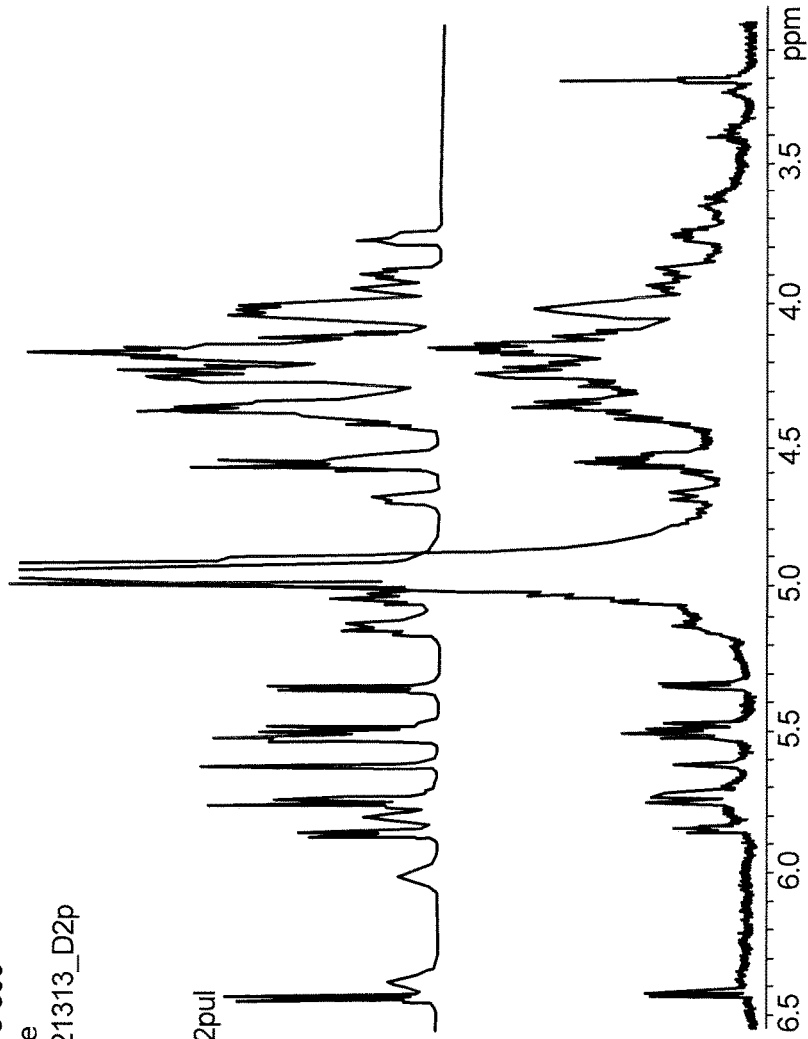
FIG. 9 shows an overlay of the $^1$H NMR spectra of a reb M standard and reb M purified following biosynthesis from reb D.

The NMR sample was dissolved in deuterated pyridine ($C_5D_5N$) and spectra were acquired on a Varian Unity Plus 600 MHz instrument using standard pulse sequences. The NMR spectra of Fraction B was compared to the NMR spectra of reb M. An overlay of the two spectra (FIG. 9) showed consistency of peaks of Fraction B with reb M. A table of the NMR assignments for reb M is shown below:

| $^1H$ and $^{13}C$ NMR spectral data for Rebaudioside M in $C_5D_5N$ [a-c]. | | |
|---|---|---|
| Position | $^{13}C$ NMR | $^1H$ NMR |
| 1 | 40.3 | 0.75 t (13.2) |
|  |  | 1.76 m |
| 2 | 19.6 | 1.35 m |
|  |  | 2.24 m |
| 3 | 38.4 | 1.01 m |
|  |  | 2.30 d (13.3) |
| 4 | 44.3 | — |
| 5 | 57.4 | 1.06 d (12.8) |
| 6 | 23.5 | 2.23 m |
|  |  | 2.41 q (13.2) |
| 7 | 42.6 | 1.41 m |
|  |  | 1.80 m |
| 8 | 41.2 | — |
| 9 | 54.3 | 0.91 d (7.7) |
| 10 | 39.7 | — |
| 11 | 20.2 | 1.65 m |
|  |  | 1.75 m |
| 12 | 38.5 | 1.86 m |
|  |  | 2.73 m |
| 13 | 87.6 | — |
| 14 | 43.3 | 2.02 m |
|  |  | 2.74 m |
| 15 | 46.5 | 1.88 d (16.4) |
|  |  | 2.03 m |
| 16 | 153.3 | — |
| 17 | 104.9 | 4.90 s |
|  |  | 5.69 s |
| 18 | 28.2 | 1.32 s |
| 19 | 176.9 | — |
| 20 | 16.8 | 1.38 s |
| 1' | 94.9 | 6.39 d (8.2) |
| 2' | 76.9 | 4.51 t (8.5) |
| 3' | 88.6 | 5.09 t (8.5) |
| 4' | 70.1 | 4.18 m |
| 5' | 78.4 | 4.13 m |
| 6' | 61.8 | 4.20 m |
|  |  | 4.31 m |
| 1'' | 96.2 | 5.46 d (7.1) |
| 2'' | 81.4 | 4.13 m |
| 3'' | 87.9 | 4.98 t (8.5) |
| 4'' | 70.4 | 4.07 t (9.6) |
| 5'' | 77.7 | 3.94 m |
| 6'' | 62.6 | 4.19 m |
|  |  | 4.32 m |
| 1''' | 104.8 | 5.48 d (7.7) |
| 2''' | 75.8 | 4.15 m |
| 3''' | 78.6 | 4.13 m |
| 4''' | 73.2 | 3.98 m |
| 5''' | 77.6 | 3.74 ddd (2.8, 6.4, 9.9) |
| 6''' | 64.0 | 4.27 m |
|  |  | 4.51 m |
| 1'''' | 103.9 | 5.45 d (7.5) |
| 2'''' | 75.6 | 3.98 m |
| 3'''' | 77.8 | 4.50 t (7.8) |
| 4'''' | 71.3 | 4.14 m |
| 5'''' | 78.0 | 3.99 m |
| 6'''' | 62.1 | 4.20 m |
|  |  | 4.32 m |
| 1''''' | 104.2 | 5.81 d (7.2) |
| 2''''' | 75.5 | 4.20 m |
| 3''''' | 78.4 | 4.20 m |
| 4''''' | 73.6 | 4.10 m |
| 5''''' | 77.8 | 3.90 ddd (2.8, 6.4, 9.9) |
| 6''''' | 64.0 | 4.32 m |
|  |  | 4.64 d (10.3) |
| 1'''''' | 104.1 | 5.31 d (8.0) |
| 2'''''' | 75.5 | 3.95 m |
| 3'''''' | 78.0 | 4.37 t (9.1) |
| 4'''''' | 71.1 | 4.10 m |
| 5'''''' | 78.1 | 3.85 ddd (1.7, 6.1, 9.9) |
| 6'''''' | 62.1 | 4.10 m |
|  |  | 4.32 m |

[a] assignments made on the basis of COSY, HMQC and HMBC correlations;
[b] Chemical shift values are in δ (ppm);
[c] Coupling constants are in Hz.

Figure 10:
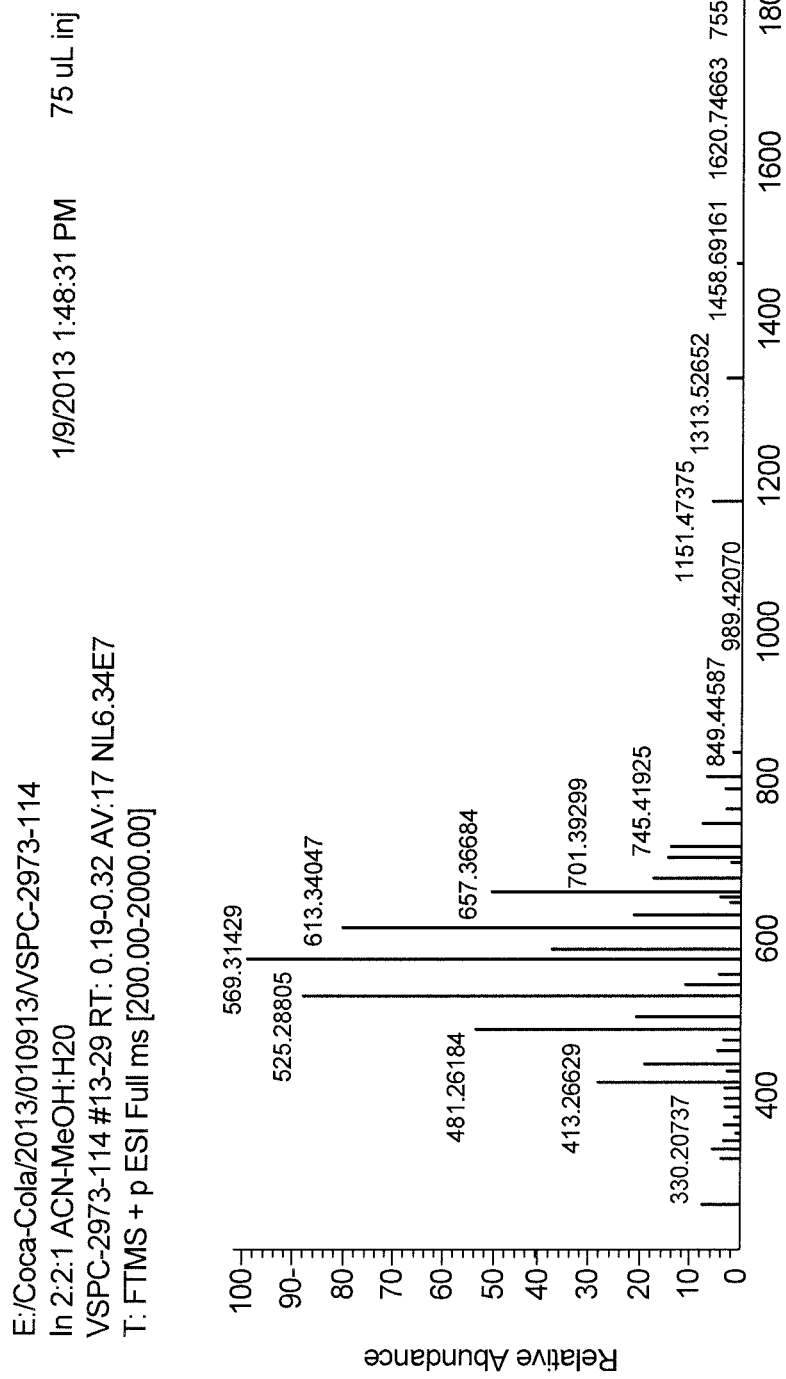
FIG. 10 shows the HRMS spectrum of reb M purified following biocatalytic production from reb D.

HRMS (FIG. 10) was generated with a Waters Premier Quadropole Time-of-Flight (Q-TOF) mass spectrometer equipped with an electrospray ionization source operated in the positive-ion mode. The sample was dissolved in methanol and eluted in 2:2:1 methanol: acetonitrile: water and introduced via infusion using the onboard syringe pump. The presence of reb M was confirmed by a [M+Na]$^+$ adduct at m/z 1313.5265, which corresponds to a molecular formula of $C_{56}H_{90}O_{33}$

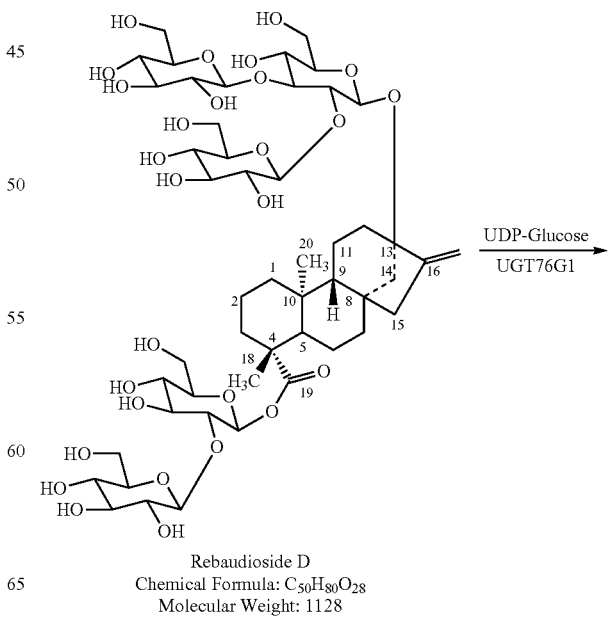

Rebaudioside D
Chemical Formula: $C_{50}H_{80}O_{28}$
Molecular Weight: 1128

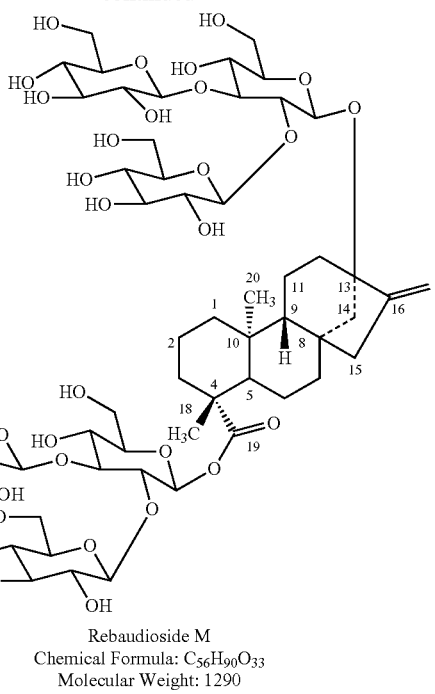

Rebaudioside M
Chemical Formula: $C_{56}H_{90}O_{33}$
Molecular Weight: 1290

Example 39

Isolation and Characterization of Reb D2

Crude Reaction Sample.

The sample, Lot CB-2977-106, used for isolation, was prepared according to Example 22 with UGTSL (GI #460409128).

HPLC Analysis.

Preliminary HPLC analyses of samples were performed using a Waters 2695 Alliance System with the following method: Phenomenex Synergi Hydro-RP, 4.6×250 mm, 4 µm (p/n 00G-4375-E0); Column Temp: 55° C.; Mobile Phase A: 0.0284% ammonium acetate ($NH_4OAc$) and 0.0116% acetic acid (HOAc) in water; Mobile Phase B: Acetonitrile (MeCN); Flow Rate: 1.0 mL/min; Injection volume: 10 µL. Detection was by UV (210 nm) and CAD.

Gradient:

| Time (min) | % A | % B |
| --- | --- | --- |
| 0.0-8.5 | 75 | 25 |
| 10.0 | 71 | 29 |
| 16.5 | 70 | 30 |
| 18.5-24.5 | 66 | 34 |
| 26.5-29.0 | 48 | 52 |
| 31-37 | 30 | 70 |
| 38 | 75 | 25 |

Analyses of semi-preparative purification fractions were performed with the following method: Waters Atlantis dC18, 4.6×100 mm, 5 µm (p/n 186001340); Mobile Phase A: 25% MeCN in water; Mobile Phase B: 30% MeCN in water; Flow Rate: 1.0 mL/min; Injection volume: 10 µL. Detection was by CAD.

Gradient:

| Time (min) | % A | % B |
| --- | --- | --- |
| 0.0-5.0 | 100 | 0 |
| 20 | 20 | 80 |
| 25 | 20 | 80 |
| 30 | 100 | 0 |

LC-MS.

Preliminary analysis of the semi-synthetic steviol glycoside mixture was carried out on a Waters AutoPurification HPLC/MS System with a Waters 3100 Mass Detector operating in negative ion mode. Analysis of the sample was performed using the following method: Phenomenex Synergi Hydro-RP, 4.6×250 mm, 4 µm (p/n 00G-4375-E0); Column Temp: 55° C.; Mobile Phase A: 0.0284% $NH_4OAc$ and 0.0116% HOAc in water; Mobile Phase B: Acetonitrile; Flow Rate: 1.0 mL/min; Injection volume: 10 µL. Detection was by UV (210 nm), and MSD (−ESI m/z 500-2000). Gradient conditions were as listed above.

Isolation by HPLC.

The purification was performed in two steps. The first method used for the semi-preparative purification is summarized below. Column: Waters Atlantis dC18, 30×100 mm, 5 (p/n 186001375); Mobile Phase A: 25% MeCN in water; Mobile Phase B: 30% MeCN in water; Flow Rate: 45 mL/min; Injection load: 160 mg dissolved in 20 mL of water. Detection was by UV (205 nm).

Gradient:

| Time (min) | % A | % B |
| --- | --- | --- |
| 0.0-5.0 | 100 | 0 |
| 20 | 20 | 80 |
| 25 | 20 | 80 |
| 30 | 100 | 0 |

The secondary purification used the same column and conditions, but isocratic mobile phase: 20% MeCN in water.

Purification from Natural Extracts.

The purification was performed in three steps. The first method used for the preparative purification is summarized below. Primary Process: Waters Symmetry C18, 50×250 mm, 7 µm (p/n WAT248000); Isocratic mobile phase: 50% methanol (MeOH) in water with 0.05% HOAc; Flow Rate: 85 mL/min; Injection load: 6 g crude extract dissolved in 50 mL of mobile phase. Detection was by UV (210 nm). Following the elution of target analytes, the column was flushed with 85% MeOH in water.

Secondary Process: Waters Symmetry Shield RP18, 50×250 mm, 7 µm (p/n WAT248000); Isocratic mobile phase: 20% MeCN in water; Flow Rate: 100 mL/min; Injection load: 0.5 g primary fraction dissolved in 30 mL of water. Detection was by UV (210 nm).

Tertiary Process: Waters Symmetry Shield RP18, 50×250 mm, 7 µm (p/n WAT248000); Isocratic mobile phase: 20% MeCN in water; Flow Rate: 100 mL/min; Injection load: 0.5 g secondary fraction dissolved in 30 mL of water. Detection was by UV (210 nm).

MS and MS/MS.

MS and MS/MS data were generated with a Waters QT of Premier mass spectrometer equipped with an electrospray ionization source. Samples were analyzed by negative ESI. Samples were diluted with $H_2O$:acetonitrile (1:1) by 50 fold and introduced via infusion using the onboard syringe pump. The samples were diluted to yield good s/n which occurred at an approximate concentration of 0.01 mg/mL.

NMR.

The sample was prepared by dissolving 1-2 mg in 150 μL of pyridine-$d_5$ and NMR data were acquired on a Bruker Avance 500 MHz instrument with a 2.5 mm inverse detection probe. The NMR spectrum was referenced to the residual solvent signal ($\delta_H$ 8.74 and $\delta_C$ 150.35 for pyridine-$d_5$).

Results and Discussion

Isolation and Purification.

Figure 11:
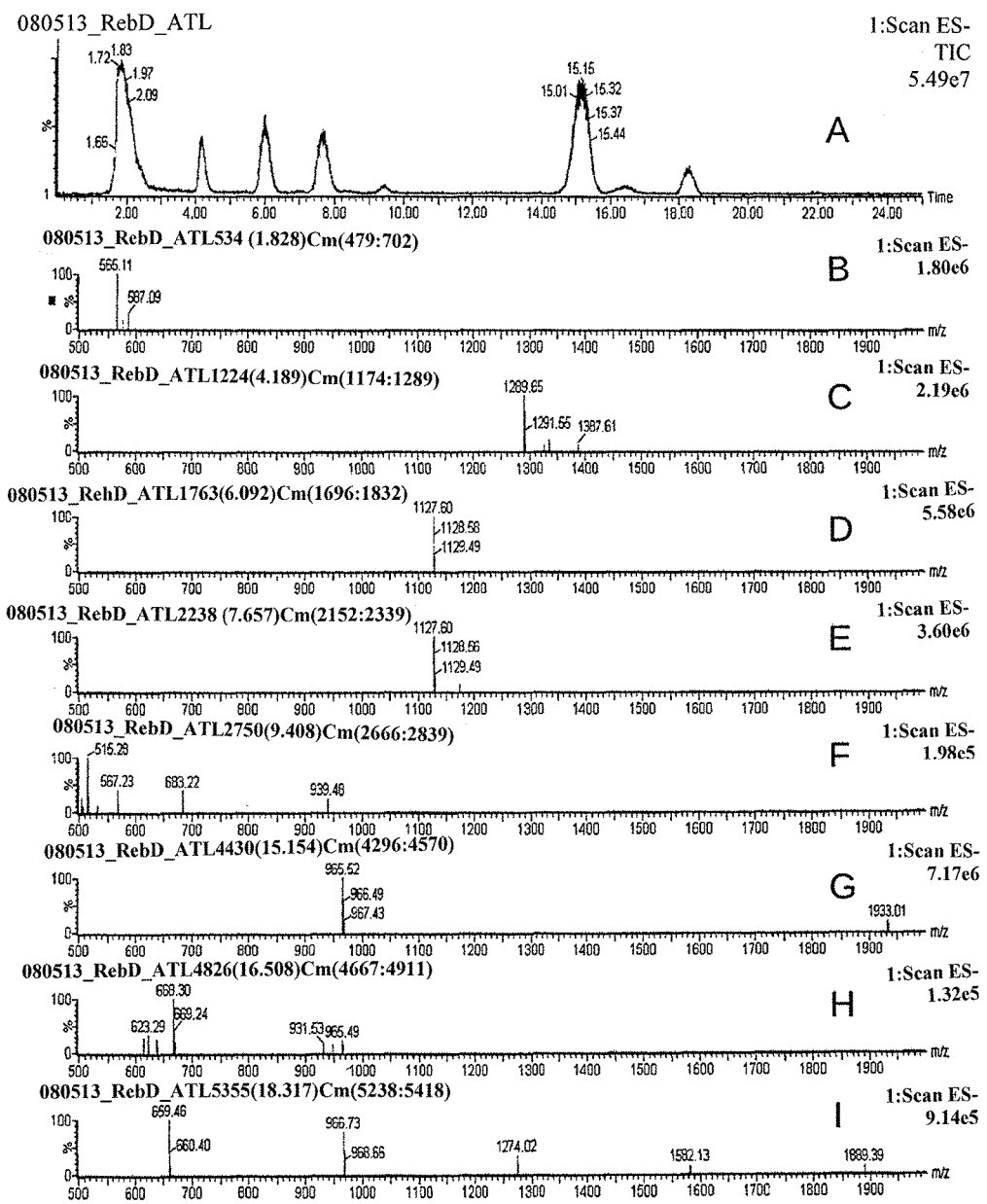
FIG. 11 shows LC-MS analysis of semi-synthetic steviol glycoside mixture, Lot number CB-2977-106, showing TIC (A), MS of peak at 1.8 min (B), MS of reb M2 peak at 4.1 min (C), MS of reb D peak at 6.0 min (D), MS of reb D2 peak at 7.7 min (E), MS of peak at 9.4 min (F), MS of rebaudioside A peak at 15.2 min (G), MS of peak at 16.5 min (H), and MS of peak at 18.3 min (I).

Isolation was performed on steviol glycoside mixture, Lot number CB-2977-106, prepared according to Example 22 with UGTSL (GI #460409128) The material was analyzed by LC-MS using the method described above and results are provided in FIG. 11. The targeted peak of interest was that at 7.7 min in the TIC chromatogram. The mass spectrum of this peak provided a [M-H]⁻ ion at m/z 1127.6. The provided sample was preliminarily processed in a single injection (160 mg) using the first method condition provided above. This method fractionated the material into 'polar' and 'non-polar' mixtures of glycosides. The 'polar' mixture was then reprocessed using the second-step conditions above. The semi-preparative HPLC trace is provided in FIG. 12. From this semi-preparative collection, the compound was isolated with a purity>99% (CAD, AUC). The fraction analysis is provided in FIG. 13. Following the purification, the combined fractions were concentrated by rotary evaporation at 35° C. and lyophilized. Approximately 1-2 mg was obtained for characterization.

Mass Spectrometry.

The ESI-TOF mass spectrum acquired by infusing a sample showed a [M-H]⁻ ion at m/z 1127.4709. The mass of the [M-H]⁻ ion was in good agreement with the molecular formula $C_{50}H_{80}O_{28}$ (calcd for $C_{50}H_{79}O_{28}$: 1127.4758, error: −4.3 ppm). The MS data confirmed a nominal mass of 1128 Daltons with the molecular formula, $C_{50}H_{80}O_{28}$.

The MS/MS spectrum (selecting the [M-H]⁻ ion at m/z 1127.5 for fragmentation) indicated the loss of two glucose units and sequential loss of three glucose moieties at m/z 641.3187, 479.2655 and 317.2065.

NMR Spectroscopy.

Figure 14:
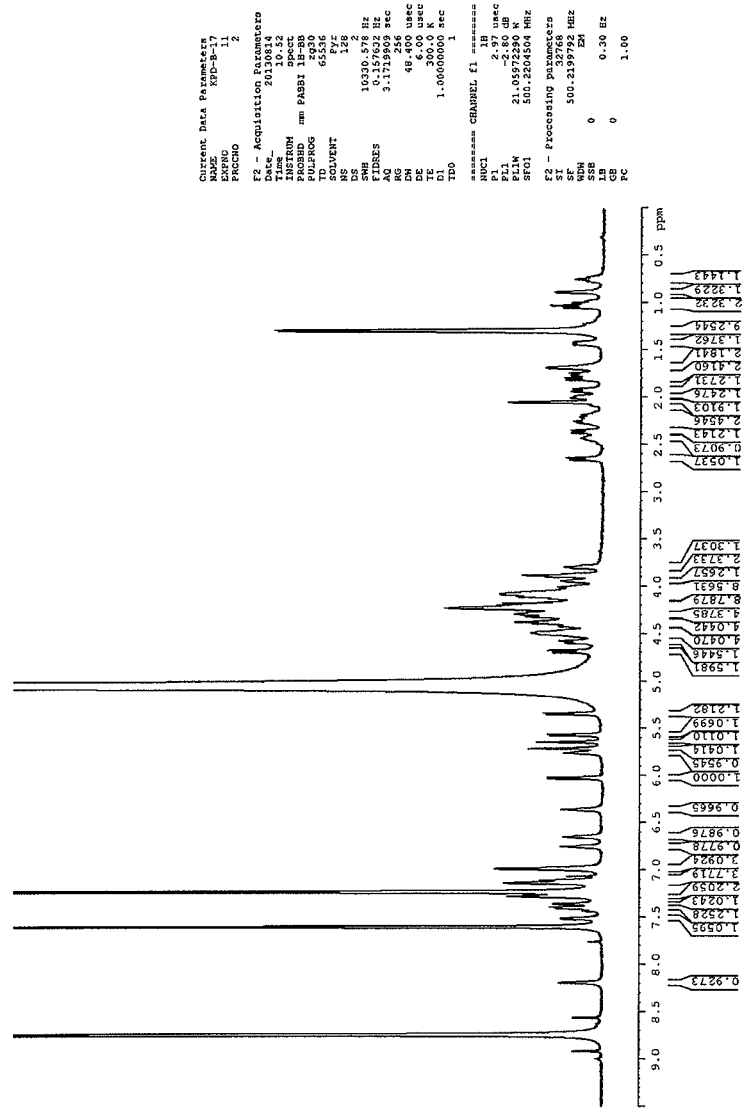
FIG. 14 shows the $^1$H NMR spectrum of reb D2 (500 MHz, pyridine-$d_5$).
Figure 15:
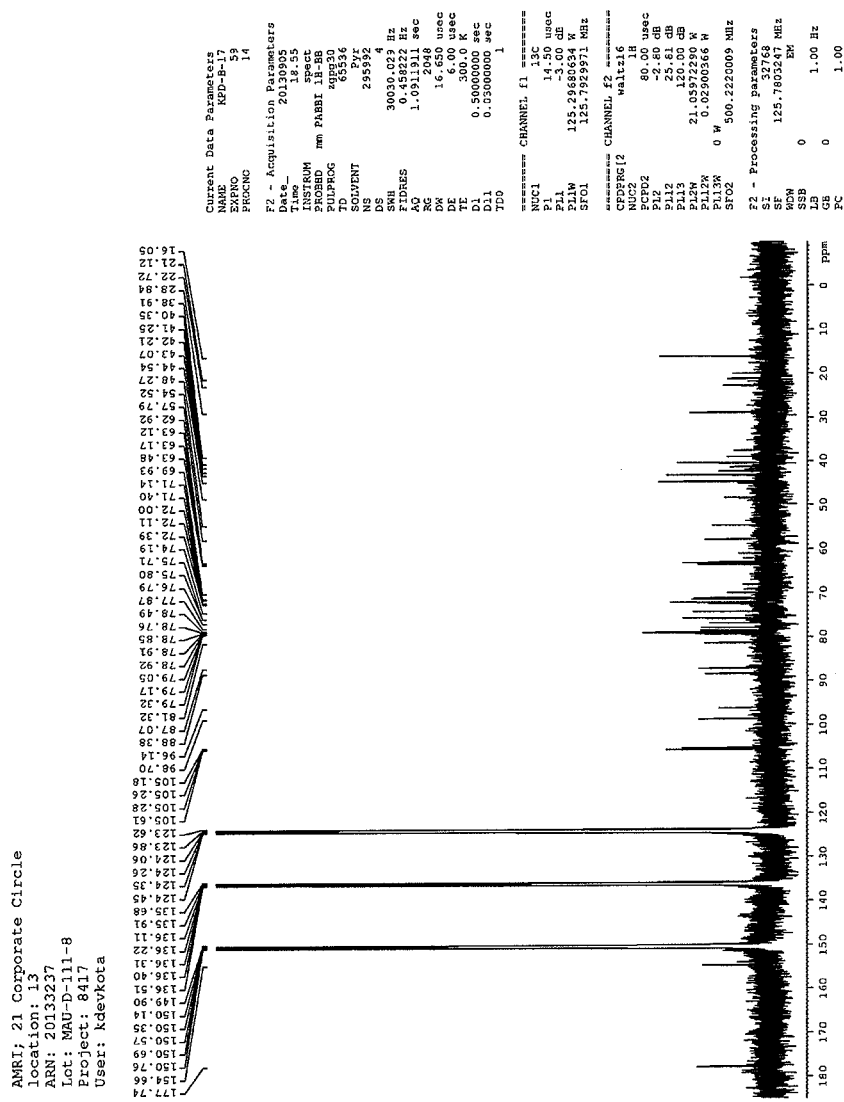
FIG. 15 shows the $^{13}$C NMR spectrum of reb D2 (125 MHz, pyridine-$d_5$).
Figure 16:
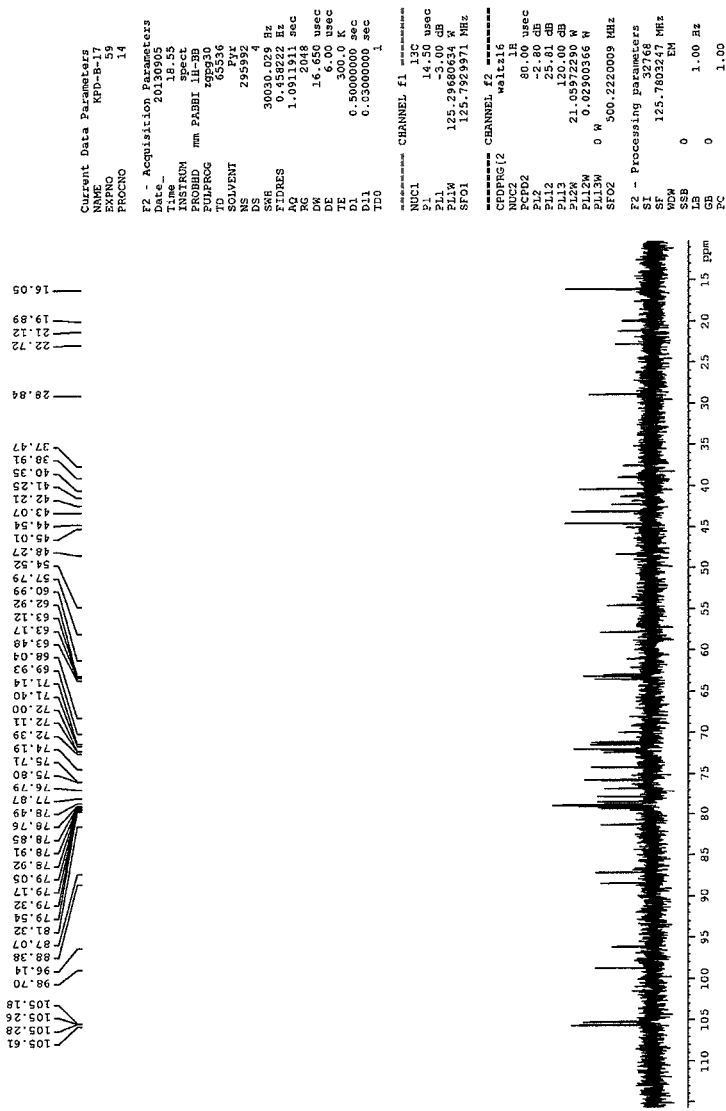
FIG. 16 shows an expansion of the $^{13}$C NMR spectrum of reb D2 (125 MHz, pyridine-$d_5$).
Figure 17:
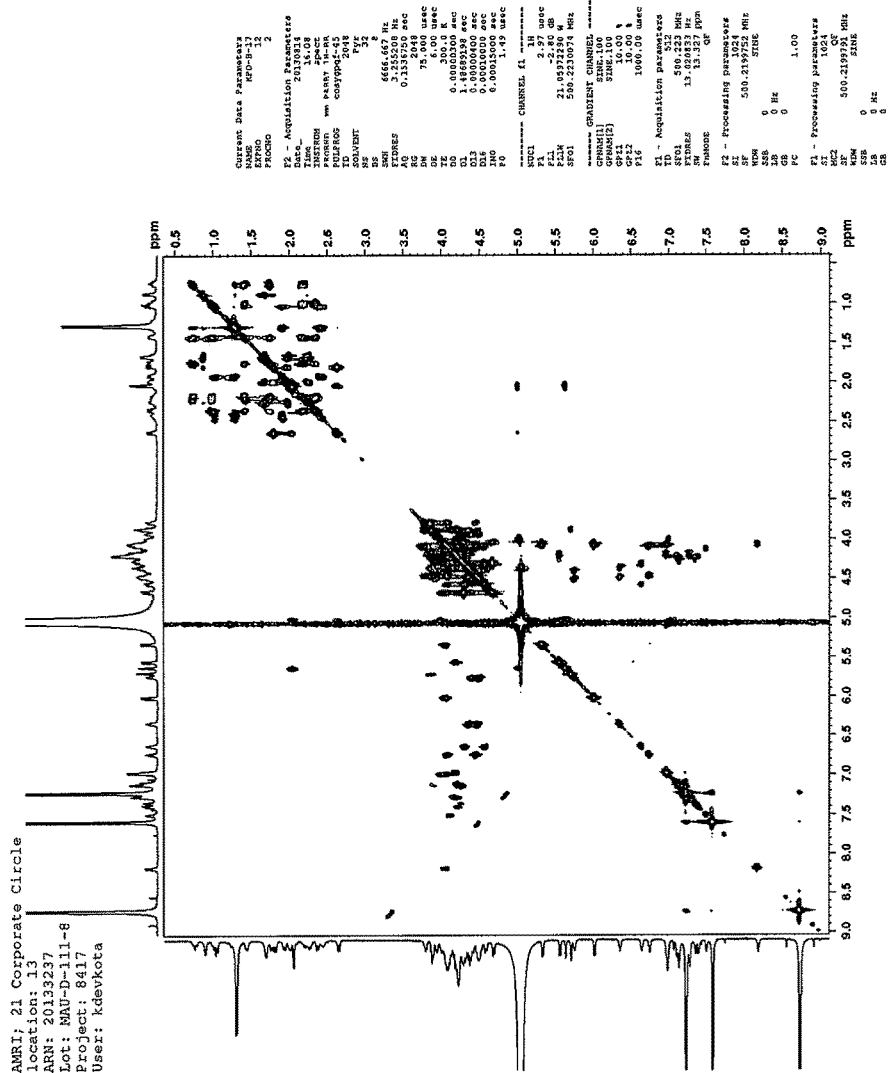
FIG. 17 shows the $^1$H-$^1$H COSY Spectrum of reb D2 (500 MHz, pyridine-$d_5$).
Figure 18:
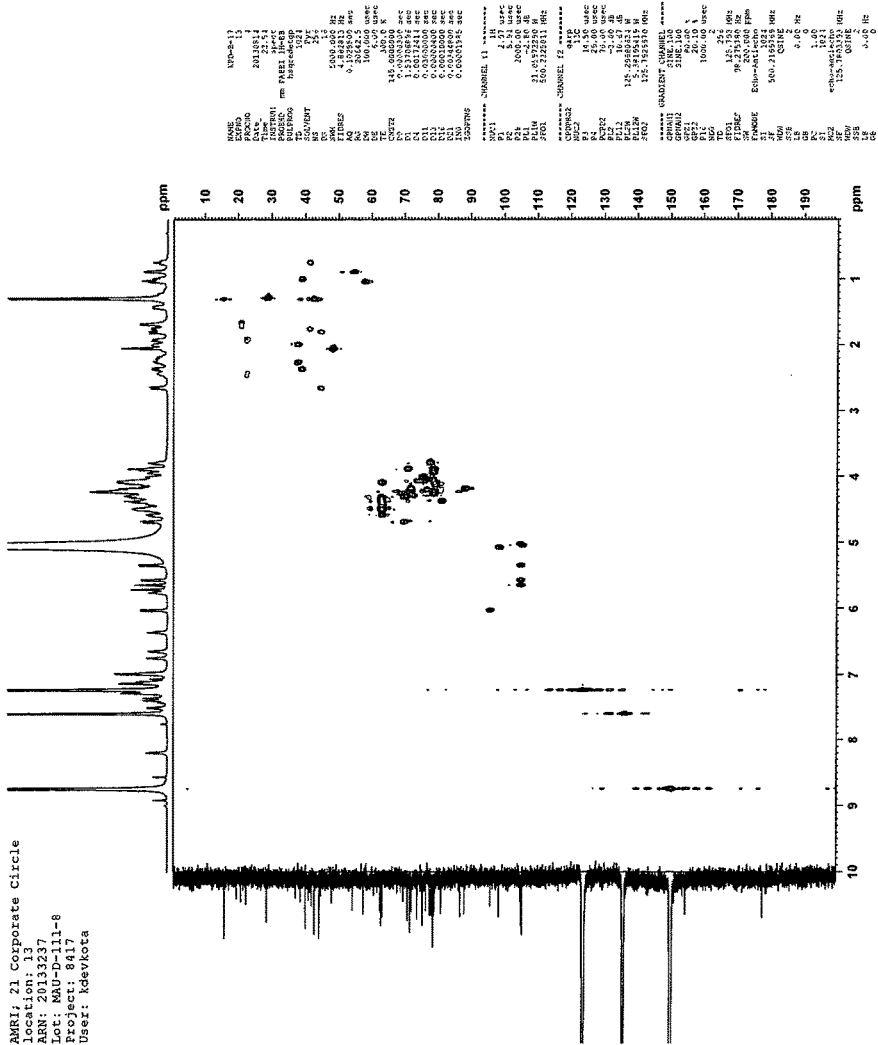
FIG. 18 shows the HSQC-DEPT spectrum of reb D2 (500 MHz, pyridine-$d_5$).
Figure 19:
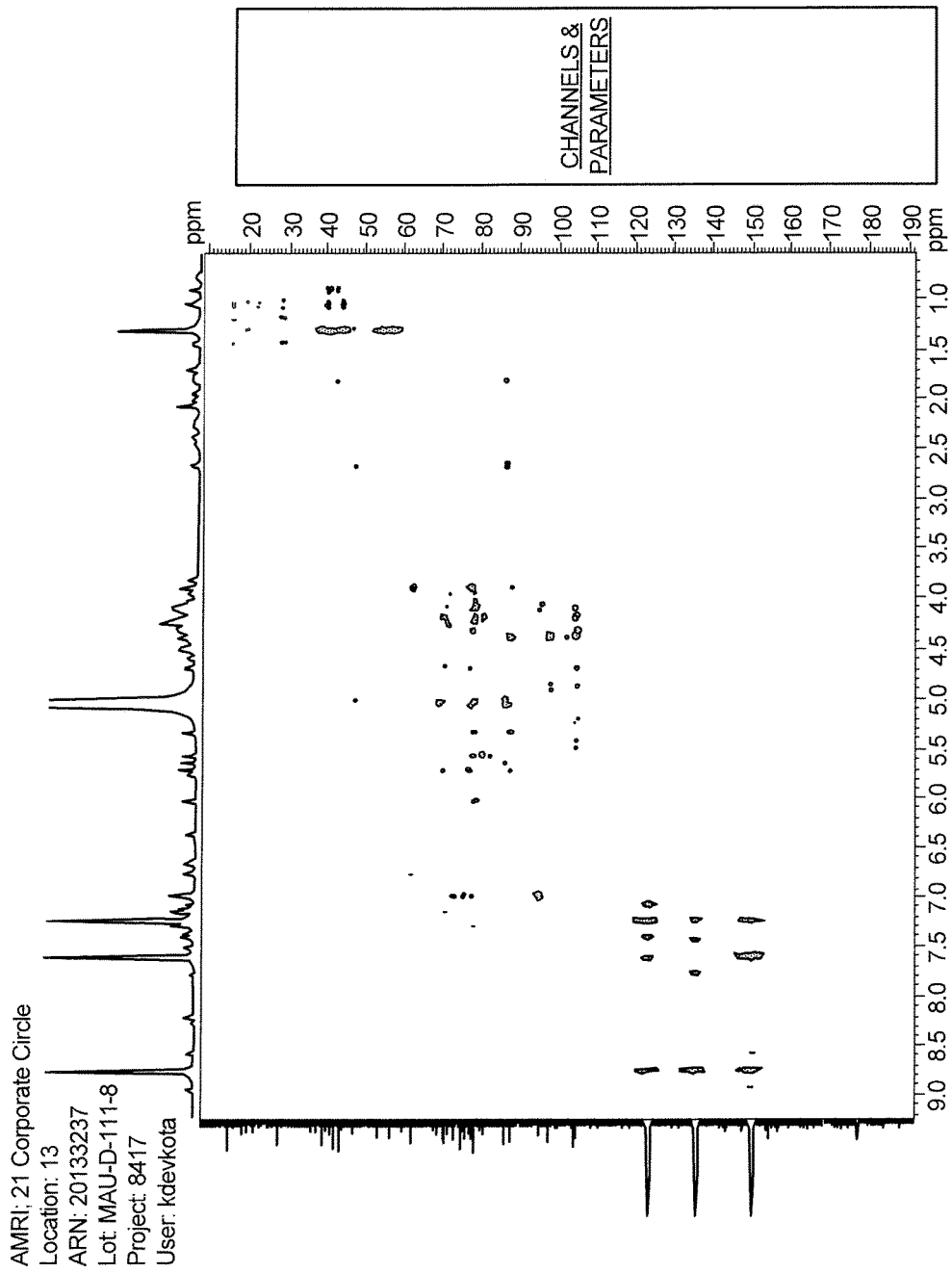
FIG. 19 shows the HMBC spectrum of reb D2.
Figure 20:
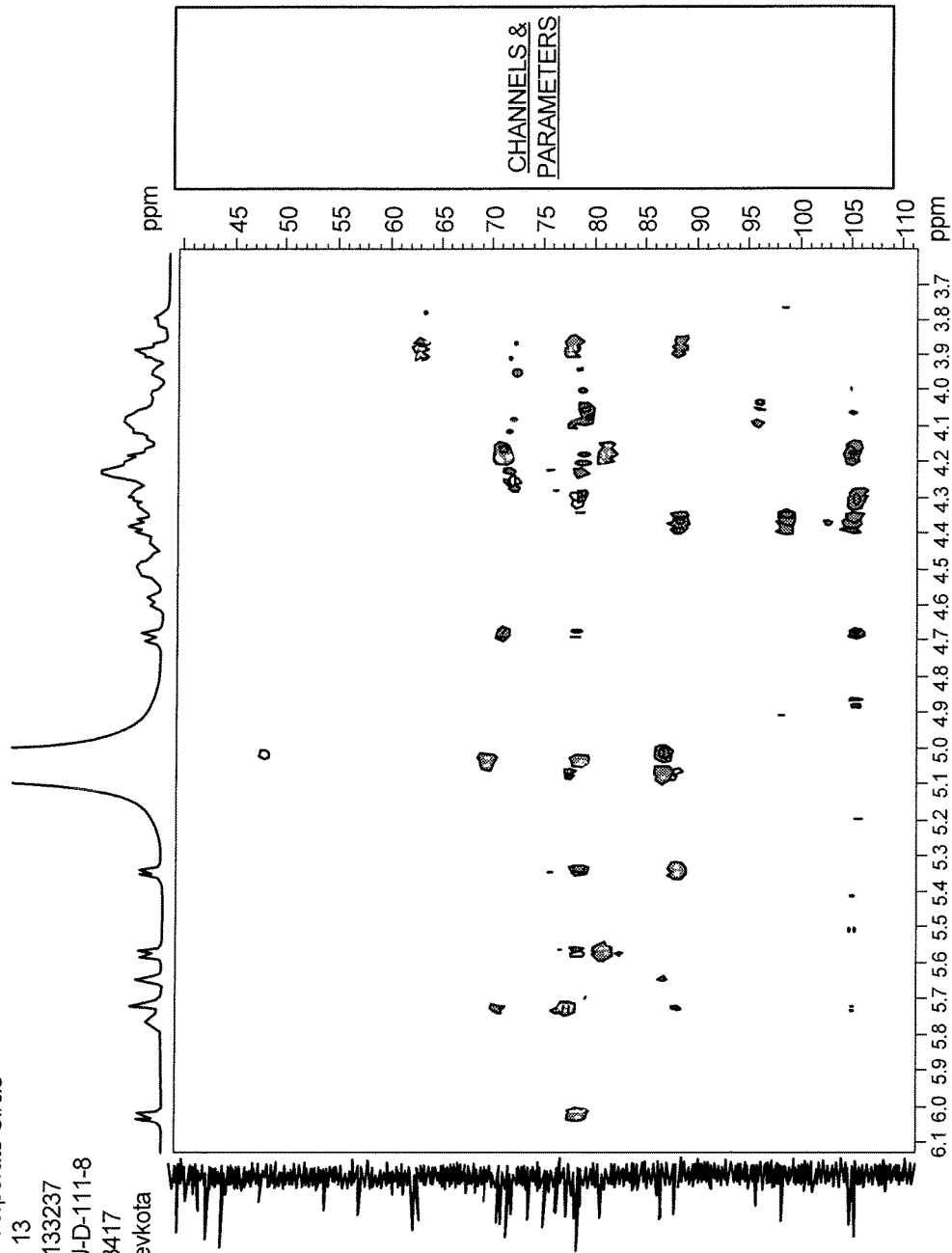
FIG. 20 shows an expansion of HMBC spectrum of reb D2 (500 MHz, pyridine-$d_5$).
Figure 21:
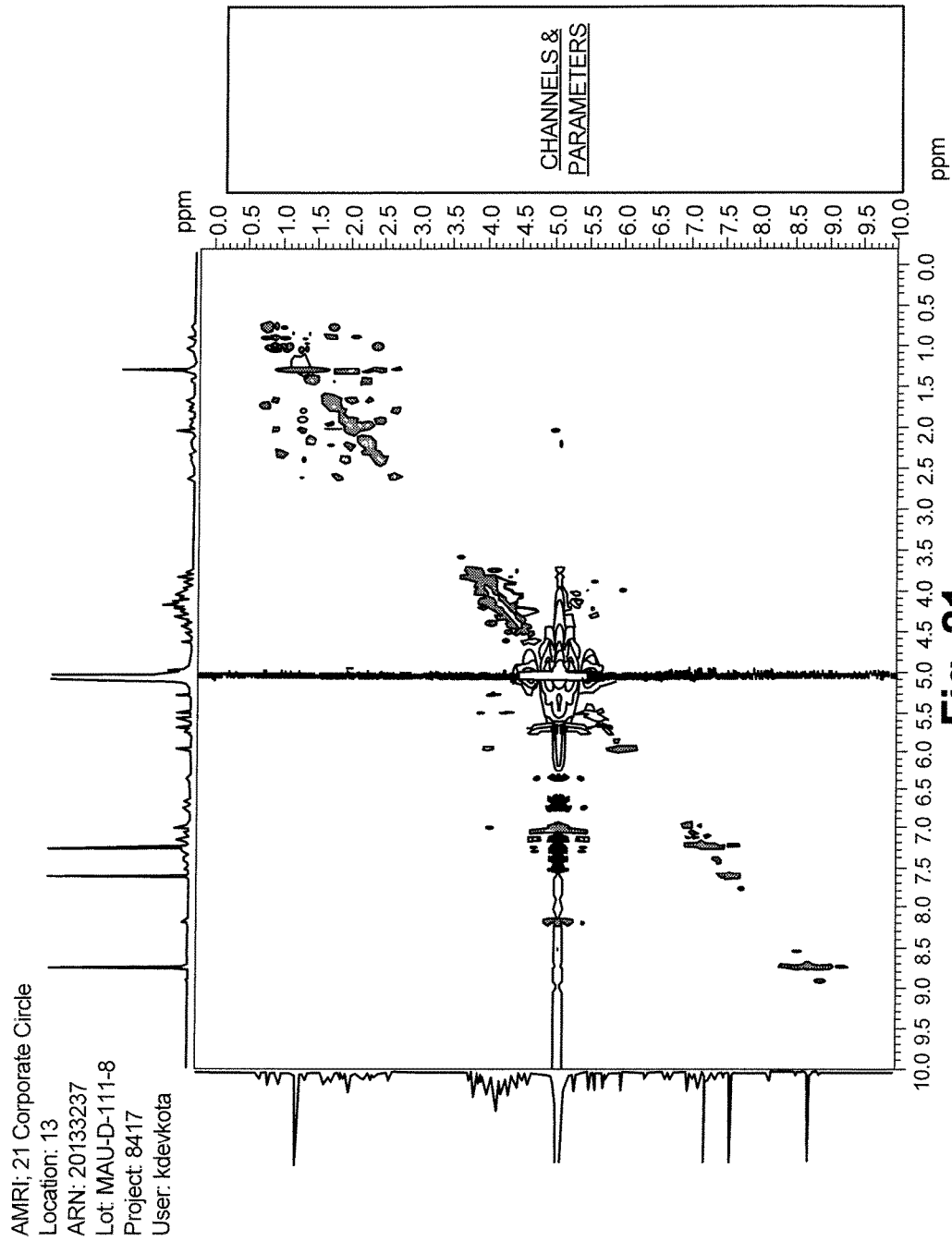
FIG. 21 shows the $^1$H NMR spectrum of reb M2 (500 MHz, $D_2O$).
Figure 22:
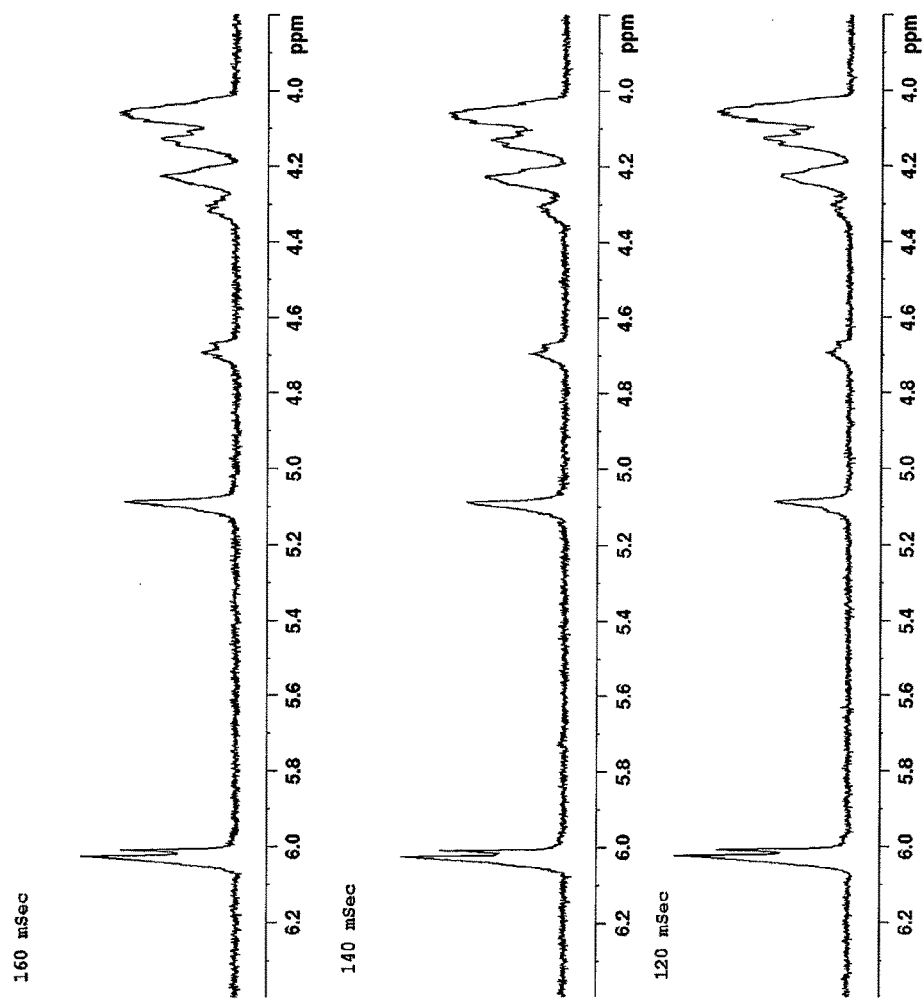
FIG. 22 shows the $^{13}$C NMR spectrum of reb M2 (125 MHz, $D_2O$/TSP).
Figure 23:
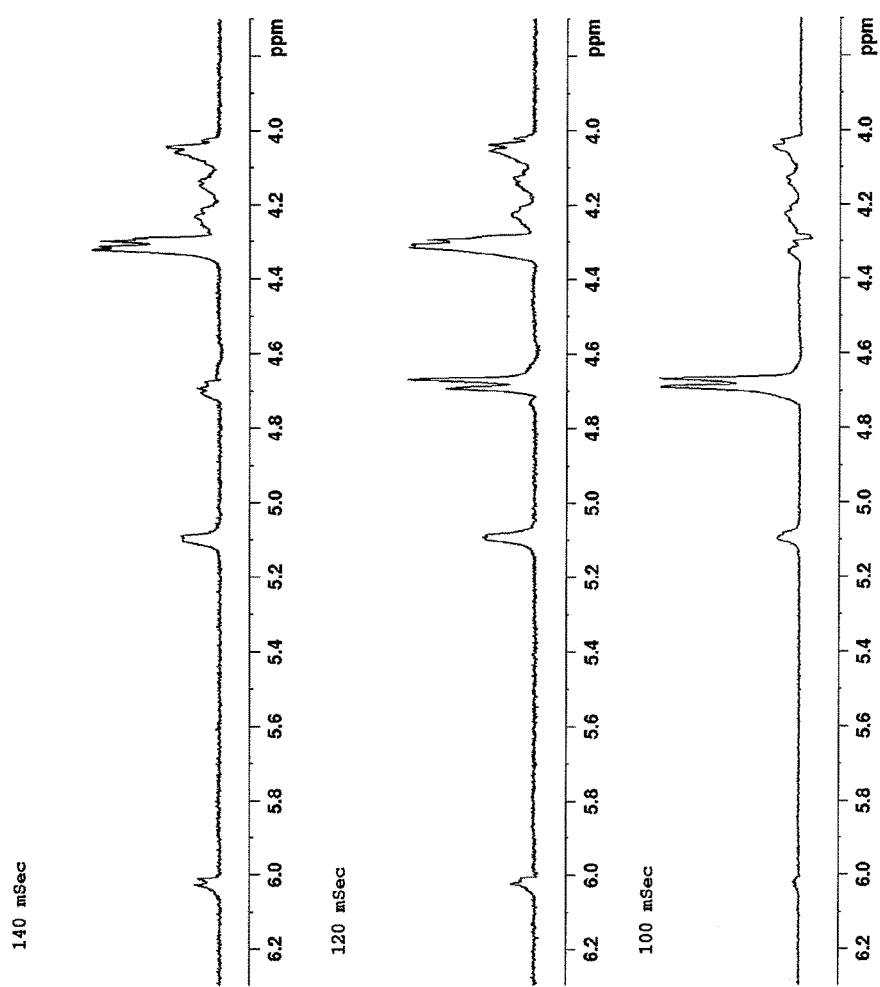
FIG. 23 shows an expansion of the $^{13}$C NMR spectrum of reb M2 (125 MHz, $D_2O$/TSP).
Figure 24:
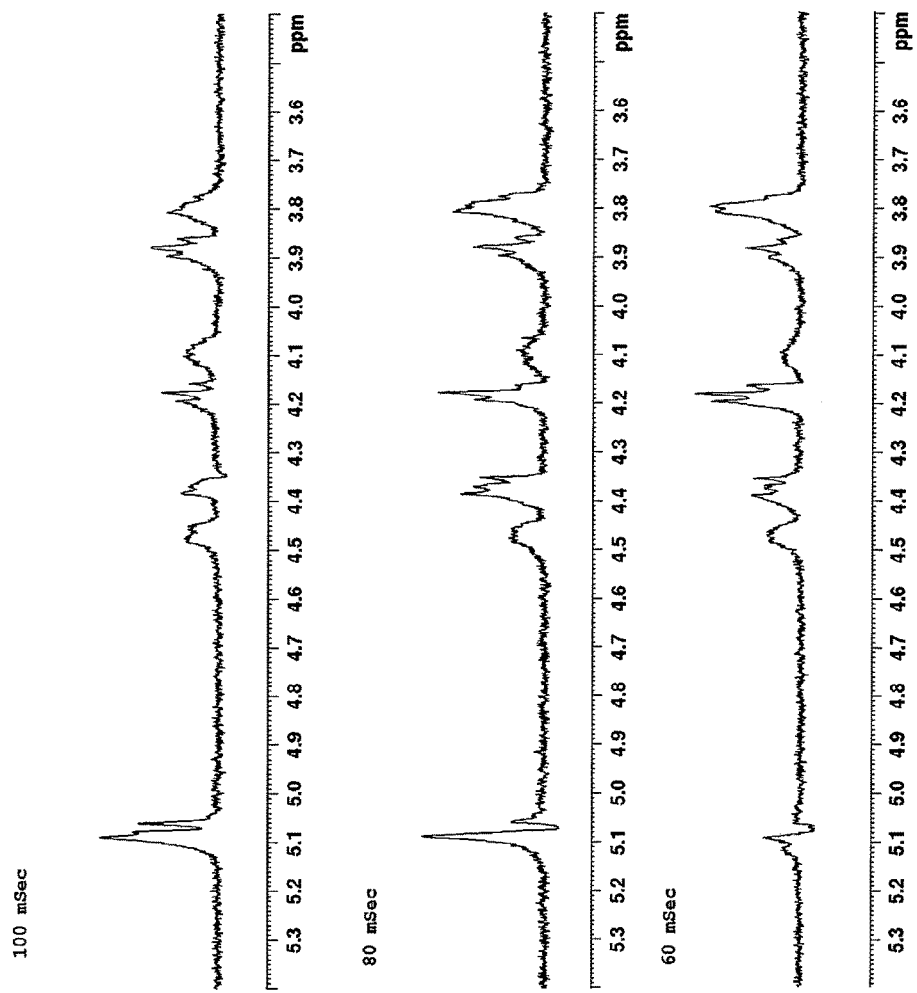
FIG. 24 shows the $^1$H-$^1$H COSY spectrum of reb M2 (500 MHz, $D_2O$).
Figure 25:
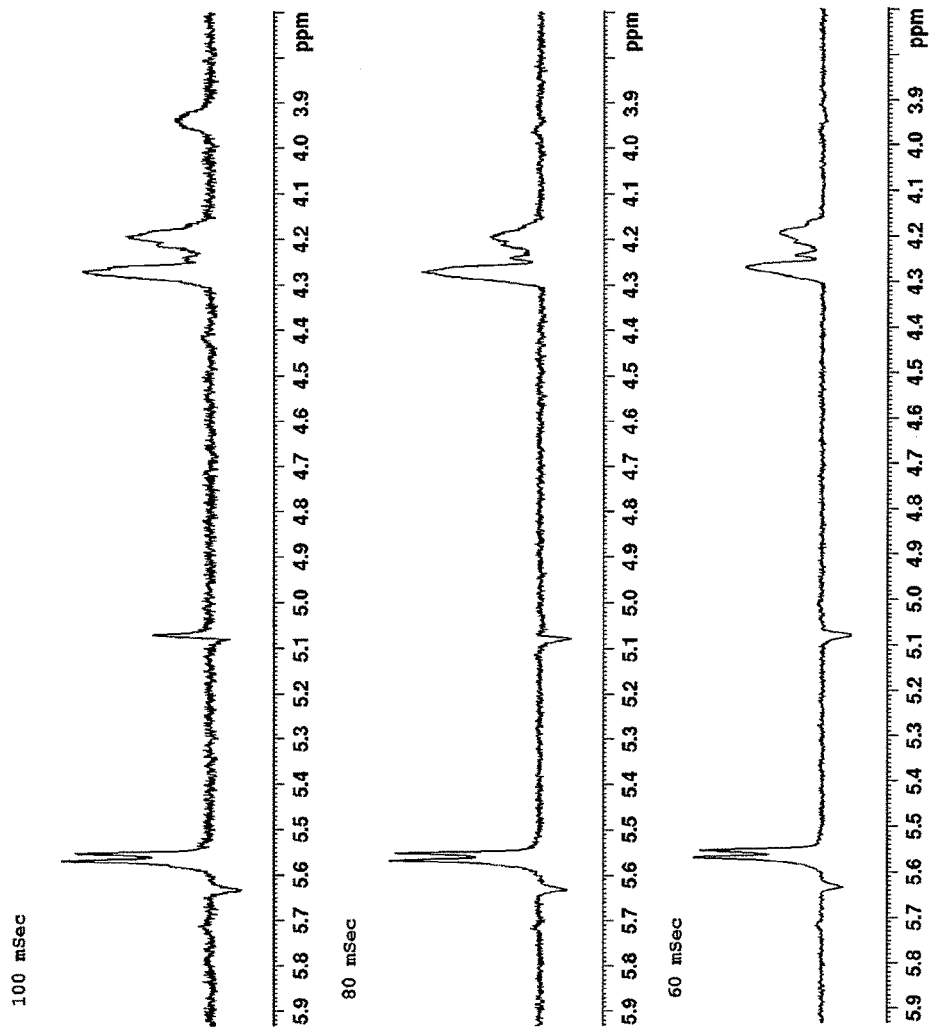
FIG. 25 shows the HSQC-DEPT spectrum of reb M2 (500 MHz, $D_2O$).
Figure 26:
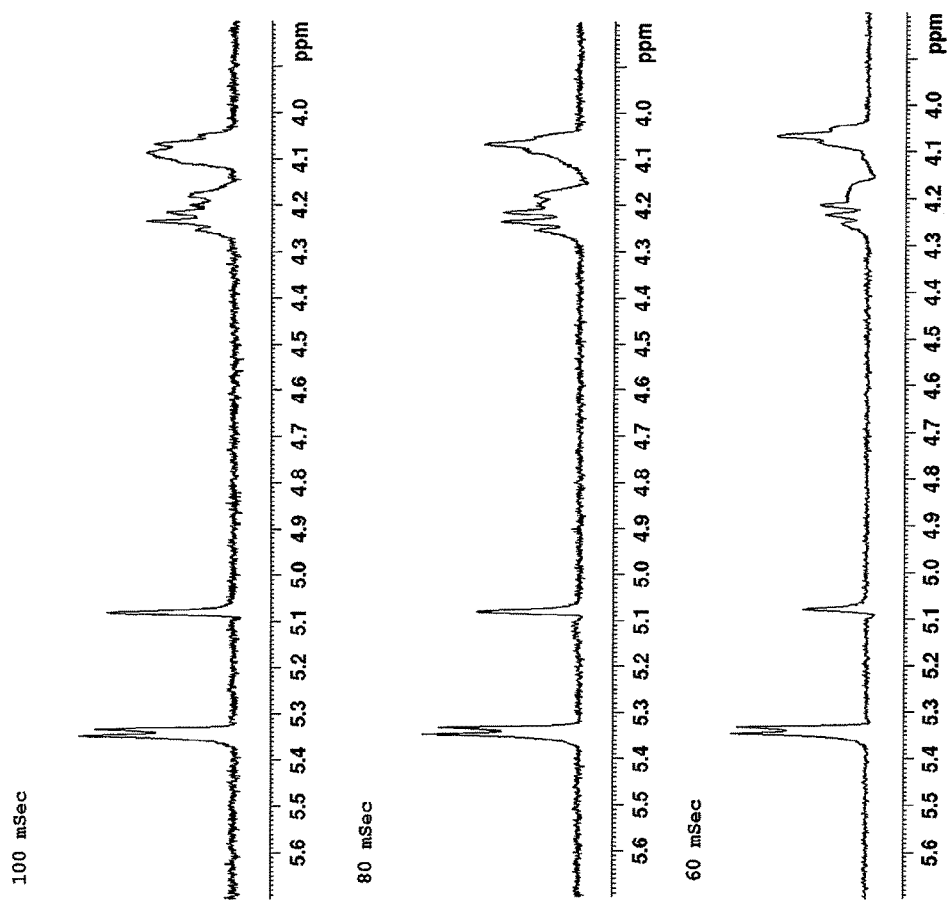
FIG. 26 shows the HMBC spectrum of reb M2 (500 MHz, $D_2O$).

A series of NMR experiments including ¹H NMR (FIG. 14), ¹³C NMR (FIGS. 15 and 16), ¹H-¹H COSY (FIG. 17), HSQC-DEPT (FIG. 18), HMBC (FIGS. 19 and 20), NOESY (FIG. 21) and 1D-TOCSY (FIG. 22-26) were performed to allow assignment of the compound. In the ¹H NMR acquired after ~46 hrs of sample preparation (FIGS. 27-28), the anomeric resonance at $\delta_H$ 5.04 is resolved which was obscured by the solvent (HOD) in the original spectrum (FIG. 14)

The ¹H, ¹H-¹H COSY, ¹H-¹³C HSQC-DEPT and ¹H-¹³C HMBC NMR data indicated that the central core of the glycoside is a diterpene. The presence of five anomeric protons observed in the ¹H and ¹H-¹³C HSQC-DEPT spectra confirm five sugar units in the structure. The methylene ¹³C resonance at $\delta_C$ 69.9 in the ¹H-¹³C HSQC-DEPT spectrum indicated the presence of a sugar linkage in the structure. The linkages of sugar units were assigned using ¹H-¹³C HMBC and 1D-TOCSY correlations.

A HMBC correlation from the methyl protons at $\delta_H$ 1.29 to the carbonyl at $\delta_C$ 177.7 allowed assignment of one of the tertiary methyl groups (C-18) as well as C-19 and provided a starting point for the assignment of the rest of the aglycone. Additional HMBC correlations from the methyl protons (H-18) to carbons at $\delta_C$ 38.9, 45.0, and 57.8 allowed assignment of C-3, C-4, and C-5. Analysis of the ¹H-¹³C HSQC-DEPT data indicated that the carbon at $\delta_C$ 38.9 was a methylene group and the carbon at $\delta_C$ 57.8 was a methine which were assigned as C-3 and C-5, respectively. This left the carbon at $\delta_C$ 45.0, which did not show a correlation in the HSQC-DEPT spectrum, to be assigned as the quaternary carbon, C-4. The ¹H chemical shifts for C-3 ($\delta_H$ 0.98 and 2j.36) and C-5 ($\delta_H$ 1.04) were assigned using the HSQC-DEPT data. A COSY correlation between one of the H-3 protons ($\delta_H$ 0.98) and a proton at $\delta_H$ 1.43 allowed assignment of one of the H-2 protons which in turn showed a correlation with a proton at $\delta_H$ 0.75 which was assigned to C-1. The remaining ¹H and ¹³C chemical shifts for C-1 and C-2 were then assigned on the basis of additional COSY and HSQC-DEPT correlations and are summarized in the table below.

¹H and ¹³C NMR (500 and 125 MHz, pyridine-$d_5$), Assignments of Reb D2.

| Position | Reb D2 ¹³C | ¹H |
|---|---|---|
| 1 | 41.3 | 0.75 t (11.0) |
|  |  | 1.76 m |
| 2 | 19.9 | 1.43 m |
|  |  | 2.20 m |
| 3 | 38.9 | 0.98 m |
|  |  | 2.36 d (12.1) |
| 4 | 45.0 | — |
| 5 | 57.8 | 1.04 d (12.5) |
| 6 | 22.7 | 1.92 m |
|  |  | 2.43 m |
| 7 | 42.2 | 1.22 m |
|  |  | 1.30 m |
| 8 | 43.1 | — |
| 9 | 54.5 | 0.88 brs |
| 10 | 40.3 | — |
| 11 | 21.1 | 1.65 m |
|  |  | 1.69 m |
| 12 | 37.5 | 1.99 m |
|  |  | 2.25 m |
| 13 | 87.1 | — |
| 14 | 44.5 | 1.80 d (11.7) |
|  |  | 2.65 d (11.7) |
| 15 | 48.3 | 1.31 m |
|  |  | 2.04 brs |
| 16 | 154.7 | — |
| 17 | 105.2 | 5.01 s |
|  |  | 5.64 s |
| 18 | 28.8 | 1.29 s |
| 19 | 177.7 | — |
| 20 | 16.0 | 1.30 s |

The other tertiary methyl singlet, observed at $\delta_H$ 1.30 showed HMBC correlations to C-1 and C-5 and was assigned as C-20. The methyl protons showed additional HMBC correlations to a quaternary carbon ($\delta_C$ 40.3) and a methine carbon ($\delta_C$ 54.5) which were assigned as C-10 and C-9, respectively. COSY correlations between H-5 ($\delta_H$ 1.04) and protons at $\delta_H$ 1.92 and 2.43 then allowed assignment of the H-6 protons which in turn showed correlations to protons at $\delta_H$ 1.22 and 1.30 which were assigned to C-7. The ¹³C chemical shifts for C-6 ($\delta_C$ 22.7) and C-7 ($\delta_C$ 42.2) were then determined from the HSQC-DEPT data. COSY correlations between H-9 ($\delta_H$ 0.88) and protons at $\delta_H$ 1.65 and 1.69 allowed assignment of the H-11 protons which in turn showed COSY correlations to protons at $\delta_H$ 1.99 and 2.25 which were assigned as the H-12 protons. The HSQC-DEPT data was then used to assign C-11 ($\delta_C$ 21.1) and C-12 ($\delta_C$ 37.5). HMBC correlations from the H-12 proton ($\delta_H$ 2.25) to carbons at $\delta_C$ 87.1 and 154.7 allowed assignment of C-13 and C-16, respectively. The olefinic protons observed at $\delta_H$ 5.01 and 5.64 showed HMBC correlations to C-13 and were assigned to C-17 ($\delta_C$ 105.2 via HSQC-DEPT). The olefinic protons H-17 and the methine proton H-9 showed HMBC correlations to a carbon at $\delta_C$ 48.3 which was assigned as C-15. An additional HMBC correlation from H-9 to a methylene carbon at $\delta_C$ 44.5 then allowed assignment of C-14. The $^1$H chemical shifts at C-14 ($\delta_H$ 1.80 and 2.65) and C-15 $\delta_H$ 1.31 and 2.04) were assigned using the HSQC-DEPT data.

Correlations observed in the NOESY spectrum were used to assign the relative stereochemistry of the central diterpene core. In the NOESY spectrum, NOE correlations were observed between H-14 and H-20 indicating that H-14 and H-20 are on the same face of the rings. Similarly, NOE correlations were observed between H-9 and H-5; H-9 and H-18 as well as H-5 and H-18 but NOE correlations were not observed between H-9 and H-14 indicating that H-5, H-9 and H-18 were on the opposite face of the rings compared to H-14 and H-20 as presented in FIG. 21. These data thus indicated that the relative stereochemistry in the central core was retained during the glycosylation step.

The key HMBC and COSY correlations used to assign the aglycone region are provided below:

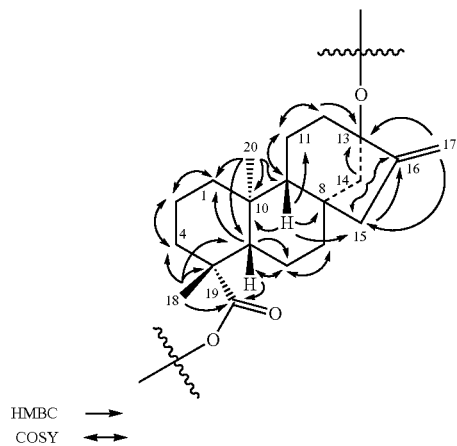

HMBC →
COSY ↔

Analysis of the $^1$H-$^{13}$C HSQC-DEPT data confirmed the presence of five anomeric protons. Three of the anomeric protons were well resolved at $\delta_H$ 6.02 ($\delta_C$ 96.1), 5.57 ($\delta_C$ 105.3), and 5.34 ($\delta_C$ 105.3) in the $^1$H NMR spectrum. The remaining two anomeric protons observed at $\delta_H$ 5.04 ($\delta_C$ 105.6) and 5.07 ($\delta_C$ 98.7) which were obscured by solvent (HOD) resonance in the $^1$H spectrum were identified by $^1$H-$^{13}$C HSQC-DEPT data. The anomeric proton observed at $\delta_H$ 6.02 showed HMBC correlation to C-19 which indicated that it corresponds to the anomeric proton of Glc$_I$. Similarly, the anomeric proton observed at $\delta_H$ 5.07 showed an HMBC correlation to C-13 allowing it to be assigned as the anomeric proton of Glc$_{II}$.

The Glc$_I$ anomeric proton ($\delta_H$ 6.02) showed a COSY correlation to a proton at $\delta_H$ 4.07 was assigned as Glc$_I$ H-2 which in turn showed a COSY correlation to a proton at $\delta_H$ 4.22 (Glc$_I$ H-3) which showed a COSY correlation with a proton at $\delta_H$ 4.12 (Glc$_I$ H-4). Due to data overlap, the COSY spectrum did not allow assignment of H-5 or the H-6 protons. Therefore, a series of 1D-TOCSY experiments were performed using selective irradiation of the Glc$_I$ anomeric proton with several different mixing times. In addition to confirming the assignments for Glc$_I$ H-2 through H-4, the 1D-TOCSY data showed a proton at $\delta_H$ 4.04 assigned as Glc$_I$ H-5 and a proton at $\delta_H$ 4.68 assigned as one of the Glc$_I$ H-6 protons. The latter proton was also used for 1D-TOCSY experiments. The selective irradiation of H-6 with several different mixing times also confirmed the assignment of Glc$_I$ H-1 to H-5 as well as the remaining methylene proton of H-6 ($\delta_H$ 4.30). Assignment of the $^{13}$C chemical shifts for Glc$_I$ C-2 ($\delta_C$ 74.2), C-3 ($\delta_C$ 79.1), C-4 ($\delta_C$ 72.1), C-5 ($\delta_C$ 78.5), and C-6 ($\delta_C$ 69.9) was determined using the $^1$H-$^{13}$C HSQC-DEPT data to complete the assignment of Glc$_I$. Furthermore, the presence of a methylene $^{13}$C resonance at $\delta_C$ 69.9 in the $^1$H-$^{13}$C HSQC-DEPT spectrum indicated a 1→6 sugar linkage of Glc$_I$ in the structure.

Out of four remaining unassigned glucose moieties, one was assigned as a substituent at C-6 of Glc$_I$ on the basis of $^1$H-$^{13}$C HSQC-DEPT, HMBC, and 1D-TOCSY correlations. The relatively downfield shift of a methylene $^{13}$C resonance of Glc$_I$ at $\delta_C$ 69.9 in the HSQC-DEPT spectrum indicated a 1→6 sugar linkage of Glc$_I$. The anomeric proton observed at $\delta_H$ 5.04 showed HMBC correlation to Glc$_I$ C-6 and was assigned as the anomeric proton of Glc$_V$. Similarly, methylene protons of Glc$_I$ showed HMBC correlations to anomeric carbon of Glc$_V$ confirming the presence of a 1→6 sugar linkage between Glc$_I$ and Glc$_V$. The Glc$_V$ anomeric proton showed a COSY correlation to a proton at $\delta_H$ 4.00 which was assigned as Glc$_V$ H-2 which in turn showed a COSY correlation to a proton at $\delta_H$ 4.22 (Glc$_V$ H-3). Due to data overlap, the COSY spectrum did not allow assignment of Glc$_V$ H-4 based on the COSY correlation of Glc$_V$ H-3. However, in the HMBC spectrum, Glc$_V$ H-3 showed a correlation to Glc$_V$ C-5 ($\delta_C$ 78.9). In HSQC-DEPT spectrum, Glc$_V$ C-5 showed a correlation to $\delta_H$ 3.89 (Glc$_V$ H-5). The Glc$_V$ H-5 showed COSY correlations to $\delta_H$ 4.21, 4.37, and 4.48. In the HSQC-DEPT spectrum, $\delta_H$ 4.21 showed a correlation to $\delta_C$ 71.4 (Glc$_V$ H-4), while $\delta_H$ 4.37 and 4.48 showed a correlation to $\delta_C$ 63.1 and were assigned to Glc$_V$ H-6a and H-6b, respectively. Assignment of the $^{13}$C chemical shifts for Glc$_V$ C-2 ($\delta_C$ 75.7) and C-3 ($\delta_C$ 79.1) was determined using the $^1$H-$^{13}$C HSQC-DEPT data to complete the assignment of Glc$_V$.

A summary of the $^1$H and $^{13}$C chemical shifts for the glycoside at C-19 are shown in the following table:

| $^1$H and $^{13}$C NMR (500 and 125 MHz, pyridine-d$_5$), Assignments of the reb D2 C-19 glycoside. | | |
|---|---|---|
| | Reb D2 | |
| Position | $^{13}$C | $^1$H |
| Glc$_I$-1 | 96.1 | 6.02 d (8.1) |
| Glc$_I$-2 | 74.2 | 4.07 m |
| Glc$_I$-3 | 79.1# | 4.22 m# |
| Glc$_I$-4 | 72.1 | 4.12 m |
| Glc$_I$-5 | 78.5 | 4.04 m |
| Glc$_I$-6 | 69.9 | 4.30 m |
| | | 4.68 d (10.7) |
| Glc$_V$-1 | 105.6 | 5.04 (8.1) |
| Glc$_V$-2 | 75.7 | 4.00 m |
| Glc$_V$-3 | 79.1# | 4.22 m# |
| Glc$_V$-4 | 71.4 | 4.21 m |
| Glc$_V$-5 | 78.9 | 3.89 m |
| Glc$_V$-6 | 63.1 | 4.37 m |
| | | 4.48 m |

$^1$H and $^{13}$C values can be exchangeable between positions Glc$_I$-3, Glc$_V$-3 and Glc$_{II}$-3.

A summary of the key HMBC, COSY, and 1D-TOCSY correlations used to assign the C-19 glycoside region are provided below.

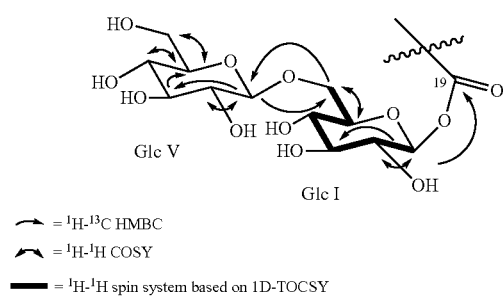

→ = ¹H-¹³C HMBC
⌒ = ¹H-¹H COSY
━ = ¹H-¹H spin system based on 1D-TOCSY

Assignment of Glc$_{II}$ was carried out in a similar manner. The Glc$_{II}$ anomeric proton ($\delta_H$ 5.07) showed a COSY correlation to a proton at $\delta_H$ 4.37, assigned as Glc$_{II}$ H-2, which in turn showed a COSY correlation to a proton at $\delta_H$ 4.18 (Glc$_{II}$ H-3). This latter proton showed an additional correlation with a proton at $\delta_H$ 3.88 (Glc$_{II}$ H-4) which also showed a COSY correlation to a proton at $\delta_H$ 3.79 (Glc$_{II}$ H-5). Glc$_{II}$ H-5 also showed a COSY correlation to Glc$_{II}$ H-6 protons ($\delta_H$ 4.08 and 4.46). Assignment of the $^{13}$C chemical shifts for Glc$_{II}$ C-2 ($\delta_C$ 81.3), C-3 ($\delta_C$ 88.4), C-4 ($\delta_C$ 71.1), C-5 ($\delta_C$ 77.9), and C-6 ($\delta_C$ 63.2) was determined using the HSQC-DEPT data. HMBC correlations from Glc$_{II}$ H-3 to C-2 and C-4 and also from Glc$_{II}$ H-4 to C-2 and C-5 confirmed the assignments made above. Additional HMBC correlations of Glc$_{II}$ H-4 to Glc$_{II}$ C-6 further support to complete the assignment of Glc$_{II}$.

Two of the remaining unassigned glucose moieties were assigned as substituents at C-2 and C-3 of Glc$_{II}$ on the basis of HMBC correlations. The anomeric proton observed at $\delta_H$ 5.57 showed a HMBC correlation to Glc$_{II}$ C-2 and was assigned as the anomeric proton of Glc$_{III}$. The anomeric proton observed at $\delta_H$ 5.34 showed a HMBC correlation to Glc$_{II}$ C-3 and was assigned as the anomeric proton of Glc$_{IV}$. The reciprocal HMBC correlations from Glc$_{II}$ H-2 to the anomeric carbon of Glc$_{III}$ and from Glc$_{II}$ H-3 to the anomeric carbon of Glc$_{IV}$ were also observed.

The anomeric proton of Glc$_{III}$ ($\delta_H$ 5.57) showed a COSY correlation with a proton at $\delta_H$ 4.19 which was assigned as Glc$_{III}$ H-2. Due to data overlap, the COSY spectrum did not allow assignment of H-3 to H-6 protons. Therefore, a series of 1D-TOCSY experiments were performed using selective irradiation of the Glc$_{III}$ anomeric proton with several different mixing times. In addition to confirming the assignments for Glc$_{III}$ H-2, the 1D-TOCSY data showed protons at $\delta_H$ 4.24 (Glc$_{III}$ H-3), $\delta_H$ 4.27 (Glc$_{III}$ H-4), and $\delta_H$ 3.94 (Glc$_{III}$ H-5). Once H-4 was assigned using 1D-TOCSY data, COSY correlations from H-4 to H-5 and in turn to H-6 were used to assign H-6. In the COSY spectrum, Glc$_{III}$ H-4 showed a correlation to Glc$_{III}$ H-5, which in turn showed COSY correlations to $\delta_H$ 4.41 and 4.50 of Glc$_{III}$ H-6a and H-6b, respectively. The $^{13}$C chemical shifts for Glc$_{III}$ C-2 ($\delta_C$ 76.8), C-3 ($\delta_C$ 78.9), C-4 ($\delta_C$ 72.4), C-5 ($\delta_C$ 78.8), and C-6 ($\delta_C$ 63.5) were then determined using the $^1$H-$^{13}$C HSQC-DEPT correlations to complete the assignment of Glc$_{III}$.

The anomeric proton of Glc$_{IV}$ ($\delta_H$ 5.34) showed a COSY correlation with a proton at $\delta_H$ 4.06 which was assigned as Glc$_{IV}$ H-2. Due to data overlap, the COSY spectrum did not allow assignment of H-3 to H-6 protons. Therefore, a series of 1D-TOCSY experiments were performed using selective irradiation of the Glc$_{IV}$ anomeric proton with several different mixing times. In addition to confirming the assignments for Glc$_{IV}$ H-2, the 1D-TOCSY data showed protons at $\delta_H$ 4.22 (Glc$_{IV}$ H-3), $\delta_H$ 4.18 (Glc$_{IV}$ H-4), and $\delta_H$ 4.10 (Glc$_{IV}$ H-5). Once H-4 was assigned using 1D-TOCSY data, COSY correlations from H-4 to H-5 and in turn to H-6 were used to assign H-6. In the COSY spectrum, Glc$_{IV}$ H-4 showed a correlation to Glc$_{IV}$ H-5, which in turn showed COSY correlations to $\delta_H$ 4.32 and 4.58, Glc$_{IV}$ H-6a and H-6b, respectively. The $^{13}$C chemical shifts for Glc$_{IV}$ C-2 ($\delta_C$ 75.8), C-3 ($\delta_C$ 78.9), C-4 ($\delta_C$ 72.0), C-5 ($\delta_C$ 79.3), and C-6 ($\delta_C$ 62.9) were then determined using the $^1$H-$^{13}$C HSQC-DEPT correlations to complete the assignment of Glc$_{IV}$.

Figure 27:
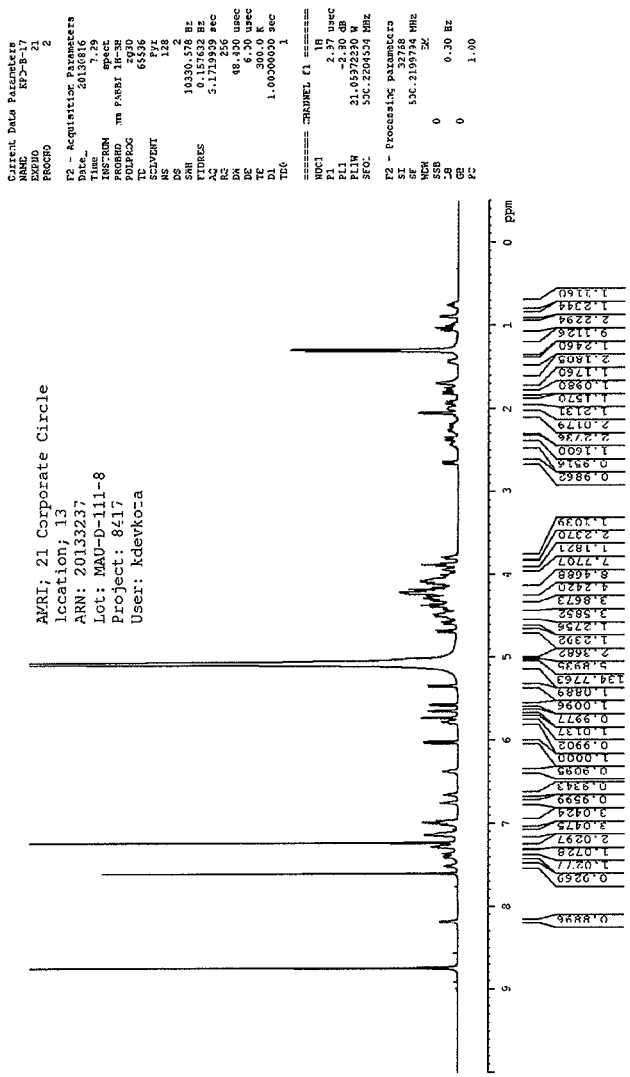
FIG. 27 shows an expansion of HMBC spectrum of reb M2 (500 MHz, $D_2O$).
Figure 28:
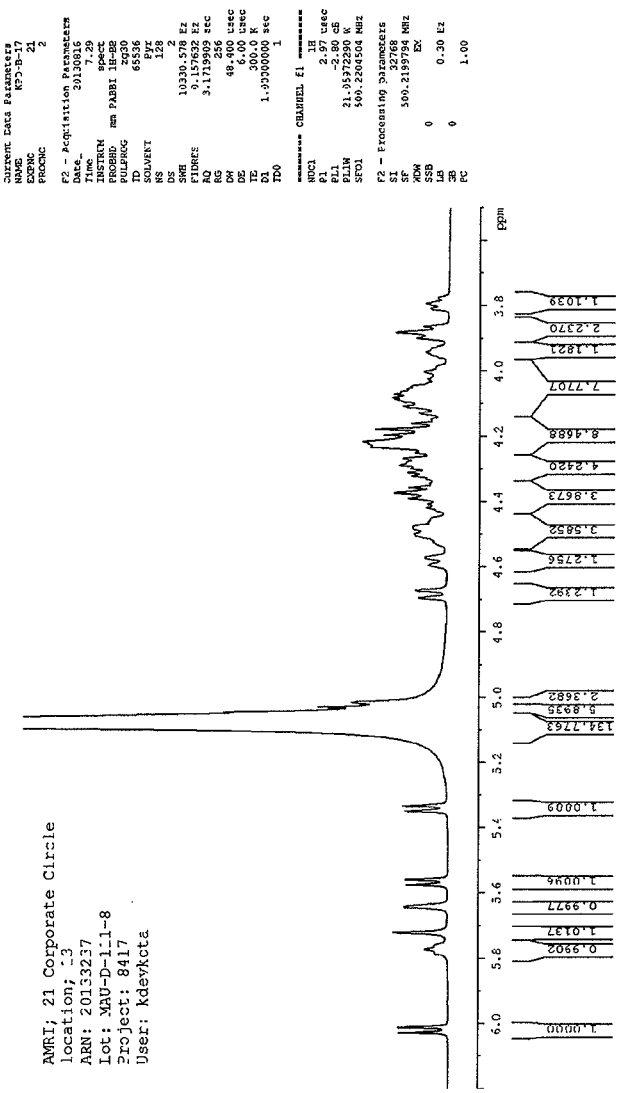
FIG. 28 shows another HMBC spectrum of reb M2.

The large coupling constants observed for the anomeric protons of the glucose moieties at $\delta_H$ 6.02 (d, J=8.1 Hz), 5.57 (d, J=7.6 Hz), 5.34 (d, J=7.9 Hz) and $\delta_H$ 5.04 (d, J=8.1 Hz), suggested their β-orientation (FIGS. 14, 27, and 28). While the remaining anomeric proton at $\delta_H$ 5.07 was obscured by the solvent resonance (HDO) it's coupling constant (J=~8 Hz) evident from 1D TOCSY data (FIG. 24) also indicated β-orientation.

A summary of the and $^{13}$C chemical shifts for the glycoside at C-13 are shown in the table below:

$^1$H and $^{13}$C NMR (500 and 125 MHz, pyridine-d$_5$), Assignments of the Reb D2 C-13 glycoside.

| Position | Reb D2 | |
|---|---|---|
| | $^{13}$C | $^1$H |
| Glc$_{II}$-1 | 98.7 | 5.07 (~8)* |
| Glc$_{II}$-2 | 81.3 | 4.37 m |
| Glc$_{II}$-3 | 88.4 | 4.18 m |
| Glc$_{II}$-4 | 71.1 | 3.88 m |
| Glc$_{II}$-5 | 77.9 | 3.79 m |
| Glc$_{II}$-6 | 63.2 | 4.08 m |
| | | 4.47 m |
| Glc$_{III}$-1 | 105.3 | 5.57 d (7.6) |
| Glc$_{III}$-2 | 76.8 | 4.19 m |
| Glc$_{III}$-3 | 78.9 | 4.24 m |
| Glc$_{III}$-4 | 72.4 | 4.27 m |
| Glc$_{III}$-5 | 78.8 | 3.94 m |
| Glc$_{III}$-6 | 63.5 | 4.41 m |
| | | 4.50 m |
| Glc$_{IV}$-1 | 105.3 | 5.34 d (7.9) |
| Glc$_{IV}$-2 | 75.8 | 4.06 m |
| Glc$_{IV}$-3 | 78.9# | 4.22 m# |
| Glc$_{IV}$-4 | 72.0 | 4.18 m |
| Glc$_{IV}$-5 | 79.3 | 4.10 m |
| Glc$_{IV}$-6 | 62.9 | 4.32 m |
| | | 4.58 m |

*Anomeric proton was obscured by solvent (HDO) resonance, coupling constant value obtained from 1D-TOCSY data.
$^1$H and $^{13}$C values can be exchangeable between Glc$_I$-3, Glc$_V$-3 and Glc$_{IV}$-3.

A summary of the key HMBC, COSY, and 1D-TOCSY correlations used to assign the C-13 glycoside region are provided below:

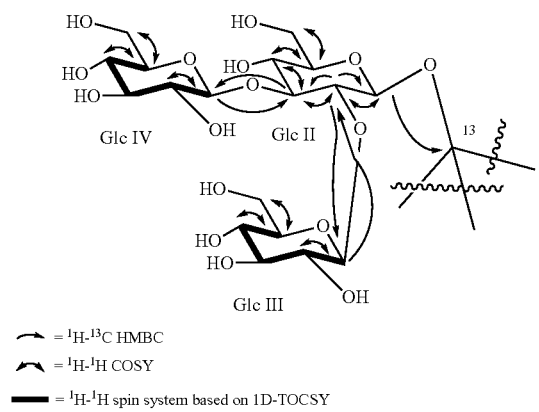

⌒ = ¹H-¹³C HMBC
⌒ = ¹H-¹H COSY
▬ = ¹H-¹H spin system based on 1D-TOCSY

NMR and MS analyses allowed a full assignment of structure, shown below. The chemical name of the compound is 13-[(2-O-β-D-glucopyranosyl-3-O-β-D-glucopyranosyl-β-D-glucopyranosyl)oxy] ent-kaur-16-en-19-oic acid-[(6-O-β-D-glucopyranosyl-β-D-glucopyranosyl) ester] (rebaudioside D2 or reb D2). The compound is an isomer of rebaudioside D.

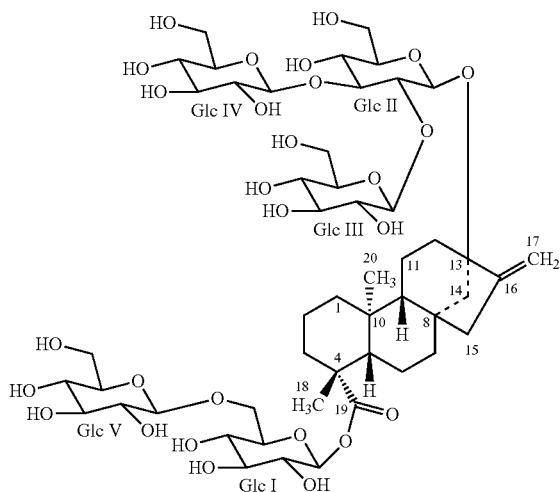

Example 40

Isolation and Characterization of Reb M2

Crude Reaction Sample.

The sample, Lot CB-2977-106, used for isolation was prepared according to Example 22 with UGTSL (GI #460409128).

HPLC Analysis.

Preliminary HPLC analyses was performed using a Waters 2695 Alliance System with the following method: Phenomenex Synergi Hydro-RP, 4.6×250 mm, 4 µm (p/n 00G-4375-E0); Column Temp: 55° C.; Mobile Phase A: 0.0284% NH₄OAc and 0.0116% HOAc in water; Mobile Phase B: Acetonitrile (MeCN); Flow Rate: 1.0 mL/min; Injection volume: 10 µL. Detection was by UV (210 nm) and CAD.

Gradient:

| Time (min) | % A | % B |
|---|---|---|
| 0.0-5.0 | 100 | 0 |
| 20 | 20 | 80 |
| 25 | 20 | 80 |
| 30 | 100 | 0 |

Analyses of semi-preparative purification fractions were performed with the following method: Waters Atlantis dC18, 4.6×100 mm, 5 µm (p/n 186001340); Mobile Phase A: 25% MeCN in water; Mobile Phase B: 30% MeCN in water; Flow Rate: 1.0 mL/min; Injection volume: 10 Detection was by CAD.

Gradient:

| Time (min) | % A | % B |
|---|---|---|
| 0.0-8.5 | 75 | 25 |
| 10.0 | 71 | 29 |
| 16.5 | 70 | 30 |
| 18.5-24.5 | 66 | 34 |
| 26.5-29.0 | 48 | 52 |
| 31-37 | 30 | 70 |
| 38 | 75 | 25 |

LC-MS.

Preliminary analysis of the semi-synthetic steviol glycoside mixture was carried out on a Waters AutoPurification HPLC/MS System with a Waters 3100 Mass Detector operating in negative ion mode. Analysis of the sample was performed using the following method: Phenomenex Synergi Hydro-RP, 4.6×250 mm, 4 µm (p/n 00G-4375-E0); Column Temp: 55° C.; Mobile Phase A: 0.0284% NH₄OAc and 0.0116% HOAc in water; Mobile Phase B: MeCN; Flow Rate: 1.0 mL/min; Injection volume: 10 µL. Detection was by UV (210 nm), and MSD (−ESI m/z 500-2000). Gradient conditions were as listed above.

Isolation by HPLC.

The purification was performed in two steps. The first method used for the semi-preparative purification is summarized below. Column: Waters Atlantis dC18, 30×100 mm, 5 µm (p/n 186001375); Mobile Phase A: 25% MeCN in water; Mobile Phase B: 30% MeCN in water; Flow Rate: 45 mL/min; Injection load: 160 mg dissolved in 20 mL of water. Detection was by UV (205 nm).

Gradient:

| Time (min) | % A | % B |
|---|---|---|
| 0.0-5.0 | 100 | 0 |
| 20 | 20 | 80 |
| 25 | 20 | 80 |
| 30 | 100 | 0 |

The secondary purification used the same column and conditions, but isocratic mobile phase: 20% MeCN in water.

MS and MS/MS.

MS and MS/MS data were generated with a Waters QTof Premier mass spectrometer equipped with an electrospray ionization source. Samples were analyzed by negative ESI. Samples were diluted with H₂O:MeCN (1:1) by 50 fold and introduced via infusion using the onboard syringe pump. The samples were diluted to yield good s/n which occurred at an approximate concentration of 0.01 mg/mL.

NMR.

The sample was prepared by dissolving ~1.0 mg in 150 μL of D$_2$O and NMR data were acquired on a Bruker Avance 500 MHz instrument with a 2.5 mm inverse detection probe. The $^1$H NMR and $^{13}$C NMR spectra were referenced to the residual solvent signal HDO ($\delta_H$ 4.79 ppm) and TSP ($\delta_C$ 0.00 ppm), respectively.

Results and Discussion

Isolation and Purification.

Figure 12:
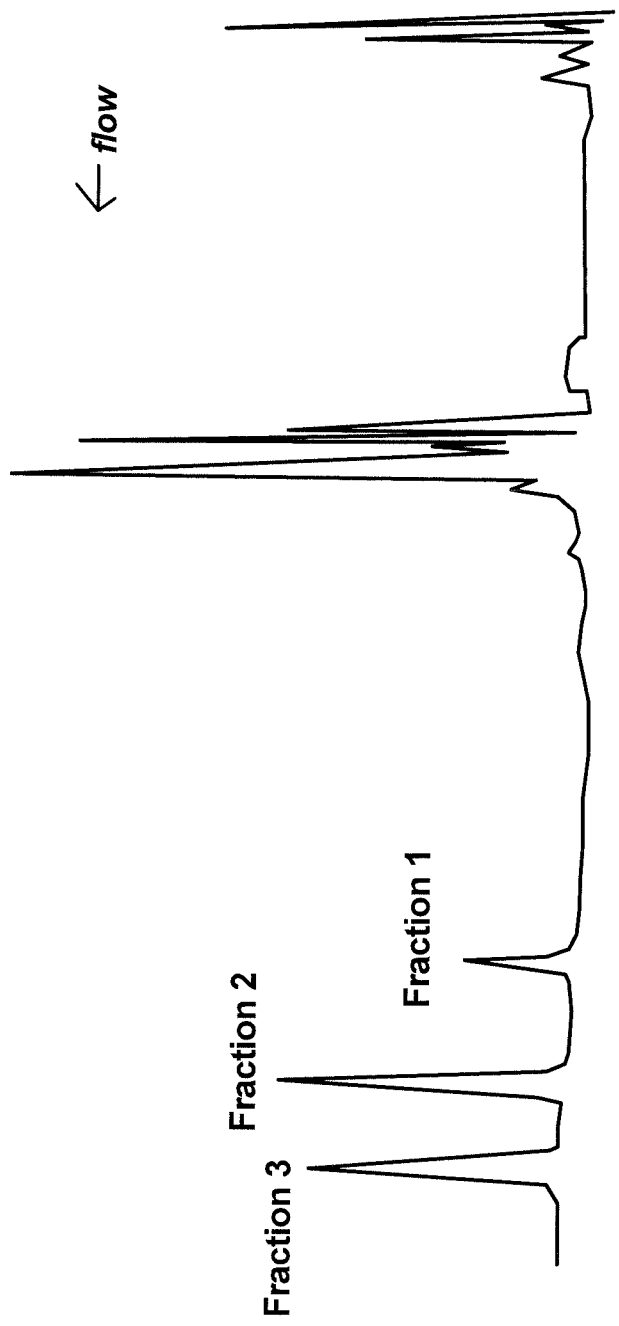
FIG. 12 shows the trace of semi-synthetic steviol glycoside mixture, Lot number CB-2977-106. Chromatogram gridlines are not homogeneous as the detector was re-calibrated 14 min following injection.
Figure 13:
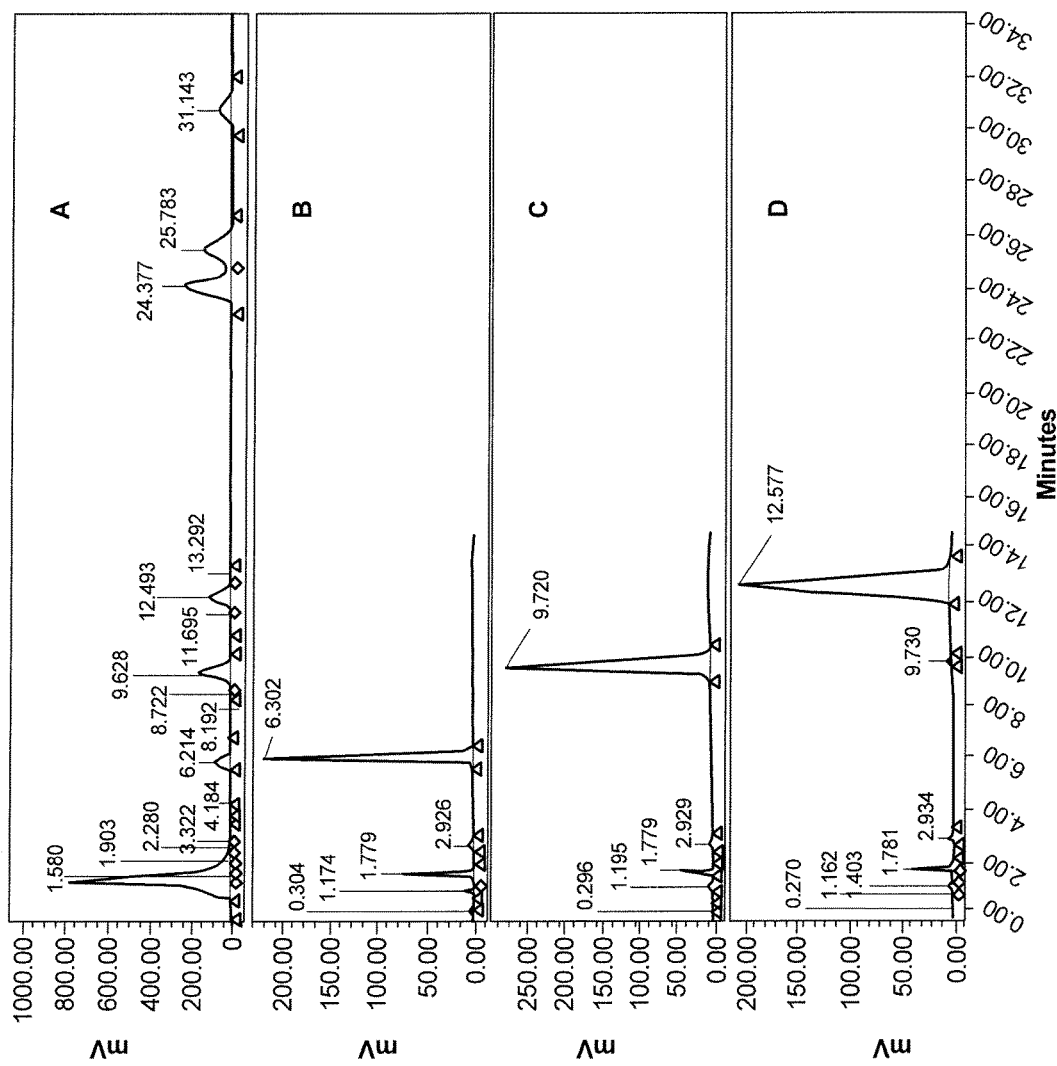
FIG. 13 shows HPLC analysis of semi-synthetic steviol glycoside mixture, Lot number CB-2977-106 (A), Isolated reb M2 (B), isolated reb D (C) and isolated reb D2 (D).

Isolation was performed using on a steviol glycoside mixture, Lot number CB-2977-106, prepared according to Example 22 with UGTSL (GI #460409128). The material was analyzed by LC-MS using the method described above (FIG. 11). The targeted peak of interest was that at 4.1 min in the TIC chromatogram. The mass spectrum of this peak provided a [M-H]$^-$ ion at m/z 1289.7. The provided sample was preliminarily processed in a single injection (160 mg) using the first method condition provided above. This method fractionated the material into 'polar' and 'non-polar' mixtures of glycosides. The 'polar' mixture was then reprocessed using the second-step conditions provided above. The semi-preparative HPLC trace is shown in FIG. 12. From this semi-preparative collection, the peak was isolated with a purity>99% (CAD, AUC). The fraction analysis is provided in FIG. 13. Following the purification, the fractions were concentrated by rotary evaporation at 35° C. and lyophilized. Approximately 1 mg was obtained.

Mass Spectrometry.

The ESI-TOF mass spectrum acquired by infusing a sample of CC-00300 showed a [M-H]$^-$ ion at m/z 1289.5266. The mass of the [M-H]$^-$ ion was in good agreement with the molecular formula C$_{56}$H$_{90}$O$_{33}$ (calcd for C$_{56}$H$_{89}$O$_{33}$: 1289.5286, error: -1.6 ppm) expected for reb M2. The MS data confirmed that CC-00300 has a nominal mass of 1290 Daltons with the molecular formula, C$_{56}$H$_{90}$O$_{33}$.

The MS/MS spectrum (selecting the [M-H]$^-$ ion at m/z 1289.5 for fragmentation) indicated the loss of three glucose units at m/z 803.3688 and sequential loss of three glucose moieties at m/z 641.3165, 479.2633 and 317.2082.

NMR Spectroscopy.

Figure 29:
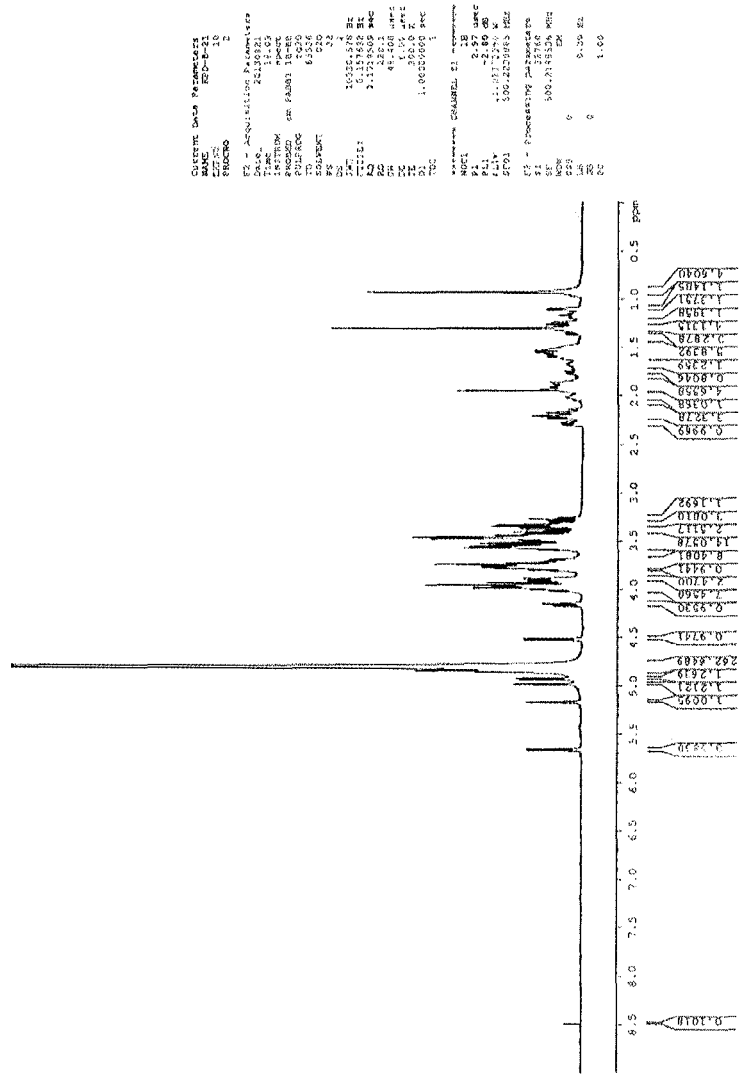
FIG. 29 shows a $^1$H NMR spectrum of reb M2.
Figure 30:
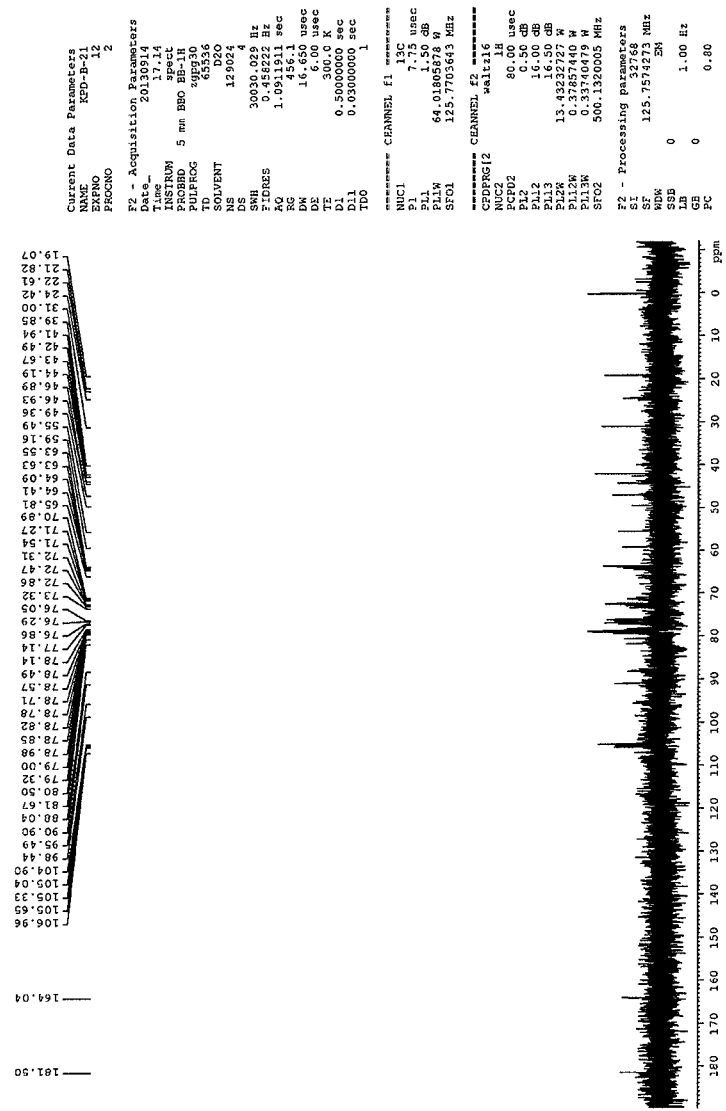
FIG. 30 shows a $^{13}$C NMR spectrum of reb M2.
Figure 31:
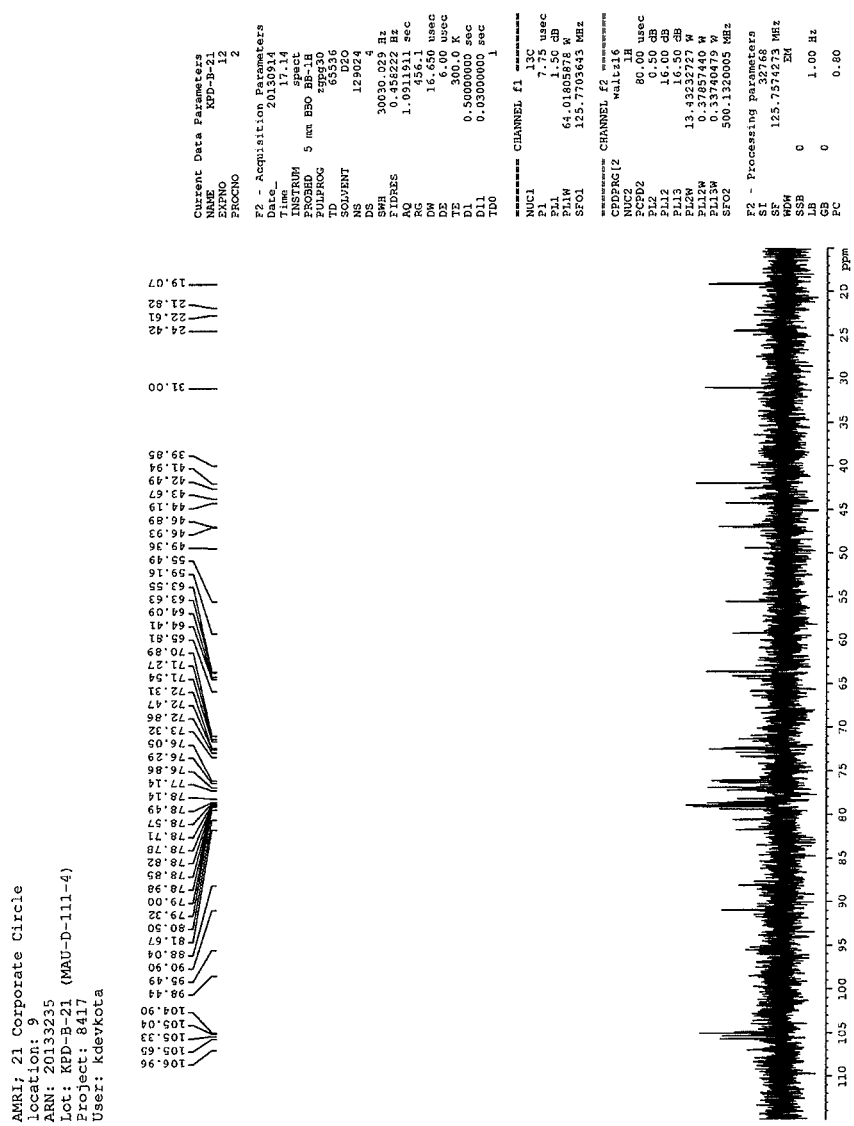
FIG. 31 shows another $^{13}$C NMR spectrum of reb M2.
Figure 32:
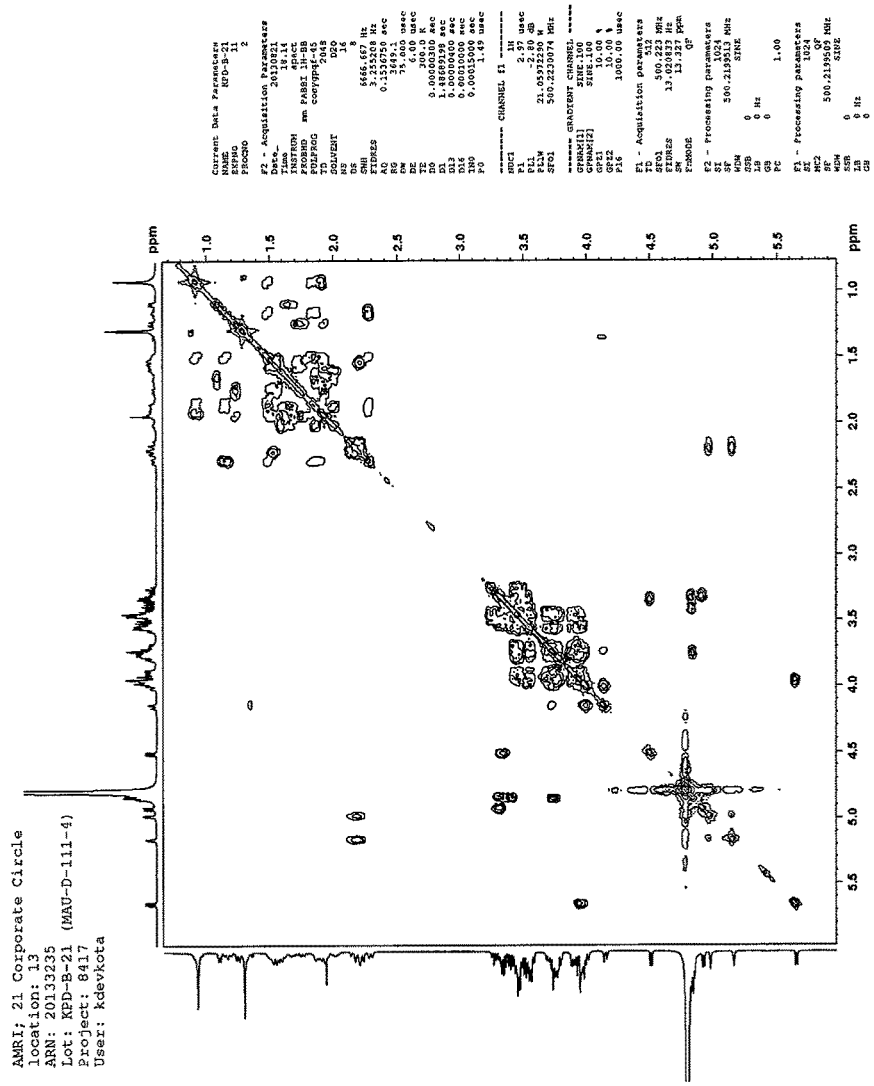
FIG. 32 shows a $^1$H-$^1$H COSY spectrum of reb M2.
Figure 33:
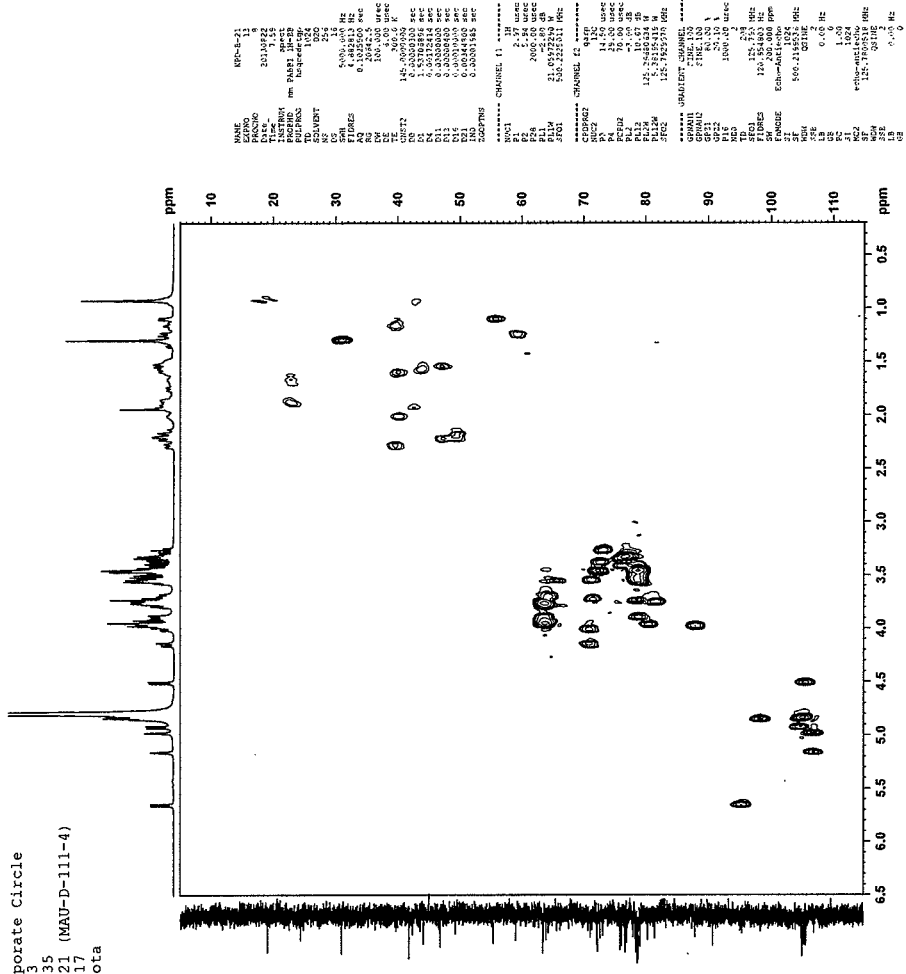
FIG. 33 shows a HSQC-DEPT spectrum of reb M2.
Figure 34:
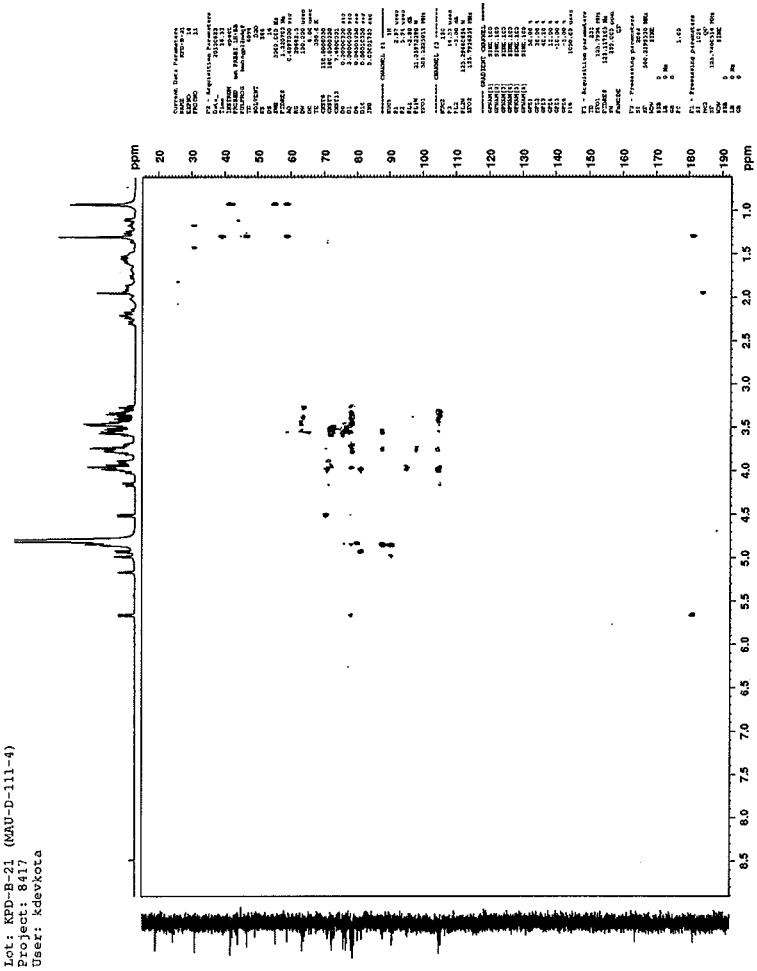
FIG. 34 shows an HMBC spectrum of reb M2.
Figure 35:
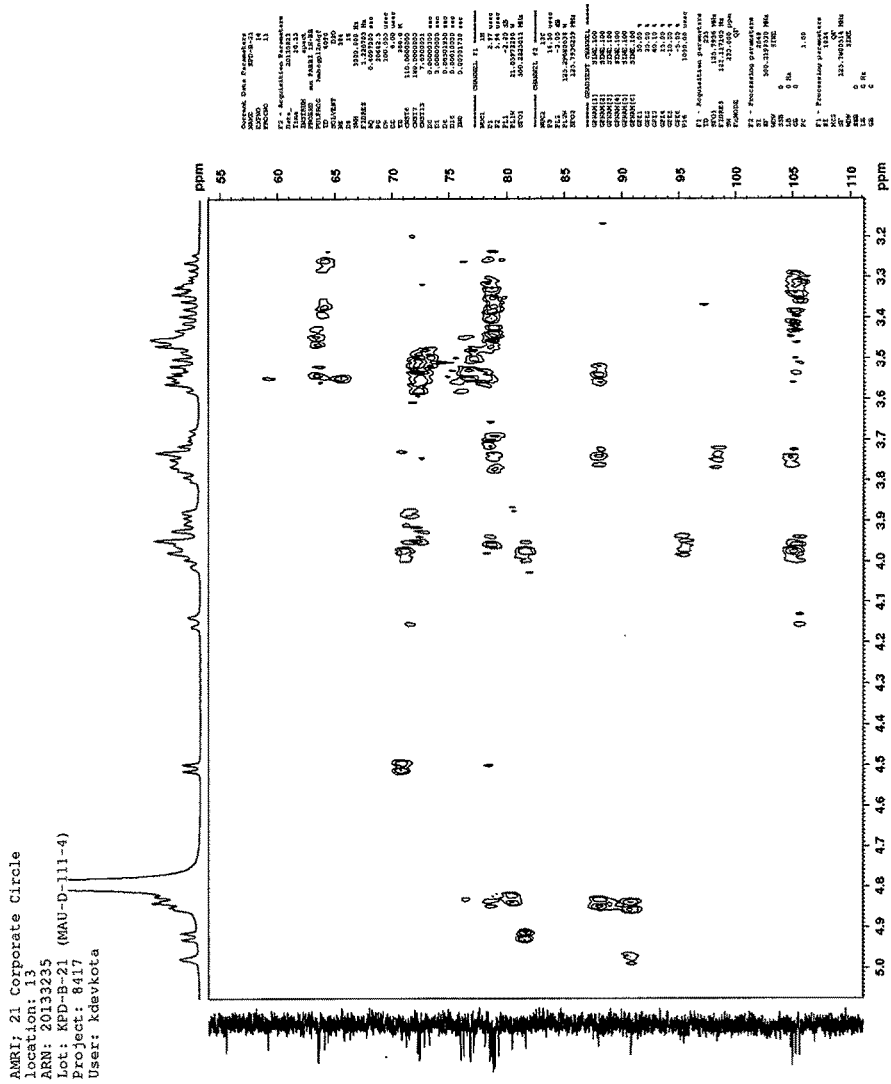
FIG. 35 shows another HMBC spectrum of reb M2.
Figure 36:
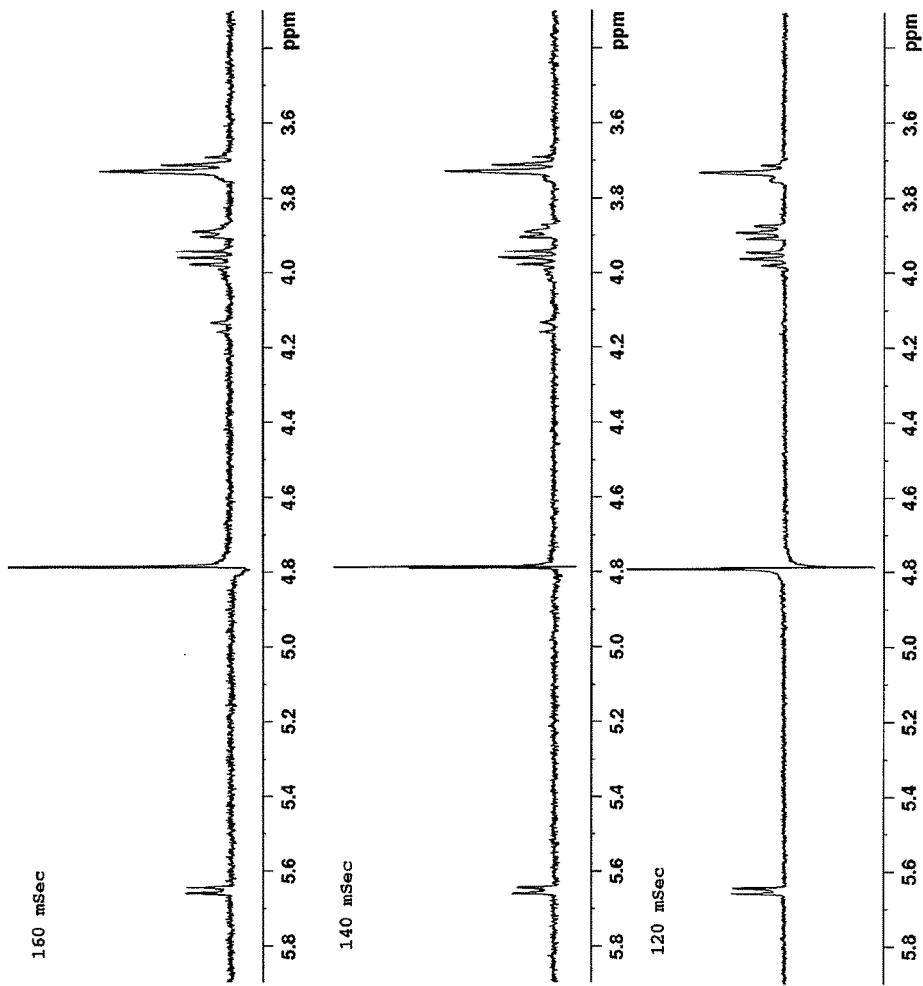
FIG. 36 shows a 1D-TOCSY spectrum of reb M2.
Figure 37:
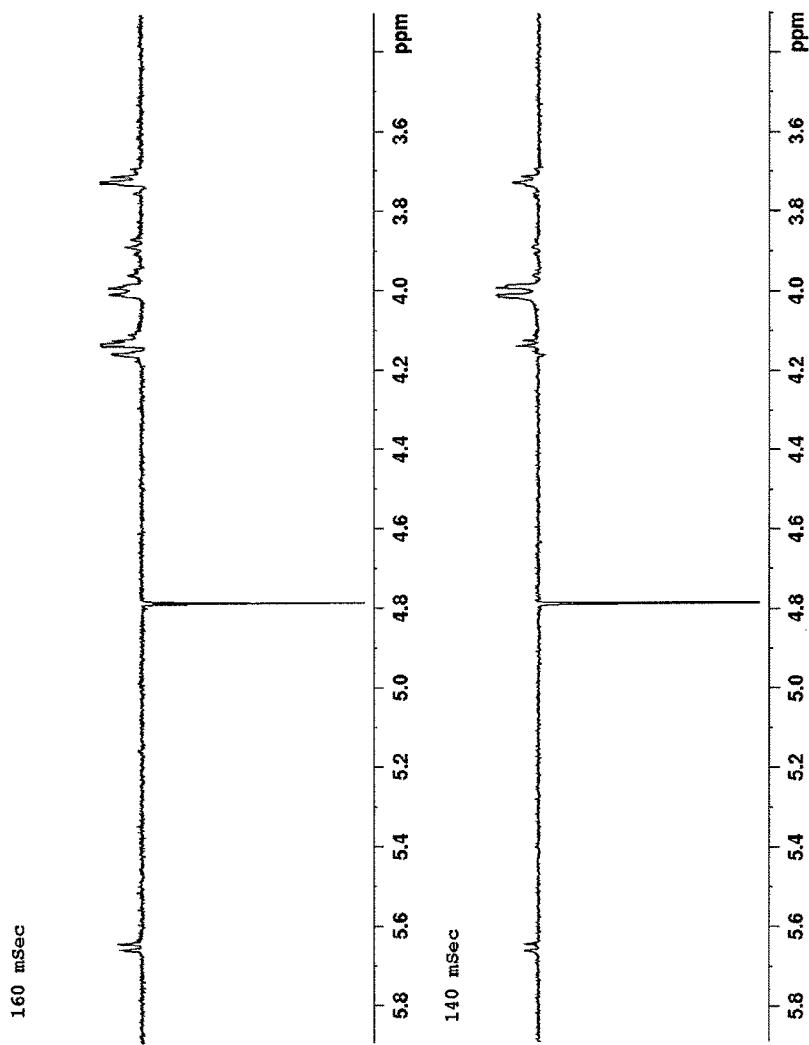
FIG. 37 shows a 1D-TOCSY spectrum of reb M2.
Figure 38:
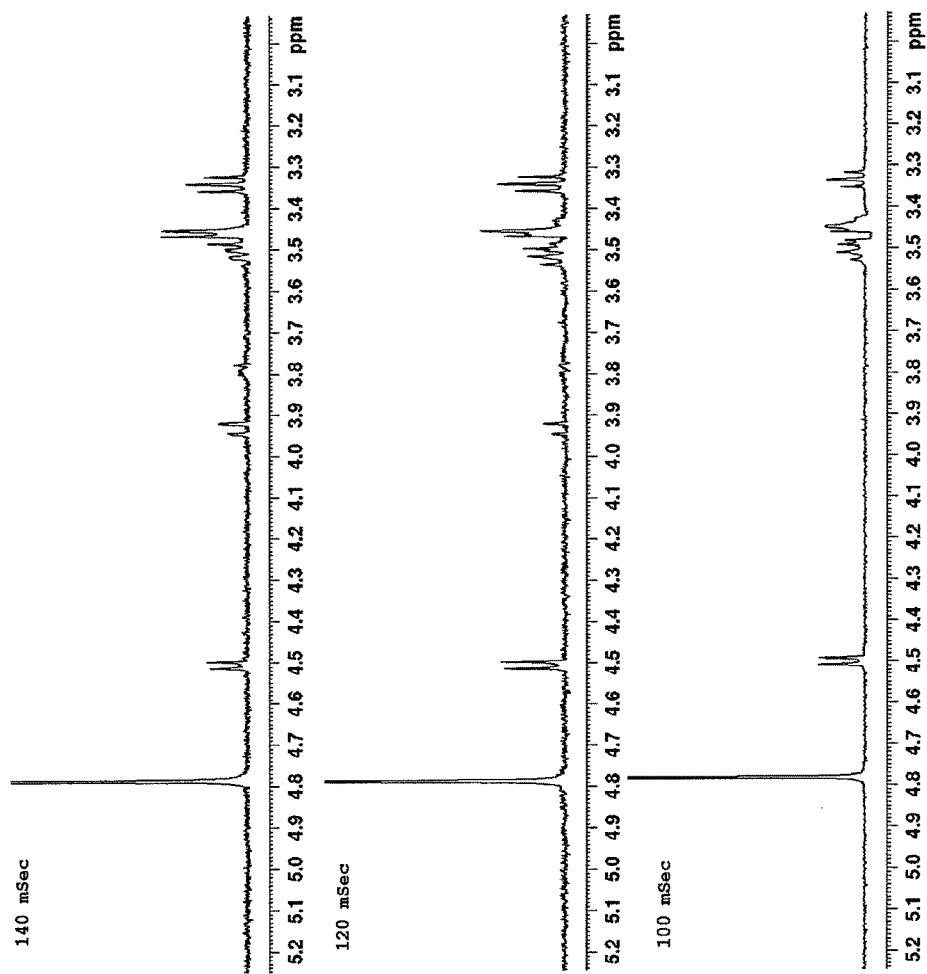
FIG. 38 shows a 1D-TOCSY spectrum of reb M2.
Figure 39:
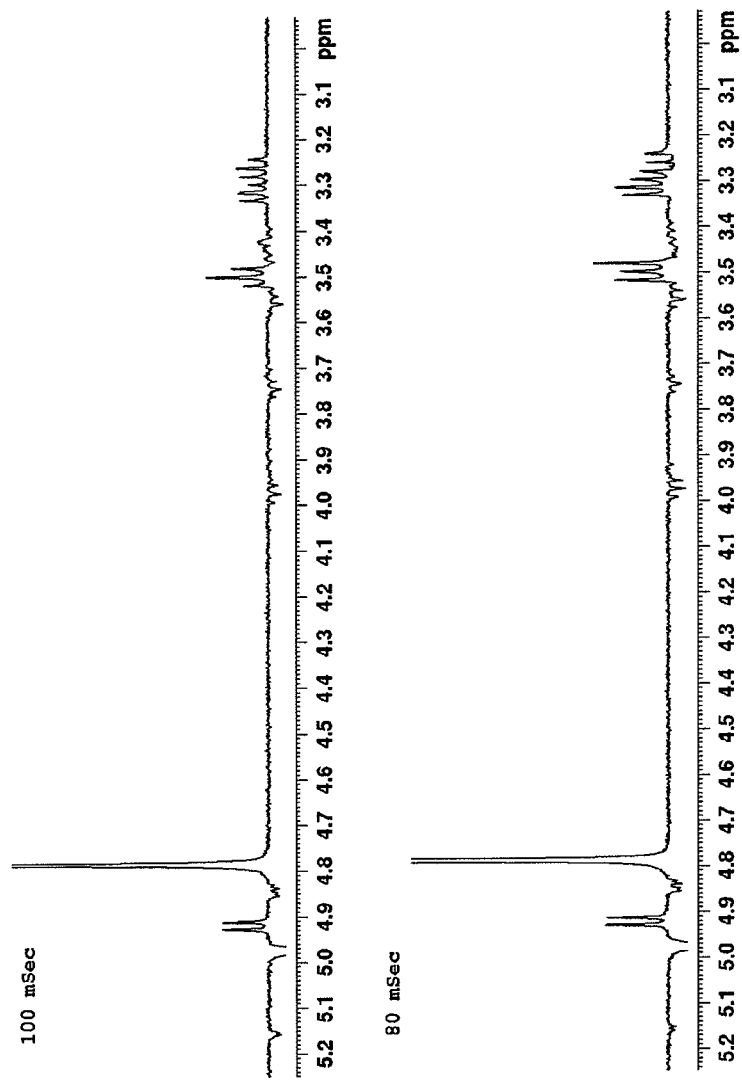
FIG. 39 shows a 1D-TOCSY spectrum of reb M2.

A series of NMR experiments including $^1$H NMR (FIG. 29), $^{13}$C NMR (FIGS. 30 and 31), $^1$H-$^1$H COSY (FIG. 32), HSQC-DEPT (FIG. 33), HMBC (FIGS. 34 and 35), and 1D-TOCSY (FIG. 36-39) were performed to allow assignment of reb M2.

The $^1$H, $^1$H-$^1$H COSY, $^1$H-$^{13}$C HSQC-DEPT and $^1$H-$^{13}$C HMBC NMR data indicated that the central core of the glycoside is a diterpene. The presence of six anomeric protons observed in the $^1$H and $^1$H-$^{13}$C HSQC-DEPT spectra confirm six sugar units in the structure. The methylene $^{13}$C resonance at $\delta_C$ 70.9 in the $^1$H-$^{13}$C HSQC-DEPT spectrum indicated the presence of a 1→6 sugar linkage in the structure. The linkages of sugar units were assigned using $^1$H-$^{13}$C HMBC and 1D-TOCSY correlations.

A HMBC correlation from the methyl protons at $\delta_H$ 1.29 to the carbonyl at $\delta_C$ 181.5 allowed assignment of one of the tertiary methyl groups (C-18) as well as C-19 and provided a starting point for the assignment of the rest of the aglycone. Additional HMBC correlations from the methyl protons (H-18) to carbons at $\delta_C$ 39.8, 43.7, and 59.2 allowed assignment of C3, C4, and C5. Analysis of the $^1$H-$^{13}$C HSQC-DEPT data indicated that the carbon at $\delta_C$ 39.8 was a methylene group and the carbon at $\delta_C$ 59.2 was a methine which were assigned as C-3 and C-5, respectively. This left the carbon at $\delta_C$ 43.7, which did not show a correlation in the HSQC-DEPT spectrum, to be assigned as the quaternary carbon, C-4. The $^1$H chemical shifts for C-3 ($\delta_H$ 1.16 and 2.28) and C-5 ($\delta_H$ 1.24) were assigned using the HSQC-DEPT data. A COSY correlation between one of the H-3 protons ($\delta_H$ 1.16) and a proton at $\delta_H$ 1.49 allowed assignment of one of the H-2 protons which in turn showed a correlation with a proton at $\delta_H$ 0.92 which was assigned to C-1. The remaining $^1$H and $^{13}$C chemical shifts for C-1 and C-2 were then assigned on the basis of additional COSY and HSQC-DEPT correlations and are summarized in the table below.

| $^1$H NMR (500 MHz, D$_2$O) and $^{13}$C NMR (125 MHz, D$_2$O/TSP) Assignments of the Reb M2 aglycone. | | |
|---|---|---|
| Position | $^{13}$C | $^1$H |
| 1 | 41.9 | 0.92 m |
|   |      | 1.93 m |
| 2 | 21.8 | 1.49 m |
|   |      | 1.86 m |
| 3 | 39.8 | 1.16 m |
|   |      | 2.28 d (13.4) |
| 4 | 43.7 | — |
| 5 | 59.2 | 1.24 d (12.1) |
| 6 | 24.4 | 1.73 m |
|   |      | 1.94 m |
| 7 | 44.2 | 1.49 m |
|   |      | 1.56 m |
| 8 | 46.9 | — |
| 9 | 55.5 | 1.09 d (7.7) |
| 10 | 42.4 | — |
| 11 | 22.6 | 1.66 m |
|    |      | 1.70 m |
| 12 | 39.9 | 1.60 m |
|    |      | 2.00 m |
| 13 | 90.9 | — |
| 14 | 46.9 | 1.53 d (12.6) |
|    |      | 2.21 d (13.6) |
| 15 | 49.4 | 2.15 d (17.2) |
|    |      | 2.18 d (18.1) |
| 16 | 164.0 | — |
| 17 | 107.0 | 4.98 s |
|    |       | 5.16 s |
| 18 | 31.0 | 1.29 s |
| 19 | 181.5 | — |
| 20 | 19.1 | 0.92 s |

The other tertiary methyl singlet, observed at $\delta_H$ 0.92 showed HMBC correlations to C-1 and C-5 and was assigned as C-20. The methyl protons showed additional HMBC correlations to a quaternary carbon ($\delta_C$ 42.4) and a methine ($\delta_C$ 55.5) which were assigned as C-10 and C-9, respectively. COSY correlations between H-5 ($\delta_H$ 1.24) and protons at $\delta_H$ 1.73 and 1.94 then allowed assignment of the H-6 protons which in turn showed correlations to protons at $\delta_H$ 1.49 and 1.56 which were assigned to C-7. The $^{13}$C chemical shifts for C-6 ($\delta_C$ 24.4) and C-7 ($\delta_C$ 44.2) were then determined from the HSQC-DEPT data. COSY correlations between H-9 ($\delta_H$ 1.09) and protons at $\delta_H$ 1.66 and 1.70 allowed assignment of the H-11 protons which in turn showed COSY correlations to protons at $\delta_H$ 1.60 and 2.00 which were assigned as the H-12 protons. The HSQC-DEPT data was then used to assign C-11 ($\delta_C$ 22.6) and C-12 ($\delta_C$ 39.9). The olefinic protons observed at $\delta_H$ 4.98 and 5.16 showed HMBC correlations to C-13 ($\delta_C$ 90.9) and were assigned to C-17 ($\delta_C$ 107.0 via HSQC-DEPT). The olefinic protons H-17 showed HMBC correlations to a carbon at $\delta_C$ 49.4 which was assigned as C-15. An additional HMBC correlation from H-9 to a methylene carbon at $\delta_C$ 46.9 then allowed assignment of C-14. The $^1$H chemical shifts at C-14 ($\delta_H$ 1.53 and 2.21) and C-15 ($\delta_H$ 2.15 and 2.18) were assigned using the HSQC-DEPT data.

A summary of the key HMBC and COSY correlations used to assign the aglycone region are provided below:

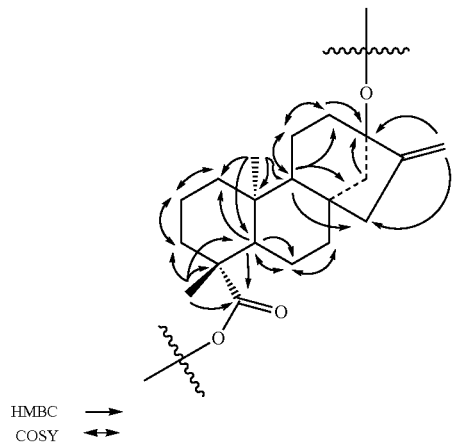

HMBC →
COSY ↔

Analysis of the $^1$H-$^{13}$C HSQC-DEPT data confirmed the presence of six anomeric protons. Three of the anomeric protons were well resolved at $\delta_H$ 5.65 ($\delta_C$ 95.5), 4.92 ($\delta_C$ 104.9), and 4.50 ($\delta_C$ 105.7) in the $^1$H NMR spectrum. The remaining three anomeric protons observed at $\delta_H$ 4.85 ($\delta_C$ 98.4), 4.84 ($\delta_C$ 105.0), and 4.83 ($\delta_C$ 105.3) were overlapped by the residual solvent resonance in the $^1$H spectrum. The anomeric proton observed at $\delta_H$ 5.65 showed a HMBC correlation to C-19 which indicated that it corresponds to the anomeric proton of Glc$_I$. Similarly, the anomeric proton observed at $\delta_H$ 4.85 showed a HMBC correlation to C-13 allowing it to be assigned as the anomeric proton of Glc$_{II}$.

The Glc$_I$ anomeric proton ($\delta_H$ 5.65) showed a COSY correlation to a proton at $\delta_H$ 3.96 which was assigned as Glc$_I$ H-2 which in turn showed a COSY correlation to a proton at $\delta_H$ 3.89 (Glc$_I$ H-3) which showed a COSY correlation with a proton at $\delta_H$ 3.71 (Glc$_I$ H-4). Due to data overlap, the COSY spectrum did not allow assignment of the H-5 or H-6 protons. Therefore, a series of 1D-TOCSY experiments were performed using selective irradiation of the Glc$_I$ anomeric proton with several different mixing times. In addition to confirming the assignments for Glc$_I$ H-2 through H-4, the 1D-TOCSY data showed a proton at $\delta_H$ 3.73 assigned as Glc$_I$ H-5 and a proton at $\delta_H$ 4.15 assigned as one of the Glc$_I$ H-6 protons. The latter proton was also used for 1D-TOCSY experiments. The selective irradiation of H-6 with several different mixing times also confirmed the assignment of Glc$_I$ H-1 to H-5 as well as the remaining methylene proton of H-6 ($\delta_H$ 4.00). Assignment of the $^{13}$C chemical shifts for Glc$_I$ C-2 ($\delta_C$ 80.5), C-3 ($\delta_C$ 79.0), C-4 ($\delta_C$ 71.5), C-5 ($\delta_C$ 79.0), and C-6 ($\delta_C$ 70.9) was determined using the $^1$H-$^{13}$C HSQC-DEPT data to complete the assignment of Glc$_I$. Furthermore, the presence of a methylene $^{13}$C resonance at $\delta_C$ 70.9 in the $^1$H-$^{13}$C HSQC-DEPT spectrum indicated a 1→6 sugar linkage of Glc$_I$ in the structure.

Two of the unassigned glucose moieties were assigned as substituents at C-2 and C-6 of Glc$_I$ on the basis of HMBC correlations. The anomeric proton observed at $\delta_H$ 4.83 showed an HMBC correlation to Glc$_I$ C-2 and was assigned as the anomeric proton of Glc$_V$. The anomeric proton observed at $\delta_H$ 4.50 showed a HMBC correlation to Glc$_I$ C-6 and was assigned as the anomeric proton of Glc$_{VI}$. The reciprocal HMBC correlations from Glc$_I$ H-2 to the anomeric carbon of Glc$_V$ and from Glc$_I$ H-6 to the anomeric carbon of Glc$_{VI}$ were also observed.

The anomeric proton of Glc$_V$ ($\delta_H$ 4.83) showed a COSY correlation with a proton at $\delta_H$ 3.32 which was assigned as Glc$_V$ H-2. The Glc$_V$ H-2 in turn showed a COSY correlation to a proton at $\delta_H$ 3.51 (Glc$_V$ H-3). This latter proton showed an additional correlation with a proton at $\delta_H$ 3.38 (Glc$_V$ H-4). H-4 also showed a COSY correlation to a proton at $\delta_H$ 3.55 (Glc$_V$ H-5) and Glc$_V$ H-5 in turn showed a COSY correlation to Glc$_V$ H-6 protons ($\delta_H$ 3.76 and 3.97). Assignment of the $^{13}$C chemical shifts for Glc$_V$ C-2 ($\delta_C$ 78.5), C-3 ($\delta_C$ 78.7), C-4 ($\delta_C$ 72.9), C-5 ($\delta_C$ 78.8), and C-6 ($\delta_C$ 63.6) was determined using the HSQC-DEPT data. HMBC correlations from Glc$_V$ H-3 to C-2 and C-4 and also from Glc$_V$ H-4 to C-3 and C-6 confirmed the assignments made above to complete the assignment of Glc$_V$.

Another glucose moiety was assigned as a substituent at C-6 of Glc$_I$ on the basis of $^1$H-$^{13}$C HSQC-DEPT and HMBC correlations. The relatively downfield shift of a methylene $^{13}$C resonance of Glc$_I$ at $\delta_C$ 70.9 in the HSQC-DEPT spectrum indicated a 1-46 sugar linkage of Glc$_I$. The anomeric proton observed at $\delta_H$ 4.50 showed a HMBC correlation to Glc$_I$ C-6 and was assigned as the anomeric proton of Glc$_{VI}$. Similarly, methylene protons of Glc$_I$ showed HMBC correlations to the anomeric carbon of Glc$_{VI}$ and this confirmed the presence of a 1→6 sugar linkage between Glc$_I$ and Glc$_{VI}$. The Glc$_{VI}$ anomeric proton showed a COSY correlation to a proton at $\delta_H$ 3.33 which was assigned as Glc$_{VI}$ H-2 which in turn showed a COSY correlation to a proton at $\delta_H$ 3.49 (Glc$_{VI}$ H-3). Due to data overlap, the COSY spectrum did not allow assignment of Glc$_V$ H-4 to H-6 based on the COSY correlations. Therefore, a series of 1D-TOCSY experiments were performed using selective irradiation of the Glc$_{VI}$ anomeric proton with different mixing times. In addition to confirming the assignments for Glc$_{VI}$ H-2 through H-3, the 1D-TOCSY data showed protons at $\delta_H$ 3.45 (Glc$_{VI}$ H-4) and $\delta_H$ 3.48 (Glc$_{VI}$ H-5) and protons at $\delta_H$ 3.92 and 3.94 assigned for Glc$_{VI}$ H-6 protons. Assignment of the $^{13}$C chemical shifts for Glc$_{VI}$ C-2 ($\delta_C$ 78.1), C-3 ($\delta_C$ 78.6), C-4 ($\delta_C$ 72.3), C-5 ($\delta_C$ 78.8), and C-6 ($\delta_C$ 64.1) was determined using the $^1$H-$^{13}$C HSQC-DEPT data to complete the assignment of Glc$_{VI}$.

A summary of the $^1$H and $^{13}$C chemical shifts for the glycoside at C-19 are found in the table below:

| H NMR (500 MHz, D$_2$O) and $^{13}$C NMR (125 MHz, D$_2$O/TSP) Assignments of the Reb M2 glycoside. | | |
| --- | --- | --- |
| Position | $^{13}$C | $^1$H |
| Glc$_I$-1 | 95.5 | 5.65 d (7.6) |
| Glc$_I$-2 | 80.5 | 3.96 m |
| Glc$_I$-3 | 79.0 | 3.89 m |
| Glc$_I$-4 | 71.5 | 3.71 m |
| Glc$_I$-5 | 79.0 | 3.73 m |
| Glc$_I$-6 | 70.9 | 4.00 m |
|  |  | 4.15 d (11.7) |
| Glc$_V$-1 | 105.3* | 4.83* d (8.0) |
| Glc$_V$-2 | 78.5 | 3.32 m |
| Glc$_V$-3 | 78.7 | 3.51 m |
| Glc$_V$-4 | 72.9 | 3.38 m |
| Glc$_V$-5 | 78.8 | 3.55 m |
| Glc$_V$-6 | 63.6 | 3.76 m |
|  |  | 3.97 m |
| Glc$_{VI}$-1 | 105.7 | 4.50 d (7.9) |
| Glc$_{VI}$-2 | 78.1 | 3.33 m |
| Glc$_{VI}$-3 | 78.6 | 3.49 m |
| Glc$_{VI}$-4 | 72.3 | 3.45 m |
| Glc$_{VI}$-5 | 78.8 | 3.48 m |

-continued

| H NMR (500 MHz, D$_2$O) and $^{13}$C NMR (125 MHz, D$_2$O/TSP) Assignments of the Reb M2 glycoside. | | |
|---|---|---|
| Position | $^{13}$C | $^1$H |
| Glc$_{II}$-6 | 64.1 | 3.92 m |
|  |  | 3.94 m |

*$^1$H and $^{13}$C values can be exchangeable with Glc$_{II}$-1 of the following table.

A summary of the key HMBC, COSY, and 1D-TOCSY correlations used to assign the C-19 glycoside region are provided below:

| $^1$H NMR (500 MHz, D$_2$O) and $^{13}$C NMR (125 MHz, D$_2$O/TSP) Assignments of the Reb M2 glycoside. | | |
|---|---|---|
| Position | $^{13}$C$^\#$ | $^1$H |
| Glc$_{II}$-1 | 98.4 | 4.85 d (7.8) |
| Glc$_{II}$-2 | 81.7 | 3.75 m |
| Glc$_{II}$-3 | 88.0 | 3.98 m |
| Glc$_{II}$-4 | 71.3 | 3.54 m |
| Glc$_{II}$-5 | 80.5 | 3.96 m |
| Glc$_{II}$-6 | 63.6 | 3.45 m |
|  |  | 3.77 m |
| Glc$_{III}$-1 | 104.9 | 4.92 d (7.9) |
| Glc$_{III}$-2 | 76.3 | 3.32 m |
| Glc$_{III}$-3 | 78.8 | 3.51 m |
| Glc$_{III}$-4 | 73.3 | 3.26 t (9.5) |
| Glc$_{III}$-5 | 78.8 | 3.44 m |
| Glc$_{III}$-6 | 64.4 | 3.75 m |
|  |  | 3.94 m |
| Glc$_{IV}$-1 | 105.0 | 4.84 d (7.8) |
| Glc$_{IV}$-2 | 76.1 | 3.41 m |
| Glc$_{IV}$-3 | 78.8 | 3.46 m |
| Glc$_{IV}$-4 | 72.5 | 3.45 m |
| Glc$_{IV}$-5 | 81.7 | 3.75 m |
| Glc$_{IV}$-6 | 65.8 | 3.55 m |
|  |  | 3.78 m |

Assignment of Glc$_{II}$ was carried out in a similar manner. The Glc$_{II}$ anomeric proton ($\delta_H$ 4.85) showed a COSY correlation to a proton at $\delta_H$ 3.75 which was assigned as Glc$_{II}$ H-2 which in turn showed a COSY correlation to a proton at $\delta_H$ 3.98 (Glc$_{II}$ H-3). This latter proton showed an additional correlation with a proton at $\delta_H$ 3.54 (Glc$_{II}$ H-4). H-4 also showed a COSY correlation to a proton at $\delta_H$ 3.96 (Glc$_{II}$ H-5). Glc$_{II}$ H-5 also showed a COSY correlation to Glc$_{II}$ H-6 protons ($\delta_H$ 3.77 and 3.45). Assignment of the $^{13}$C chemical shifts for Glc$_{II}$ C-2 ($\delta_C$ 81.7), C-3 ($\delta_C$ 88.0), C-4 ($\delta_C$ 71.3), C-5 ($\delta_C$ 80.5), and C-6 ($\delta_C$ 63.6) was determined using the HSQC-DEPT data. HMBC correlations from Glc$_{II}$ H-3 to C-2 and C-4 and also from Glc$_{II}$ H-4 to C-3 and C-6 confirmed the assignments made above to complete the assignment of Glc$_{II}$.

Two of the remaining unassigned glucose moieties were assigned as substituents at C-2 and C-3 of Glc$_{II}$ on the basis of HMBC correlations. The anomeric proton observed at $\delta_H$ 4.92 showed a HMBC correlation to Glc$_{II}$ C-2 and was assigned as the anomeric proton of Glc$_{III}$. The anomeric proton observed at $\delta_H$ 4.84 showed a HMBC correlation to Glc$_{II}$ C-3 and was assigned as the anomeric proton of Glc$_{IV}$. The reciprocal HMBC correlations between Glc$_{II}$ H-2 and the anomeric carbon of Glc$_{III}$ and between Glcn H-3 and the anomeric carbon of Glc$_{IV}$ were also observed.

The anomeric proton of Glc$_{iii}$ ($\delta_H$ 4.92) showed a COSY correlation with a proton at $\delta_H$ 3.32 which was assigned as Glc$_{III}$ H-2. Due to data overlap, the COSY spectrum did not allow assignment of H-3 to H-6 protons. Therefore, a series of 1D-TOCSY experiments were performed using selective irradiation of the Glc$_{III}$ anomeric proton with different mixing times. In addition to confirming the assignments for Glc$_{III}$ H-2, the 1D-TOCSY data showed protons at $\delta_H$ 3.51 (Glc$_{III}$ H-3), $\delta_H$ 3.26 (Glc$_{iii}$ H-4), and $\delta_H$ 3.44 (Glc$_{iii}$ H-5). Once H-4 was assigned using 1D-TOCSY data, COSY correlations from H-4 to H-5 and in turn to H-6 were used to assign H-6. In the COSY spectrum, Glc$_{iii}$ H-4 showed a correlation to Glc$_{III}$ H-5, which in turn showed COSY correlations to $\delta_H$ 3.94 and 3.75 of Glc$_{iii}$ H-6a and H-6b, respectively. The $^{13}$C chemical shifts for Glc$_{III}$ C-2 ($\delta_C$ 76.3), C-3 ($\delta_C$ 78.8), C-4 ($\delta_C$ 73.3), C-5 ($\delta_C$ 78.8), and C-6 ($\delta_C$ 64.4) were then determined using the $^1$H-$^{13}$C HSQC-DEPT correlations to complete the assignment of Glc$_{III}$.

The anomeric proton of Glc$_{IV}$ ($\delta_H$ 4.84) which showed a COSY correlation to a proton at $\delta_H$ 3.41 was assigned as Glc$_{IV}$ H-2 which in turn showed a COSY correlation to a proton at $\delta_H$ 3.46 (Glc$_{IV}$ H-3). This latter proton showed an additional correlation with a proton at $\delta_H$ 3.45 (Glc$_{IV}$ H-4) which also showed a COSY correlation to a proton at $\delta_H$ 3.75 (Glc$_{IV}$ H-5). Glc$_{IV}$ H-5 also showed a COSY correlation to Glc$_{IV}$ H-6 protons OH 3.55 and 3.78). Assignment of the $^{13}$C chemical shifts for Glc$_{IV}$ C-2 ($\delta_C$ 76.1), C-3 ($\delta_C$ 78.8), C-4 ($\delta_C$ 72.5), C-5 ($\delta_C$ 81.7), and C-6 ($\delta_C$ 65.8) was determined using the HSQC-DEPT data. HMBC correlations from Glc$_{IV}$ H-3 to C-4 and C-5 and also from Glc$_{IV}$ H-4 to C-3 and C-6 confirmed the assignments made above to complete the assignment of Glc$_{IV}$.

A summary of the $^1$H and $^{13}$C chemical shifts for the glycoside at C-13 are found in the following table:

| $^1$H NMR (500 MHz, D$_2$O) and $^{13}$C NMR (125 MHz, D$_2$O/TSP) Assignments of the Reb M2 glycoside. | | |
|---|---|---|
| Position | $^{13}$C$^\#$ | $^1$H |
| Glc$_{II}$-1 | 98.4 | 4.85 d (7.8) |
| Glc$_{II}$-2 | 81.7 | 3.75 m |
| Glc$_{II}$-3 | 88.0 | 3.98 m |
| Glc$_{II}$-4 | 71.3 | 3.54 m |
| Glc$_{II}$-5 | 80.5 | 3.96 m |
| Glc$_{II}$-6 | 63.6 | 3.45 m |
|  |  | 3.77 m |
| Glc$_{III}$-1 | 104.9 | 4.92 d (7.9) |
| Glc$_{III}$-2 | 76.3 | 3.32 m |
| Glc$_{III}$-3 | 78.8 | 3.51 m |
| Glc$_{III}$-4 | 73.3 | 3.26 t (9.5) |
| Glc$_{III}$-5 | 78.8 | 3.44 m |
| Glc$_{III}$-6 | 64.4 | 3.75 m |
|  |  | 3.94 m |
| Glc$_{IV}$-1 | 105.0 | 4.84 d (7.8) |
| Glc$_{IV}$-2 | 76.1 | 3.41 m |
| Glc$_{IV}$-3 | 78.8 | 3.46 m |
| Glc$_{IV}$-4 | 72.5 | 3.45 m |
| Glc$_{IV}$-5 | 81.7 | 3.75 m |
| Glc$_{IV}$-6 | 65.8 | 3.55 m |
|  |  | 3.78 m |

A summary of the key HMBC, COSY, and 1D-TOCSY correlations used to assign the C-13 glycoside region are provided below:

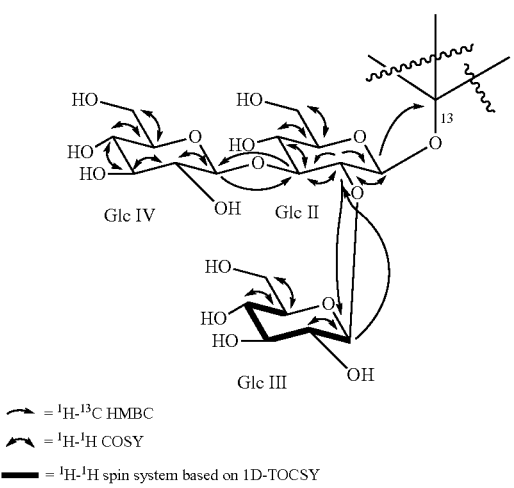

= ¹H-¹³C HMBC
= ¹H-¹H COSY
= ¹H-¹H spin system based on 1D-TOCSY

NMR and MS analyses allowed a full assignment of its structure, shown below. The chemical name of the compound is 13-[(2-O-β-D-glucopyranosyl-3-O-β-D-glucopyranosyl-β-D-glucopyranosyl)oxy] ent-kaur-16-en-19-oic acid-[(2-O-β-D-glucopyranosyl-6-O-β-D-glucopyranosyl-β-D-glucopyranosyl) ester] (rebaudioside M2 or reb M2). The compound is an isomer of rebaudioside M.

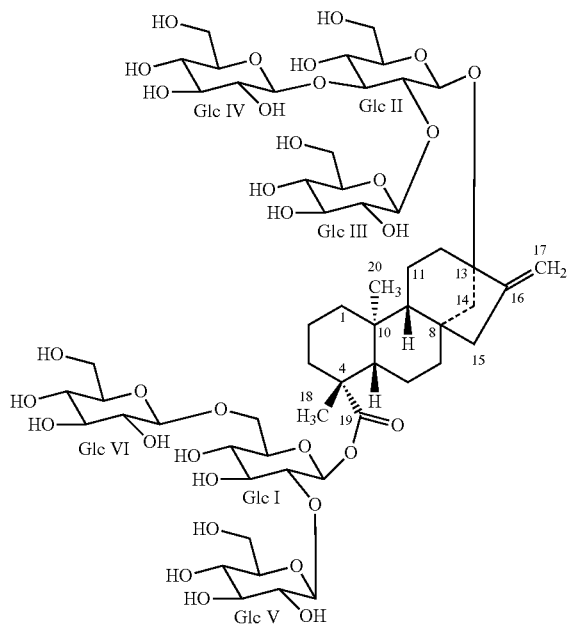

Example 41

Directed Evolution of UGT76G1 for the Conversion of Rebaudioside D to Rebaudioside M (Round 2)

The most active clone from the first round of directed evolution of UGT76G1 (see EXAMPLE 26 UGT76G1var94 containing mutations: Q266E_P272A_R334K_G348P_L379G) was chosen as baseline clone for round 2. A list of 53 mutations was established containing different identified positive mutations from the first round and new mutations obtained by DNA2.0 ProteinGPS™ strategy. This list of mutations was subsequently used to design 92 variant genes that contained each 3 different mutations. After codon-optimized for expression in E. coli the genes were synthesized, subcloned in the pET30a+ plasmid and used for transformation of E. coli BL21 (DE3) chemically competent cells. The obtained cells were grown in Petri-dishes on solid LB medium in the presence of Kanamycin. Suitable colonies were selected and allowed to grow in liquid LB medium in tubes. Glycerol was added to the suspension as cryoprotectant and 400 µL aliquots were stored at −20° C. and at −80° C.

These storage aliquots of E. coli BL21(DE3) containing the pET30a+_UGT76G1var plasmids were thawed and added to LBGKP medium (20 g/L Luria Broth Lennox; 50 mM PIPES buffer pH 7.00; 50 mM Phosphate buffer pH 7.00; 2.5 g/L glucose and 50 mg/L of Kanamycine). This culture was allowed to shake in a 96 microtiter plate at 30° C. for 8 h.

3.95 mL of production medium containing 60 g/L of Overnight Express™ Instant TB medium (Novagen®), 10 g/L of glycerol and 50 mg/L of Kanamycin was inoculated with 50 µL of above described culture. In a 48 deepwell plate the resulting culture was allowed to stir at 20° C. The cultures gave significant growth and a good OD (600 nm) was obtained. After 44 h, the cells were harvested by centrifugation and frozen.

Lysis was performed by addition of Bugbuster® Master mix (Novagen®) to the thawed cells and the lysate was recovered by centrifugation. Activity tests were performed with 100 µL of fresh lysate that was added to a solution of Rebaudioside D (final concentration 0.5 mM), MgCl$_2$ (final concentration 3 mM) and UDP-Glucose (final concentration 2.5 mM) in 50 mM phosphate buffer pH 7.2.

The reaction was allowed to run at 30° C. and samples were taken after 2, 4, 7 and 24 h. to determine conversion and initial rate by HPLC (CAD detection) using the analytical method that was described above for the transformation of Rebaudioside D to Rebaudioside M. In parallel the experiments were performed with baseline clone, Round1-Var94. The conversion after 22 h. and initial rate for this baseline clone was defined as 100% and the normalized conversions and initial rates for the round 2 clones are depicted in the following table:

| Clone | Mutations* | Normalized conversion Reb D to Reb M after 22 h. | Normalized initial rate (0-4 h) |
|---|---|---|---|
| Round1-Var94 | UGT76G1 (Q266E_P272A_R334K_G348P_L379G) baseline clone | 100% | 100% |
| Round2-Var1 | Round1-Var94 (A213N_P348G_I411V) | 70% | 86% |
| Round2-Var2 | Round1-Var94 (K303G_I423M_Q425E) | 120% | 134% |
| Round2-Var3 | Round1-Var94 (V20L_N138K_S147G) | 14% | 15% |
| Round2-Var4 | Round1-Var94 (I16V_V133A_L299I) | 37% | 43% |

-continued

| Clone | Mutations* | Normalized conversion Reb D to Reb M after 22 h. | Normalized initial rate (0-4 h) |
|---|---|---|---|
| Round2-Var5 | Round1-Var94 (S241V_S274G_Q432E) | 75% | 72% |
| Round2-Var6 | Round1-Var94 (I16V_L139V_I218V) | 62% | 68% |
| Round2-Var7 | Round1-Var94 (K334R_N409K_Q432E) | 104% | 92% |
| Round2-Var8 | Round1-Var94 (I15L_R141T_I407V) | 17% | 26% |
| Round2-Var9 | Round1-Var94 (R141T_K303G_G379L) | 31% | 42% |
| Round2-Var10 | Round1-Var94 (I190L_K303G_P348G) | 131% | 149% |
| Round2-Var11 | Round1-Var94 (E266Q_F314S_N409R) | 106% | 132% |
| Round2-Var12 | Round1-Var94 (V133A_I295V_K303G) | 43% | 49% |
| Round2-Var13 | Round1-Var94 (I16V_S241V_N409R) | 80% | 79% |
| Round2-Var14 | Round1-Var94 (A239V_K334R_G379L) | 58% | 55% |
| Round2-Var15 | Round1-Var94 (I190L_K393R_V396L) | 118% | 126% |
| Round2-Var16 | Round1-Var94 (L101F_I295M_K393R) | 84% | 89% |
| Round2-Var17 | Round1-Var94 (A239V_E266Q_Q425E) | 96% | 101% |
| Round2-Var18 | Round1-Var94 (V20L_I190L_I423M) | 98% | 98% |
| Round2-Var19 | Round1-Var94 (V20L_G379L_S456L) | 84% | 81% |
| Round2-Var20 | Round1-Var94 (K334R_P348G_N409R) | 73% | 73% |
| Round2-Var21 | Round1-Var94 (E231A_S241V_E449D) | 53% | 50% |
| Round2-Var22 | Round1-Var94 (K188R_L299I_V394I) | 56% | 59% |
| Round2-Var23 | Round1-Var94 (E231A_S274G_V394I) | 110% | 124% |
| Round2-Var24 | Round1-Var94 (S42A_I295V_Q432E) | 71% | 78% |
| Round2-Var25 | Round1-Var94 (A213N_A272P_K334R) | 95% | 80% |
| Round2-Var26 | Round1-Var94 (L158Y_S274K_N409K) | 80% | 50% |
| Round2-Var27 | Round1-Var94 (K188R_I295M_Q425E) | 132% | 116% |
| Round2-Var28 | Round1-Var94 (I15L_I295M_V394I) | 53% | 36% |
| Round2-Var29 | Round1-Var94 (V133A_A239V_V394I) | 47% | 30% |
| Round2-Var30 | Round1-Var94 (L158Y_F314S_K316R) | 107% | 72% |
| Round2-Var31 | Round1-Var94 (L158Y_A239V_A272P) | 54% | 30% |
| Round2-Var32 | Round1-Var94 (F46I_D301N_V396L) | 109% | 101% |
| Round2-Var33 | Round1-Var94 (L101F_I218V_Q432E) | 78% | 54% |
| Round2-Var34 | Round1-Var94 (I16V_F46I_I295M) | 110% | 95% |
| Round2-Var35 | Round1-Var94 (A213N_E266S_I407V) | 98% | 79% |
| Round2-Var36 | Round1-Var94 (A239V_S274K_I295M) | 102% | 89% |
| Round2-Var37 | Round1-Var94 (A239V_F314S_S450K) | 105% | 99% |
| Round2-Var38 | Round1-Var94 (L139V_K188R_D301N) | 66% | 51% |
| Round2-Var39 | Round1-Var94 (I45V_I218V_S274K) | 87% | 58% |
| Round2-Var40 | Round1-Var94 (S241V_K303G_V394I) | 78% | 57% |
| Round2-Var41 | Round1-Var94 (R141T_S274G_K334R) | 41% | 28% |
| Round2-Var42 | Round1-Var94 (V217L_S274G_L299I) | 47% | 34% |
| Round2-Var43 | Round1-Var94 (S274G_D301N_P348G) | 98% | 91% |
| Round2-Var44 | Round1-Var94 (E231A_N409R_S450K) | 87% | 65% |
| Round2-Var45 | Round1-Var94 (R64H_E231A_K316R) | 88% | 64% |
| Round2-Var46 | Round1-Var94 (V394I_N409K_I411V) | 110% | 100% |
| Round2-Var47 | Round1-Var94 (I45V_I295M_K303G) | 113% | 88% |
| Round2-Var48 | Round1-Var94 (L101F_V396L_L398V) | 46% | 43% |
| Round2-Var49 | Round1-Var94 (N27S_L101F_S447A) | 54% | 37% |
| Round2-Var50 | Round1-Var94 (S274G_F314S_L398V) | 129% | 156% |
| Round2-Var51 | Round1-Var94 (E266Q_L299I_K393R) | 70% | 51% |
| Round2-Var52 | Round1-Var94 (V217L_E266S_V394I) | 62% | 48% |
| Round2-Var53 | Round1-Var94 (N138K_A272P_N409R) | 118% | 102% |
| Round2-Var54 | Round1-Var94 (E266S_F314S_Q432E) | 124% | 146% |
| Round2-Var55 | Round1-Var94 (D301N_G379L_L398V) | 56% | 45% |
| Round2-Var56 | Round1-Var94 (F46I_E266S_K334R) | 123% | 142% |
| Round2-Var57 | Round1-Var94 (A272P_V394I_Q432E) | 133% | 142% |
| Round2-Var58 | Round1-Var94 (V394I_I407V_S456L) | 118% | 114% |
| Round2-Var59 | Round1-Var94 (I218V_E266Q_I423M) | 106% | 98% |
| Round2-Var60 | Round1-Var94 (A272P_G379L_I407V) | 80% | 63% |
| Round2-Var61 | Round1-Var94 (E231A_K303G_S456L) | 113% | 110% |
| Round2-Var62 | Round1-Var94 (I190L_E266Q_I407V) | 150% | 167% |
| Round2-Var63 | Round1-Var94 (N27S_L139V_I295V) | 43% | 25% |
| Round2-Var64 | Round1-Var94 (V217L_I423M_S447A) | 67% | 51% |
| Round2-Var65 | Round1-Var94 (L158Y_E266S_E449D) | 68% | 43% |
| Round2-Var66 | Round1-Var94 (S42A_F46I_I407V) | 160% | 203% |
| Round2-Var67 | Round1-Var94 (N138K_E231A_D301N) | 118% | 93% |
| Round2-Var68 | Round1-Var94 (K188R_G379L_N409R) | 52% | 35% |
| Round2-Var69 | Round1-Var94 (I15L_E231A_V396L) | 38% | 22% |
| Round2-Var70 | Round1-Var94 (E231A_Q425E_Q432E) | 115% | 119% |
| Round2-Var71 | Round1-Var94 (D301N_K316R_Q425E) | 126% | 121% |
| Round2-Var72 | Round1-Var94 (L139V_I295M_F314S) | 76% | 91% |
| Round2-Var73 | Round1-Var94 (S147G_E266S_D301N) | 30% | 18% |
| Round2-Var74 | Round1-Var94 (R64H_S147G_S447A) | 23% | 12% |
| Round2-Var75 | Round1-Var94 (S42A_K303G_L398V) | 95% | 110% |
| Round2-Var76 | Round1-Var94 (I45V_D301N_E449D) | 62% | 60% |
| Round2-Var77 | Round1-Var94 (V133A_E266S_I411V) | 37% | 28% |
| Round2-Var78 | Round1-Var94 (I45V_N409R_Q425E) | 63% | 59% |

-continued

| Clone | Mutations* | Normalized conversion Reb D to Reb M after 22 h. | Normalized initial rate (0-4 h) |
|---|---|---|---|
| Round2-Var79 | Round1-Var94 (R141T_A272P_F314S) | 23% | 10% |
| Round2-Var80 | Round1-Var94 (E266S_S274G_N409R) | 81% | 91% |
| Round2-Var81 | Round1-Var94 (N409K_Q425E_S450K) | 81% | 84% |
| Round2-Var82 | Round1-Var94 (N27S_R64H_K393R) | 47% | 37% |
| Round2-Var83 | Round1-Var94 (S42A_A213N_V217L) | 62% | 46% |
| Round2-Var84 | Round1-Var94 (N27S_S274K_I407V) | 49% | 44% |
| Round2-Var85 | Round1-Var94 (I411V_Q425E_S456L) | 75% | 81% |
| Round2-Var86 | Round1-Var94 (A239V_K316R_E449D) | 83% | 72% |
| Round2-Var87 | Round1-Var94 (S147G_A239V_P348G) | 18% | 7% |
| Round2-Var88 | Round1-Var94 (V20L_S274G_S450K) | 71% | 68% |
| Round2-Var89 | Round1-Var94 (F314S_V394I_S447A) | 88% | 123% |
| Round2-Var90 | Round1-Var94 (R64H_E266Q_I295M) | 45% | 47% |
| Round2-Var91 | Round1-Var94 (N138K_I295V_I407V) | 50% | 51% |
| Round2-Var92 | Round1-Var94 (I15L_P348G_Q432E) | 18% | 13% |

*Mutations are noted as follows: reference gene-original amino acid-position-new amino acid: For example the mutation of an alanine at position 33 to a glycine for variant 94 from the first round of directed evolution of UGT76G1 is noted as Round1-Var94 (A33G)

Modeling of these results allowed to obtain a ranking of the effect of each mutation. The following mutations were determined as being beneficial for activity: S42A, F46I, I190L, S274G, I295M, K303G, F314S, K316R, K393R, V394I, I407V, N409K, N409R, Q425E, Q432E, S447A, S456L.

Example 42

In Vivo Production of AtSUS

```
                                            SEQ ID 13
AtSUS
>gi|79328294|ref|NP_001031915.1| sucrose synthase
1 [Arabidopsis thaliana]
MANAERMITRVHSQRERLNETLVSERNEVLALLSRVEAKGKGILQQNQII

AEFEALPEQTRKKLEGGPFFDLLKSTQEAIVLPPWVALAVRPRPGVWEYL

RVNLHALVVEELQPAEFLHFKEELVDGVKNGNFTLELDFEPFNASIPRPT

LHKYIGNGVDFLNRHLSAKLFHDKESLLPLLKFLRLHSHQGKNLMLSEKI

QNLNTLQHTLRKAEEYLAELKSETLYEEFEAKFEEIGLERGWGDNAERVL

DMIRLLLDLLEAPDPCTLETFLGRVPMVFNVVILSPHGYFAQDNVLGYPD

TGGQVVYILDQVRALEIEMLQRIKQQGLNIKPRILILTRLLPDAVGTTCG

ERLERVYDSEYCDILRVPFRTEKGIVRKWISRFEVWPYLETYTEDAAVEL

SKELNGKPDLIIGNYSDGNLVASLLAHKLGVTQCTIAHALEKTKYPDSDI

YWKKLDDKYHFSCQFTADIFAMNHTDFIITSTFQEIAGSKETVGQYESHT

AFTLPGLYRVVHGIDVFDPKFNIVSPGADMSIYFPYTEEKRRLTKFHSEI

EELLYSDVENKEHLCVLKDKKKPILFTMARLDRVKNLSGLVEWYGKNTRL

RELANLVVVGGDRRKESKDNEEKAEMKKMYDLIEEYKLNGQFRWISSQMD

RVRNGELYRYICDTKGAFVQPALYEAFGLTVVEAMTCGLPTFATCKGGPA

EIIVHGKSGFHIDPYHGDQAADTLADFFTKCKEDPSHWDEISKGGLQRIE

EKYTWQIYSQRLLTLTGVYGFWKHVSNLDRLEARRYLEMFYALKYRPLAQ

AVPLAQDD
```

The synthetic gene of AtSuS that was codon optimized for expression in *E. coli* and subcloned in the pET30a+ plasmid using the NdeI and XhoI restriction sites. The pET30A+ vector containing the AtSUS gene was used to transform electrocompetent *E. coli* B121(DE3) cells. The obtained cells were grown in petri-dishes in the presence of Kanamycin and suitable colonies were selected and allowed to grow in liquid LB medium (erlenmeyer flasks). Glycerol was added to the suspension as cryoprotectant and 400 µL aliquots were stored at −20° C. and at −80° C.

The storage aliquots of *E. coli* BL21(DE3) containing the pET30A+_AtSUS plasmids were thawed and added to 30 mL of LBGKP medium (20 g/L Luria Broth Lennox; 50 mM PIPES buffer pH 7.00; 50 mM Phosphate buffer pH 7.00; 2.5 g/L glucose and 50 mg/L of Kanamycine). This culture was allowed to shake at 135 rpm at 30° C. for 8 h.

The production medium contained 60 g/L of overnight express instant TB medium (Novagen), 10 g/L of glycerol and 50 mg/L of Kanamycine. The preculture was added to 800 mL of this medium and the solution was allowed to stir at 20° C. while taking samples to measure the OD and pH. The culture gave significant growth and a good OD was obtained. After 40 h, the cells were harvested by centrifugation and frozen to obtain 30.1 g of cell wet weight.

Lysis was performed by Fastprep (MP Biomedicals, Lysing matrix B, speed 6.0, 3×40 sec) with a cell suspension of 200 mg of cells in 1.0 mL of 50 mM Tris buffer pH 7.5. The lysate was recovered by centrifugation and used fresh.

Example 43

Figure 69:
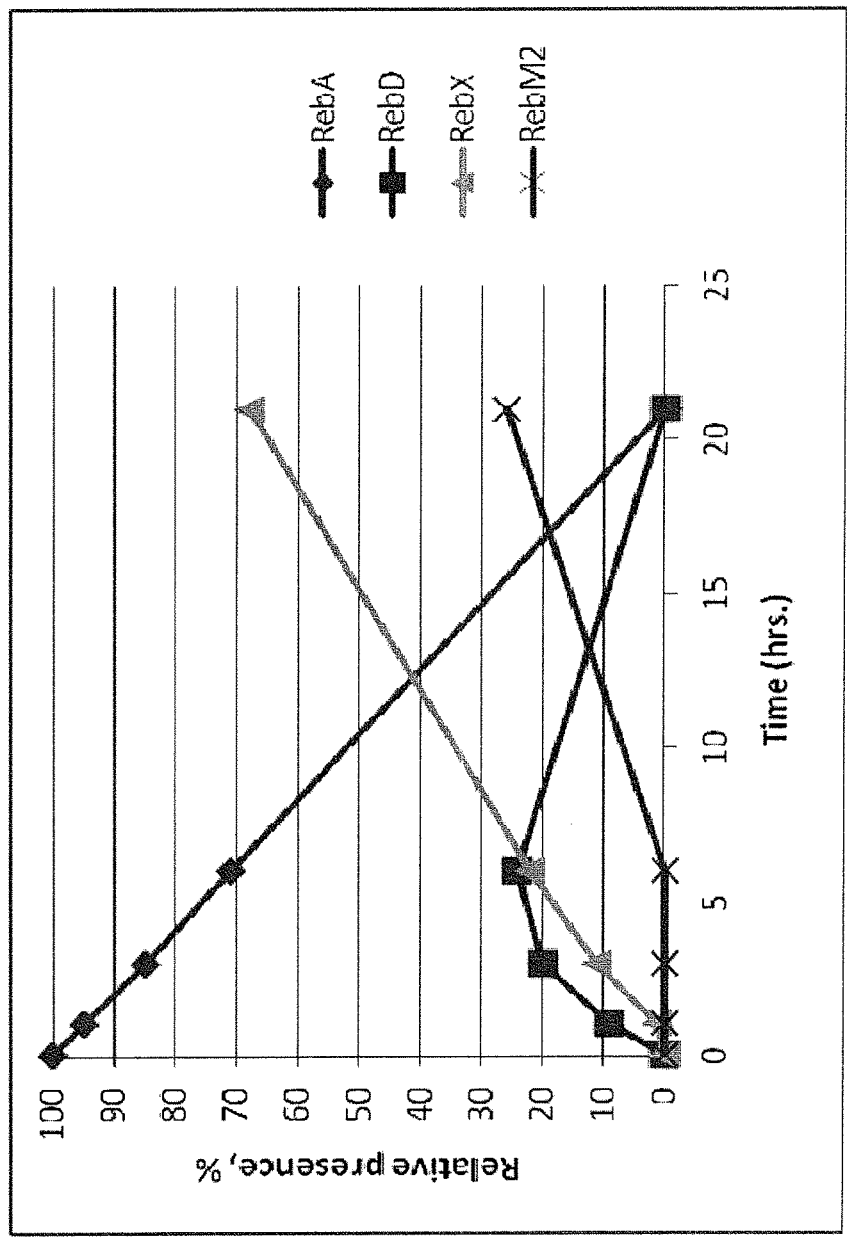
FIG. 69 shows the results of an HPLC analysis.

Conversion of Rebaudioside A to Rebaudioside M with In Situ Prepared UDP-Glucose Using UGTSL2, UGT76G1-R1-F12 and AtSUS The reaction was performed at 1 mL scale using 100 mM of sucrose, 3 mM of $MgCl_2$, 0.25 mM of UDP and 0.5 mM of Rebaudioside A in potassium phosphate buffer (50 mM final concentration, pH 7.5). The reaction was started by adding 15 µL of UGTSL2 (see EXAMPLE 27) lysate (2 U/mL), 150 µL of UGT76G1var94 (see EXAMPLE 26) (2.5 U/mL) and 15 µL of AtSUS (see EXAMPLE 42) (400 U/mL). The reaction was followed by HPLC after quenching 125 µL samples with 10 µL of 2 N $H_2SO_4$ and 115 µL of 60% methanol. 68% of Rebaudioside M and 26% of Rebaudioside M2 was obtained after 21 h of reaction time. The results are presented in FIG. 69.

Although various embodiments of the present invention have been disclosed in the foregoing description for purposes of illustration, it should be understood that a variety of changes, modifications and substitutions may be incorporated without departing from either the spirit of scope of the present invention.

We claim:

1. A method for preparing reb D2 comprising:
   a. contacting a starting composition comprising reb A with UDP-glucosyltransferase, to produce a composition comprising reb D2; and
   b. isolating the composition comprising reb D2.

2. The method of claim 1, further comprising purifying the composition comprising reb D2 to provide reb D2 having a purity greater than about 95% by weight on an anhydrous basis.

3. A method for preparing reb M2 comprising:
   a. contacting a starting composition comprising reb D2 with UDP-glucosyltransferase to produce a composition comprising reb M2; and
   b. isolating the composition comprising reb M2.

4. The method of claim 3, further comprising purifying the composition comprising reb M2 to provide reb M2 having a purity greater than about 95% by weight on an anhydrous basis.

* * * * *

SEQUENCE LISTING

<160> NUMBER OF SEQ ID NOS: 13

<210> SEQ ID NO 1
<211> LENGTH: 1397
<212> TYPE: DNA
<213> ORGANISM: Escherichia coli

<400> SEQUENCE: 1

| | | | | | | |
|---|---|---|---|---|---|---|
| ccatggccca | tatggaaaac | aaaaccgaaa | ccaccgttcg | tcgtcgtcgc | cgtattattc | 60 |
| tgtttccggt | tccgtttcag | ggtcatatta | atccgattct | gcagctggca | aatgtgctgt | 120 |
| atagcaaagg | ttttagcatt | accattttc | ataccaattt | taacaaaccg | aaaaccagca | 180 |
| attatccgca | ttttaccttt | cgctttattc | tggataatga | tccgcaggat | gaacgcatta | 240 |
| gcaatctgcc | gacacatggt | ccgctggcag | gtatgcgtat | tccgattatt | aacgaacatg | 300 |
| gtgcagatga | actgcgtcgt | gaactggaac | tgctgatgct | ggcaagcgaa | gaagatgaag | 360 |
| aagttagctg | tctgattacc | gatgcactgt | ggtattttgc | acagagcgtt | gcagatagcc | 420 |
| tgaatctgcg | tcgtctggtt | ctgatgacca | gcagcctgtt | taactttcat | gcacatgtta | 480 |
| gcctgccgca | gtttgatgaa | ctgggttatc | tggatccgga | tgataaaacc | cgtctggaag | 540 |
| aacaggcaag | cggttttccg | atgctgaaag | tgaaagatat | caaaagcgcc | tatagcaatt | 600 |
| ggcagattct | gaaagaaatt | ctgggcaaaa | tgattaaaca | gaccaaagca | agcagcggtg | 660 |
| ttatttggaa | tagctttaaa | gaactggaag | aaagcgaact | ggaaaccgtg | attcgtgaaa | 720 |
| ttccggcacc | gagcttttctg | attccgctgc | cgaaacatct | gaccgcaagc | agcagcagcc | 780 |
| tgctggatca | tgatcgtacc | gttttttcagt | ggctggatca | gcagcctccg | agcagcgttc | 840 |
| tgtatgttag | ctttggtagc | accagcgaag | ttgatgaaaa | agattttctg | gaaattgccc | 900 |
| gtggtctggt | tgatagcaaa | cagagctttc | tgtgggttgt | tcgtccgggt | tttgttaaag | 960 |
| gtagcacctg | ggttgaaccg | ctgccggatg | ttttctcggg | tgaacgtggt | cgtattgtta | 1020 |
| aatgggttcc | gcagcaagaa | gttctggcac | acggcgcaat | tggtgcattt | tggacccata | 1080 |
| gcggttggaa | tagcaccctg | gaaagcgttt | gtgaaggtgt | tccgatgatt | tttagcgatt | 1140 |
| ttggtctgga | tcagccgctg | aatgcacgtt | atatgagtga | tgttctgaaa | gtgggtgtgt | 1200 |
| atctggaaaa | tggttgggaa | cgtggtgaaa | ttgcaaatgc | aattcgtcgt | gttatggtgg | 1260 |
| atgaagaagg | tgaatatatt | cgtcagaatg | cccgtgttct | gaaacagaaa | gcagatgtta | 1320 |
| gcctgatgaa | aggtggtagc | agctatgaaa | gcctggaaag | tctggttagc | tatattagca | 1380 |
| gcctgtaata | actcgag | | | | | 1397 |

<210> SEQ ID NO 2
<211> LENGTH: 1442
<212> TYPE: DNA
<213> ORGANISM: Escherichia coli

<400> SEQUENCE: 2

| | | | | | | |
|---|---|---|---|---|---|---|
| ccatggcaca | tatggcaacc | agcgatagca | ttgttgatga | tcgtaaacag | ctgcatgttg | 60 |
| caacctttcc | gtggctggca | tttggtcata | ttctgccgta | tctgcagctg | agcaaactga | 120 |
| ttgcagaaaa | aggtcataaa | gtgagctttc | tgagcaccac | ccgtaatatt | cagcgtctga | 180 |
| gcagccatat | tagtccgctg | attaatgttg | ttcagctgac | cctgcctcgt | gttcaagaac | 240 |
| tgccggaaga | tgccgaagca | accaccgatg | ttcatccgga | agatattccg | tatctgaaaa | 300 |
| aagcaagtga | tggtctgcag | ccggaagtta | cccgttttct | ggaacagcat | agtccggatt | 360 |
| ggatcatcta | tgattatacc | cattattggc | tgccgagcat | tgcagcaagc | ctgggtatta | 420 |

```
gccgtgcaca ttttagcgtt accacccccgt gggcaattgc atatatgggt ccgagcgcag    480
atgcaatgat taatggtagt gatggtcgta ccaccgttga agatctgacc acccctccga    540
aatggtttcc gtttccgacc aaagtttgtt ggcgtaaaca tgatctggca cgtctggttc    600
cgtataaagc accgggtatt agtgatggtt atcgtatggg tctggttctg aaaggtagcg    660
attgtctgct gagcaaatgc tatcatgaat ttggcaccca gtggctgccg ctgctggaaa    720
ccctgcatca ggttccggtt gttccggtgg gtctgctgcc tccggaagtt ccgggtgatg    780
aaaaagatga aacctgggtt agcatcaaaa atggctgga tggtaaacag aaaggtagcg    840
tggtttatgt tgcactgggt agcgaagttc tggttagcca gaccgaagtt gttgaactgg    900
cactgggtct ggaactgagc ggtctgccgt ttgtttgggc atatcgtaaa ccgaaaggtc    960
cggcaaaaag cgatagcgtt gaactgccgg atggttttgt tgaacgtacc cgtgatcgtg    1020
gtctggtttg gaccagctgg gcacctcagc tgcgtattct gagccatgaa agcgtttgtg    1080
gttttctgac ccattgtggt agcggtagca ttgtggaagg tctgatgttt ggtcatccgc    1140
tgattatgct gccgattttt ggtgatcagc cgctgaatgc acgtctgctg aagataaac    1200 aggttggtat tgaaattccg cgtaatgaag aagatggttg cctgaccaaa gaaagcgttg    1260
cacgtagcct gcgtagcgtt gttgttgaaa agaaggcga atctataaa gccaatgcac    1320 gtgaactgag caaaatctat aatgatacca agtggaaaa agaatatgtg agccagttcg    1380
tggattatct ggaaaaaaac acccgtgcag ttgccattga tcacgaaagc taatgactcg    1440
ag                                                                     1442

<210> SEQ ID NO 3
<211> LENGTH: 472
<212> TYPE: PRT
<213> ORGANISM: Oryza sativa

<400> SEQUENCE: 3

Met Asp Asp Ala His Ser Ser Gln Ser Pro Leu His Val Val Ile Phe
1               5                   10                  15

Pro Trp Leu Ala Phe Gly His Leu Leu Pro Cys Leu Asp Leu Ala Glu
            20                  25                  30

Arg Leu Ala Ala Arg Gly His Arg Val Ser Phe Val Ser Thr Pro Arg
        35                  40                  45

Asn Leu Ala Arg Leu Pro Pro Val Arg Pro Glu Leu Ala Glu Leu Val
    50                  55                  60

Asp Leu Val Ala Leu Pro Leu Pro Arg Val Asp Gly Leu Pro Asp Gly
65                  70                  75                  80

Ala Glu Ala Thr Ser Asp Val Pro Phe Asp Lys Phe Glu Leu His Arg
                85                  90                  95

Lys Ala Phe Asp Gly Leu Ala Ala Pro Phe Ser Ala Phe Leu Asp Thr
            100                 105                 110

Ala Cys Ala Gly Gly Lys Arg Pro Asp Trp Val Leu Ala Asp Leu Met
        115                 120                 125

His His Trp Val Ala Leu Ala Ser Gln Glu Arg Gly Val Pro Cys Ala
    130                 135                 140

Met Ile Leu Pro Cys Ser Ala Val Val Ala Ser Ala Pro Pro
145                 150                 155                 160

Thr Glu Ser Ser Ala Asp Gln Arg Glu Ala Ile Val Arg Ser Met Gly
                165                 170                 175

Thr Ala Ala Pro Ser Phe Glu Ala Lys Arg Ala Thr Glu Glu Phe Ala
```

```
                    180                 185                 190
Thr Glu Gly Ala Ser Gly Val Ser Ile Met Thr Arg Tyr Ser Leu Thr
                195                 200                 205
Leu Gln Arg Ser Lys Leu Val Ala Met Arg Ser Cys Pro Glu Leu Glu
            210                 215                 220
Pro Gly Ala Phe Thr Ile Leu Thr Arg Phe Tyr Gly Lys Pro Val Val
225                 230                 235                 240
Pro Phe Gly Leu Leu Pro Pro Arg Pro Asp Gly Ala Arg Gly Val Ser
                245                 250                 255
Lys Asn Gly Lys His Asp Ala Ile Met Gln Trp Leu Asp Ala Gln Pro
            260                 265                 270
Ala Lys Ser Val Val Tyr Val Ala Leu Gly Ser Glu Ala Pro Met Ser
            275                 280                 285
Ala Asp Leu Leu Arg Glu Leu Ala His Gly Leu Asp Leu Ala Gly Thr
            290                 295                 300
Arg Phe Leu Trp Ala Met Arg Lys Pro Ala Gly Val Asp Ala Asp Ser
305                 310                 315                 320
Val Leu Pro Ala Gly Phe Leu Gly Arg Thr Gly Glu Arg Gly Leu Val
                325                 330                 335
Thr Thr Arg Trp Ala Pro Gln Val Ser Ile Leu Ala His Ala Ala Val
                340                 345                 350
Cys Ala Phe Leu Thr His Cys Gly Trp Gly Ser Val Val Glu Gly Leu
                355                 360                 365
Gln Phe Gly His Pro Leu Ile Met Leu Pro Ile Leu Gly Asp Gln Gly
            370                 375                 380
Pro Asn Ala Arg Ile Leu Glu Gly Arg Lys Leu Gly Val Ala Val Pro
385                 390                 395                 400
Arg Asn Asp Glu Asp Gly Ser Phe Asp Arg Gly Val Ala Gly Ala
                405                 410                 415
Val Arg Ala Val Val Glu Glu Gly Lys Thr Phe Phe Ala Asn
                420                 425                 430
Ala Arg Lys Leu Gln Glu Ile Val Ala Asp Arg Glu Arg Glu Glu Arg
            435                 440                 445
Cys Ile Asp Glu Phe Val Gln His Leu Thr Ser Trp Asn Glu Leu Lys
            450                 455                 460
Asn Asn Ser Asp Gly Gln Tyr Pro
465                 470

<210> SEQ ID NO 4
<211> LENGTH: 502
<212> TYPE: PRT
<213> ORGANISM: Avena strigosa

<400> SEQUENCE: 4

Met Ala Val Lys Asp Glu Gln Gln Ser Pro Leu His Ile Leu Leu Phe
1               5                   10                  15
Pro Phe Leu Ala Pro Gly His Leu Ile Pro Ile Ala Asp Met Ala Ala
                20                  25                  30
Leu Phe Ala Ser Arg Gly Val Arg Cys Thr Ile Leu Thr Thr Pro Val
            35                  40                  45
Asn Ala Ala Ile Ile Arg Ser Ala Val Asp Arg Ala Asn Asp Ala Phe
        50                  55                  60
Arg Gly Ser Asp Cys Pro Ala Ile Asp Ile Ser Val Val Pro Phe Pro
65                  70                  75                  80
```

```
Asp Val Gly Leu Pro Pro Gly Val Glu Asn Gly Asn Ala Leu Thr Ser
             85                  90                  95

Pro Ala Asp Arg Leu Lys Phe Phe Gln Ala Val Ala Glu Leu Arg Glu
            100                 105                 110

Pro Phe Asp Arg Phe Leu Ala Asp Asn His Pro Asp Ala Val Val Ser
            115                 120                 125

Asp Ser Phe Phe His Trp Ser Thr Asp Ala Ala Glu His Gly Val
            130                 135                 140

Pro Arg Leu Gly Phe Leu Gly Ser Ser Met Phe Ala Gly Ser Cys Asn
145                 150                 155                 160

Glu Ser Thr Leu His Asn Asn Pro Leu Glu Thr Ala Ala Asp Asp Pro
                165                 170                 175

Asp Ala Leu Val Ser Leu Pro Gly Leu Pro His Arg Val Glu Leu Arg
            180                 185                 190

Arg Ser Gln Met Met Asp Pro Lys Lys Arg Pro Asp His Trp Ala Leu
            195                 200                 205

Leu Glu Ser Val Asn Ala Ala Asp Gln Lys Ser Phe Gly Glu Val Phe
            210                 215                 220

Asn Ser Phe His Glu Leu Glu Pro Asp Tyr Val Glu His Tyr Gln Thr
225                 230                 235                 240

Thr Leu Gly Arg Arg Thr Trp Leu Val Gly Pro Val Ala Leu Ala Ser
                245                 250                 255

Lys Asp Met Ala Gly Arg Gly Ser Thr Ser Ala Arg Ser Pro Asp Ala
            260                 265                 270

Asp Ser Cys Leu Arg Trp Leu Asp Thr Lys Gln Pro Gly Ser Val Val
            275                 280                 285

Tyr Val Ser Phe Gly Thr Leu Ile Arg Phe Ser Pro Ala Glu Leu His
            290                 295                 300

Glu Leu Ala Arg Gly Leu Asp Leu Ser Gly Lys Asn Phe Val Trp Val
305                 310                 315                 320

Leu Gly Arg Ala Gly Pro Asp Ser Ser Glu Trp Met Pro Gln Gly Phe
            325                 330                 335

Ala Asp Leu Ile Thr Pro Arg Gly Asp Arg Gly Phe Ile Ile Arg Gly
            340                 345                 350

Trp Ala Pro Gln Met Leu Ile Leu Asn His Arg Ala Leu Gly Gly Phe
            355                 360                 365

Val Thr His Cys Gly Trp Asn Ser Thr Leu Glu Ser Val Ser Ala Gly
            370                 375                 380

Val Pro Met Val Thr Trp Pro Arg Phe Ala Asp Gln Phe Gln Asn Glu
385                 390                 395                 400

Lys Leu Ile Val Glu Val Leu Lys Val Gly Val Ser Ile Gly Ala Lys
            405                 410                 415

Asp Tyr Gly Ser Gly Ile Glu Asn His Asp Val Ile Arg Gly Glu Val
            420                 425                 430

Ile Ala Glu Ser Ile Gly Lys Leu Met Gly Ser Ser Glu Glu Ser Asp
            435                 440                 445

Ala Ile Gln Arg Lys Ala Lys Asp Leu Gly Ala Glu Ala Arg Ser Ala
            450                 455                 460

Val Glu Asn Gly Gly Ser Ser Tyr Asn Asp Val Gly Arg Leu Met Asp
465                 470                 475                 480

Glu Leu Met Ala Arg Arg Ser Ser Val Lys Val Gly Glu Asp Ile Ile
            485                 490                 495

Pro Thr Asn Asp Gly Leu
```

-continued

500

<210> SEQ ID NO 5
<211> LENGTH: 470
<212> TYPE: PRT
<213> ORGANISM: Solanum lycopersicum

<400> SEQUENCE: 5

```
Met Ser Pro Lys Leu His Lys Glu Leu Phe His Ser Leu Tyr Lys
1               5                   10                  15

Lys Thr Arg Ser Asn His Thr Met Ala Thr Leu Lys Val Leu Met Phe
                20                  25                  30

Pro Phe Leu Ala Tyr Gly His Ile Ser Pro Tyr Leu Asn Val Ala Lys
            35                  40                  45

Lys Leu Ala Asp Arg Gly Phe Leu Ile Tyr Phe Cys Ser Thr Pro Ile
    50                  55                  60

Asn Leu Lys Ser Thr Ile Glu Lys Ile Pro Glu Lys Tyr Ala Asp Ser
65                  70                  75                  80

Ile His Leu Ile Glu Leu His Leu Pro Glu Leu Pro Gln Leu Pro Pro
                85                  90                  95

His Tyr His Thr Thr Asn Gly Leu Pro Pro Asn Leu Asn Gln Val Leu
            100                 105                 110

Gln Lys Ala Leu Lys Met Ser Lys Pro Asn Phe Ser Lys Ile Leu Gln
        115                 120                 125

Asn Leu Lys Pro Asp Leu Val Ile Tyr Asp Ile Leu Gln Arg Trp Ala
    130                 135                 140

Lys His Val Ala Asn Glu Gln Asn Ile Pro Ala Val Lys Leu Leu Thr
145                 150                 155                 160

Ser Gly Ala Ala Val Phe Ser Tyr Phe Phe Asn Val Leu Lys Lys Pro
                165                 170                 175

Gly Val Glu Phe Pro Phe Pro Gly Ile Tyr Leu Arg Lys Ile Glu Gln
            180                 185                 190

Val Arg Leu Ser Glu Met Met Ser Lys Ser Asp Lys Glu Lys Glu Leu
        195                 200                 205

Glu Asp Asp Asp Asp Asp Leu Leu Val Asp Gly Asn Met Gln
    210                 215                 220

Ile Met Leu Met Ser Thr Ser Arg Thr Ile Glu Ala Lys Tyr Ile Asp
225                 230                 235                 240

Phe Cys Thr Ala Leu Thr Asn Trp Lys Val Val Pro Val Gly Pro Pro
                245                 250                 255

Val Gln Asp Leu Ile Thr Asn Asp Val Asp Asp Met Glu Leu Ile Asp
            260                 265                 270

Trp Leu Gly Thr Lys Asp Glu Asn Ser Thr Val Phe Val Ser Phe Gly
        275                 280                 285

Ser Glu Tyr Phe Leu Ser Lys Glu Asp Met Glu Glu Val Ala Phe Ala
    290                 295                 300

Leu Glu Leu Ser Asn Val Asn Phe Ile Trp Val Ala Arg Phe Pro Lys
305                 310                 315                 320

Gly Glu Glu Arg Asn Leu Glu Asp Ala Leu Pro Lys Gly Phe Leu Glu
                325                 330                 335

Arg Ile Gly Glu Arg Gly Arg Val Leu Asp Lys Phe Ala Pro Gln Pro
            340                 345                 350

Arg Ile Leu Asn His Pro Ser Thr Gly Gly Phe Ile Ser His Cys Gly
        355                 360                 365
```

Trp Asn Ser Ala Met Glu Ser Ile Asp Phe Gly Val Pro Ile Ile Ala
    370                 375                 380

Met Pro Met His Leu Asp Gln Pro Met Asn Ala Arg Leu Ile Val Glu
385                 390                 395                 400

Leu Gly Val Ala Val Glu Ile Val Arg Asp Asp Gly Lys Ile His
                405                 410                 415

Arg Gly Glu Ile Ala Glu Thr Leu Lys Gly Val Ile Thr Gly Lys Thr
                420                 425                 430

Gly Glu Lys Leu Arg Ala Lys Val Arg Asp Ile Ser Lys Asn Leu Lys
                435                 440                 445

Thr Ile Arg Asp Glu Met Asp Ala Ala Glu Glu Leu Ile Gln
    450                 455                 460

Leu Cys Arg Asn Gly Asn
465                 470

<210> SEQ ID NO 6
<211> LENGTH: 464
<212> TYPE: PRT
<213> ORGANISM: Oryza sativa

<400> SEQUENCE: 6

Met His Val Val Met Leu Pro Trp Leu Ala Phe Gly His Ile Leu Pro
1               5                   10                  15

Phe Ala Glu Phe Ala Lys Arg Val Ala Arg Gln Gly His Arg Val Thr
                20                  25                  30

Leu Phe Ser Thr Pro Arg Asn Thr Arg Arg Leu Ile Asp Val Pro Pro
            35                  40                  45

Ser Leu Ala Gly Arg Ile Arg Val Asp Ile Pro Leu Pro Arg Val
    50                  55                  60

Glu His Leu Pro Glu His Ala Glu Ala Thr Ile Asp Leu Pro Ser Asn
65                  70                  75                  80

Asp Leu Arg Pro Tyr Leu Arg Arg Ala Tyr Asp Glu Ala Phe Ser Arg
                85                  90                  95

Glu Leu Ser Arg Leu Leu Gln Glu Thr Gly Pro Ser Arg Pro Asp Trp
                100                 105                 110

Val Leu Ala Asp Tyr Ala Ala Tyr Trp Ala Pro Ala Ala Ala Ser Arg
            115                 120                 125

His Gly Val Pro Cys Ala Phe Leu Ser Leu Phe Gly Ala Ala Ala Leu
    130                 135                 140

Cys Phe Phe Gly Pro Ala Glu Thr Leu Gln Gly Arg Gly Pro Tyr Ala
145                 150                 155                 160

Lys Thr Glu Pro Ala His Leu Thr Ala Val Pro Glu Tyr Val Pro Phe
                165                 170                 175

Pro Thr Thr Val Ala Phe Arg Gly Asn Glu Ala Arg Glu Leu Phe Lys
            180                 185                 190

Pro Ser Leu Ile Pro Asp Glu Ser Gly Val Ser Glu Ser Tyr Arg Phe
    195                 200                 205

Ser Gln Ser Ile Glu Gly Cys Gln Leu Val Ala Val Arg Ser Asn Gln
210                 215                 220

Glu Phe Glu Pro Glu Trp Leu Glu Leu Leu Gly Glu Leu Tyr Gln Lys
225                 230                 235                 240

Pro Val Ile Pro Ile Gly Met Phe Pro Pro Pro Pro Gln Asp Val
                245                 250                 255

Ala Gly His Glu Glu Thr Leu Arg Trp Leu Asp Arg Gln Glu Pro Asn
            260                 265                 270

```
Ser Val Val Tyr Ala Ala Phe Gly Ser Glu Val Lys Leu Thr Ala Glu
            275                 280                 285

Gln Leu Gln Arg Ile Ala Leu Gly Leu Glu Ala Ser Glu Leu Pro Phe
    290                 295                 300

Ile Trp Ala Phe Arg Ala Pro Pro Asp Ala Gly Asp Gly Asp Gly Leu
305                 310                 315                 320

Pro Gly Gly Phe Lys Glu Arg Val Asn Gly Arg Gly Val Val Cys Arg
                325                 330                 335

Gly Trp Val Pro Gln Val Lys Phe Leu Ala His Ala Ser Val Gly Gly
                340                 345                 350

Phe Leu Thr His Ala Gly Trp Asn Ser Ile Ala Glu Gly Leu Ala Asn
            355                 360                 365

Gly Val Arg Leu Val Leu Pro Leu Met Phe Glu Gln Gly Leu Asn
    370                 375                 380

Ala Arg Gln Leu Ala Glu Lys Val Ala Val Glu Val Ala Arg Asp
385                 390                 395                 400

Glu Asp Asp Gly Ser Phe Ala Ala Asn Asp Ile Val Asp Ala Leu Arg
                405                 410                 415

Arg Val Met Val Gly Glu Glu Gly Asp Glu Phe Gly Val Lys Val Lys
            420                 425                 430

Glu Leu Ala Lys Val Phe Gly Asp Asp Glu Val Asn Asp Arg Tyr Val
            435                 440                 445

Arg Asp Phe Leu Lys Cys Leu Ser Glu Tyr Lys Met Gln Arg Gln Gly
            450                 455                 460

<210> SEQ ID NO 7
<211> LENGTH: 515
<212> TYPE: PRT
<213> ORGANISM: Arabidopsis lyrata

<400> SEQUENCE: 7

Met Asp Asp Lys Lys Glu Glu Val Met His Ile Ala Met Phe Pro Trp
1               5                   10                  15

Leu Ala Met Gly His Leu Leu Pro Phe Leu Arg Leu Ser Lys Leu Leu
            20                  25                  30

Ala Gln Lys Gly His Lys Ile Ser Phe Ile Ser Thr Pro Arg Asn Ile
        35                  40                  45

Leu Arg Leu Pro Lys Leu Pro Ser Asn Leu Ser Ser Ser Ile Thr Phe
    50                  55                  60

Val Ser Phe Pro Leu Pro Ser Ile Ser Gly Leu Pro Pro Ser Ser Glu
65                  70                  75                  80

Ser Ser Met Asp Val Pro Tyr Asn Lys Gln Gln Ser Leu Lys Ala Ala
            85                  90                  95

Phe Asp Leu Leu Gln Pro Pro Leu Thr Glu Phe Leu Arg Leu Ser Ser
            100                 105                 110

Pro Asp Trp Ile Ile Tyr Asp Tyr Ala Ser His Trp Leu Pro Ser Ile
        115                 120                 125

Ala Lys Glu Leu Gly Ile Ser Lys Ala Phe Phe Ser Leu Phe Asn Ala
    130                 135                 140

Ala Thr Leu Cys Phe Met Gly Pro Ser Ser Leu Ile Glu Glu Ser
145                 150                 155                 160

Arg Ser Thr Pro Glu Asp Phe Thr Val Val Pro Pro Trp Val Pro Phe
                165                 170                 175

Lys Ser Thr Ile Val Phe Arg Tyr His Glu Val Ser Arg Tyr Val Glu
```

```
            180                 185                 190
Lys Thr Asp Glu Asp Val Thr Gly Val Ser Asp Ser Val Arg Phe Gly
        195                 200                 205

Tyr Thr Ile Asp Gly Ser Asp Ala Val Phe Val Arg Ser Cys Pro Glu
        210                 215                 220

Phe Glu Pro Glu Trp Phe Ser Leu Leu Gln Asp Leu Tyr Arg Lys Pro
225                 230                 235                 240

Val Phe Pro Ile Gly Phe Leu Pro Pro Val Ile Glu Asp Asp Asp Asp
                245                 250                 255

Asp Thr Thr Trp Val Arg Ile Lys Glu Trp Leu Asp Lys Gln Arg Val
            260                 265                 270

Asn Ser Val Val Tyr Val Ser Leu Gly Thr Glu Ala Ser Leu Arg Arg
        275                 280                 285

Glu Glu Leu Thr Glu Leu Ala Leu Gly Leu Glu Lys Ser Glu Thr Pro
        290                 295                 300

Phe Phe Trp Val Leu Arg Asn Glu Pro Gln Ile Pro Asp Gly Phe Glu
305                 310                 315                 320

Glu Arg Val Lys Gly Arg Gly Met Val His Val Gly Trp Val Pro Gln
                325                 330                 335

Val Lys Ile Leu Ser His Glu Ser Val Gly Gly Phe Leu Thr His Cys
            340                 345                 350

Gly Trp Asn Ser Val Val Glu Gly Ile Gly Phe Gly Lys Val Pro Ile
        355                 360                 365

Phe Leu Pro Val Leu Asn Glu Gln Gly Leu Asn Thr Arg Leu Leu Gln
370                 375                 380

Gly Lys Gly Leu Gly Val Glu Val Leu Arg Asp Glu Arg Asp Gly Ser
385                 390                 395                 400

Phe Gly Ser Asp Ser Val Ala Asp Ser Val Arg Leu Val Met Ile Asp
                405                 410                 415

Asp Ala Gly Glu Glu Ile Arg Glu Lys Val Lys Leu Met Lys Gly Leu
            420                 425                 430

Phe Gly Asn Met Asp Glu Asn Ile Arg Tyr Val Asp Glu Leu Val Gly
        435                 440                 445

Phe Met Arg Asn Asp Glu Ser Ser Gln Leu Lys Glu Glu Glu Glu Glu
        450                 455                 460

Asp Asp Cys Ser Asp Asp Gln Ser Ser Glu Val Ser Ser Glu Thr Asp
465                 470                 475                 480

Glu Lys Glu Leu Asn Leu Asp Leu Lys Glu Glu Lys Arg Arg Ile Ser
                485                 490                 495

Val Tyr Lys Ser Leu Ser Ser Glu Phe Asp Asp Tyr Val Ala Asn Glu
            500                 505                 510

Lys Met Gly
        515

<210> SEQ ID NO 8
<211> LENGTH: 772
<212> TYPE: PRT
<213> ORGANISM: Oryza sativa

<400> SEQUENCE: 8

Met His Val Val Ile Cys Pro Leu Leu Ala Phe Gly His Leu Leu Pro
1               5                   10                  15

Cys Leu Asp Leu Ala Gln Arg Leu Ala Cys Gly His Arg Val Ser Phe
            20                  25                  30
```

```
Val Ser Thr Pro Arg Asn Ile Ser Arg Leu Pro Pro Val Arg Pro Ser
        35                  40                  45

Leu Ala Pro Leu Val Ser Phe Val Ala Leu Pro Leu Pro Arg Val Glu
 50                  55                  60

Gly Leu Pro Asn Gly Ala Glu Ser Thr His Asn Val Pro His Asp Arg
 65                  70                  75                  80

Pro Asp Met Val Glu Leu His Leu Arg Ala Phe Asp Gly Leu Ala Ala
                 85                  90                  95

Pro Phe Ser Glu Phe Leu Gly Thr Ala Cys Ala Asp Trp Val Met Pro
            100                 105                 110

Thr Ser Ser Ala Pro Arg Gln Thr Leu Ser Ser Asn Ile His Arg Asn
        115                 120                 125

Ser Ser Arg Pro Gly Thr Pro Ala Pro Ser Gly Arg Leu Leu Cys Pro
130                 135                 140

Ile Thr Pro His Ser Asn Thr Leu Glu Arg Ala Ala Glu Lys Leu Val
145                 150                 155                 160

Arg Ser Ser Arg Gln Asn Ala Arg Ala Arg Ser Leu Leu Ala Phe Thr
                165                 170                 175

Ser Pro Pro Leu Pro Tyr Arg Asp Val Phe Arg Ser Leu Leu Gly Leu
            180                 185                 190

Gln Met Gly Arg Lys Gln Leu Asn Ile Ala His Glu Thr Asn Gly Arg
        195                 200                 205

Arg Thr Gly Thr Leu Pro Leu Asn Leu Cys Arg Trp Met Trp Lys Gln
210                 215                 220

Arg Arg Cys Gly Lys Leu Arg Pro Ser Asp Val Glu Phe Asn Thr Ser
225                 230                 235                 240

Arg Ser Asn Glu Ala Ile Ser Pro Ile Gly Ala Ser Leu Val Asn Leu
                245                 250                 255

Gln Ser Ile Gln Ser Pro Asn Pro Arg Ala Val Leu Pro Ile Ala Ser
            260                 265                 270

Ser Gly Val Arg Ala Val Phe Ile Gly Arg Ala Arg Thr Ser Thr Pro
        275                 280                 285

Thr Pro Pro His Ala Lys Pro Ala Arg Ser Ala Ala Pro Arg Ala His
290                 295                 300

Arg Pro Pro Ser Ser Val Met Asp Ser Gly Tyr Ser Ser Ser Tyr Ala
305                 310                 315                 320

Ala Ala Ala Gly Met His Val Val Ile Cys Pro Trp Leu Ala Phe Gly
                325                 330                 335

His Leu Leu Pro Cys Leu Asp Leu Ala Gln Arg Leu Ala Ser Arg Gly
            340                 345                 350

His Arg Val Ser Phe Val Ser Thr Pro Arg Asn Ile Ser Arg Leu Pro
        355                 360                 365

Pro Val Arg Pro Ala Leu Ala Pro Leu Val Ala Phe Val Ala Leu Pro
370                 375                 380

Leu Pro Arg Val Glu Gly Leu Pro Asp Gly Ala Glu Ser Thr Asn Asp
385                 390                 395                 400

Val Pro His Asp Arg Pro Asp Met Val Glu Leu His Arg Arg Ala Phe
                405                 410                 415

Asp Gly Leu Ala Ala Pro Phe Ser Glu Phe Leu Gly Thr Ala Cys Ala
            420                 425                 430

Asp Trp Val Ile Val Asp Val Phe His His Trp Ala Ala Ala Ala Ala
        435                 440                 445

Leu Glu His Lys Val Pro Cys Ala Met Met Leu Leu Gly Ser Ala His
```

```
                450                 455                 460
Met Ile Ala Ser Ile Ala Asp Arg Arg Leu Glu Arg Ala Glu Thr Glu
465                 470                 475                 480

Ser Pro Ala Ala Ala Gly Gln Gly Arg Pro Ala Ala Pro Thr Phe
                485                 490                 495

Glu Val Ala Arg Met Lys Leu Ile Arg Thr Lys Gly Ser Ser Gly Met
                500                 505                 510

Ser Leu Ala Glu Arg Phe Ser Leu Thr Leu Ser Arg Ser Ser Leu Val
                515                 520                 525

Val Gly Arg Ser Cys Val Glu Phe Glu Pro Glu Thr Val Pro Leu Leu
                530                 535                 540

Ser Thr Leu Arg Gly Lys Pro Ile Thr Phe Leu Gly Leu Met Pro Pro
545                 550                 555                 560

Leu His Glu Gly Arg Arg Glu Asp Gly Glu Asp Ala Thr Val Arg Trp
                565                 570                 575

Leu Asp Ala Gln Pro Ala Lys Ser Val Val Tyr Val Ala Leu Gly Ser
                580                 585                 590

Glu Val Pro Leu Gly Val Glu Lys Val His Glu Leu Ala Leu Gly Leu
                595                 600                 605

Glu Leu Ala Gly Thr Arg Phe Leu Trp Ala Leu Arg Lys Pro Thr Gly
                610                 615                 620

Val Ser Asp Ala Asp Leu Leu Pro Ala Gly Phe Glu Glu Arg Thr Arg
625                 630                 635                 640

Gly Arg Gly Val Val Ala Thr Arg Trp Val Pro Gln Met Ser Ile Leu
                645                 650                 655

Ala His Ala Ala Val Gly Ala Phe Leu Thr His Cys Gly Trp Asn Ser
                660                 665                 670

Thr Ile Glu Gly Leu Met Phe Gly His Pro Leu Ile Met Leu Pro Ile
                675                 680                 685

Phe Gly Asp Gln Gly Pro Asn Ala Arg Leu Ile Glu Ala Lys Asn Ala
                690                 695                 700

Gly Leu Gln Val Ala Arg Asn Asp Gly Asp Gly Ser Phe Asp Arg Glu
705                 710                 715                 720

Gly Val Ala Ala Ala Ile Arg Ala Val Ala Val Glu Glu Glu Ser Ser
                725                 730                 735

Lys Val Phe Gln Ala Lys Ala Lys Lys Leu Gln Glu Ile Val Ala Asp
                740                 745                 750

Met Ala Cys His Glu Arg Tyr Ile Asp Gly Phe Ile Gln Gln Leu Arg
                755                 760                 765

Ser Tyr Lys Asp
770

<210> SEQ ID NO 9
<211> LENGTH: 442
<212> TYPE: PRT
<213> ORGANISM: Escherichia coli

<400> SEQUENCE: 9

Met Ala Thr Asn Leu Arg Val Leu Met Phe Pro Trp Leu Ala Tyr Gly
1               5                   10                  15

His Ile Ser Pro Phe Leu Asn Ile Ala Lys Gln Leu Ala Asp Arg Gly
                20                  25                  30

Phe Leu Ile Tyr Leu Cys Ser Thr Arg Ile Asn Leu Glu Ser Ile Ile
                35                  40                  45
```

Lys Lys Ile Pro Glu Lys Tyr Ala Asp Ser Ile His Leu Ile Glu Leu
 50                  55                  60

Gln Leu Pro Glu Leu Pro Glu Leu Pro His Tyr His Thr Thr Asn
 65                  70                  75                  80

Gly Leu Pro Pro His Leu Asn Pro Thr Leu His Lys Ala Leu Lys Met
                 85                  90                  95

Ser Lys Pro Asn Phe Ser Arg Ile Leu Gln Asn Leu Lys Pro Asp Leu
            100                 105                 110

Leu Ile Tyr Asp Val Leu Gln Pro Trp Ala Glu His Val Ala Asn Glu
            115                 120                 125

Gln Asn Ile Pro Ala Gly Lys Leu Leu Thr Ser Cys Ala Ala Val Phe
130                 135                 140

Ser Tyr Phe Phe Ser Phe Arg Lys Asn Pro Gly Val Glu Phe Pro Phe
145                 150                 155                 160

Pro Ala Ile His Leu Pro Glu Val Glu Lys Val Lys Ile Arg Glu Ile
                165                 170                 175

Leu Ala Lys Glu Pro Glu Glu Gly Gly Arg Leu Asp Glu Gly Asn Lys
            180                 185                 190

Gln Met Met Leu Met Cys Thr Ser Arg Thr Ile Glu Ala Lys Tyr Ile
            195                 200                 205

Asp Tyr Cys Thr Glu Leu Cys Asn Trp Lys Val Val Pro Val Gly Pro
            210                 215                 220

Pro Phe Gln Asp Leu Ile Thr Asn Asp Ala Asp Asn Lys Glu Leu Ile
225                 230                 235                 240

Asp Trp Leu Gly Thr Lys His Glu Asn Ser Thr Val Phe Val Ser Phe
                245                 250                 255

Gly Ser Glu Tyr Phe Leu Ser Lys Glu Asp Met Glu Glu Val Ala Phe
            260                 265                 270

Ala Leu Glu Leu Ser Asn Val Asn Phe Ile Trp Val Ala Arg Phe Pro
            275                 280                 285

Lys Gly Glu Glu Arg Asn Leu Glu Asp Ala Leu Pro Lys Gly Phe Leu
            290                 295                 300

Glu Arg Ile Gly Glu Arg Gly Arg Val Leu Asp Lys Phe Ala Pro Gln
305                 310                 315                 320

Pro Arg Ile Leu Asn His Pro Ser Thr Gly Gly Phe Ile Ser His Cys
                325                 330                 335

Gly Trp Asn Ser Ala Met Glu Ser Ile Asp Phe Gly Val Pro Ile Ile
            340                 345                 350

Ala Met Pro Ile His Asn Asp Gln Pro Ile Asn Ala Lys Leu Met Val
            355                 360                 365

Glu Leu Gly Val Ala Val Glu Ile Val Arg Asp Asp Asp Gly Lys Ile
370                 375                 380

His Arg Gly Glu Ile Ala Glu Thr Leu Lys Ser Val Val Thr Gly Glu
385                 390                 395                 400

Thr Gly Glu Ile Leu Arg Ala Lys Val Arg Glu Ile Ser Lys Asn Leu
                405                 410                 415

Lys Ser Ile Arg Asp Glu Glu Met Asp Ala Val Ala Glu Glu Leu Ile
            420                 425                 430

Gln Leu Cys Arg Asn Ser Asn Lys Ser Lys
            435                 440

<210> SEQ ID NO 10
<211> LENGTH: 454
<212> TYPE: PRT

<213> ORGANISM: Escherichia coli

<400> SEQUENCE: 10

```
Met Gly Thr Glu Val Thr Val His Lys Asn Thr Leu Arg Val Leu Met
1               5                   10                  15

Phe Pro Trp Leu Ala Tyr Gly His Ile Ser Pro Phe Leu Asn Val Ala
            20                  25                  30

Lys Lys Leu Val Asp Arg Gly Phe Leu Ile Tyr Leu Cys Ser Thr Ala
        35                  40                  45

Ile Asn Leu Lys Ser Thr Ile Lys Lys Ile Pro Glu Lys Tyr Ser Asp
    50                  55                  60

Ser Ile Gln Leu Ile Glu Leu His Leu Pro Leu Pro Glu Leu Pro
65                  70                  75                  80

Pro His Tyr His Thr Thr Asn Gly Leu Pro Pro His Leu Asn His Thr
                85                  90                  95

Leu Gln Lys Ala Leu Lys Met Ser Lys Pro Asn Phe Ser Lys Ile Leu
            100                 105                 110

Gln Asn Leu Lys Pro Asp Leu Val Ile Tyr Asp Leu Gln Gln Trp
        115                 120                 125

Ala Glu Gly Val Ala Asn Glu Gln Asn Ile Pro Ala Val Lys Leu Leu
    130                 135                 140

Thr Ser Gly Ala Ala Val Leu Ser Tyr Phe Phe Asn Leu Val Lys Lys
145                 150                 155                 160

Pro Gly Val Glu Phe Pro Phe Pro Ala Ile Tyr Leu Arg Lys Asn Glu
                165                 170                 175

Leu Glu Lys Met Ser Glu Leu Leu Ala Gln Ser Ala Lys Asp Lys Glu
            180                 185                 190

Pro Asp Gly Val Asp Pro Phe Ala Asp Gly Asn Met Gln Val Met Leu
        195                 200                 205

Met Ser Thr Ser Arg Ile Ile Glu Ala Lys Tyr Ile Asp Tyr Phe Ser
    210                 215                 220

Gly Leu Ser Asn Trp Lys Val Val Pro Val Gly Pro Pro Val Gln Asp
225                 230                 235                 240

Pro Ile Ala Asp Asp Ala Asp Glu Met Glu Leu Ile Asp Trp Leu Gly
                245                 250                 255

Lys Lys Asp Glu Asn Ser Thr Val Phe Val Ser Phe Gly Ser Glu Tyr
            260                 265                 270

Phe Leu Ser Lys Glu Asp Arg Glu Glu Ile Ala Phe Gly Leu Glu Leu
        275                 280                 285

Ser Asn Val Asn Phe Ile Trp Val Ala Arg Phe Pro Lys Gly Glu Glu
    290                 295                 300

Gln Asn Leu Glu Asp Ala Leu Pro Lys Gly Phe Leu Glu Arg Ile Gly
305                 310                 315                 320

Asp Arg Gly Arg Val Leu Asp Lys Phe Ala Pro Gln Pro Arg Ile Leu
                325                 330                 335

Asn His Pro Ser Thr Gly Gly Phe Ile Ser His Cys Gly Trp Asn Ser
            340                 345                 350

Val Met Glu Ser Val Asp Phe Gly Val Pro Ile Ile Ala Met Pro Ile
        355                 360                 365

His Leu Asp Gln Pro Met Asn Ala Arg Leu Ile Val Glu Leu Gly Val
    370                 375                 380

Ala Val Glu Ile Val Arg Asp Asp Tyr Gly Lys Ile His Arg Glu Glu
385                 390                 395                 400
```

```
Ile Ala Glu Ile Leu Lys Asp Val Ile Ala Gly Lys Ser Gly Glu Asn
                405                 410                 415

Leu Lys Ala Lys Met Arg Asp Ile Ser Lys Asn Leu Lys Ser Ile Arg
            420                 425                 430

Asp Glu Glu Met Asp Thr Ala Ala Glu Glu Leu Ile Gln Leu Cys Lys
        435                 440                 445

Asn Ser Pro Lys Leu Lys
    450

<210> SEQ ID NO 11
<211> LENGTH: 458
<212> TYPE: PRT
<213> ORGANISM: Stevia rebaudiana

<400> SEQUENCE: 11

Met Glu Asn Lys Thr Glu Thr Thr Val Arg Arg Arg Arg Ile Ile
1               5                   10                  15

Leu Phe Pro Val Pro Phe Gln Gly His Ile Asn Pro Ile Leu Gln Leu
            20                  25                  30

Ala Asn Val Leu Tyr Ser Lys Gly Phe Ser Ile Thr Ile Phe His Thr
        35                  40                  45

Asn Phe Asn Lys Pro Lys Thr Ser Asn Tyr Pro His Phe Thr Phe Arg
    50                  55                  60

Phe Ile Leu Asp Asn Asp Pro Gln Asp Glu Arg Ile Ser Asn Leu Pro
65                  70                  75                  80

Thr His Gly Pro Leu Ala Gly Met Arg Ile Pro Ile Ile Asn Glu His
                85                  90                  95

Gly Ala Asp Glu Leu Arg Arg Glu Leu Glu Leu Leu Met Leu Ala Ser
            100                 105                 110

Glu Glu Asp Glu Glu Val Ser Cys Leu Ile Thr Asp Ala Leu Trp Tyr
        115                 120                 125

Phe Ala Gln Ser Val Ala Asp Ser Leu Asn Leu Arg Arg Leu Val Leu
    130                 135                 140

Met Thr Ser Ser Leu Phe Asn Phe His Ala His Val Ser Leu Pro Gln
145                 150                 155                 160

Phe Asp Glu Leu Gly Tyr Leu Asp Pro Asp Asp Lys Thr Arg Leu Glu
                165                 170                 175

Glu Gln Ala Ser Gly Phe Pro Met Leu Lys Val Lys Asp Ile Lys Ser
            180                 185                 190

Ala Tyr Ser Asn Trp Gln Ile Leu Lys Glu Ile Leu Gly Lys Met Ile
        195                 200                 205

Lys Gln Thr Lys Ala Ser Ser Gly Val Ile Trp Asn Ser Phe Lys Glu
    210                 215                 220

Leu Glu Glu Ser Glu Leu Glu Thr Val Ile Arg Glu Ile Pro Ala Pro
225                 230                 235                 240

Ser Phe Leu Ile Pro Leu Pro Lys His Leu Thr Ala Ser Ser Ser Ser
                245                 250                 255

Leu Leu Asp His Asp Arg Thr Val Phe Gln Trp Leu Asp Gln Gln Pro
            260                 265                 270

Pro Ser Ser Val Leu Tyr Val Ser Phe Gly Ser Thr Ser Glu Val Asp
        275                 280                 285

Glu Lys Asp Phe Leu Glu Ile Ala Arg Gly Leu Val Asp Ser Lys Gln
    290                 295                 300

Ser Phe Leu Trp Val Val Arg Pro Gly Phe Val Lys Gly Ser Thr Trp
305                 310                 315                 320
```

```
Val Glu Pro Leu Pro Asp Gly Phe Leu Gly Glu Arg Gly Arg Ile Val
            325                 330                 335

Lys Trp Val Pro Gln Gln Glu Val Leu Ala His Gly Ala Ile Gly Ala
            340                 345                 350

Phe Trp Thr His Ser Gly Trp Asn Ser Thr Leu Glu Ser Val Cys Glu
            355                 360                 365

Gly Val Pro Met Ile Phe Ser Asp Phe Gly Leu Asp Gln Pro Leu Asn
            370                 375                 380

Ala Arg Tyr Met Ser Asp Val Leu Lys Val Gly Val Tyr Leu Glu Asn
385                 390                 395                 400

Gly Trp Glu Arg Gly Glu Ile Ala Asn Ala Ile Arg Arg Val Met Val
            405                 410                 415

Asp Glu Glu Gly Glu Tyr Ile Arg Gln Asn Ala Arg Val Leu Lys Gln
            420                 425                 430

Lys Ala Asp Val Ser Leu Met Lys Gly Gly Ser Ser Tyr Glu Ser Leu
            435                 440                 445

Glu Ser Leu Val Ser Tyr Ile Ser Ser Leu
450                 455

<210> SEQ ID NO 12
<211> LENGTH: 470
<212> TYPE: PRT
<213> ORGANISM: jSolanum lycopersicum

<400> SEQUENCE: 12

Met Ser Pro Lys Leu His Lys Glu Leu Phe His Ser Leu Tyr Lys
1               5                   10                  15

Lys Thr Arg Ser Asn His Thr Met Ala Thr Leu Lys Val Leu Met Phe
            20                  25                  30

Pro Phe Leu Ala Tyr Gly His Ile Ser Pro Tyr Leu Asn Val Ala Lys
            35                  40                  45

Lys Leu Ala Asp Arg Gly Phe Leu Ile Tyr Phe Cys Ser Thr Pro Ile
            50                  55                  60

Asn Leu Lys Ser Thr Ile Glu Lys Ile Pro Glu Lys Tyr Ala Asp Ser
65                  70                  75                  80

Ile His Leu Ile Glu Leu His Leu Pro Glu Leu Pro Gln Leu Pro Pro
            85                  90                  95

His Tyr His Thr Thr Asn Gly Leu Pro Pro Asn Leu Asn Gln Val Leu
            100                 105                 110

Gln Lys Ala Leu Lys Met Ser Lys Pro Asn Phe Ser Lys Ile Leu Gln
            115                 120                 125

Asn Leu Lys Pro Asp Leu Val Ile Tyr Asp Ile Leu Gln Arg Trp Ala
            130                 135                 140

Lys His Val Ala Asn Glu Gln Asn Ile Pro Ala Val Lys Leu Leu Thr
145                 150                 155                 160

Ser Gly Ala Ala Val Phe Ser Tyr Phe Phe Asn Val Leu Lys Lys Pro
            165                 170                 175

Gly Val Glu Phe Pro Phe Pro Gly Ile Tyr Leu Arg Lys Ile Glu Gln
            180                 185                 190

Val Arg Leu Ser Glu Met Met Ser Lys Ser Asp Lys Glu Lys Glu Leu
            195                 200                 205

Glu Asp Asp Asp Asp Asp Asp Leu Leu Val Asp Gly Asn Met Gln
            210                 215                 220

Ile Met Leu Met Ser Thr Ser Arg Thr Ile Glu Ala Lys Tyr Ile Asp
```

```
               225                 230                 235                 240
        Phe Cys Thr Ala Leu Thr Asn Trp Lys Val Pro Val Gly Pro Pro
                        245                 250                 255

Val Gln Asp Leu Ile Thr Asn Asp Val Asp Met Glu Leu Ile Asp
                        260                 265                 270

Trp Leu Gly Thr Lys Asp Glu Asn Ser Thr Val Phe Val Ser Phe Gly
                        275                 280                 285

Ser Glu Tyr Phe Leu Ser Lys Glu Asp Met Glu Glu Val Ala Phe Ala
                        290                 295                 300

Leu Glu Leu Ser Asn Val Asn Phe Ile Trp Val Ala Arg Phe Pro Lys
        305                 310                 315                 320

Gly Glu Glu Arg Asn Leu Glu Asp Ala Leu Pro Lys Gly Phe Leu Glu
                        325                 330                 335

Arg Ile Gly Glu Arg Gly Arg Val Leu Asp Lys Phe Ala Pro Gln Pro
                        340                 345                 350

Arg Ile Leu Asn His Pro Ser Thr Gly Gly Phe Ile Ser His Cys Gly
                        355                 360                 365

Trp Asn Ser Ala Met Glu Ser Ile Asp Phe Gly Val Pro Ile Ile Ala
                        370                 375                 380

Met Pro Met His Leu Asp Gln Pro Met Asn Ala Arg Leu Ile Val Glu
        385                 390                 395                 400

Leu Gly Val Ala Val Glu Ile Val Arg Asp Asp Gly Lys Ile His
                        405                 410                 415

Arg Gly Glu Ile Ala Glu Thr Leu Lys Gly Val Ile Thr Gly Lys Thr
                        420                 425                 430

Gly Glu Lys Leu Arg Ala Lys Val Arg Asp Ile Ser Lys Asn Leu Lys
                        435                 440                 445

Thr Ile Arg Asp Glu Glu Met Asp Ala Ala Ala Glu Glu Leu Ile Gln
                        450                 455                 460

Leu Cys Arg Asn Gly Asn
        465                 470

<210> SEQ ID NO 13
<211> LENGTH: 808
<212> TYPE: PRT
<213> ORGANISM: Escherichia coli

<400> SEQUENCE: 13

Met Ala Asn Ala Glu Arg Met Ile Thr Arg Val His Ser Gln Arg Glu
        1               5                   10                  15

Arg Leu Asn Glu Thr Leu Val Ser Glu Arg Asn Glu Val Leu Ala Leu
                        20                  25                  30

Leu Ser Arg Val Glu Ala Lys Gly Lys Gly Ile Leu Gln Gln Asn Gln
                        35                  40                  45

Ile Ile Ala Glu Phe Glu Ala Leu Pro Glu Gln Thr Arg Lys Lys Leu
        50                  55                  60

Glu Gly Gly Pro Phe Phe Asp Leu Leu Lys Ser Thr Gln Glu Ala Ile
        65                  70                  75                  80

Val Leu Pro Pro Trp Val Ala Leu Ala Val Arg Pro Arg Pro Gly Val
                        85                  90                  95

Trp Glu Tyr Leu Arg Val Asn Leu His Ala Leu Val Val Glu Glu Leu
                        100                 105                 110

Gln Pro Ala Glu Phe Leu His Phe Lys Glu Glu Leu Val Asp Gly Val
                        115                 120                 125
```

```
Lys Asn Gly Asn Phe Thr Leu Glu Leu Asp Phe Glu Pro Phe Asn Ala
130                 135                 140

Ser Ile Pro Arg Pro Thr Leu His Lys Tyr Ile Gly Asn Gly Val Asp
145                 150                 155                 160

Phe Leu Asn Arg His Leu Ser Ala Lys Leu Phe His Asp Lys Glu Ser
                165                 170                 175

Leu Leu Pro Leu Leu Lys Phe Leu Arg Leu His Ser His Gln Gly Lys
            180                 185                 190

Asn Leu Met Leu Ser Glu Lys Ile Gln Asn Leu Asn Thr Leu Gln His
        195                 200                 205

Thr Leu Arg Lys Ala Glu Glu Tyr Leu Ala Glu Leu Lys Ser Glu Thr
210                 215                 220

Leu Tyr Glu Glu Phe Glu Ala Lys Phe Glu Glu Ile Gly Leu Glu Arg
225                 230                 235                 240

Gly Trp Gly Asp Asn Ala Glu Arg Val Leu Asp Met Ile Arg Leu Leu
                245                 250                 255

Leu Asp Leu Leu Glu Ala Pro Asp Pro Cys Thr Leu Glu Thr Phe Leu
            260                 265                 270

Gly Arg Val Pro Met Val Phe Asn Val Ile Leu Ser Pro His Gly
        275                 280                 285

Tyr Phe Ala Gln Asp Asn Val Leu Gly Tyr Pro Asp Thr Gly Gly Gln
290                 295                 300

Val Val Tyr Ile Leu Asp Gln Val Arg Ala Leu Glu Ile Glu Met Leu
305                 310                 315                 320

Gln Arg Ile Lys Gln Gln Gly Leu Asn Ile Lys Pro Arg Ile Leu Ile
                325                 330                 335

Leu Thr Arg Leu Leu Pro Asp Ala Val Gly Thr Thr Cys Gly Glu Arg
            340                 345                 350

Leu Glu Arg Val Tyr Asp Ser Glu Tyr Cys Asp Ile Leu Arg Val Pro
        355                 360                 365

Phe Arg Thr Glu Lys Gly Ile Val Arg Lys Trp Ile Ser Arg Phe Glu
370                 375                 380

Val Trp Pro Tyr Leu Glu Thr Tyr Thr Glu Asp Ala Ala Val Glu Leu
385                 390                 395                 400

Ser Lys Glu Leu Asn Gly Lys Pro Asp Leu Ile Ile Gly Asn Tyr Ser
                405                 410                 415

Asp Gly Asn Leu Val Ala Ser Leu Leu Ala His Lys Leu Gly Val Thr
            420                 425                 430

Gln Cys Thr Ile Ala His Ala Leu Glu Lys Thr Lys Tyr Pro Asp Ser
        435                 440                 445

Asp Ile Tyr Trp Lys Lys Leu Asp Asp Lys Tyr His Phe Ser Cys Gln
450                 455                 460

Phe Thr Ala Asp Ile Phe Ala Met Asn His Thr Asp Phe Ile Ile Thr
465                 470                 475                 480

Ser Thr Phe Gln Glu Ile Ala Gly Ser Lys Glu Thr Val Gly Gln Tyr
                485                 490                 495

Glu Ser His Thr Ala Phe Thr Leu Pro Gly Leu Tyr Arg Val Val His
            500                 505                 510

Gly Ile Asp Val Phe Asp Pro Lys Phe Asn Ile Val Ser Pro Gly Ala
        515                 520                 525

Asp Met Ser Ile Tyr Phe Pro Tyr Thr Glu Glu Lys Arg Arg Leu Thr
530                 535                 540

Lys Phe His Ser Glu Ile Glu Glu Leu Leu Tyr Ser Asp Val Glu Asn
```

```
545                550                555                560
Lys Glu His Leu Cys Val Leu Lys Asp Lys Lys Pro Ile Leu Phe
            565                570                575

Thr Met Ala Arg Leu Asp Arg Val Lys Asn Leu Ser Gly Leu Val Glu
            580                585                590

Trp Tyr Gly Lys Asn Thr Arg Leu Arg Glu Leu Ala Asn Leu Val Val
            595                600                605

Val Gly Gly Asp Arg Arg Lys Glu Ser Lys Asp Asn Glu Glu Lys Ala
            610                615                620

Glu Met Lys Lys Met Tyr Asp Leu Ile Glu Glu Tyr Lys Leu Asn Gly
625                630                635                640

Gln Phe Arg Trp Ile Ser Ser Gln Met Asp Arg Val Arg Asn Gly Glu
                645                650                655

Leu Tyr Arg Tyr Ile Cys Asp Thr Lys Gly Ala Phe Val Gln Pro Ala
                660                665                670

Leu Tyr Glu Ala Phe Gly Leu Thr Val Val Glu Ala Met Thr Cys Gly
                675                680                685

Leu Pro Thr Phe Ala Thr Cys Lys Gly Gly Pro Ala Glu Ile Ile Val
            690                695                700

His Gly Lys Ser Gly Phe His Ile Asp Pro Tyr His Gly Asp Gln Ala
705                710                715                720

Ala Asp Thr Leu Ala Asp Phe Phe Thr Lys Cys Lys Glu Asp Pro Ser
                725                730                735

His Trp Asp Glu Ile Ser Lys Gly Gly Leu Gln Arg Ile Glu Glu Lys
            740                745                750

Tyr Thr Trp Gln Ile Tyr Ser Gln Arg Leu Leu Thr Leu Thr Gly Val
            755                760                765

Tyr Gly Phe Trp Lys His Val Ser Asn Leu Asp Arg Leu Glu Ala Arg
            770                775                780

Arg Tyr Leu Glu Met Phe Tyr Ala Leu Lys Tyr Arg Pro Leu Ala Gln
785                790                795                800

Ala Val Pro Leu Ala Gln Asp Asp
            805
```